United States Patent [19]
Nagase et al.

[11] Patent Number: 6,156,762
[45] Date of Patent: Dec. 5, 2000

[54] INDOLOMORPHINAN DERIVATIVE AND AGENT FOR CURING AND PREVENTING CEREBRAL DISORDER

[75] Inventors: Hiroshi Nagase; Yoshifumi Imamura; Junichi Hirokawa; Susumu Matsuda; Yasushi Miyauchi, all of Kanagawa, Japan

[73] Assignee: Toray Industries, Inc., Japan

[21] Appl. No.: 09/142,794

[22] PCT Filed: Jan. 13, 1998

[86] PCT No.: PCT/JP98/00092

§ 371 Date: Sep. 24, 1998

§ 102(e) Date: Sep. 24, 1998

[87] PCT Pub. No.: WO98/31684

PCT Pub. Date: Jul. 23, 1998

[30] Foreign Application Priority Data

Jan. 16, 1997 [JP] Japan ................................ 9-005829

[51] Int. Cl.[7] ...................... A61K 31/485; C07D 489/10
[52] U.S. Cl. ................................ 514/279; 546/26; 546/28; 546/31; 546/35; 546/36
[58] Field of Search .................. 514/279; 546/26, 546/28, 31, 35, 36, 37

[56] References Cited

U.S. PATENT DOCUMENTS 5,852,030 12/1998 Nagase et al. .......................... 514/279

FOREIGN PATENT DOCUMENTS

WO 95/31463 11/1995 WIPO .
WO 95/31464 11/1995 WIPO .

Primary Examiner—Charamjit S. Aulakh
Attorney, Agent, or Firm—Austin R. Miller

[57] ABSTRACT

The present invention provides an indolomorphinan derivative or a pharmacologically acceptable acid addition salt thereof, and an agent for curing and preventing cerebral disorders composed of the derivative and salt thereof, which is represented by the following formula (I):

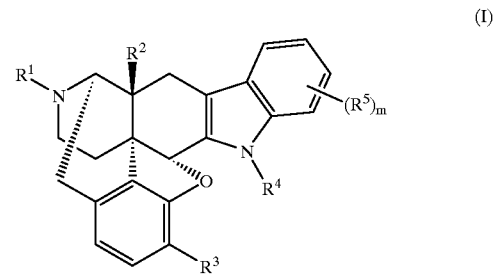

(I)

[wherein $R^1$ represents cyclopropylmethyl or the like; $R^2$ and $R^3$ each represent hydroxy methoxy, or the like; $R^4$ represents hydrogen, methyl, benzyl, 3-isothiocyanatopropyl, or the like; and $(R^5)_m$ represents hydrogen, substituted benzo, or the like]. The compounds of the present invention have the excellent effect of preventing damage of the cerebral nerve cells. Therefore, the compounds of the present invention are useful as medicines used for curing and preventing various cerebral diseases such as cerebral stroke, traumatic cerebral diseases, cerebral edema, and cerebral neurodegenerative diseases, ameliorating after-effects thereof, and preventing the recurrence thereof by inhibiting various ischemic, hemorrhagic or traumatic cerebral disorders, and damages of the cerebral nerve cells caused by various nerve degenerations.

17 Claims, No Drawings

INDOLOMORPHINAN DERIVATIVE AND AGENT FOR CURING AND PREVENTING CEREBRAL DISORDER

CROSS REFERENCE TO RELATED APPLICATIONS

This application is a 371 of PCT/JP98/00092 filed Jan. 13, 1998 now WO98/31684 and claims priority of Japanese Application No. 5829, filed Jan. 16, 1997.

TECHNICAL FIELD

The present invention relates to indolomorphinan derivatives or pharmacologically acceptable acid addition salts thereof, and an agent for curing and preventing cerebral disorders comprising the derivatives or salts thereof, and particularly to a medicine useful for ameliorating various cerebral diseases and aftereffects thereof, and preventing the recurrence thereof.

BACKGROUND ART

In recent years, diseases in the cerebral region such as various cerebrovascular diseases have increased with the arrival of the aging society. Cerebrovascular diseases are possibly caused by aging, hypertension, arterial sclerosis, hyperlipidemia, and the like, and are generally referred to as "cerebral stroke". In a broad sense, cerebral vascular diseases possibly include functional disorders of the brain due to head trauma.

Cerebral stroke is roughly classified into ischemic (infarcted) diseases and hemorrhagic diseases. Examples of the former include cerebral infarction (cerebral thrombosis, cerebral embolism(, and the like, and examples of the latter include cerebral hemorrhage, subarachnoid hemorrhage, and the like. In these diseases, the blood flow is clogged due to a cerebrovascular disorder, and thus glucose and oxygen, which are energy sources of the action of the cerebral nerve cells, are insufficiently supplied, resulting in various damage of the nerve cells. These diseases are fundamentally caused by death of the cerebral nerve cells of a damage area and the periphery thereof. Such cerebrovascular diseases cause occurrence of various aftereffects such as cerebrovascular dementia, which are critical medical and social problems at present.

Medicines which have been developed as agents for curing such cerebrovascular diseases in Japan are mainly used for ameliorating aftereffects such as psychoneurosis and the like, and main medicines have the function to increase the amount of the blood flow to the brain to promote the supply of glucose and oxygen to an ischemic area. From the viewpoint of the functional mechanism, these medicines are expressed by vague terms such as medicines for ameliorating the cerebral blood flow, medicines for activating cerebral metabolism, and medicines for ameliorating cerebral function. However, almost all of these medicines are effective in ameliorating marginal symptoms such as volition disorders, affective disorders, behavioral abnormality, and the like, while the activity to the nucleus symptoms of dementia such as memory disorders and the like is considered as doubtful. Also some anti cerebral edema agents, antithrombotic agents, and thrombolytic agents are clinically used, particularly, in the acute stage of a cerebrovascular disease. These agents also have no direct action on the cerebral nerve cells, but are used only for symptomatic therapy. In any case, the above present medicines have substantially no effect on damage of the cerebral nerve cells in cerebrovascular diseases, and have no action to inhibit directly the death of the cerebral nerve cells.

As described above, there is now no medicine effective against damage of the cerebral nerve cells which are fundamental causes of cerebrovascular diseases. It is known that the degree of such damage has correlation to the ischemia time the cerebral blood flow is clogged, and a long ischemia time causes organic damage to the cerebral nerve cells which are not ameliorated even by recovery of the blood flow. For such cerebrovascular disorders, it is important to cure the disorders in the acute stage within 24 hours from the occurrence of the disease. Therefore, there is now demand for developing, as early as possible, a medicine which has the effect of securely protecting damages of the cerebral nerve cells and which is easy to use.

In addition to such cerebrovascular disorders, an increase in cerebral neurodegenerative diseases such as Alzheimer's disease is also a problem, and approach for elucidating causes and developing a therapeutic method is actively carried out in various fields. Although the main object of the approach is to activate, particularly, the acetylcholine nervous system, approach is also carried out by employing the neuroprotective action by a substance related to a nerve growth factor, a neurotrophic factor for the death of the nerve cells due to cerebral neurodegenerative diseases. Also the effect of a medicine having the cerebral neuroprotective action is expected.

The present invention relates to an agent for curing and preventing cerebral disorders, and an object of the present invention is to provide a medicine useful for ameliorating various cerebral diseases and aftereffects thereof, and preventing the recurrence thereof. Particularly, the present invention provides a medicine useful for curing and preventing cerebral stroke, traumatic cerebral disease, cerebral edema, and cerebral neurodegenerative diseases by inhibiting various ischemic, hemorrhagic or traumatic cerebral disorders and damage of the cerebral nerve cells caused by various nerve degeneration, to protect the cerebral nerve cells.

DISCLOSURE OF THE INVENTION

The object can be achieved by the present invention described below.

The present invention relates to an agent for curing and preventing cerebral disorders comprising an indolomorphinan derivative or a pharmacologically acceptable acid addition salt thereof, which is represented by the following formula (I):

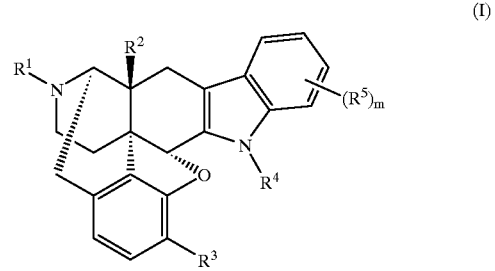

wherein $R^1$ represents hydrogen, alkyl having a carbon number of 1 to 5, cycloalkylalkyl having a carbon number of 4 to 7, cycloalkenylalkyl having a carbon number of 5 to 7, aryl having a carbon number of 6 to 12, aralky having a carbon number of 7 to 13, alkenyl having a carbon number of 2 to 7, furan-2-ylalkyl (wherein an alkyl moiety has a carbon number of 1 to 5), or thiophene-2-ylalkyl (wherein an alkyl moiety has a carbon number of 1 to 5);

wherein $R^2$ and $R^3$ independently represent hydrogen, hydroxy, alkoxy having a carbon number of 1 to 5, alkanoyloxy having a carbon number of 1 to 5, aralkyloxy having a carbon number of 7 to 13, or arylcarbnyloxy having a carbon number of 7 to 13;

wherein $R^4$ represents hydrogen, alkyl having a carbon number of 1 to 8, aralkyl having a carbon number of 7 to 13 (which may be substituted by at least one substituent $R^{15}$), or $R^6$;

$R^6$ represents alkanoyl having a carbon number of 1 to 5, arylcarbonyl having a carbon number of 7 to 13 (which may be substituted by at least one substituent $R^{15}$), alkylsulfonyl having a carbon number of 1 to 5, arylsulfonyl having a carbon number of 6 to 12 (which may be substituted by at least one substituent $R^{15}$), aralkylsulfonyl having a carbon number of 7 to 13 (which may be substituted by at least one substituent $R^{15}$), or $(CH_2)_i-R^{16}$;

$R^{15}$ represents fluoro, chloro, bromo, iodo, nitro, amino, hydroxy, alkyl having a carbon number of 1 to 5, alkoxy having a carbon number of 1 to 5, isothiocyanoto, trifluoromethyl, trifluoromethoxy, or cyano;

i represents an integer of 1 to 8;

$R^{16}$ represents $OR^7$, $NR^7F^{7'}$, nitro, cyano, isocyano, isocyanato, isothiocyanato, $COOR^7$, $CONR^7R^7$, $NR^7CHO$, $NR^7(CO)-R^9$, $NR^7(CO)NR^8R^9$, $NR^7(C=S)NR^8R^9$, $NR^7(CO))-R^9$, or $NR^7(C=S)O-R^9$ (wherein $R^7$, $R^{8'}$, $R^8$ independently represent hydrogen or alkyl having a carbon number of 1 to 5);

$R^9$ represents alkyl having a carbon number of 1 to 5, aryl having a carbon number of 6 to 12 (which may be substituted by at least one substituent $R^{15}$), heteroaryl having a hetero atom number of 1 to 3 and a carbon number of 3 to 11 (wherein a hetero atom is O, N or S, and which may be substituted by at least one substituent $R^{15}$), aralkyl having a carbon number of 7 to 13 (which may be substituted by at least one substituent $R^{15}$), or arylalkenyl having a carbon number of 8 to 15 (wherein an aryl moiety may be substituted by at least one substituent $R^{15}$);

m represents an integer of 0 to 4;

$R^5$ represents each of m substituents on the benzene ring, such as fluoro, chloro, bromo, amino, alkyl having a carbon number of 1 to 8, cycloalkyl having a carbon number of 3 to 7, or alkoxy having a carbon number of 1 to 5 (wherein when $R^4$ is $R^6$, $R^5$ represents $R^{11}$), or two $R^5$ substituted at adjacent carbons form together a fused ring structure A (wherein residual 0 to 2 substituents $R^5$ each represent $R^{11}$ or form another fused ring structure A);

the fused ring structure A is a benzo, indeno or naphtho structure which is unsubstituted or substituted by 1 to 4 substituents $R^{10}$;

$R^{10}$ and $R^{11}$ independently represent (1) fluoro, chloro, bromo, iodo, nitro, alkyl having a carbon number of 1 to 8, alkoxy having a carbon number of 1 to 5, isothiocyanato, trifluoromethyl, trifluoromethoxy, cyano, phenyl, hydroxyalkyl having a carbon number of 1 to 3, $SR^{12}$, $SOR^{12}$, $SO_2R^{12}$, $(CH_2)_kCO_2R^{12}$, $SO_2NR^{13}R^{14}$, $(CH_2)_kNR^{13}R^{14}$, or $(CH_2)_kN(R^{13})COR^{14}$ (wherein k represents an integer of 0 to 5, $R^{12}$ represents alkyl having a carbon number of 1 to 5, $R^{13}$ and $R^{14}$ independently represent hydrogen, alkyl having a carbon number of 1 to 5, or cycloalkylalkyl having a carbon number of 4 to 6), and/or (2) $R^{10}$ and $R^{11}$ substituted at adjacent carbons with a ring junction therebetween form together any one of ethano, propano and o-benzeno bridged structures $R^{10}-R^{11}$; and formula (I) includes (+) form, (−) form and (±) form.

The present invention also relates to indolomorphinan derivatives and pharmacologically acceptable addition salts thereof represented by the following formula (II):

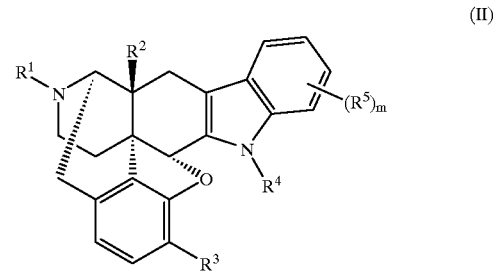

(II)

wherein $R^1$, $R^2$, $R^3$, $R^4$, $R^{15}$, i, $R^6$, $R^{16}$, $R^7$, $R^{7'}$, $R^8$, $R^9$, m, $R^5$, A, $R^{10}$, k, $R^{12}$, $R^{13}$ and $R^{14}$ are defined as the same as described above (wherein when $R^4$ is hydrogen, alkyl having a carbon number of 1 to 8 or aralkyl having a carbon number of 7 to 13, m is an integer of 2 to 4, two $R^5$ groups form together a fused ring structure A, and each of the residual 0 to 2 $R^5$ groups must be $R^{11}$ (wherein when the fused ring structure A is benzo, at least one $R^{10}$ and one $R^{11}$ substituted at adjacent carbons with a ring junction therebetween must form together a bridged structure $R^{10}-R^{11}$ which must be any one of ethano, propano and o-benzo), or must form another fused ring structure A), and formula (II) includes (+) form, (−) form and (±) form.

BEST MODE FOR CARRYING OUT THE INVENTION

Preferred embodiments of the agent for curing and preventing cerebral disorders comprising an indolomorphinan derivative or a pharmacologically acceptable acid addition salt thereof represented by formula (I) of the present invention are as follows.

$R^1$ is preferably hydrogen, alkyl having a carbon number of 1 to 5, cycloalkylmethyl having a carbon number of 4 to 7, cycloalkyenylmethyl having a carbon number of 5 to 7, phenyl, naphthyl, phenylalkyl having a carbon number of 7 to 13, alkenyl having a carbon number of 2 to 7, furan-2-ylalkyl having a carbon number of 1 to 5 (wherein the carbon number indicates the number of the carbons of the alkyl moiety of furan-2-ylalkyl), or thiophene-2-ylalkyl having a carbon number of 1 to 5 (wherein the carbon number indicates the number of the carbons of the alkyl moiety of thiophene-2-ylalkyl), and more preferably hydrogen, methyl, ethyl, propyl, butyl, cyclopropylmethyl, cyclobutylmethyl, cyclopentylmethyl, benzyl, phenetyl, allyl, 2-butenyl, 3-butenyl, 2-methyl-2-butenyl, 3-methyl-2-butenyl, 3-methyl-3-butenyl, furan-2-ylmethyl, or thiophene-2-ylmethyl. Of these groups, hydrogen methyl, cyloopropylmethyl, cyclobutylmethyl, benzyl, phenetyl, and ally are preferred.

$R^2$ and $R^3$ are preferably hydrogen, hydroxy, methoxy, ethyoxy, propoxy, acetoxy, benzyloxy, or benzoyloxy. Of tehse groups, $R^2$ is more preferably hydroxy, methoxy, or acetoxy, and $R^3$ is more preferably hydrogen, hydroxy or methoxy.

$R^4$ is preferably hydrogen, methyl, ethyl, butyl, benzyl, phenetyl, or 3-phenylpropyl, and other preferably groups as $R^4$ include groups preferably for $R^6$, such as acetyl, benzoyl, methanesulfonyl, benzenesulfonyl, benzylsulfonyl, $(CH_2)_2$—$R^{16}$, $(CH_2)_3$—$R^{16}$, $(CH_2)_4$—$R^{16}$ and the like.

Of these groups $R^4$, when $R^4$ is benzyl, phenetyl, 3-phenylpropyl, benzoyl, benzenesulfonyl or benzylsulfonyl, an aryl moiety may be substituted by a substituent $R^{15}$, wherein $R^{15}$ is one or two substituents which are the same or different and preferably selected from fluoro, chloro, bromo, nitro, amino, methyl, methoxy, isothiocyanato, trifluoromethyl, trifluoromethoxy, and cyano, and particularly one substituent preferably selected from fluoro, chloro, bromo, nitro, methyl, methoxy, and trifluoromethyl.

In the above description, $R^{16}$ is preferably hydroxy, methoxy, ethoxy, amino, methylamino, dimethylamino, nitro, cyano, isocyano, isocyanato, istiocyanato, COOH, COOMe, COOEt, $CONH_2$, NHCHO, NH(CH)—$R^9$, NH(CO)NH—$R^9$, NH(C=S)NH—$R^9$, NH(CO))—$R^9$, or NH(C=S)O—$R^9$. Of these groups, hydroxy, methoxy, amino, nitro, cyano, isothiocyanato, COOH, COOMe, COOEt, NHCHO, NH(CO)—$R^9$, NH(CO)NH—$R^9$, and NH(C=S)NH—$R^9$ are particularly preferable.

In this case, $R^9$ is preferably methyl, phenyl, naphthyl, furly, thienyl, pyrrolyl, pryidyl, indolyl, quinolyl, benzyl, or cinnamyl. In these groups $R^9$ except methyl, the aryl moiety may be substituted by a substituent $R^{15}$. In this case, as $R^{15}$, one or the same or different two substituents are preferably selected from fluoro, chloro, bromo, nitro, amino, methyl, methoxy, isothiocyanato, trifluoromethyl, trifluoromethoxy and cyano, and, particularly, one substituent is preferably selected from fluoro, chloro, bromo, nitro, methyl, methoxy, and trifluoromethyl.

Of these groups $R^4$, preferably examples of $R^4$ include hydrogen, methyl, ethyl, butyl, benzyl, fluorobenzyl, chlorobenzyl, bromobenzyl, methylbenzyl, methoxybenzyl, nitrobenzyl, (tirfluoromethyl)benzyl, 2-phneytyl, 3-phenylpropyl, acetyl, benzoyl, methanesulfonyl, benzenesulfonyl, toluenesulfonyl, benzylsulfonyl, $(CH)_2$OH, $(CH_2)_2$OMe, $(CH_2)_2$OEt, $(CH_2)_n$$NH_2$, $(CH_2)_2$$NO_2$, $(CH_2)$CN, $(CH_2)_2$NCS, $(CH_{22}$COOH, $(CH_2)_2$COOMe, $(CH_2)_2$COOEt, $(CH_2)_2$NHCHO, $(CH_2)_2$NH(CO)Ph, $(CH_2)_N$ NH(CO)-cinnamyl, $(CH_2)_N$NH(CO)—(trifluoromethyl) cinnamyl, $(CH_2)_2$NH(CO)-pyridyl, $(CH_2)_2$NH(CO)NHPh, $(CH_2)_2$NH(C=S)NHPh, $(CH_20_N$NH(C=S)NHCH$_2$Ph, $(CH_2)_3$OH, $(CH_2)_3$OMe, $(CH_2)_3$OEt, $(CH_2)_3$$NH_2$, $(CH_2)_3$$NO_2$, $(CH_2)_3$CN, $(CH_2)_3$NCS, $(CH_2)_3$COOH, $(CH_2)_3$COOMe, $(CH_2)_3$COOEt, $(CH_2)_3$NHCHO, $(CH_2)_3$NH(CO)Ph, $(CH_2)_3$NH(CO)-cinnamyl, $(CH_2)_3$NH(CO)-(trifluoromethyl) cinnamyl, $(CH_2)_3$NH(CO)-pyridyl, $(CH_2)_3$NH(CO)NHPh, $(CH_2)_3$NH(C=S)NHPh, $(CH_2)_3$NH(C=S)NHCH$_2$Ph, $(CH_2)_4$OH, $(CH_2)_4$OMe, $(CH_2)_4$OEt, $(CH_2)_4$$NH_2$, $(CH_2)_4$$NO_2$, $(CH_2)_4$CN, $(CH_{24}$NCS, $(CH_2)_4$COOH, $(CH_2)_4$COOMe, $(CH_2)_4$COOEt, $(CH_2)_4$NHCHO, $(CH_2)_4$NH(CO)Ph, $(CH_2)_4$NH(CO)-cinnamyl, $(CH_2)_4$NH(CO)-(trifluoromethyl) cinnamyl, $(CH_2)_4$NH(CO)-pyridyl, $(CH_2)_4$NH(CO)NHPh, $(C_2)_4$NH(C=S)NHPh,$(CH_2)_4$NH(C=S)NHCH$_2$Ph, and the like. However, $R^4$ is not limited to these groups.

When $R^5$ does not form the fused ring structure A, $R^5$ is preferably fluoro, chloro, bromo, amino, methyl, ethyl, propyl, butyl, heptyl, cyclopentyl, cyclopentyl, cyclohexyl, methoxy or ethoxy, and more preferably fluoro, chloro, bromo, methyl, heptyl, cyclopentyl, cyclohexyl or methoxy.

However, when $R^4$ is $R^6$, $R^5$ presents $R^{11}$. In this case, groups as $R^{11}$ include fluoro, chloro, bromo, iodo, nitro, methyl, ethyl, propyl, butyl, heptyl, methoxy, isothiocyanato, trifluoromethyl, trifluoromethoxy, cyano, phenyl, hydroxymethyl, hydroxyethyl, hyroxyprpyl, $SR^{12}$, $SOR^{12}$, $SO_2R^{12}$, $CH_2CO_2R^{12}$, $(CH_2)_2CO_2R^{12}$, $(CH_2)_3CO_2R^{12}$, $SO_2NR^{13}R^{14}$, $CH_2NR^{13}R^{14}$, $(CH_2)_2NR^{13}R^{14}$, $(CH_2)_3NR^{13}R^{14}$, $C_2N(R^{13})COR^{14}$, $(CH_2)_2N(R^{13})COR^{14}$, and $(CH_2)_3N(R^{13})COR^{14}$. Of these groups, fluoro, chloro, bromo, nitro, methyl, ethyl, heptyl, methoxy, isothiocyanato, trifluoromethyl, trifluoromethoxy, cyano, phenyl, hydroxymethyl, hydroxyethyl, hydroxypropyl, $SR^{12}M$ $SOR^{12}SO_2R^{12}$, $CH_2CO_2R^{12}$, $(CH_2)_2CO_2R^{12}$, $(CH_2)$[<i]nf3$CO_2R^{12}$, $SO_2NR^{13}R^{14}$, $CONR^{13}R^{14}$, $CH_2NR^{13}R^{14}$, $(CH_2)_2NR^{13}R^{14}$, $(CH_2)_3NR^{13}R^{14}$, $CH_2N(R^{13})COR^{14}$, $(CH_2)_2N(R^{13})COR^{14}$, and $(CH_2)_3N(R^{13})COR^{14}$ are preferably. In this case, $R^{12}$is preferably methyl or ethyl, $R^{13}$ is preferably hydrogen or methyl, and $R^{14}$ is preferably hydrogen, methyl, ethyl, propyl, butyl, cyclopropylmethyl, or cyclobutylmethyl. When two groups $R^5$ form a fused ring structure A together, the residual 0 to 2 groups $R^5$ are $R^{11}$, or the residual two $R^5$ form another fused ring structure A together. The fused ring structure A is preferably a benzo structure unsubstituted or substituted by 1 or 2groups $R^{10}$, or an indeno or naphtho structure unsubstituted by $R^{10}$. Particularly, a benzo structure unsubstituted or unsubstituted by one $R^{10}$ is preferably. For example, tow $R^5$ groups form a benzo structure as the fused ring structure A, examples of compounds of formula (I) include compounds represented by the following formulae (IIIa), (IIIb), (IIIc) and (IIId). However, the compounds of formula (I) are not limited to these compounds.

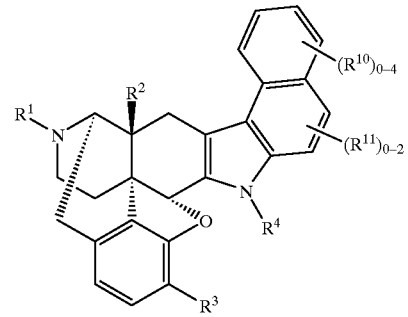

(IIIa)

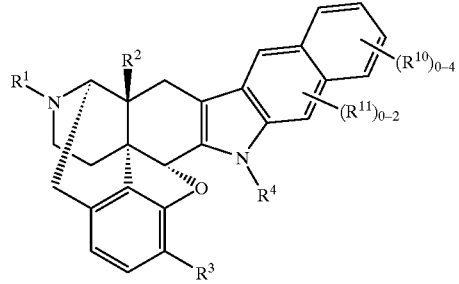

(IIIb)

(IIIc)

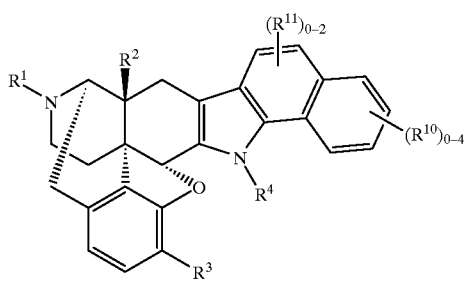

(IVb)

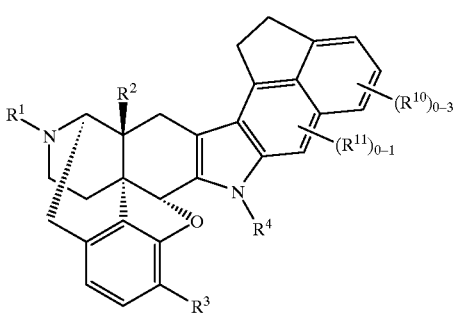

(IIId)

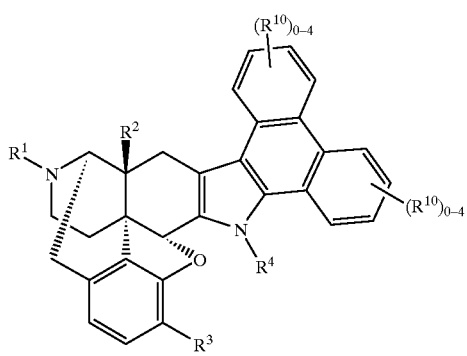

(IVc)

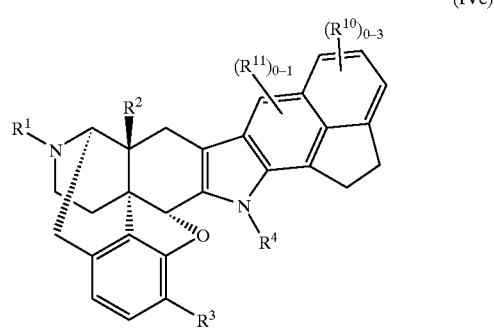

Each of $R^{10}$ and $R^{11}$ is preferably fluoro, chloro, bromo, iodo, nitro, methyl, ethyl, propyl, butyl, methoxy, isothiocyanato, trifluoromethyl, trifluoromethyl, cyano, phenyl, hydroxymethyl, hydroxyethyl, hydroxypropyl, $SR^{12}$, $SOR^{12}$, $SO_2R^{12}$, $CH_2CO_2R^{12}$, $(CH_2)_2CO_2R^{12}$, $(CH_2CO_2R^{12}$, $SO_2NR^{13}R^{14}$, $CONR^{13}R^{14}$, $CH_2NR^{13}R^{14}$, $(CH_2)_2NR^{13}R^{14}$, $(CH_2)_3NR^{13}R^{14}$, $CH_2N(R^{13})COR^{14}$, $(CH_2)_2N(R^{13})COR^{14}$, or $(CH_2)_3N(R^{13})COR^{14}$. In this case, $R^{12}$ is preferably methyl or ethyl, $R^{13}$ is preferably hydrogen, methyl or ethyl, and $R^{14}$ is preferably hydrogen, ethyl, propyl, butyl, cyclopropylmethyl, or cyclobutylmethyl. $R^{10}$ and $R^{11}$ may form a bridged structure of $R^{10}$–$R^{11}$ together. In this case, an ethano or o-benzeno structure is preferable as the bridged structure. For example, the bridged structure is ethano, and the fused ring structure A is benzo, examples of compounds of formula (I) include compounds represented by the following formulae (IVa), (IVb), (IVc) and (IVd). The compounds of formula (I) are not limited to these compounds.

(IVa)

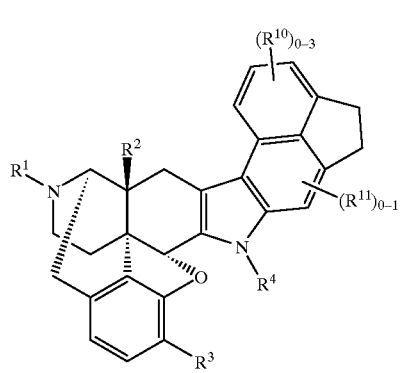

(IVd)

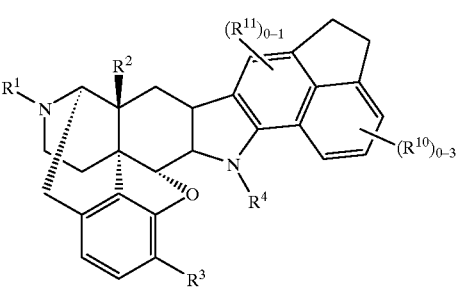

The substituents in preferred embodiments of the indolomorphinan derivatives or pharmacologically acceptable acid addition salts thereof represented by formula (II) of the present invention are basically the same as those in preferred embodiments of the agent for curing and preventing cerebral disorder comprising the indolomorphinan derivatives or pharmacologically acceptable acid addition salts thereof represented by formula (I) of the present invention. However, when $R^4$ is hydrogen, alkyl having a carbon number of 1 to 8, or aralkyl having a carbon number of 7 to 13, m is an integer of 2 to 4, two $R^5$ groups necessarily form a fused ring structure A, and the residual 0 or 2 $R^5$ groups are each $R^{11}$ or form another fused ring structure A together. In this case, the fused ring structure A is preferably a benzo structure substituted by 1 or 2 substituents $R^{10}$, or an indeno or naphtho structure unsubstituted by $R^{10}$. Particularly, when the fused ring structure A is a benzo structure substituted by 1 or 2 substituents $R^{10}$, at least one substituent $R^{10}$ and a substituent $R^{11}$ of adjacent carbon with a ring junction therebetween necessarily form a bridged structure $R^{10}$–$R^{11}$, ethano and o-benzeno structures are preferable.

Preferably examples of pharmacologically acceptable acid addition salts include inorganic salts such as a hydrochloride, a sulfate, a nitrate, a hydrobromide, a hydroiodide, a phosphate, and the like; organic carboxylates such as acetate, a lactate, a citrate, an oxalate, a glutarate, a malate, a tartrate, a fumarate, a mandelate, a maleate, a benzoate, a phthalate, and the like; organic sulfonates such as a methanesulfonate, an elthanesulfonate, a benzenesulfonate, a p-toluenesulfonate, a cophorsulfonate, and the like. Particularly, a hydrochloride, a phosphate, a tartrate, a methanesulfonate, and the like are preferable, but, of course, the salts are not limited to these salts.

Of the compounds of formula (I) of the present invention, compound 1 is designated 17-cycloproplymethyl-3,14β-dihydroxy-6,7-dehydro-4,5α-epoxy-6,7,2',3'-indolomorphinan in which $R^1$ is cyclopropylmethyl, $R^2$ and $R^3$ are each hydroxy, $R^4$ is hydrogen, and m is 0.

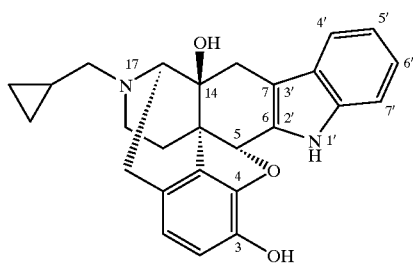

1

Of the compounds of formula (I) of the present invention, compound 2 is designated 17-cyclopropylmethyl-3,14β-dihydroxy-6,7-dehydro-4,5α-epoxy-6,7,2',3'-benzoindolo)morphinan in which $R^1$ is cyclopropylmethyl, $R^2$ and $R^3$ are each hydroxy, $R^4$ is hydrogen, m is 2, and two $R^5$ groups are substituents at the 6' and 7'-positions of the indole ring and form a benzo ring together as the fused ring structure A.

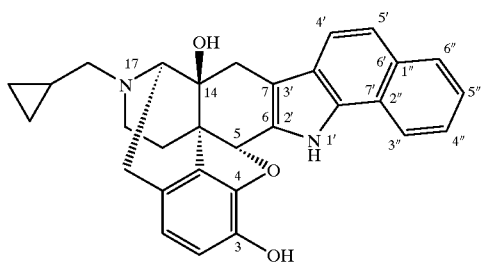

2

Of the compounds of formula (I) of the present invention, compound 3 is designated 17-cyclopropylmethyl-3,14β-dihydroxy-6,7-dehydro-4,5α-epoxy-6,7,2',3'-(5',6''-ethano-6', 7'-benziondolo)morphinan in which $R^1$ is cyclopropylmethyl, $R^2$ and $R^3$ are each hydroxy, $R^4$ is hydrogen, m is 3, two $R^5$ groups are substituents at the 6' and 7'-positions of the indole ring and form a benzo ring substituted by one $R^{10}$ together as the fused ring structure A, and the residual one $R^5$ is $R^{11}$ as a substituent at the 5'-position of the indole ring forms an ethano structure as a bridges structure $R^{10}$–$R^{11}$ together with $R^{10}$ as a substituent at the 6''-position of the benzene ring adjacent to $R^{11}$ with the ring junction therebetween.

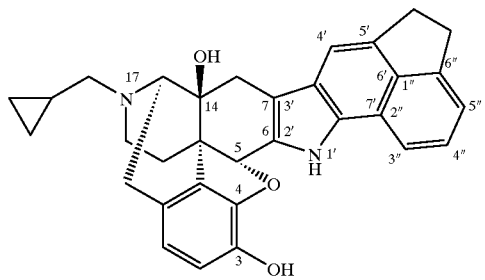

3

Although examples of compounds as the indolomorphinan derivatives represented by formula (I) of the present invention include the following compounds listed in tables, the present invention not limited to these compounds.

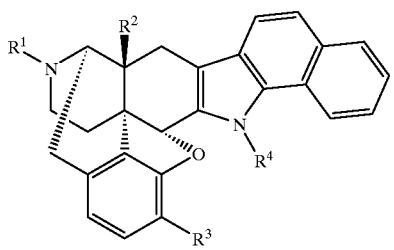

| $R^1$ | $R^2$ | $R^3$ | $R^4$ |
|---|---|---|---|
| cyclopropylmethyl | OH | OH | H |
| cyclopropylmethyl | OH | OMe | H |
| cyclobutylmethyl | OH | OH | H |
| cyclobutylmethyl | OH | OMe | H |
| allyl | OH | OH | H |
| allyl | OH | OMe | H |
| H | OH | OH | H |
| H | OH | OMe | H |
| Me | OH | OH | H |
| Me | OH | OMe | H |
| benzyl | OH | OH | H |
| benzyl | OH | OMe | H |
| 2-phenethyl | OH | OH | H |
| 2-phenethyl | OH | OMe | H |
| cyclopropylmethyl | OH | OH | Me |
| cyclopropylmethyl | OH | OMe | Me |
| cyclobutylmethyl | OH | OH | Me |
| cyclobutylmethyl | OH | OMe | Me |
| allyl | OH | OH | Me |
| allyl | OH | OMe | Me |
| H | OH | OH | Me |
| H | OH | OMe | Me |
| Me | OH | OH | Me |
| Me | OH | OMe | Me |
| benzyl | OH | OH | Me |
| benzyl | OH | OMe | Me |
| 2-phenethyl | OH | OH | Me |
| 2-phenethyl | OH | OMe | Me |
| cyclopropylmethyl | OH | OH | Et |
| cyclopropylmethyl | OH | OMe | Et |
| cyclobutylmethyl | OH | OH | Et |
| cyclobutylmethyl | OH | OMe | Et |
| allyl | OH | OH | Et |
| allyl | OH | OMe | Et |
| H | OH | OH | Et |
| H | OH | OMe | Et |
| Me | OH | OH | Et |
| Me | OH | OMe | Et |
| benzyl | OH | OH | Et |
| benzyl | OH | OMe | Et |
| 2-phenethyl | OH | OH | Et |

-continued

| | | | |
|---|---|---|---|
| 2-phenethyl | OH | OMe | Et |
| cyclopropylmethyl | OH | OH | Bu |
| cyclopropylmethyl | OH | OMe | Bu |
| cyclobutylmethyl | OH | OH | Bu |
| cyclobutylmethyl | OH | OMe | Bu |
| allyl | OH | OH | Bu |
| allyl | OH | OMe | Bu |
| H | OH | OH | Bu |
| H | OH | OMe | Bu |
| Me | OH | OH | Bu |
| Me | OH | OMe | Bu |
| benzyl | OH | OH | Bu |
| benzyl | OH | OMe | Bu |
| 2-phenethyl | OH | OH | Bu |
| 2-phenethyl | OH | OMe | Bu |
| cyclopropylmethyl | OH | OH | PhCH$_2$ |
| cyclopropylmethyl | OH | OMe | PhCH$_2$ |
| cyclobutylmethyl | OH | OH | PhCH$_2$ |
| cyclobutylmethyl | OH | OMe | PhCH$_2$ |
| allyl | OH | OH | PhCH$_2$ |
| allyl | OH | OMe | PhCH$_2$ |
| H | OH | OH | PhCH$_2$ |
| H | OH | OMe | PhCH$_2$ |
| Me | OH | OH | PhCH$_2$ |
| Me | OH | OMe | PhCH$_2$ |
| benzyl | OH | OH | PhCH$_2$ |
| benzyl | OH | OMe | PhCH$_2$ |
| 2-phenethyl | OH | OH | PhCH$_2$ |
| 2-phenethyl | OH | OMe | PhCH$_2$ |
| cyclopropylmethyl | OH | OH | (F—C$_9$H$_4$)CH$_2$ |
| cyclopropylmethyl | OH | OMe | (F—C$_9$H$_4$)CH$_2$ |
| cyclobutylmethyl | OH | OH | (F—C$_6$H$_4$)CH$_2$ |
| cyclobutylmethyl | OH | OMe | (F—C$_6$H$_4$)CH$_2$ |
| allyl | OH | OH | (F—C$_6$H$_4$)CH$_2$ |
| allyl | OH | OMe | (F—C$_6$H$_4$)CH$_2$ |
| H | OH | OH | (F—C$_6$H$_4$)CH$_2$ |
| H | OH | OMe | (F—C$_6$H$_4$)CH$_2$ |
| Me | OH | OH | (F—C$_6$H$_4$)CH$_2$ |
| Me | OH | OMe | (F—C$_6$H$_4$)CH$_2$ |
| benzyl | OH | OH | (F—C$_6$H$_4$)CH$_2$ |
| benzyl | OH | OMe | (F—C$_6$H$_4$)CH$_2$ |
| 2-phenethyl | OH | OH | (F—C$_6$H$_4$)CH$_2$ |
| 2-phenethyl | OH | OMe | (F—C$_6$H$_4$)CH$_2$ |
| cyclopropylmethyl | OH | OH | (Cl—C$_6$H$_4$)CH$_2$ |
| cyclopropylmethyl | OH | OMe | (Cl—C$_6$H$_4$)CH$_2$ |
| cyclobutylmethyl | OH | OH | (Cl—C$_6$H$_4$)CH$_2$ |
| cyclobutylmethyl | OH | OMe | (Cl—C$_6$H$_4$)CH$_2$ |
| allyl | OH | OH | (Cl—C$_6$H$_4$)CH$_2$ |
| allyl | OH | OMe | (Cl—C$_6$H$_4$)CH$_2$ |
| H | OH | OH | (Cl—C$_6$H$_4$)CH$_2$ |
| H | OH | OMe | (Cl—C$_6$H$_4$)CH$_2$ |
| Me | OH | OH | (Cl—C$_6$H$_4$)CH$_2$ |
| Me | OH | OMe | (Cl—C$_6$H$_4$)CH$_2$ |
| benzyl | OH | OH | (Cl—C$_6$H$_4$)CH$_2$ |
| benzyl | OH | OMe | (Cl—C$_6$H$_4$)CH$_2$ |
| 2-phenethyl | OH | OH | (Cl—C$_6$H$_4$)CH$_2$ |
| 2-phenethyl | OH | OMe | (Cl—C$_6$H$_4$)CH$_2$ |
| cyclopropylmethyl | OH | OH | (Br—C$_6$H$_4$)CH$_2$ |
| cyclopropylmethyl | OH | OMe | (Br—C$_6$H$_4$)CH$_2$ |
| cyclobutylmethyl | OH | OH | (Br—C$_6$H$_4$)CH$_2$ |
| cyclobutylmethyl | OH | OMe | (Br—C$_6$H$_4$)CH$_2$ |
| allyl | OH | OH | (Br—C$_9$H$_4$)CH$_2$ |
| allyl | OH | OMe | (Br—C$_9$H$_4$)CH$_2$ |
| H | OH | OH | (Br—C$_9$H$_4$)CH$_2$ |
| H | OH | OMe | (Br—C$_6$H$_4$)CH$_2$ |
| Me | OH | OH | (Br—C$_9$H$_4$)CH$_2$ |
| Me | OH | OMe | (Br—C$_9$H$_4$)CH$_2$ |
| benzyl | OH | OH | (Br—C$_9$H$_4$)CH$_2$ |
| benzyl | OH | OMe | (Br—C$_9$H$_4$)CH$_2$ |
| 2-phenethyl | OH | OH | (Br—C$_9$H$_4$)CH$_2$ |
| 2-phenethyl | OH | OMe | (Br—C$_9$H$_4$)CH$_2$ |
| cyclopropylmethyl | OH | OH | (Me—C$_6$H$_4$)CH$_2$ |
| cyclopropylmethyl | OH | OMe | (Me—C$_6$H$_4$)CH$_2$ |
| cyclobutylmethyl | OH | OH | (Me—C$_6$H$_4$)CH$_2$ |
| cyclobutylmethyl | OH | OMe | (Me—C$_6$H$_4$)CH$_2$ |
| allyl | OH | OH | (Me—C$_6$H$_4$)CH$_2$ |
| allyl | OH | OMe | (Me—C$_6$H$_4$)CH$_2$ |
| H | OH | OH | (Me—C$_6$H$_4$)CH$_2$ |
| H | OH | OMe | (Me—C$_6$H$_4$)CH$_2$ |
| Me | OH | OH | (Me—C$_9$H$_4$)CH$_2$ |
| Me | OH | OMe | (Me—C$_9$H$_4$)CH$_2$ |
| benzyl | OH | OH | (Me—C$_9$H$_4$)CH$_2$ |
| benzyl | OH | OMe | (Me—C$_9$H$_4$)CH$_2$ |
| 2-phenethyl | OH | OH | (Me—C$_6$H$_4$)CH$_2$ |
| 2-phenethyl | OH | OMe | (Me—C$_6$H$_4$)CH$_2$ |
| cyclopropylmethyl | OH | OH | (MeO—C$_6$H$_4$)CH$_2$ |
| cyclopropylmethyl | OH | OMe | (MeO—C$_6$H$_4$)CH$_2$ |
| cyclobutylmethyl | OH | OH | (MeO—C$_6$H$_4$)CH$_2$ |
| cyclobutylmethyl | OH | OMe | (MeO—C$_6$H$_4$)CH$_2$ |
| allyl | OH | OH | (MeO—C$_6$H$_4$)CH$_2$ |
| allyl | OH | OMe | (MeO—C$_6$H$_4$)CH$_2$ |
| H | OH | OH | (MeO—C$_6$H$_4$)CH$_2$ |
| H | OH | OMe | (MeO—C$_6$H$_4$)CH$_2$ |
| Me | OH | OH | (MeO—C$_6$H$_4$)CH$_2$ |
| Me | OH | OMe | (MeO—C$_6$H$_4$)CH$_2$ |
| benzyl | OH | OH | (MeO—C$_6$H$_4$)CH$_2$ |
| benzyl | OH | OMe | (MeO—C$_6$H$_4$)CH$_2$ |
| 2-phenethyl | OH | OH | (MeO—C$_6$H$_4$)CH$_2$ |
| 2-phenethyl | OH | OMe | (MeO—C$_6$H$_4$)CH$_2$ |
| cyclopropylmethyl | OH | OH | (O$_2$N—C$_6$H$_4$)CH$_2$ |
| cyclopropylmethyl | OH | OMe | (O$_2$N—C$_6$H$_4$)CH$_2$ |
| cyclobutylmethyl | OH | OH | (O$_2$N—C$_6$H$_4$)CH$_2$ |
| cyclobutylmethyl | OH | OMe | (O$_2$N—C$_6$H$_4$)CH$_2$ |
| allyl | OH | OH | (O$_2$N—C$_6$H$_4$)CH$_2$ |
| allyl | OH | OMe | (O$_2$N—C$_6$H$_4$)CH$_2$ |
| H | OH | OH | (O$_2$N—C$_6$H$_4$)CH$_2$ |
| H | OH | OMe | (O$_2$N—C$_6$H$_4$)CH$_2$ |
| Me | OH | OH | (O$_2$N—C$_6$H$_4$)CH$_2$ |
| Me | OH | OMe | (O$_2$N—C$_6$H$_4$)CH$_2$ |
| benzyl | OH | OH | (O$_2$N—C$_6$H$_4$)CH$_2$ |
| benzyl | OH | OMe | (O$_2$N—C$_6$H$_4$)CH$_2$ |
| 2-phenethyl | OH | OH | (O$_2$N—C$_9$H$_4$)CH$_2$ |
| 2-phenethyl | OH | OMe | (O$_2$N—C$_6$H$_4$)CH$_2$ |
| cyclopropylmethyl | OH | OH | (F$_3$C—C$_6$H$_4$)CH$_2$ |
| cyclopropylmethyl | OH | OMe | (F$_3$C—C$_6$H$_4$)CH$_2$ |
| cyclobutylmethyl | OH | OH | (F$_3$C—C$_6$H$_4$)CH$_2$ |
| cyclobutylmethyl | OH | OMe | (F$_3$C—C$_6$H$_4$)CH$_2$ |
| allyl | OH | OH | (F$_3$C—C$_6$H$_4$)CH$_2$ |
| allyl | OH | OMe | (F$_3$C—C$_6$H$_4$)CH$_2$ |
| H | OH | OH | (F$_3$C—C$_9$H$_4$)CH$_2$ |
| H | OH | OMe | (F$_3$C—C$_9$H$_4$)CH$_2$ |
| Me | OH | OH | (F$_3$C—C$_9$H$_4$)CH$_2$ |
| Me | OH | OMe | (F$_3$C—C$_9$H$_4$)CH$_2$ |
| benzyl | OH | OH | (F$_3$C—C$_9$H$_4$)CH$_2$ |
| benzyl | OH | OMe | (F$_3$C—C$_9$H$_4$)CH$_2$ |
| 2-phenethyl | OH | OH | (F$_3$C—C$_9$H$_4$)CH$_2$ |
| 2-phenethyl | OH | OMe | (F$_3$C—C$_9$H$_4$)CH$_2$ |
| cyclopropylmethyl | OH | OH | Ph(CH$_2$)$_2$ |
| cyclopropylmethyl | OH | OMe | Ph(CH$_2$)$_2$ |
| cyclobutylmethyl | OH | OH | Ph(CH$_2$)$_2$ |
| cyclobutylmethyl | OH | OMe | Ph(CH$_2$)$_2$ |
| allyl | OH | OH | Ph(CH$_2$)$_2$ |
| allyl | OH | OMe | Ph(CH$_2$)$_2$ |
| H | OH | OH | Ph(CH$_2$)$_2$ |
| H | OH | OMe | Ph(CH$_2$)$_2$ |
| Me | OH | OH | Ph(CH$_2$)$_2$ |
| Me | OH | OMe | Ph(CH$_2$)$_2$ |
| benzyl | OH | OH | Ph(CH$_2$)$_2$ |
| benzyl | OH | OMe | Ph(CH$_2$)$_2$ |
| 2-phenethyl | OH | OH | Ph(CH$_2$)$_2$ |
| 2-phenethyl | OH | OMe | Ph(CH$_2$)$_2$ |
| cyclopropylmethyl | OH | OH | Ph(CH$_2$)$_3$ |
| cyclopropylmethyl | OH | OMe | Ph(CH$_2$)$_3$ |
| cyclobutylmethyl | OH | OH | Ph(CH$_2$)$_3$ |
| cyclobutylmethyl | OH | OMe | Ph(CH$_2$)$_3$ |
| allyl | OH | OH | Ph(CH$_2$)$_3$ |
| allyl | OH | OMe | Ph(CH$_2$)$_3$ |
| H | OH | OH | Ph(CH$_2$)$_3$ |
| H | OH | OMe | Ph(CH$_2$)$_3$ |
| Me | OH | OH | Ph(CH$_2$)$_3$ |
| Me | OH | OMe | Ph(CH$_2$)$_3$ |
| benzyl | OH | OH | Ph(CH$_2$)$_3$ |
| benzyl | OH | OMe | Ph(CH$_2$)$_3$ |
| 2-phenethyl | OH | OH | Ph(CH$_2$)$_3$ |
| 2-phenethyl | OH | OMe | Ph(CH$_2$)$_3$ |
| cyclopropylmethyl | OH | OH | MeCO |
| cyclopropylmethyl | OH | OMe | MeCO |
| cyclobutylmethyl | OH | OH | MeCO |

-continued

| | | | |
|---|---|---|---|
| cyclobutylmethyl | OH | OMe | MeCO |
| allyl | OH | OH | MeCO |
| allyl | OH | OMe | MeCO |
| H | OH | OH | MeCO |
| H | OH | OMe | MeCO |
| Me | OH | OH | MeCO |
| Me | OH | OMe | MeCO |
| benzyl | OH | OH | MeCO |
| benzyl | OH | OMe | MeCO |
| 2-phenethyl | OH | OH | MeCO |
| 2-phenethyl | OH | OMe | MeCO |
| cyclopropylmethyl | OH | OH | PhCO |
| cyclopropylmethyl | OH | OMe | PhCO |
| cyclobutylmethyl | OH | OH | PhCO |
| cyclobutylmethyl | OH | OMe | PhCO |
| allyl | OH | OH | PhCO |
| allyl | OH | OMe | PhCO |
| H | OH | OH | PhCO |
| H | OH | OMe | PhCO |
| Me | OH | OH | PhCO |
| Me | OH | OMe | PhCO |
| benzyl | OH | OH | PhCO |
| benzyl | OH | OMe | PhCO |
| 2-phenethyl | OH | OH | PhCO |
| 2-phenethyl | OH | OMe | PhCO |
| cyclopropylmethyl | OH | OH | $MeSO_2$ |
| cyclopropylmethyl | OH | OMe | $MeSO_2$ |
| cyclobutylmethyl | OH | OH | $MeSO_2$ |
| cyclobutylmethyl | OH | OMe | $MeSO_2$ |
| allyl | OH | OH | $MeSO_2$ |
| allyl | OH | OMe | $MeSO_2$ |
| H | OH | OH | $MeSO_2$ |
| H | OH | OMe | $MeSO_2$ |
| Me | OH | OH | $MeSO_2$ |
| Me | OH | OMe | $MeSO_2$ |
| benzyl | OH | OH | $MeSO_2$ |
| benzyl | OH | OMe | $MeSO_2$ |
| 2-phenethyl | OH | OH | $MeSO_2$ |
| 2-phenethyl | OH | OMe | $MeSO_2$ |
| cyclopropylmethyl | OH | OH | $PhSO_2$ |
| cyclopropylmethyl | OH | OMe | $PhSO_2$ |
| cyclobutylmethyl | OH | OH | $PhSO_2$ |
| cyclobutylmethyl | OH | OMe | $PhSO_2$ |
| allyl | OH | OH | $PhSO_2$ |
| allyl | OH | OMe | $PhSO_2$ |
| H | OH | OH | $PhSO_2$ |
| H | OH | OMe | $PhSO_2$ |
| Me | OH | OH | $PhSO_2$ |
| Me | OH | OMe | $PhSO_2$ |
| benzyl | OH | OH | $PhSO_2$ |
| benzyl | OH | OMe | $PhSO_2$ |
| 2-phenethyl | OH | OH | $PhSO_2$ |
| 2-phenethyl | OH | OMe | $PhSO_2$ |
| cyclopropylmethyl | OH | OH | $(Me-C_6H_4)SO_2$ |
| cyclopropylmethyl | OH | OMe | $(Me-C_6H_4)SO_2$ |
| cyclobutylmethyl | OH | OH | $(Me-C_6H_4)SO_2$ |
| cyclobutylmethyl | OH | OMe | $(Me-C_6H_4)SO_2$ |
| allyl | OH | OH | $(Me-C_6H_5)SO_2$ |
| allyl | OH | OMe | $(Me-C_6H_5)SO_2$ |
| H | OH | OH | $(Me-C_6H_4)SO_2$ |
| H | OH | OMe | $(Me-C_6H_4)SO_2$ |
| Me | OH | OH | $(Me-C_6H_4)SO_2$ |
| Me | OH | OMe | $(Me-C_6H_4)SO_2$ |
| benzyl | OH | OH | $(Me-C_6H_4)SO_2$ |
| benzyl | OH | OMe | $(Me-C_6H_4)SO_2$ |
| 2-phenethyl | OH | OH | $(Me-C_6H_4)SO_2$ |
| 2-phenethyl | OH | OMe | $(Me-C_6H_4)SO_2$ |
| cyclopropylmethyl | OH | OH | $PhCH_2SO_2$ |
| cyclopropylmethyl | OH | OMe | $PhCH_2SO_2$ |
| cyclobutylmethyl | OH | OH | $PhCH_2SO_2$ |
| cyclobutylmethyl | OH | OMe | $PhCH_2SO_2$ |
| allyl | OH | OH | $PhCH_2SO_2$ |
| allyl | OH | OMe | $PhCH_2SO_2$ |
| H | OH | OH | $PhCH_2SO_2$ |
| H | OH | OMe | $PhCH_2SO_2$ |
| Me | OH | OH | $PhCH_2SO_2$ |
| Me | OH | OMe | $PhCH_2SO_2$ |
| benzyl | OH | OH | $PhCH_2SO_2$ |
| benzyl | OH | OMe | $PhCH_2SO_2$ |
| 2-phenethyl | OH | OH | $PhCH_2SO_2$ |
| 2-phenethyl | OH | OMe | $PhCH_2SO_2$ |

-continued

| $R^1$ | $R^2$ | $R^3$ | i | $R^{16}$ |
|---|---|---|---|---|
| cyclopropylmethyl | OH | OH | 2 | OH |
| cyclopropylmethyl | OH | OMe | 2 | OH |
| cyclobutylmethyl | OH | OH | 2 | OH |
| cyclobutylmethyl | OH | OMe | 2 | OH |
| allyl | OH | OH | 2 | OH |
| allyl | OH | OMe | 2 | OH |
| H | OH | OH | 2 | OH |
| H | OH | OMe | 2 | OH |
| Me | OH | OH | 2 | OH |
| Me | OH | OMe | 2 | OH |
| benzyl | OH | OH | 2 | OH |
| benzyl | OH | OMe | 2 | OH |
| 2-phenethyl | OH | OH | 2 | OH |
| 2-phenethyl | OH | OMe | 2 | OH |
| cyclopropylmethyl | OH | OH | 2 | OMe |
| cyclopropylmethyl | OH | OMe | 2 | OMe |
| cyclobutylmethyl | OH | OH | 2 | OMe |
| cyclobutylmethyl | OH | OMe | 2 | OMe |
| allyl | OH | OH | 2 | OMe |
| allyl | OH | OMe | 2 | OMe |
| H | OH | OH | 2 | OMe |
| H | OH | OMe | 2 | OMe |
| Me | OH | OH | 2 | OMe |
| Me | OH | OMe | 2 | OMe |
| benzyl | OH | OH | 2 | OMe |
| benzyl | OH | OMe | 2 | OMe |
| 2-phenethyl | OH | OH | 2 | OMe |
| 2-phenethyl | OH | OMe | 2 | OMe |
| cyclopropylmethyl | OH | OH | 2 | OEt |
| cyclopropylmethyl | OH | OMe | 2 | OEt |
| cyclobutylmethyl | OH | OH | 2 | OEt |
| cyclobutylmethyl | OH | OMe | 2 | OEt |
| allyl | OH | OH | 2 | OEt |
| allyl | OH | OMe | 2 | OEt |
| H | OH | OH | 2 | OEt |
| H | OH | OMe | 2 | OEt |
| Me | OH | OH | 2 | OEt |
| Me | OH | OMe | 2 | OEt |
| benzyl | OH | OH | 2 | OEt |
| benzyl | OH | OMe | 2 | OEt |
| 2-phenethyl | OH | OH | 2 | OEt |
| 2-phenethyl | OH | OMe | 2 | OEt |
| cyclopropylmethyl | OH | OH | 2 | $NH_2$ |
| cyclopropylmethyl | OH | OMe | 2 | $NH_2$ |
| cyclobutylmethyl | OH | OH | 2 | $NH_2$ |
| cyclobutylmethyl | OH | OMe | 2 | $NH_2$ |
| allyl | OH | OH | 2 | $NH_2$ |
| allyl | OH | OMe | 2 | $NH_2$ |
| H | OH | OH | 2 | $NH_2$ |
| H | OH | OMe | 2 | $NH_2$ |
| Me | OH | OH | 2 | $NH_2$ |
| Me | OH | OMe | 2 | $NH_2$ |
| benzyl | OH | OH | 2 | $NH_2$ |
| benzyl | OH | OMe | 2 | $NH_2$ |
| 2-phenethyl | OH | OH | 2 | $NH_2$ |
| 2-phenethyl | OH | OMe | 2 | $NH_2$ |
| cyclopropylmethyl | OH | OH | 2 | $NO_2$ |
| cyclopropylmethyl | OH | OMe | 2 | $NO_2$ |
| cyclobutylmethyl | OH | OH | 2 | $NO_2$ |
| cyclobutylmethyl | OH | OMe | 2 | $NO_2$ |
| allyl | OH | OH | 2 | $NO_2$ |

-continued

| | | | | |
|---|---|---|---|---|
| allyl | OH | OMe | 2 | NO$_2$ |
| H | OH | OH | 2 | NO$_2$ |
| H | OH | OMe | 2 | NO$_2$ |
| Me | OH | OH | 2 | NO$_2$ |
| Me | OH | OMe | 2 | NO$_2$ |
| benzyl | OH | OH | 2 | NO$_2$ |
| benzyl | OH | OMe | 2 | NO$_2$ |
| 2-phenethyl | OH | OH | 2 | NO$_2$ |
| 2-phenethyl | OH | OMe | 2 | NO$_2$ |
| cyclopropylmethyl | OH | OH | 2 | CN |
| cyclopropylmethyl | OH | OMe | 2 | CN |
| cyclobutylmethyl | OH | OH | 2 | CN |
| cyclobutylmethyl | OH | OMe | 2 | CN |
| allyl | OH | OH | 2 | CN |
| allyl | OH | OMe | 2 | CN |
| H | OH | OH | 2 | CN |
| H | OH | OMe | 2 | CN |
| Me | OH | OH | 2 | CN |
| Me | OH | OMe | 2 | CN |
| benzyl | OH | OH | 2 | CN |
| benzyl | OH | OMe | 2 | CN |
| 2-phenethyl | OH | OH | 2 | CN |
| 2-phenethyl | OH | OMe | 2 | CN |
| cyclopropylmethyl | OH | OH | 2 | NCS |
| cyclopropylmethyl | OH | OMe | 2 | NCS |
| cyclobutylmethyl | OH | OH | 2 | NCS |
| cyclobutylmethyl | OH | OMe | 2 | NCS |
| allyl | OH | OH | 2 | NCS |
| allyl | OH | OMe | 2 | NCS |
| H | OH | OH | 2 | NCS |
| H | OH | OMe | 2 | NCS |
| Me | OH | OH | 2 | NCS |
| Me | OH | OMe | 2 | NCS |
| benzyl | OH | OH | 2 | NCS |
| benzyl | OH | OMe | 2 | NCS |
| 2-phenethyl | OH | OH | 2 | NCS |
| 2-phenethyl | OH | OMe | 2 | NCS |
| cyclopropylmethyl | OH | OH | 2 | COOH |
| cyclopropylmethyl | OH | OMe | 2 | COOH |
| cyclobutylmethyl | OH | OH | 2 | COOH |
| cyclobutylmethyl | OH | OMe | 2 | COOH |
| allyl | OH | OH | 2 | COOH |
| allyl | OH | OMe | 2 | COOH |
| H | OH | OH | 2 | COOH |
| H | OH | OMe | 2 | COOH |
| Me | OH | OH | 2 | COOH |
| Me | OH | OMe | 2 | COOH |
| benzyl | OH | OH | 2 | COOH |
| benzyl | OH | OMe | 2 | COOH |
| 2-phenethyl | OH | OH | 2 | COOH |
| 2-phenethyl | OH | OMe | 2 | COOH |
| cyclopropylmethyl | OH | OH | 2 | COOMe |
| cyclopropylmethyl | OH | OMe | 2 | COOMe |
| cyclobutylmethyl | OH | OH | 2 | COOMe |
| cyclobutylmethyl | OH | OMe | 2 | COOMe |
| allyl | OH | OH | 2 | COOMe |
| allyl | OH | OMe | 2 | COOMe |
| H | OH | OH | 2 | COOMe |
| H | OH | OMe | 2 | COOMe |
| Me | OH | OH | 2 | COOMe |
| Me | OH | OMe | 2 | COOMe |
| benzyl | OH | OH | 2 | COOMe |
| benzyl | OH | OMe | 2 | COOMe |
| 2-phenethyl | OH | OH | 2 | COOMe |
| 2-phenethyl | OH | OMe | 2 | COOMe |
| cyclopropylmethyl | OH | OH | 2 | COOEt |
| cyclopropylmethyl | OH | OMe | 2 | COOEt |
| cyclobutylmethyl | OH | OH | 2 | COOEt |
| cyclobutylmethyl | OH | OMe | 2 | COOEt |
| allyl | OH | OH | 2 | COOEt |
| allyl | OH | OMe | 2 | COOEt |
| H | OH | OH | 2 | COOEt |
| H | OH | OMe | 2 | COOEt |
| Me | OH | OH | 2 | COOEt |
| Me | OH | OMe | 2 | COOEt |
| benzyl | OH | OH | 2 | COOEt |
| benzyl | OH | OMe | 2 | COOEt |
| 2-phenethyl | OH | OH | 2 | COOEt |
| 2-phenethyl | OH | OMe | 2 | COOEt |
| cyclopropylmethyl | OH | OH | 2 | NHCHO |
| cyclopropylmethyl | OH | OMe | 2 | NHCHO |
| cyclobutylmethyl | OH | OH | 2 | NHCHO |
| cyclobutylmethyl | OH | OMe | 2 | NHCHO |
| allyl | OH | OH | 2 | NHCHO |
| allyl | OH | OMe | 2 | NHCHO |
| H | OH | OH | 2 | NHCHO |
| H | OH | OMe | 2 | NHCHO |
| Me | OH | OH | 2 | NHCHO |
| Me | OH | OMe | 2 | NHCHO |
| benzyl | OH | OH | 2 | NHCHO |
| benzyl | OH | OMe | 2 | NHCHO |
| 2-phenethyl | OH | OH | 2 | NHCHO |
| 2-phenethyl | OH | OMe | 2 | NHCHO |
| cyclopropylmethyl | OH | OH | 2 | NHCO—Me |
| cyclopropylmethyl | OH | OMe | 2 | NHCO—Me |
| cyclobutylmethyl | OH | OH | 2 | NHCO—Me |
| cyclobutylmethyl | OH | OMe | 2 | NHCO—Me |
| allyl | OH | OH | 2 | NHCO—Me |
| allyl | OH | OMe | 2 | NHCO—Me |
| H | OH | OH | 2 | NHCO—Me |
| H | OH | OMe | 2 | NHCO—Me |
| Me | OH | OH | 2 | NHCO—Me |
| Me | OH | OMe | 2 | NHCO—Me |
| benzyl | OH | OH | 2 | NHCO—Me |
| benzyl | OH | OMe | 2 | NHCO—Me |
| 2-phenethyl | OH | OH | 2 | NHCO—Me |
| 2-phenethyl | OH | OMe | 2 | NHCO—Me |
| cyclopropylmethyl | OH | OH | 2 | NHCO—Ph |
| cyclopropylmethyl | OH | OMe | 2 | NHCO—Ph |
| cyclobutylmethyl | OH | OH | 2 | NHCO—Ph |
| cyclobutylmethyl | OH | OMe | 2 | NHCO—Ph |
| allyl | OH | OH | 2 | NHCO—Ph |
| allyl | OH | OMe | 2 | NHCO—Ph |
| H | OH | OH | 2 | NHCO—Ph |
| H | OH | OMe | 2 | NHCO—Ph |
| Me | OH | OH | 2 | NHCO—Ph |
| Me | OH | OMe | 2 | NHCO—Ph |
| benzyl | OH | OH | 2 | NHCO—Ph |
| benzyl | OH | OMe | 2 | NHCO—Ph |
| 2-phenethyl | OH | OH | 2 | NHCO—Ph |
| 2-phenethyl | OH | OMe | 2 | NHCO—Ph |
| cyclopropylmethyl | OH | OH | 2 | NHCO—(CH$_2$)$_5$Ph |
| cyclopropylmethyl | OH | OMe | 2 | NHCO—(CH$_2$)$_5$Ph |
| cyclobutylmethyl | OH | OH | 2 | NHCO—(CH$_2$)$_5$Ph |
| cyclobutylmethyl | OH | OMe | 2 | NHCO—(CH$_2$)$_5$Ph |
| allyl | OH | OH | 2 | NHCO—(CH$_2$)$_5$Ph |
| allyl | OH | OMe | 2 | NHCO—(CH$_2$)$_5$Ph |
| H | OH | OH | 2 | NHCO—(CH$_2$)$_5$Ph |
| H | OH | OMe | 2 | NHCO—(CH$_2$)$_5$Ph |
| Me | OH | OH | 2 | NHCO—(CH$_2$)$_5$Ph |
| Me | OH | OMe | 2 | NHCO—(CH$_2$)$_5$Ph |
| benzyl | OH | OH | 2 | NHCO—(CH$_2$)$_5$Ph |
| benzyl | OH | OMe | 2 | NHCO—(CH$_2$)$_5$Ph |
| 2-phenethyl | OH | OH | 2 | NHCO—(CH$_2$)$_5$Ph |
| 2-phenethyl | OH | OMe | 2 | NHCO—(CH$_2$)$_5$Ph |
| cyclopropylmethyl | OH | OH | 2 | NHCO-cinnamyl |
| cyclopropylmethyl | OH | OMe | 2 | NHCO-cinnamyl |
| cyclobutylmethyl | OH | OH | 2 | NHCO-cinnamyl |
| cyclobutylmethyl | OH | OMe | 2 | NHCO-cinnamyl |
| allyl | OH | OH | 2 | NHCO-cinnamyl |
| allyl | OH | OMe | 2 | NHCO-cinnamyl |
| H | OH | OH | 2 | NHCO-cinnamyl |
| H | OH | OMe | 2 | NHCO-cinnamyl |
| Me | OH | OH | 2 | NHCO-cinnamyl |
| Me | OH | OM | 2 | NHCO-cinnamyl |
| benzyl | OH | OH | 2 | NHCO-cinnamyl |
| benzyl | OH | OMe | 2 | NHCO-cinnamyl |
| 2-phenethyl | OH | OH | 2 | NHCO-cinnamyl |
| 2-phenethyl | OH | OMe | 2 | NHCO-cinnamyl |
| cyclopropylmethyl | OH | OH | 2 | NHCO—(CF$_3$-cinnamyl) |
| cyclopropylmethyl | OH | OMe | 2 | NHCO—(CF$_3$-cinnamyl) |
| cyclobutylmethyl | OH | OH | 2 | NHCO—(CF$_3$-cinnamyl) |
| cyclobutylmethyl | OH | OMe | 2 | NHCO—(CF$_3$-cinnamyl) |
| allyl | OH | OH | 2 | NHCO—(CF$_3$-cinnamyl) |
| allyl | OH | OMe | 2 | NHCO—(CF$_3$-cinnamyl) |
| H | OH | OH | 2 | NHCO—(CF$_3$-cinnamyl) |
| H | OH | OMe | 2 | NHCO—(CF$_3$-cinnamyl) |
| Me | OH | OH | 2 | NHCO—(CF$_3$-cinnamyl) |

-continued

| | | | | |
|---|---|---|---|---|
| Me | OH | OMe | 2 | NHCO—(CF$_3$-cinnamyl) |
| benzyl | OH | OH | 2 | NHCO—(CF$_3$-cinnamyl) |
| benzyl | OH | OMe | 2 | NHCO—(CF$_3$-cinnamyl) |
| 2-phenethyl | OH | OH | 2 | NHCO—(CF$_3$-cinnamyl) |
| 2-phenethyl | OH | OMe | 2 | NHCO—(CF$_3$-cinnamyl) |
| cyclopropylmethyl | OH | OH | 2 | NHCO-pyridyl |
| cyclopropylmethyl | OH | OMe | 2 | NHCO-pyridyl |
| cyclobutylmethyl | OH | OH | 2 | NHCO-pyridyl |
| cyclobutylmethyl | OH | OMe | 2 | NHCO-pyridyl |
| allyl | OH | OH | 2 | NHCO-pyridyl |
| allyl | OH | OMe | 2 | NHCO-pyridyl |
| H | OH | OH | 2 | NHCO-pyridyl |
| H | OH | OMe | 2 | NHCO-pyridyl |
| Me | OH | OH | 2 | NHCO-pyridyl |
| Me | OH | OMe | 2 | NHCO-pyridyl |
| benzyl | OH | OH | 2 | NHCO-pyridyl |
| benzyl | OH | OMe | 2 | NHCO-pyridyl |
| 2-phenethyl | OH | OH | 2 | NHCO-pyridyl |
| 2-phenethyl | OH | OMe | 2 | NHCO-pyridyl |
| cyclopropylmethyl | OH | OH | 2 | NHCO—NHPh |
| cyclopropylmethyl | OH | OMe | 2 | NHCO—NHPh |
| cyclobutylmethyl | OH | OH | 2 | NHCO—NHPh |
| cyclobutylmethyl | OH | OMe | 2 | NHCO—NHPh |
| allyl | OH | OH | 2 | NHCO—NHPh |
| allyl | OH | OMe | 2 | NHCO—NHPh |
| H | OH | OH | 2 | NHCO—NHPh |
| H | OH | OMe | 2 | NHCO—NHPh |
| Me | OH | OH | 2 | NHCO—NHPh |
| Me | OH | OMe | 2 | NHCO—NHPh |
| benzyl | OH | OH | 2 | NHCO—NHPh |
| benzyl | OH | OMe | 2 | NHCO—NHPh |
| 2-phenethyl | OH | OH | 2 | NHCO—NHPh |
| 2-phenethyl | OH | OMe | 2 | NHCO—NHPh |
| cyclopropylmethyl | OH | OH | 2 | NHCS—NHPh |
| cyclopropylmethyl | OH | OMe | 2 | NHCS—NHPh |
| cyclobutylmethyl | OH | OH | 2 | NHCS—NHPh |
| cyclobutylmethyl | OH | OMe | 2 | NHCS—NHPh |
| allyl | OH | OH | 2 | NHCS—NHPh |
| allyl | OH | OMe | 2 | NHCS—NHPh |
| H | OH | OH | 2 | NHCS—NHPh |
| H | OH | OMe | 2 | NHCS—NHPh |
| Me | OH | OH | 2 | NHCS—NHPh |
| Me | OH | OMe | 2 | NHCS—NHPh |
| benzyl | OH | OH | 2 | NHCS—NHPh |
| benzyl | OH | OMe | 2 | NHCS—NHPh |
| 2-phenethyl | OH | OH | 2 | NHCS—NHPh |
| 2-phenethyl | OH | OMe | 2 | NHCS—NHPh |
| cyclopropylmethyl | OH | OH | 2 | NHCS—NHCH$_2$Ph |
| cyclopropylmethyl | OH | OMe | 2 | NHCS—NHCH$_2$Ph |
| cyclobutylmethyl | OH | OH | 2 | NHCS—NHCH$_2$Ph |
| cyclobutylmethyl | OH | OMe | 2 | NHCS—NHCH$_2$Ph |
| allyl | OH | OH | 2 | NHCS—NHCH$_2$Ph |
| allyl | OH | OMe | 2 | NHCS—NHCH$_2$Ph |
| H | OH | OH | 2 | NHCS—NHCH$_2$Ph |
| H | OH | OMe | 2 | NHCS—NHCH$_2$Ph |
| Me | OH | OH | 2 | NHCS—NHCH$_2$Ph |
| Me | OH | OMe | 2 | NHCS—NHCH$_2$Ph |
| benzyl | OH | OH | 2 | NHCS—NHCH$_2$Ph |
| benzyl | OH | OMe | 2 | NHCS—NHCH$_2$Ph |
| 2-phenethyl | OH | OH | 2 | NHCS—NHCH$_2$Ph |
| 2-phenethyl | OH | OMe | 2 | NHCS—NHCH$_2$Ph |
| cyclopropylmethyl | OH | OH | 3 | OH |
| cyclopropylmethyl | OH | OMe | 3 | OH |
| cyclobutylmethyl | OH | OH | 3 | OH |
| cyclobutylmethyl | OH | OMe | 3 | OH |
| allyl | OH | OH | 3 | OH |
| allyl | OH | OMe | 3 | OH |
| H | OH | OH | 3 | OH |
| H | OH | OMe | 3 | OH |
| Me | OH | OH | 3 | OH |
| Me | OH | OMe | 3 | OH |
| benzyl | OH | OH | 3 | OH |
| benzyl | OH | OMe | 3 | OH |
| 2-phenethyl | OH | OH | 3 | OH |
| 2-phenethyl | OH | OMe | 3 | OH |
| cyclopropylmethyl | OH | OH | 3 | OMe |
| cyclopropylmethyl | OH | OMe | 3 | OMe |
| cyclobutylmethyl | OH | OH | 3 | OMe |
| cyclobutylmethyl | OH | OMe | 3 | OMe |
| allyl | OH | OH | 3 | OMe |
| allyl | OH | OMe | 3 | OMe |
| H | OH | OH | 3 | OMe |
| H | OH | OMe | 3 | OMe |
| Me | OH | OH | 3 | OMe |
| Me | OH | OMe | 3 | OMe |
| benzyl | OH | OH | 3 | OMe |
| benzyl | OH | OMe | 3 | OMe |
| 2-phenethyl | OH | OH | 3 | OMe |
| 2-phenethyl | OH | OMe | 3 | OMe |
| cyclopropylmethyl | OH | OH | 3 | OEt |
| cyclopropylmethyl | OH | OMe | 3 | OEt |
| cyclobutylmethyl | OH | OH | 3 | OEt |
| cyclobutylmethyl | OH | OMe | 3 | OEt |
| allyl | OH | OH | 3 | OEt |
| allyl | OH | OMe | 3 | OEt |
| H | OH | OH | 3 | OEt |
| H | OH | OMe | 3 | OEt |
| Me | OH | OH | 3 | OEt |
| Me | OH | OMe | 3 | OEt |
| benzyl | OH | OH | 3 | OEt |
| benzyl | OH | OMe | 3 | OEt |
| 2-phenethyl | OH | OH | 3 | OEt |
| 2-phenethyl | OH | OMe | 3 | OEt |
| cyclopropylmethyl | OH | OH | 3 | NH$_2$ |
| cyclopropylmethyl | OH | OMe | 3 | NH$_2$ |
| cyclobutylmethyl | OH | OH | 3 | NH$_2$ |
| cyclobutylmethyl | OH | OMe | 3 | NH$_2$ |
| allyl | OH | OH | 3 | NH$_2$ |
| allyl | OH | OMe | 3 | NH$_2$ |
| H | OH | OH | 3 | NH$_2$ |
| H | OH | OMe | 3 | NH$_2$ |
| Me | OH | OH | 3 | NH$_2$ |
| Me | OH | OMe | 3 | NH$_2$ |
| benzyl | OH | OH | 3 | NH$_2$ |
| benzyl | OH | OMe | 3 | NH$_2$ |
| 2-phenethyl | OH | OH | 3 | NH$_2$ |
| 2-phenethyl | OH | OMe | 3 | NH$_2$ |
| cyclopropylmethyl | OH | OH | 3 | NO$_2$ |
| cyclopropylmethyl | OH | OMe | 3 | NO$_2$ |
| cyclobutylmethyl | OH | OH | 3 | NO$_2$ |
| cyclobutylmethyl | OH | OMe | 3 | NO$_2$ |
| allyl | OH | OH | 3 | NO$_2$ |
| allyl | OH | OMe | 3 | NO$_2$ |
| H | OH | OH | 3 | NO$_2$ |
| H | OH | OMe | 3 | NO$_2$ |
| Me | OH | OH | 3 | NO$_2$ |
| Me | OH | OMe | 3 | NO$_2$ |
| benzyl | OH | OH | 3 | NO$_2$ |
| benzyl | OH | OMe | 3 | NO$_2$ |
| 2-phenethyl | OH | OH | 3 | NO$_2$ |
| 2-phenethyl | OH | OMe | 3 | NO$_2$ |
| cyclopropylmethyl | OH | OH | 3 | CN |
| cyclopropylmethyl | OH | OMe | 3 | CN |
| cyclobutylmethyl | OH | OH | 3 | CN |
| cyclobutylmethyl | OH | OMe | 3 | CN |
| allyl | OH | OH | 3 | CN |
| allyl | OH | OMe | 3 | CN |
| H | OH | OH | 3 | CN |
| H | OH | OMe | 3 | CN |
| Me | OH | OH | 3 | CN |
| Me | OH | OMe | 3 | CN |
| benzyl | OH | OH | 3 | CN |
| benzyl | OH | OMe | 3 | CN |
| 2-phenethyl | OH | OH | 3 | CN |
| 2-phenethyl | OH | OMe | 3 | CN |
| cyclopropylmethyl | OH | OH | 3 | NCS |
| cyclopropylmethyl | OH | OMe | 3 | NCS |
| cyclobutylmethyl | OH | OH | 3 | NCS |
| cyclobutylmethyl | OH | OMe | 3 | NCS |
| allyl | OH | OH | 3 | NCS |
| allyl | OH | OMe | 3 | NCS |
| H | OH | OH | 3 | NCS |
| H | OH | OMe | 3 | NCS |
| Me | OH | OH | 3 | NCS |
| Me | OH | OMe | 3 | NCS |
| benzyl | OH | OH | 3 | NCS |
| benzyl | OH | OMe | 3 | NCS |
| 2-phenethyl | OH | OH | 3 | NCS |

| | | | | |
|---|---|---|---|---|
| 2-phenethyl | OH | OMe | 3 | NCS |
| cyclopropylmethyl | OH | OH | 3 | COOH |
| cyclopropylmethyl | OH | OMe | 3 | COOH |
| cyclobutylmethyl | OH | OH | 3 | COOH |
| cyclobutylmethyl | OH | OMe | 3 | COOH |
| allyl | OH | OH | 3 | COOH |
| allyl | OH | OMe | 3 | COOH |
| H | OH | OH | 3 | COOH |
| H | OH | OMe | 3 | COOH |
| Me | OH | OH | 3 | COOH |
| Me | OH | OMe | 3 | COOH |
| benzyl | OH | OH | 3 | COOH |
| benzyl | OH | OMe | 3 | COOH |
| 2-phenethyl | OH | OH | 3 | COOH |
| 2-phenethyl | OH | OMe | 3 | COOH |
| cyclopropylmethyl | OH | OH | 3 | COOMe |
| cyclopropylmethyl | OH | OMe | 3 | COOMe |
| cyclobutylmethyl | OH | OH | 3 | COOMe |
| cyclobutylmethyl | OH | OMe | 3 | COOMe |
| allyl | OH | OH | 3 | COOMe |
| allyl | OH | OMe | 3 | COOMe |
| H | OH | OH | 3 | COOMe |
| H | OH | OMe | 3 | COOMe |
| Me | OH | OH | 3 | COOMe |
| Me | OH | OMe | 3 | COOMe |
| benzyl | OH | OH | 3 | COOMe |
| benzyl | OH | OMe | 3 | COOMe |
| 2-phenethyl | OH | OH | 3 | COOMe |
| 2-phenethyl | OH | OMe | 3 | COOMe |
| cyclopropylmethyl | OH | OH | 3 | COOEt |
| cyclopropylmethyl | OH | OMe | 3 | COOEt |
| cyclobutylmethyl | OH | OH | 3 | COOEt |
| cyclobutylmethyl | OH | OMe | 3 | COOEt |
| allyl | OH | OH | 3 | COOEt |
| allyl | OH | OMe | 3 | COOEt |
| H | OH | OH | 3 | COOEt |
| H | OH | OMe | 3 | COOEt |
| Me | OH | OH | 3 | COOEt |
| Me | OH | OMe | 3 | COOEt |
| benzyl | OH | OH | 3 | COOEt |
| benzyl | OH | OMe | 3 | COOEt |
| 2-phenethyl | OH | OH | 3 | COOEt |
| 2-phenethyl | OH | OMe | 3 | COOEt |
| cyclopropylmethyl | OH | OH | 3 | NHCHO |
| cyclopropylmethyl | OH | OMe | 3 | NHCHO |
| cyclobutylmethyl | OH | OH | 3 | NHCHO |
| cyclobutylmethyl | OH | OMe | 3 | NHCHO |
| allyl | OH | OH | 3 | NHCHO |
| allyl | OH | OMe | 3 | NHCHO |
| H | OH | OH | 3 | NHCHO |
| H | OH | OMe | 3 | NHCHO |
| Me | OH | OH | 3 | NHCHO |
| Me | OH | OMe | 3 | NHCHO |
| benzyl | OH | OH | 3 | NHCHO |
| benzyl | OH | OMe | 3 | NHCHO |
| 2-phenethyl | OH | OH | 3 | NHCHO |
| 2-phenethyl | OH | OMe | 3 | NHCHO |
| cyclopropylmethyl | OH | OH | 3 | NHCO—Me |
| cyclopropylmethyl | OH | OMe | 3 | NHCO—Me |
| cyclobutylmethyl | OH | OH | 3 | NHCO—Me |
| cyclobutylmethyl | OH | OMe | 3 | NHCO—Me |
| allyl | OH | OH | 3 | NHCO—Me |
| allyl | OH | OMe | 3 | NHCO—Me |
| H | OH | OH | 3 | NHCO—Me |
| H | OH | OMe | 3 | NHCO—Me |
| Me | OH | OH | 3 | NHCO—Me |
| Me | OH | OMe | 3 | NHCO—Me |
| benzyl | OH | OH | 3 | NHCO—Me |
| benzyl | OH | OMe | 3 | NHCO—Me |
| 2-phenethyl | OH | OH | 3 | NHCO—Me |
| 2-phenethyl | OH | OMe | 3 | NHCO—Me |
| cyclopropylmethyl | OH | OH | 3 | NHCO—Ph |
| cyclopropylmethyl | OH | OMe | 3 | NHCO—Ph |
| cyclobutylmethyl | OH | OH | 3 | NHCO—Ph |
| cyclobutylmethyl | OH | OMe | 3 | NHCO—Ph |
| allyl | OH | OH | 3 | NHCO—Ph |
| allyl | OH | OMe | 3 | NHCO—Ph |
| H | OH | OH | 3 | NHCO—Ph |
| H | OH | OMe | 3 | NHCO—Ph |
| Me | OH | OH | 3 | NHCO—Ph |
| Me | OH | OMe | 3 | NHCO—Ph |
| benzyl | OH | OH | 3 | NHCO—Ph |
| benzyl | OH | OMe | 3 | NHCO—Ph |
| 2-phenethyl | OH | OH | 3 | NHCO—Ph |
| 2-phenethyl | OH | OMe | 3 | NHCO—Ph |
| cyclopropylmethyl | OH | OH | 3 | NHCO—$(CH_2)_5$Ph |
| cyclopropylmethyl | OH | OMe | 3 | NHCO—$(CH_2)_5$Ph |
| cyclobutylmethyl | OH | OH | 3 | NHCO—$(CH_2)_5$Ph |
| cyclobutylmethyl | OH | OMe | 3 | NHCO—$(CH_2)_5$Ph |
| allyl | OH | OH | 3 | NHCO—$(CH_2)_5$Ph |
| allyl | OH | OMe | 3 | NHCO—$(CH_2)_5$Ph |
| H | OH | OH | 3 | NHCO—$(CH_2)_5$Ph |
| H | OH | OMe | 3 | NHCO—$(CH_2)_5$Ph |
| Me | OH | OH | 3 | NHCO—$(CH_2)_5$Ph |
| Me | OH | OMe | 3 | NHCO—$(CH_2)_5$Ph |
| benzyl | OH | OH | 3 | NHCO—$(CH_2)_5$Ph |
| benzyl | OH | OMe | 3 | NHCO—$(CH_2)_5$Ph |
| 2-phenethyl | OH | OH | 3 | NHCO—$(CH_2)_5$Ph |
| 2-phenethyl | OH | OMe | 3 | NHCO—$(CH_2)_5$Ph |
| cyclopropylmethyl | OH | OH | 3 | NHCO-cinnamyl |
| cyclopropylmethyl | OH | OMe | 3 | NHCO-cinnamyl |
| cyclobutylmethyl | OH | OH | 3 | NHCO-cinnamyl |
| cyclobutylmethyl | OH | OMe | 3 | NHCO-cinnamyl |
| allyl | OH | OH | 3 | NHCO-cinnamyl |
| allyl | OH | OMe | 3 | NHCO-cinnamyl |
| H | OH | OH | 3 | NHCO-cinnamyl |
| H | OH | OMe | 3 | NHCO-cinnamyl |
| Me | OH | OH | 3 | NHCO-cinnamyl |
| Me | OH | OMe | 3 | NHCO-cinnamyl |
| benzyl | OH | OH | 3 | NHCO-cinnamyl |
| benzyl | OH | OMe | 3 | NHCO-cinnamyl |
| 2-phenethyl | OH | OH | 3 | NHCO-cinnamyl |
| 2-phenethyl | OH | OMe | 3 | NHCO-cinnamyl |
| cyclopropylmethyl | OH | OH | 3 | NHCO—($CF_3$-cinnamyl) |
| cyclopropylmethyl | OH | OMe | 3 | NHCO—($CF_3$-cinnamyl) |
| cyclobutylmethyl | OH | OH | 3 | NHCO—($CF_3$-cinnamyl) |
| cyclobutylmethyl | OH | OMe | 3 | NHCO—($CF_3$-cinnamyl) |
| allyl | OH | OH | 3 | NHCO—($CF_3$-cinnamyl) |
| allyl | OH | OMe | 3 | NHCO—($CF_3$-cinnamyl) |
| H | OH | OH | 3 | NHCO—($CF_3$-cinnamyl) |
| H | OH | OMe | 3 | NHCO—($CF_3$-cinnamyl) |
| Me | OH | OH | 3 | NHCO—($CF_3$-cinnamyl) |
| Me | OH | OMe | 3 | NHCO—($CF_3$-cinnamyl) |
| benzyl | OH | OH | 3 | NHCO—($CF_3$-cinnamyl) |
| benzyl | OH | OMe | 3 | NHCO—($CF_3$-cinnamyl) |
| 2-phenethyl | OH | OH | 3 | NHCO—($CF_3$-cinnamyl) |
| 2-phenethyl | OH | OMe | 3 | NHCO—($CF_3$-cinnamyl) |
| cyclopropylmethyl | OH | OH | 3 | NHCO-pyridyl |
| cyclopropylmethyl | OH | OMe | 3 | NHCO-pyridyl |
| cyclobutylmethyl | OH | OH | 3 | NHCO-pyridyl |
| cyclobutylmethyl | OH | OMe | 3 | NHCO-pyridyl |
| allyl | OH | OH | 3 | NHCO-pyridyl |
| allyl | OH | OMe | 3 | NHCO-pyridyl |
| H | OH | OH | 3 | NHCO-pyridyl |
| H | OH | OMe | 3 | NHCO-pyridyl |
| Me | OH | OH | 3 | NHCO-pyridyl |
| Me | OH | OMe | 3 | NHCO-pyridyl |
| benzyl | OH | OH | 3 | NHCO-pyridyl |
| benzyl | OH | OMe | 3 | NHCO-pyridyl |
| 2-phenethyl | OH | OH | 3 | NHCO-pyridyl |
| 2-phenethyl | OH | OMe | 3 | NHCO-pyridyl |
| cyclopropylmethyl | OH | OH | 3 | NHCO—NHPh |
| cyclopropylmethyl | OH | OMe | 3 | NHCO—NHPh |
| cyclobutylmethyl | OH | OH | 3 | NHCO—NHPh |
| cyclobutylmethyl | OH | OMe | 3 | NHCO—NHPh |
| allyl | OH | OH | 3 | NHCO—NHPh |
| allyl | OH | OMe | 3 | NHCO—NHPh |
| H | OH | OH | 3 | NHCO—NHPh |
| H | OH | OMe | 3 | NHCO—NHPh |
| Me | OH | OH | 3 | NHCO—NHPh |
| Me | OH | OMe | 3 | NHCO—NHPh |
| benzyl | OH | OH | 3 | NHCO—NHPh |
| benzyl | OH | OMe | 3 | NHCO—NHPh |
| 2-phenethyl | OH | OH | 3 | NHCO—NHPh |
| 2-phenethyl | OH | OMe | 3 | NHCO—NHPh |
| cyclopropylmethyl | OH | OH | 3 | NHCS—NHPh |
| cyclopropylmethyl | OH | OMe | 3 | NHCS—NHPh |
| cyclobutylmethyl | OH | OH | 3 | NHCS—NHPh |

-continued

| | | | | |
|---|---|---|---|---|
| cyclobutylmethyl | OH | OMe | 3 | NHCS—NHPh |
| allyl | OH | OH | 3 | NHCS—NHPh |
| allyl | OH | OMe | 3 | NHCS—NHPh |
| H | OH | OH | 3 | NHCS—NHPh |
| H | OH | OMe | 3 | NHCS—NHPh |
| Me | OH | OH | 3 | NHCS—NHPh |
| Me | OH | OMe | 3 | NHCS—NHPh |
| benzyl | OH | OH | 3 | NHCS—NHPh |
| benzyl | OH | OMe | 3 | NHCS—NHPh |
| 2-phenethyl | OH | OH | 3 | NHCS—NHPh |
| 2-phenethyl | OH | OMe | 3 | NHCS—NHPh |
| cyclopropylmethyl | OH | OH | 3 | NHCS—NHCH$_2$Ph |
| cyclopropylmethyl | OH | OMe | 3 | NHCS—NHCH$_2$Ph |
| cyclobutylmethyl | OH | OH | 3 | NHCS—NHCH$_2$Ph |
| cyclobutylmethyl | OH | OMe | 3 | NHCS—NHCH$_2$Ph |
| allyl | OH | OH | 3 | NHCS—NHCH$_2$Ph |
| allyl | OH | OMe | 3 | NHCS—NHCH$_2$Ph |
| H | OH | OH | 3 | NHCS—NHCH$_2$Ph |
| H | OH | OMe | 3 | NHCS—NHCH$_2$Ph |
| Me | OH | OH | 3 | NHCS—NHCH$_2$Ph |
| Me | OH | OMe | 3 | NHCS—NHCH$_2$Ph |
| benzyl | OH | OH | 3 | NHCS—NHCH$_2$Ph |
| benzyl | OH | OMe | 3 | NHCS—NHCH$_2$Ph |
| 2-phenethyl | OH | OH | 3 | NHCS—NHCH$_2$Ph |
| 2-phenethyl | OH | OMe | 3 | NHCS—NHCH$_2$Ph |
| cyclopropylmethyl | OH | OH | 4 | OH |
| cyclopropylmethyl | OH | OMe | 4 | OH |
| cyclobutylmethyl | OH | OH | 4 | OH |
| cyclobutylmethyl | OH | OMe | 4 | OH |
| allyl | OH | OH | 4 | OH |
| allyl | OH | OMe | 4 | OH |
| H | OH | OH | 4 | OH |
| H | OH | OMe | 4 | OH |
| Me | OH | OH | 4 | OH |
| Me | OH | OMe | 4 | OH |
| benzyl | OH | OH | 4 | OH |
| benzyl | OH | OMe | 4 | OH |
| 2-phenethyl | OH | OH | 4 | OH |
| 2-phenethyl | OH | OMe | 4 | OH |
| cyclopropylmethyl | OH | OH | 4 | OMe |
| cyclopropylmethyl | OH | OMe | 4 | OMe |
| cyclobutylmethyl | OH | OH | 4 | OMe |
| cyclobutylmethyl | OH | OMe | 4 | OMe |
| allyl | OH | OH | 4 | OMe |
| allyl | OH | OMe | 4 | OMe |
| H | OH | OH | 4 | OMe |
| H | OH | OMe | 4 | OMe |
| Me | OH | OH | 4 | OMe |
| Me | OH | OMe | 4 | OMe |
| benzyl | OH | OH | 4 | OMe |
| benzyl | OH | OMe | 4 | OMe |
| 2-phenethyl | OH | OH | 4 | OMe |
| 2-phenethyl | OH | OMe | 4 | OMe |
| cyclopropylmethyl | OH | OH | 4 | OEt |
| cyclopropylmethyl | OH | OMe | 4 | OEt |
| cyclobutylmethyl | OH | OH | 4 | OEt |
| cyclobutylmethyl | OH | OMe | 4 | OEt |
| allyl | OH | OH | 4 | OEt |
| allyl | OH | OMe | 4 | OEt |
| H | OH | OH | 4 | OEt |
| H | OH | OMe | 4 | OEt |
| Me | OH | OH | 4 | OEt |
| Me | OH | OMe | 4 | OEt |
| benzyl | OH | OH | 4 | OEt |
| benzyl | OH | OMe | 4 | OEt |
| 2-phenethyl | OH | OH | 4 | OEt |
| 2-phenethyl | OH | OMe | 4 | OEt |
| cyclopropylmethyl | OH | OH | 4 | NH$_2$ |
| cyclopropylmethyl | OH | OMe | 4 | NH$_2$ |
| cyclobutylmethyl | OH | OH | 4 | NH$_2$ |
| cyclobutylmethyl | OH | OMe | 4 | NH$_2$ |
| allyl | OH | OH | 4 | NH$_2$ |
| allyl | OH | OMe | 4 | NH$_2$ |
| H | OH | OH | 4 | NH$_2$ |
| H | OH | OMe | 4 | NH$_2$ |
| Me | OH | OH | 4 | NH$_2$ |
| Me | OH | OMe | 4 | NH$_2$ |
| benzyl | OH | OH | 4 | NH$_2$ |
| benzyl | OH | OMe | 4 | NH$_2$ |
| 2-phenethyl | OH | OH | 4 | NH$_2$ |
| 2-phenethyl | OH | OMe | 4 | NH$_2$ |
| cyclopropylmethyl | OH | OH | 4 | NO$_2$ |
| cyclopropylmethyl | OH | OMe | 4 | NO$_2$ |
| cyclobutylmethyl | OH | OH | 4 | NO$_2$ |
| cyclobutylmethyl | OH | OMe | 4 | NO$_2$ |
| allyl | OH | OH | 4 | NO$_2$ |
| allyl | OH | OMe | 4 | NO$_2$ |
| H | OH | OH | 4 | NO$_2$ |
| H | OH | OMe | 4 | NO$_2$ |
| Me | OH | OH | 4 | NO$_2$ |
| Me | OH | OMe | 4 | NO$_2$ |
| benzyl | OH | OH | 4 | NO$_2$ |
| benzyl | OH | OMe | 4 | NO$_2$ |
| 2-phenethyl | OH | OH | 4 | NO$_2$ |
| 2-phenethyl | OH | OMe | 4 | NO$_2$ |
| cyclopropylmethyl | OH | OH | 4 | CN |
| cyclopropylmethyl | OH | OMe | 4 | CN |
| cyclobutylmethyl | OH | OH | 4 | CN |
| cyclobutylmethyl | OH | OMe | 4 | CN |
| allyl | OH | OH | 4 | CN |
| allyl | OH | OMe | 4 | CN |
| H | OH | OH | 4 | CN |
| H | OH | OMe | 4 | CN |
| Me | OH | OH | 4 | CN |
| Me | OH | OMe | 4 | CN |
| benzyl | OH | OH | 4 | CN |
| benzyl | OH | OMe | 4 | CN |
| 2-phenethyl | OH | OH | 4 | CN |
| 2-phenethyl | OH | OMe | 4 | CN |
| cyclopropylmethyl | OH | OH | 4 | NCS |
| cyclopropylmethyl | OH | OMe | 4 | NCS |
| cyclobutylmethyl | OH | OH | 4 | NCS |
| cyclobutylmethyl | OH | OMe | 4 | NCS |
| allyl | OH | OH | 4 | NCS |
| allyl | OH | OMe | 4 | NCS |
| H | OH | OH | 4 | NCS |
| H | OH | OMe | 4 | NCS |
| Me | OH | OH | 4 | NCS |
| Me | OH | OMe | 4 | NCS |
| benzyl | OH | OH | 4 | NCS |
| benzyl | OH | OMe | 4 | NCS |
| 2-phenethyl | OH | OH | 4 | NCS |
| 2-phenethyl | OH | OMe | 4 | NCS |
| cyclopropylmethyl | OH | OH | 4 | COOH |
| cyclopropylmethyl | OH | OMe | 4 | COOH |
| cyclobutylmethyl | OH | OH | 4 | COOH |
| cyclobutylmethyl | OH | OMe | 4 | COOH |
| allyl | OH | OH | 4 | COOH |
| allyl | OH | OMe | 4 | COOH |
| H | OH | OH | 4 | COOH |
| H | OH | OMe | 4 | COOH |
| Me | OH | OH | 4 | COOH |
| Me | OH | OMe | 4 | COOH |
| benzyl | OH | OH | 4 | COOH |
| benzyl | OH | OMe | 4 | OCOH |
| 2-phenethyl | OH | OH | 4 | COOH |
| 2-phenethyl | OH | OMe | 4 | COOH |
| cyclopropylmethyl | OH | OH | 4 | COOMe |
| cyclopropylmethyl | OH | OMe | 4 | COOMe |
| cyclobutylmethyl | OH | OH | 4 | COOMe |
| cyclobutylmethyl | OH | OMe | 4 | COOMe |
| allyl | OH | OH | 4 | COOMe |
| allyl | OH | OMe | 4 | COOMe |
| H | OH | OH | 4 | COOMe |
| H | OH | OMe | 4 | COOMe |
| Me | OH | OH | 4 | COOMe |
| Me | OH | OMe | 4 | COOMe |
| benzyl | OH | OH | 4 | COOMe |
| benzyl | OH | OMe | 4 | COOMe |
| 2-phenethyl | OH | OH | 4 | COOMe |
| 2-phenethyl | OH | OMe | 4 | COOMe |
| cyclopropylmethyl | OH | OH | 4 | COOEt |
| cyclopropylmethyl | OH | OMe | 4 | COOEt |
| cyclobutylmethyl | OH | OH | 4 | COOEt |
| cyclobutylmethyl | OH | OMe | 4 | COOEt |
| allyl | OH | OH | 4 | COOEt |
| allyl | OH | OMe | 4 | COOEt |
| H | OH | OH | 4 | COOEt |

| | | | | |
|---|---|---|---|---|
| H | OH | OMe | 4 | COOEt |
| Me | OH | OH | 4 | COOEt |
| Me | OH | OMe | 4 | COOEt |
| benzyl | OH | OH | 4 | COOEt |
| benzyl | OH | OMe | 4 | COOEt |
| 2-phenethyl | OH | OH | 4 | COOEt |
| 2-phenethyl | OH | OMe | 4 | COOEt |
| cyclopropylmethyl | OH | OH | 4 | NHCHO |
| cyclopropylmethyl | OH | OMe | 4 | NHCHO |
| cyclobutylmethyl | OH | OH | 4 | NHCHO |
| cyclobutylmethyl | OH | OMe | 4 | NHCHO |
| allyl | OH | OH | 4 | NHCHO |
| allyl | OH | OMe | 4 | NHCHO |
| H | OH | OH | 4 | NHCHO |
| H | OH | OMe | 4 | NHCHO |
| Me | OH | OH | 4 | NHCHO |
| Me | OH | OMe | 4 | NHCHO |
| benzyl | OH | OH | 4 | NHCHO |
| benzyl | OH | OMe | 4 | NHCHO |
| 2-phenethyl | OH | OH | 4 | NHCHO |
| 2-phenethyl | OH | OMe | 4 | NHCHO |
| cyclopropylmethyl | OH | OH | 4 | NHCO—Me |
| cyclopropylmethyl | OH | OMe | 4 | NHCO—Me |
| cyclobutylmethyl | OH | OH | 4 | NHCO—Me |
| cyclobutylmethyl | OH | OMe | 4 | NHCO—Me |
| allyl | OH | OH | 4 | NHCO—Me |
| allyl | OH | OMe | 4 | NHCO—Me |
| H | OH | OH | 4 | NHCO—Me |
| H | OH | OMe | 4 | NHCO—Me |
| Me | OH | OH | 4 | NHCO—Me |
| Me | OH | OMe | 4 | NHCO—Me |
| benzyl | OH | OH | 4 | NHCO—Me |
| benzyl | OH | OMe | 4 | NHCO—Me |
| 2-phenethyl | OH | OH | 4 | NHCO—Me |
| 2-phenethyl | OH | OMe | 4 | NHCO—Me |
| cyclopropylmethyl | OH | OH | 4 | NHCO—Ph |
| cyclopropylmethyl | OH | OMe | 4 | NHCO—Ph |
| cyclobutylmethyl | OH | OH | 4 | NHCO—Ph |
| cyclobutylmethyl | OH | OMe | 4 | NHCO—Ph |
| allyl | OH | OH | 4 | NHCO—Ph |
| allyl | OH | OMe | 4 | NHCO—Ph |
| H | OH | OH | 4 | NHCO—Ph |
| H | OH | OMe | 4 | NHCO—Ph |
| Me | OH | OH | 4 | NHCO—Ph |
| Me | OH | OMe | 4 | NHCO—Ph |
| benzyl | OH | OH | 4 | NHCO—Ph |
| benzyl | OH | OMe | 4 | NHCO—Ph |
| 2-phenethyl | OH | OH | 4 | NHCO—Ph |
| 2-phenethyl | OH | OMe | 4 | NHCO—Ph |
| cyclopropylmethyl | OH | OH | 4 | NHCO—(CH$_2$)$_5$Ph |
| cyclopropylmethyl | OH | OMe | 4 | NHCO—(CH$_2$)$_5$Ph |
| cyclobutylmethyl | OH | OH | 4 | NHCO—(CH$_2$)$_5$Ph |
| cyclobutylmethyl | OH | OMe | 4 | NHCO—(CH$_2$)$_5$Ph |
| allyl | OH | OH | 4 | NHCO—(CH$_2$)$_5$Ph |
| allyl | OH | OMe | 4 | NHCO—(CH$_2$)$_5$Ph |
| H | OH | OH | 4 | NHCO—(CH$_2$)$_5$Ph |
| H | OH | OMe | 4 | NHCO—(CH$_2$)$_5$Ph |
| Me | OH | OH | 4 | NHCO—(CH$_2$)$_5$Ph |
| Me | OH | OMe | 4 | NHCO—(CH$_2$)$_5$Ph |
| benzyl | OH | OH | 4 | NHCO—(CH$_2$)$_5$Ph |
| benzyl | OH | OMe | 4 | NHCO—(CH$_2$)$_5$Ph |
| 2-phenethyl | OH | OH | 4 | NHCO—(CH$_2$)$_5$Ph |
| 2-phenethyl | OH | OMe | 4 | NHCO—(CH$_2$)$_5$Ph |
| cyclopropylmethyl | OH | OH | 4 | NHCO-cinnamyl |
| cyclopropylmethyl | OH | OMe | 4 | NHCO-cinnamyl |
| cyclobutylmethyl | OH | OH | 4 | NHCO-cinnamyl |
| cyclobutylmethyl | OH | OMe | 4 | NHCO-cinnamyl |
| allyl | OH | OH | 4 | NHCO-cinnamyl |
| allyl | OH | OMe | 4 | NHCO-cinnamyl |
| H | OH | OH | 4 | NHCO-cinnamyl |
| H | OH | OMe | 4 | NHCO-cinnamyl |
| Me | OH | OH | 4 | NHCO-cinnamyl |
| Me | OH | OMe | 4 | NHCO-cinnamyl |
| benzyl | OH | OH | 4 | NHCO-cinnamyl |
| benzyl | OH | OMe | 4 | NHCO-cinnamyl |
| 2-phenethyl | OH | OH | 4 | NHCO-cinnamyl |
| 2-phenethyl | OH | OMe | 4 | NHCO-cinnamyl |
| cyclopropylmethyl | OH | OH | 4 | NHCO—(CF$_3$-cinnamyl) |
| cyclopropylmethyl | OH | OMe | 4 | NHCO—(CF$_3$-cinnamyl) |
| cyclobutylmethyl | OH | OH | 4 | NHCO—(CF$_3$-cinnamyl) |
| cyclobutylmethyl | OH | OMe | 4 | NHCO—(CF$_3$-cinnamyl) |
| allyl | OH | OH | 4 | NHCO—(CF$_3$-cinnamyl) |
| allyl | OH | OMe | 4 | NHCO—(CF$_3$-cinnamyl) |
| H | OH | OH | 4 | NHCO—(CF$_3$-cinnamyl) |
| H | OH | OMe | 4 | NHCO—(CF$_3$-cinnamyl) |
| Me | OH | OH | 4 | NHCO—(CF$_3$-cinnamyl) |
| Me | OH | OMe | 4 | NHCO—(CF$_3$-cinnamyl) |
| benzyl | OH | OH | 4 | NHCO—(CF$_3$-cinnamyl) |
| benzyl | OH | OMe | 4 | NHCO—(CF$_3$-cinnamyl) |
| 2-phenethyl | OH | OH | 4 | NHCO—(CF$_3$-cinnamyl) |
| 2-phenethyl | OH | OMe | 4 | NHCO—(CF$_3$-cinnamyl) |
| cyclopropylmethyl | OH | OH | 4 | NHCO-pyridyl |
| cyclopropylmethyl | OH | OMe | 4 | NHCO-pyridyl |
| cyclobutylmethyl | OH | OH | 4 | NHCO-pyridyl |
| cyclobutylmethyl | OH | OMe | 4 | NHCO-pyridyl |
| allyl | OH | OH | 4 | NHCO-pyridyl |
| allyl | OH | OMe | 4 | NHCO-pyridyl |
| H | OH | OH | 4 | NHCO-pyridyl |
| H | OH | OMe | 4 | NHCO-pyridyl |
| Me | OH | OH | 4 | NHCO-pyridyl |
| Me | OH | OMe | 4 | NHCO-pyridyl |
| benzyl | OH | OH | 4 | NHCO-pyridyl |
| benzyl | OH | OMe | 4 | NHCO-pyridyl |
| 2-phenethyl | OH | OH | 4 | NHCO-pyridyl |
| 2-phenethyl | OH | OMe | 4 | NHCO-pyridyl |
| cyclopropylmethyl | OH | OH | 4 | NHCO—NHPh |
| cyclopropylmethyl | OH | OMe | 4 | NHCO—NHPh |
| cyclobutylmethyl | OH | OH | 4 | NHCO—NHPh |
| cyclobutylmethyl | OH | OMe | 4 | NHCO—NHPh |
| allyl | OH | OH | 4 | NHCO—NHPh |
| allyl | OH | OMe | 4 | NHCO—NHPh |
| H | OH | OH | 4 | NHCO—NHPh |
| H | OH | OMe | 4 | NHCO—NHPh |
| Me | OH | OH | 4 | NHCO—NHPh |
| Me | OH | OMe | 4 | NHCO—NHPh |
| benzyl | OH | OH | 4 | NHCO—NHPh |
| benzyl | OH | OMe | 4 | NHCO—NHPh |
| 2-phenethyl | OH | OH | 4 | NHCO—NHPh |
| 2-phenethyl | OH | OMe | 4 | NHCO—NHPh |
| cyclopropylmethyl | OH | OH | 4 | NHCS—NHPh |
| cyclopropylmethyl | OH | OMe | 4 | NHCS—NHPh |
| cyclobutylmethyl | OH | OH | 4 | NHCS—NHPh |
| cyclobutylmethyl | OH | OMe | 4 | NHCS—NHPh |
| allyl | OH | OH | 4 | NHCS—NHPh |
| allyl | OH | OMe | 4 | NHCS—NHPh |
| H | OH | OH | 4 | NHCS—NHPh |
| H | OH | OMe | 4 | NHCS—NHPh |
| Me | OH | OH | 4 | NHCS—NHPh |
| Me | OH | OMe | 4 | NHCS—NHPh |
| benzyl | OH | OH | 4 | NHCS—NHPh |
| benzyl | OH | OMe | 4 | NHCS—NHPh |
| 2-phenethyl | OH | OH | 4 | NHCS—NHPh |
| 2-phenethyl | OH | OMe | 4 | NHCS—NHPh |
| cyclopropylmethyl | OH | OH | 4 | NHCS—NHCH$_2$Ph |
| cyclopropylmethyl | OH | OMe | 4 | NHCS—NHCH$_2$Ph |
| cyclobutylmethyl | OH | OH | 4 | NHCS—NHCH$_2$Ph |
| cyclobutylmethyl | OH | OMe | 4 | NHCS—NHCH$_2$Ph |
| allyl | OH | OH | 4 | NHCS—NHCH$_2$Ph |
| allyl | OH | OMe | 4 | NHCS—NHCH$_2$Ph |
| H | OH | OH | 4 | NHCS—NHCH$_2$Ph |
| H | OH | OMe | 4 | NHCS—NHCH$_2$Ph |
| Me | OH | OH | 4 | NHCS—NHCH$_2$Ph |
| Me | OH | OMe | 4 | NHCS—NHCH$_2$Ph |
| benzyl | OH | OH | 4 | NHCS—NHCH$_2$Ph |
| benzyl | OH | OMe | 4 | NHCS—NHCH$_2$Ph |
| 2-phenethyl | OH | OH | 4 | NHCS—NHCH$_2$Ph |
| 2-phenethyl | OH | OMe | 4 | NHCS—NHCH$_2$Ph |

-continued

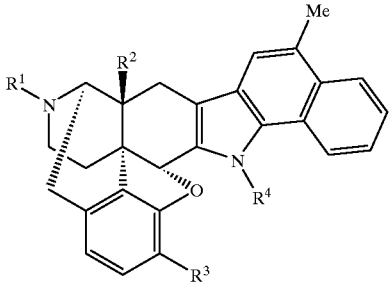

| R¹ | R² | R³ | R⁴ |
|---|---|---|---|
| cyclopropylmethyl | OH | OH | H |
| cyclopropylmethyl | OH | OMe | H |
| cyclobutylmethyl | OH | OH | H |
| cyclobutylmethyl | OH | OMe | H |
| allyl | OH | OH | H |
| allyl | OH | OMe | H |
| H | OH | OH | H |
| H | OH | OMe | H |
| Me | OH | OH | H |
| Me | OH | OMe | H |
| benzyl | OH | OH | H |
| benzyl | OH | OMe | H |
| 2-phenethyl | OH | OH | H |
| 2-phenethyl | OH | OMe | H |
| cyclopropylmethyl | OH | OH | Me |
| cyclopropylmethyl | OH | OMe | Me |
| cyclobutylmethyl | OH | OH | Me |
| cyclobutylmethyl | OH | OMe | Me |
| allyl | OH | OH | Me |
| allyl | OH | OMe | Me |
| H | OH | OH | Me |
| H | OH | OMe | Me |
| Me | OH | OH | Me |
| Me | OH | OMe | Me |
| benzyl | OH | OH | Me |
| benzyl | OH | OMe | Me |
| 2-phenethyl | OH | OH | Me |
| 2-phenethyl | OH | OMe | Me |
| cyclopropylmethyl | OH | OH | Et |
| cyclopropylmethyl | OH | OMe | Et |
| cyclobutylmethyl | OH | OH | Et |
| cyclobutylmethyl | OH | OMe | Et |
| allyl | OH | OH | Et |
| allyl | OH | OMe | Et |
| H | OH | OH | Et |
| H | OH | OMe | Et |
| Me | OH | OH | Et |
| Me | OH | OMe | Et |
| benzyl | OH | OH | Et |
| benzyl | OH | OMe | Et |
| 2-phenethyl | OH | OH | Et |
| 2-phenethyl | OH | OMe | Et |
| cyclopropylmethyl | OH | OH | Bu |
| cyclopropylmethyl | OH | OMe | Bu |
| cyclobutylmethyl | OH | OH | Bu |
| cyclobutylmethyl | OH | OMe | Bu |
| allyl | OH | OH | Bu |
| allyl | OH | OMe | Bu |
| H | OH | OH | Bu |
| H | OH | OMe | Bu |
| Me | OH | OH | Bu |
| Me | OH | OMe | Bu |
| benzyl | OH | OH | Bu |
| benzyl | OH | OMe | Bu |
| 2-phenethyl | OH | OH | Bu |
| 2-phenethyl | OH | OMe | Bu |
| cyclopropylmethyl | OH | OH | $PhCH_2$ |
| cyclopropylmethyl | OH | OMe | $PhCH_2$ |
| cylcobutylmethyl | OH | OH | $PhCH_2$ |
| cyclobutylmethyl | OH | OMe | $PhCH_2$ |
| allyl | OH | OH | $PhCH_2$ |
| allyl | OH | OMe | $PhCH_2$ |
| H | OH | OH | $PhCH_2$ |
| H | OH | OMe | $PhCH_2$ |
| Me | OH | OH | $PhCH_2$ |
| Me | OH | OMe | $PhCH_2$ |
| benzyl | OH | OH | $PhCH_2$ |
| benzyl | OH | OMe | $PhCH_2$ |
| 2-phenethyl | OH | OH | $PhCH_2$ |
| 2-phenethyl | OH | OMe | $PhCH_2$ |
| cyclopropylmethyl | OH | OH | $(F-C_6H_4)CH_2$ |
| cyclopropylmethyl | OH | OMe | $(F-C_6H_4)CH_2$ |
| cyclobutylmethyl | OH | OH | $(F-C_6H_4)CH_2$ |
| cyclobutylmethyl | OH | OMe | $(F-C_6H_4)CH_2$ |
| allyl | OH | OH | $(F-C_6H_4)CH_2$ |
| allyl | OH | OMe | $(F-C_6H_4)CH_2$ |
| H | OH | OH | $(F-C_6H_4)CH_2$ |
| H | OH | OMe | $(F-C_6H_4)CH_2$ |
| Me | OH | OH | $(F-C_6H_4)CH_2$ |
| Me | OH | OMe | $(F-C_6H_4)CH_2$ |
| benzyl | OH | OH | $(F-C_6H_4)CH_2$ |
| benzyl | OH | OMe | $(F-C_6H_4)CH_2$ |
| 2-phenethyl | OH | OH | $(F-C_6H_4)CH_2$ |
| 2-phenethyl | OH | OMe | $(F-C_6H_4)CH_2$ |
| cyclopropylmethyl | OH | OH | $(Cl-C_6H_4)CH_2$ |
| cyclopropylmethyl | OH | OMe | $(Cl-C_6H_4)CH_2$ |
| cyclobutylmethyl | OH | OH | $(Cl-C_6H_4)CH_2$ |
| cyclobutylmethyl | OH | OMe | $(Cl-C_6H_4)CH_2$ |
| allyl | OH | OH | $(Cl-C_6H_4)CH_2$ |
| allyl | OH | OMe | $(Cl-C_6H_4)CH_2$ |
| H | OH | OH | $(Cl-C_6H_4)CH_2$ |
| H | OH | OMe | $(Cl-C_6H_4)CH_2$ |
| Me | OH | OH | $(Cl-C_6H_4)CH_2$ |
| Me | OH | OMe | $(Cl-C_6H_4)CH_2$ |
| benzyl | OH | OH | $(Cl-C_6H_4)CH_2$ |
| benzyl | OH | OMe | $(Cl-C_6H_4)CH_2$ |
| 2-phenethyl | OH | OH | $(Cl-C_6H_4)CH_2$ |
| 2-phenethyl | OH | OMe | $(Cl-C_6H_4)CH_2$ |
| cyclopropylmethyl | OH | OH | $(Br-C_6H_4)CH_2$ |
| cyclopropylmethyl | OH | OMe | $(Br-C_6H_4)CH_2$ |
| cyclobutylmethyl | OH | OH | $(Br-C_6H_4)CH_2$ |
| cyclobutylmethyl | OH | OMe | $(Br-C_6H_4)CH_2$ |
| allyl | OH | OH | $(Br-C_6H_4)CH_2$ |
| allyl | OH | OMe | $(Br-C_9H_4)CH_2$ |
| H | OH | OH | $(Br-C_6H_4)CH_2$ |
| H | OH | OMe | $(Br-C_6H_4)CH_2$ |
| Me | OH | OH | $(Br-C_9H_4)CH_2$ |
| Me | OH | OMe | $(Br-C_9H_4)CH_2$ |
| benzyl | OH | OH | $(Br-C_9H_4)CH_2$ |
| benzyl | OH | OMe | $(Br-C_9H_4)CH_2$ |
| 2-phenethyl | OH | OH | $(Br-C_9H_4)CH_2$ |
| 2-phenethyl | OH | OMe | $(Br-C_9H_4)CH_2$ |
| cyclopropylmethyl | OH | OH | $(Me-C_9H_4)CH_2$ |
| cyclopropylmethyl | OH | OMe | $(Me-C_9H_4)CH_2$ |
| cyclobutylmethyl | OH | OH | $(Me-C_6H_4)CH_2$ |
| cyclobutylmethyl | OH | OMe | $(Me-C_6H_4)CH_2$ |
| allyl | OH | OH | $(Me-C_6H_4)CH_2$ |
| allyl | OH | OMe | $(Me-C_6H_4)CH_2$ |
| H | OH | OH | $(Me-C_6H_4)CH_2$ |
| H | OH | OMe | $(Me-C_6H_4)CH_2$ |
| Me | OH | OH | $(Me-C_6H_4)CH_2$ |
| Me | OH | OMe | $(Me-C_6H_4)CH_2$ |
| benzyl | OH | OH | $(Me-C_6H_4)CH_2$ |
| benzyl | OH | OMe | $(Me-C_6H_4)CH_2$ |
| 2-phenethyl | OH | OH | $(Me-C_6H_4)CH_2$ |
| 2-phenethyl | OH | OMe | $(Me-C_6H_4)CH_2$ |
| cyclopropylmethyl | OH | OH | $(MeO-C_6H_4)CH_2$ |
| cyclopropylmethyl | OH | OMe | $(MeO-C_6H_4)CH_2$ |
| cyclobutylmethyl | OH | OH | $(MeO-C_6H_4)CH_2$ |
| cyclobutylmethyl | OH | OMe | $(MeO-C_6H_4)CH_2$ |
| allyl | OH | OH | $(MeO-C_5H_4)CH_2$ |
| allyl | OH | OMe | $(MeO-C_6H_4)CH_2$ |
| H | OH | OH | $(MeO-C_6H_4)CH_2$ |
| H | OH | OMe | $(MeO-C_9H_4)CH_2$ |
| Me | OH | OH | $(MeO-C_6H_4)CH_2$ |
| Me | OH | OMe | $(MeO-C_6H_4)CH_2$ |
| benzyl | OH | OH | $(MeO-C_6H_4)CH_2$ |
| benzyl | OH | OMe | $(MeO-C_6H_4)CH_2$ |
| 2-phenethyl | OH | OH | $(MeO-C_6H_4)CH_2$ |
| 2-phenethyl | OH | OMe | $(MeO-C_6H_4)CH_2$ |
| cyclopropylmethyl | OH | OH | $(O_2N-C_6H_4)CH_2$ |

-continued

| | | | |
|---|---|---|---|
| cyclopropylmethyl | OH | OMe | (O₂N—C₆H₄)CH₂ |
| cyclobutylmethyl | OH | OH | (O₂N—C₆H₄)CH₂ |
| cyclobutylmethyl | OH | OMe | (O₂N—C₆H₄)CH₂ |
| allyl | OH | OH | (O₂N—C₆H₄)CH₂ |
| allyl | OH | OMe | (O₂N—C₆H₄)CH₂ |
| H | OH | OH | (O₂N—C₆H₄)CH₂ |
| H | OH | OMe | (O₂N—C₆H₄)CH₂ |
| Me | OH | OH | (O₂N—C₆H₄)CH₂ |
| Me | OH | OMe | (O₂N—C₆H₄)CH₂ |
| benzyl | OH | OH | (O₂N—C₆H₄)CH₂ |
| benzyl | OH | OMe | (O₂N—C₆H₄)CH₂ |
| 2-phenethyl | OH | OH | (O₂N—C₆H₄)CH₂ |
| 2-phenethyl | OH | OMe | (O₂N—C₆H₄)CH₂ |
| cyclopropylmethyl | OH | OH | (F₃C—C₆H₄)CH₂ |
| cyclopropylmethyl | OH | OMe | (F₃C—C₅H₄)CH₂ |
| cyclobutylmethyl | OH | OH | (F₃C—C₆H₄)CH₂ |
| cyclobutylmethyl | OH | OMe | (F₃C—C₆H₄)CH₂ |
| allyl | OH | OH | (F₃C—C₆H₄)CH₂ |
| allyl | OH | OMe | (F₃C—C₆H₄)CH₂ |
| H | OH | OH | (F₃C—C₉H₄)CH₂ |
| H | OH | OMe | (F₃C—C₉H₄)CH₂ |
| Me | OH | OH | (F₃C—C₉H₄)CH₂ |
| Me | OH | OMe | (F₃C—C₉H₄)CH₂ |
| benzyl | OH | OH | (F₃C—C₉H₄)CH₂ |
| benzyl | OH | OMe | (F₃C—C₉H₄)CH₂ |
| 2-phenethyl | OH | OH | (F₃C—C₉H₄)CH₂ |
| 2-phenethyl | OH | OMe | (F₃C—C₉H₄)CH₂ |
| cyclopropylmethyl | OH | OH | Ph(CH₂)₂ |
| cyclopropylmethyl | OH | OMe | Ph(CH₂)₂ |
| cyclobutylmethyl | OH | OH | Ph(CH₂)₂ |
| cyclobutylmethyl | OH | OMe | Ph(CH₂)₂ |
| allyl | OH | OH | Ph(CH₂)₂ |
| allyl | OH | OMe | Ph(CH₂)₂ |
| H | OH | OH | Ph(CH₂)₂ |
| H | OH | OMe | Ph(CH₂)₂ |
| Me | OH | OH | Ph(CH₂)₂ |
| Me | OH | OMe | Ph(CH₂)₂ |
| benzyl | OH | OH | Ph(CH₂)₂ |
| benzyl | OH | OMe | Ph(CH₂)₂ |
| 2-phenethyl | OH | OH | Ph(CH₂)₂ |
| 2-phenethyl | OH | OMe | Ph(CH₂)₂ |
| cyclopropylmethyl | OH | OH | Ph(CH₂)₃ |
| cyclopropylmethyl | OH | OMe | Ph(CH₂)₃ |
| cyclobutylmethyl | OH | OH | Ph(CH₂)₃ |
| cyclobutylmethyl | OH | OMe | Ph(CH₂)₃ |
| allyl | OH | OH | Ph(CH₂)₃ |
| allyl | OH | OMe | Ph(CH₂)₃ |
| H | OH | OH | Ph(CH₂)₃ |
| H | OH | OMe | Ph(CH₂)₃ |
| Me | OH | OH | Ph(CH₂)₃ |
| Me | OH | OMe | Ph(CH₂)₃ |
| benzyl | OH | OH | Ph(CH₂)₃ |
| benzyl | OH | OMe | Ph(CH₂)₃ |
| 2-phenethyl | OH | OH | Ph(CH₂)₃ |
| 2-phenethyl | OH | OMe | Ph(CH₂)₃ |
| cyclopropylmethyl | OH | OH | MeCO |
| cyclopropylmethyl | OH | OMe | MeCO |
| cyclobutylmethyl | OH | OH | MeCO |
| cyclobutylmethyl | OH | OMe | MeCO |
| allyl | OH | OH | MeCO |
| allyl | OH | OMe | MeCO |
| H | OH | OH | MeCO |
| H | OH | OMe | MeCO |
| Me | OH | OH | MeCO |
| Me | OH | OMe | MeCO |
| benzyl | OH | OH | MeCO |
| benzyl | OH | OMe | MeCO |
| 2-phenethyl | OH | OH | MeCO |
| 2-phenethyl | OH | OMe | MeCO |
| cyclopropylmethyl | OH | OH | PhCO |
| cyclopropylmethyl | OH | OMe | PhCO |
| cyclobutylmethyl | OH | OH | PhCO |
| cyclobutylmethyl | OH | OMe | PhCO |
| allyl | OH | OH | PhCO |
| allyl | OH | OMe | PhCO |
| H | OH | OH | PhCO |
| H | OH | OMe | PhCO |
| Me | OH | OH | PhCO |
| Me | OH | OMe | PhCO |

-continued

| | | | |
|---|---|---|---|
| benzyl | OH | OH | PhCO |
| benzyl | OH | OMe | PhCO |
| 2-phenethyl | OH | OH | PhCO |
| 2-phenethyl | OH | OMe | PhCO |
| cyclopropylmethyl | OH | OH | MeSO₂ |
| cyclopropylmethyl | OH | OMe | MeSO₂ |
| cyclobutylmethyl | OH | OH | MeSO₂ |
| cyclobutylmethyl | OH | OMe | MeSO₂ |
| allyl | OH | OH | MeSO₂ |
| allyl | OH | OMe | MeSO₂ |
| H | OH | OH | MeSO₂ |
| H | OH | OMe | MeSO₂ |
| Me | OH | OH | MeSO₂ |
| Me | OH | OMe | MeSO₂ |
| benzyl | OH | OH | MeSO₂ |
| benzyl | OH | OMe | MeSO₂ |
| 2-phenethyl | OH | OH | MeSO₂ |
| 2-phenethyl | OH | OMe | MeSO₂ |
| cyclopropylmethyl | OH | OH | PhSO₂ |
| cyclopropylmethyl | OH | OMe | PhSO₂ |
| cyclobutylmethyl | OH | OH | PhSO₂ |
| cyclobutylmethyl | OH | OMe | PhSO₂ |
| allyl | OH | OH | PhSO₂ |
| allyl | OH | OMe | PhSO₂ |
| H | OH | OH | PhSO₂ |
| H | OH | OMe | PhSO₂ |
| Me | OH | OH | PhSO₂ |
| Me | OH | OMe | PhSO₂ |
| benzyl | OH | OH | PhSO₂ |
| benzyl | OH | OMe | PhSO₂ |
| 2-phenethyl | OH | OH | PhSO₂ |
| 2-phenethyl | OH | OMe | PhSO₂ |
| cyclopropylmethyl | OH | OH | (Me—C₆H₄)SO₂ |
| cyclopropylmethyl | OH | OMe | (Me—C₆H₄)SO₂ |
| cyclobutylmethyl | OH | OH | (Me—C₆H₄)SO₂ |
| cyclobutylmethyl | OH | OMe | (Me—C₆H₄)SO₂ |
| allyl | OH | OH | (Me—C₆H₄)SO₂ |
| allyl | OH | OMe | (Me—C₆H₄)SO₂ |
| H | OH | OH | (Me—C₆H₄)SO₂ |
| H | OH | OMe | (Me—C₆H₄)SO₂ |
| Me | OH | OH | (Me—C₆H₄)SO₂ |
| Me | OH | OMe | (Me—C₆H₄)SO₂ |
| benzyl | OH | OH | (Me—C₆H₄)SO₂ |
| benzyl | OH | OMe | (Me—C₆H₄)SO₂ |
| 2-phenethyl | OH | OH | (Me—C₆H₄)SO₂ |
| 2-phenethyl | OH | OMe | (Me—C₆H₄)SO₂ |
| cyclopropylmethyl | OH | OH | PhCH₂SO₂ |
| cyclopropylmethyl | OH | OMe | PhCH₂SO₂ |
| cyclobutylmethyl | OH | OH | PhCH₂SO₂ |
| cyclobutylmethyl | OH | OMe | PhCH₂SO₂ |
| allyl | OH | OH | PhCH₂SO₂ |
| allyl | OH | OMe | PhCH₂SO₂ |
| H | OH | OH | PhCH₂SO₂ |
| H | OH | OMe | PhCH₂SO₂ |
| Me | OH | OH | PhCH₂SO₂ |
| Me | OH | OMe | PhCH₂SO₂ |
| benzyl | OH | OH | PhCH₂SO₂ |
| benzyl | OH | OMe | PhCH₂SO₂ |
| 2-phenethyl | OH | OH | PhCH₂SO₂ |
| 2-phenethyl | OH | OMe | PhCH₂SO₂ |

| R¹ | R² | R³ | i | R¹⁶ |
|---|---|---|---|---|
| cyclopropylmethyl | OH | OH | 2 | OH |
| cyclopropylmethyl | OH | OMe | 2 | OH |
| cyclobutylmethyl | OH | OH | 2 | OH |
| cyclobutylmethyl | OH | OMe | 2 | OH |
| allyl | OH | OH | 2 | OH |
| allyl | OH | OMe | 2 | OH |
| H | OH | OH | 2 | OH |
| H | OH | OMe | 2 | OH |
| Me | OH | OH | 2 | OH |
| Me | OH | OMe | 2 | OH |
| benzyl | OH | OH | 2 | OH |
| benzyl | OH | OMe | 2 | OH |
| 2-phenethyl | OH | OH | 2 | OH |
| 2-phenethyl | OH | OMe | 2 | OH |
| cyclopropylmethyl | OH | OH | 2 | OMe |
| cyclopropylmethyl | OH | OMe | 2 | OMe |
| cyclobutylmethyl | OH | OH | 2 | OMe |
| cyclobutylmethyl | OH | OMe | 2 | OMe |
| allyl | OH | OH | 2 | OMe |
| allyl | OH | OMe | 2 | OMe |
| H | OH | OH | 2 | OMe |
| H | OH | OMe | 2 | OMe |
| Me | OH | OH | 2 | OMe |
| Me | OH | OMe | 2 | OMe |
| benzyl | OH | OH | 2 | OMe |
| benzyl | OH | OMe | 2 | OMe |
| 2-phenethyl | OH | OH | 2 | OMe |
| 2-phenethyl | OH | OMe | 2 | OMe |
| cyclopropylmethyl | OH | OH | 2 | OEt |
| cyclopropylmethyl | OH | OMe | 2 | OEt |
| cyclobutylmethyl | OH | OH | 2 | OEt |
| cyclobutylmethyl | OH | OMe | 2 | OEt |
| allyl | OH | OH | 2 | OEt |
| allyl | OH | OMe | 2 | OEt |
| H | OH | OH | 2 | OEt |
| H | OH | OMe | 2 | OEt |
| Me | OH | OH | 2 | OEt |
| Me | OH | OMe | 2 | OEt |
| benzyl | OH | OH | 2 | OEt |
| benzyl | OH | OMe | 2 | OEt |
| 2-phenethyl | OH | OH | 2 | OEt |
| 2-phenethyl | OH | OMe | 2 | OEt |
| cyclopropylmethyl | OH | OH | 2 | NH₂ |
| cyclopropylmethyl | OH | OMe | 2 | NH₂ |
| cyclobutylmethyl | OH | OH | 2 | NH₂ |
| cyclobutylmethyl | OH | OMe | 2 | NH₂ |
| allyl | OH | OH | 2 | NH₂ |
| allyl | OH | OMe | 2 | NH₂ |
| H | OH | OH | 2 | NH₂ |
| H | OH | OMe | 2 | NH₂ |
| Me | OH | OH | 2 | NH₂ |
| Me | OH | OMe | 2 | NH₂ |
| benzyl | OH | OH | 2 | NH₂ |
| benzyl | OH | OMe | 2 | NH₂ |
| 2-phenethyl | OH | OH | 2 | NH₂ |
| 2-phenethyl | OH | OMe | 2 | NH₂ |
| cyclopropylmethyl | OH | OH | 2 | NO₂ |
| cyclopropylmethyl | OH | OMe | 2 | NO₂ |
| cyclobutylmethyl | OH | OH | 2 | NO₂ |
| cyclobutylmethyl | OH | OMe | 2 | NO₂ |
| allyl | OH | OH | 2 | NO₂ |
| allyl | OH | OMe | 2 | NO₂ |
| H | OH | OH | 2 | NO₂ |
| H | OH | OMe | 2 | NO₂ |
| Me | OH | OH | 2 | NO₂ |
| Me | OH | OMe | 2 | NO₂ |
| benzyl | OH | OH | 2 | NO₂ |
| benzyl | OH | OMe | 2 | NO₂ |
| 2-phenethyl | OH | OH | 2 | NO₂ |
| 2-phenethyl | OH | OMe | 2 | NO₂ |
| cyclopropylmethyl | OH | OH | 2 | CN |
| cyclopropylmethyl | OH | OMe | 2 | CN |
| cyclobutylmethyl | OH | OH | 2 | CN |
| cyclobutylmethyl | OH | OMe | 2 | CN |
| allyl | OH | OH | 2 | CN |
| allyl | OH | OMe | 2 | CN |
| H | OH | OH | 2 | CN |
| H | OH | OMe | 2 | CN |
| Me | OH | OH | 2 | CN |
| Me | OH | OMe | 2 | CN |
| benzyl | OH | OH | 2 | CN |
| benzyl | OH | OMe | 2 | CN |
| 2-phenethyl | OH | OH | 2 | CN |
| 2-phenethyl | OH | OMe | 2 | CN |
| cyclopropylmethyl | OH | OH | 2 | NCS |
| cyclopropylmethyl | OH | OMe | 2 | NCS |
| cyclobutylmethyl | OH | OH | 2 | NCS |
| cyclobutylmethyl | OH | OMe | 2 | NCS |
| allyl | OH | OH | 2 | NCS |
| allyl | OH | OMe | 2 | NCS |
| H | OH | OH | 2 | NCS |
| H | OH | OMe | 2 | NCS |
| Me | OH | OH | 2 | NCS |
| Me | OH | OMe | 2 | NCS |
| benzyl | OH | OH | 2 | NCS |
| benzyl | OH | OMe | 2 | NCS |
| 2-phenethyl | OH | OH | 2 | NCS |
| 2-phenethyl | OH | OMe | 2 | NCS |
| cyclopropylmethyl | OH | OH | 2 | COOH |
| cyclopropylmethyl | OH | OMe | 2 | COOH |
| cyclobutylmethyl | OH | OH | 2 | COOH |
| cyclobutylmethyl | OH | OMe | 2 | COOH |
| allyl | OH | OH | 2 | COOH |
| allyl | OH | OMe | 2 | COOH |
| H | OH | OH | 2 | COOH |
| H | OH | OMe | 2 | COOH |
| Me | OH | OH | 2 | COOH |
| Me | OH | OMe | 2 | COOH |
| benzyl | OH | OH | 2 | COOH |
| benzyl | OH | OMe | 2 | COOH |
| 2-phenethyl | OH | OH | 2 | COOH |
| 2-phenethyl | OH | OMe | 2 | COOH |
| cyclopropylmethyl | OH | OH | 2 | COOMe |
| cyclopropylmethyl | OH | OMe | 2 | COOMe |
| cyclobutylmethyl | OH | OH | 2 | COOMe |
| cyclobutylmethyl | OH | OMe | 2 | COOMe |
| allyl | OH | OH | 2 | COOMe |
| allyl | OH | OMe | 2 | COOMe |
| H | OH | OH | 2 | COOMe |
| H | OH | OMe | 2 | COOMe |
| Me | OH | OH | 2 | COOMe |
| Me | OH | OMe | 2 | COOMe |
| benzyl | OH | OH | 2 | COOMe |
| benzyl | OH | OMe | 2 | COOMe |
| 2-phenethyl | OH | OH | 2 | COOMe |
| 2-phenethyl | OH | OMe | 2 | COOMe |
| cyclopropylmethyl | OH | OH | 2 | COOEt |
| cyclopropylmethyl | OH | OMe | 2 | COOEt |
| cyclobutylmethyl | OH | OH | 2 | COOEt |
| cyclobutylmethyl | OH | OMe | 2 | COOEt |
| allyl | OH | OH | 2 | COOEt |
| allyl | OH | OMe | 2 | COOEt |
| H | OH | OH | 2 | COOEt |
| H | OH | OMe | 2 | COOEt |
| Me | OH | OH | 2 | COOEt |
| Me | OH | OMe | 2 | COOEt |
| benzyl | OH | OH | 2 | COOEt |
| benzyl | OH | OMe | 2 | COOEt |
| 2-phenethyl | OH | OH | 2 | COOEt |
| 2-phenethyl | OH | OMe | 2 | COOEt |
| cyclopropylmethyl | OH | OH | 2 | NHCHO |

-continued

| | | | | |
|---|---|---|---|---|
| cyclopropylmethyl | OH | OMe | 2 | NHCHO |
| cyclobutylmethyl | OH | OH | 2 | NHCHO |
| cyclobutylmethyl | OH | OMe | 2 | NHCHO |
| allyl | OH | OH | 2 | NHCHO |
| allyl | OH | OMe | 2 | NHCHO |
| H | OH | OH | 2 | NHCHO |
| H | OH | OMe | 2 | NHCHO |
| Me | OH | OH | 2 | NHCHO |
| Me | OH | OMe | 2 | NHCHO |
| benzyl | OH | OH | 2 | NHCHO |
| benzyl | OH | OMe | 2 | NHCHO |
| 2-phenethyl | OH | OH | 2 | NHCHO |
| 2-phenethyl | OH | OMe | 2 | NHCHO |
| cyclopropylmethyl | OH | OH | 2 | NHCO—Me |
| cyclopropylmethyl | OH | OMe | 2 | NHCO—Me |
| cyclobutylmethyl | OH | OH | 2 | NHCO—Me |
| cyclobutylmethyl | OH | OMe | 2 | NHCO—Me |
| allyl | OH | OH | 2 | NHCO—Me |
| allyl | OH | OMe | 2 | NHCO—Me |
| H | OH | OH | 2 | NHCO—Me |
| H | OH | OMe | 2 | NHCO—Me |
| Me | OH | OH | 2 | NHCO—Me |
| Me | OH | OMe | 2 | NHCO—Me |
| benzyl | OH | OH | 2 | NHCO—Me |
| benzyl | OH | OMe | 2 | NHCO—Me |
| 2-phenethyl | OH | OH | 2 | NHCO—Me |
| 2-phenethyl | OH | OMe | 2 | NHCO—Me |
| cyclopropylmethyl | OH | OH | 2 | NHCO—Ph |
| cyclopropylmethyl | OH | OMe | 2 | NHCO—Ph |
| cyclobutylmethyl | OH | OH | 2 | NHCO—Ph |
| cyclobutylmethyl | OH | OMe | 2 | NHCO—Ph |
| allyl | OH | OH | 2 | NHCO—Ph |
| allyl | OH | OMe | 2 | NHCO—Ph |
| H | OH | OH | 2 | NHCO—Ph |
| H | OH | OMe | 2 | NHCO—Ph |
| Me | OH | OH | 2 | NHCO—Ph |
| Me | OH | OMe | 2 | NHCO—Ph |
| benzyl | OH | OH | 2 | NHCO—Ph |
| benzyl | OH | OMe | 2 | NHCO—Ph |
| 2-phenethyl | OH | OH | 2 | NHCO—Ph |
| 2-phenethyl | OH | OMe | 2 | NHCO—Ph |
| cyclopropylmethyl | OH | OH | 2 | NHCO—$(CH_2)_5$Ph |
| cyclopropylmethyl | OH | OMe | 2 | NHCO—$(CH_2)_5$Ph |
| cyclobutylmethyl | OH | OH | 2 | NHCO—$(CH_2)_5$Ph |
| cyclobutylmethyl | OH | OMe | 2 | NHCO—$(CH_2)_5$Ph |
| allyl | OH | OH | 2 | NHCO—$(CH_2)_5$Ph |
| allyl | OH | OMe | 2 | NHCO—$(CH_2)_5$Ph |
| H | OH | OH | 2 | NHCO—$(CH_2)_5$Ph |
| H | OH | OMe | 2 | NHCO—$(CH_2)_5$Ph |
| Me | OH | OH | 2 | NHCO—$(CH_2)_5$Ph |
| Me | OH | OMe | 2 | NHCO—$(CH_2)_5$Ph |
| benzyl | OH | OH | 2 | NHCO—$(CH_2)_5$Ph |
| benzyl | OH | OMe | 2 | NHCO—$(CH_2)_5$Ph |
| 2-phenethyl | OH | OH | 2 | NHCO—$(CH_2)_5$Ph |
| 2-phenethyl | OH | OMe | 2 | NHCO—$(CH_2)_5$Ph |
| cyclopropylmethyl | OH | OH | 2 | NHCO-cinnamyl |
| cyclopropylmethyl | OH | OMe | 2 | NHCO-cinnamyl |
| cyclobutylmethyl | OH | OH | 2 | NHCO-cinnamyl |
| cyclobutylmethyl | OH | OMe | 2 | NHCO-cinnamyl |
| allyl | OH | OH | 2 | NHCO-cinnamyl |
| allyl | OH | OMe | 2 | NHCO-cinnamyl |
| H | OH | OH | 2 | NHCO-cinnamyl |
| H | OH | OMe | 2 | NHCO-cinnamyl |
| Me | OH | OH | 2 | NHCO-cinnamyl |
| Me | OH | OMe | 2 | NHCO-cinnamyl |
| benzyl | OH | OH | 2 | NHCO-cinnamyl |
| benzyl | OH | OMe | 2 | NHCO-cinnamyl |
| 2-phenethyl | OH | OH | 2 | NHCO-cinnamyl |
| 2-phenethyl | OH | OMe | 2 | NHCO-cinnamyl |
| cyclopropylmethyl | OH | OH | 2 | NHCO—($CF_3$-cinnamyl) |
| cyclopropylmethyl | OH | OMe | 2 | NHCO—($CF_3$-cinnamyl) |
| cyclobutylmethyl | OH | OH | 2 | NHCO—($CF_3$-cinnamyl) |
| cyclobutylmethyl | OH | OMe | 2 | NHCO—($CF_3$-cinnamyl) |
| allyl | OH | OH | 2 | NHCO—($CF_3$-cinnamyl) |
| allyl | OH | OMe | 2 | NHCO—($CF_3$-cinnamyl) |
| H | OH | OH | 2 | NHCO—($CF_3$-cinnamyl) |
| H | OH | OMe | 2 | NHCO—($CF_3$-cinnamyl) |
| Me | OH | OH | 2 | NHCO—($CF_3$-cinnamyl) |
| Me | OH | OMe | 2 | NHCO—($CF_3$-cinnamyl) |
| benzyl | OH | OH | 2 | NHCO—($CF_3$-cinnamyl) |
| benzyl | OH | OMe | 2 | NHCO—($CF_3$-cinnamyl) |
| 2-phenethyl | OH | OH | 2 | NHCO—($CF_3$-cinnamyl) |
| 2-phenethyl | OH | OMe | 2 | NHCO—($CF_3$-cinnamyl) |
| cyclopropylmethyl | OH | OH | 2 | NHCO-pyridyl |
| cyclopropylmethyl | OH | OMe | 2 | NHCO-pyridyl |
| cyclobutylmethyl | OH | OH | 2 | NHCO-pyridyl |
| cyclobutylmethyl | OH | OMe | 2 | NHCO-pyridyl |
| allyl | OH | OH | 2 | NHCO-pyridyl |
| allyl | OH | OMe | 2 | NHCO-pyridyl |
| H | OH | OH | 2 | NHCO-pyridyl |
| H | OH | OMe | 2 | NHCO-pyridyl |
| Me | OH | OH | 2 | NHCO-pyridyl |
| Me | OH | OMe | 2 | NHCO-pyridyl |
| benzyl | OH | OH | 2 | NHCO-pyridyl |
| benzyl | OH | OMe | 2 | NHCO-pyridyl |
| 2-phenethyl | OH | OH | 2 | NHCO-pyridyl |
| 2-phenethyl | OH | OMe | 2 | NHCO-pyridyl |
| cyclopropylmethyl | OH | OH | 2 | NHCO—NHPh |
| cyclopropylmethyl | OH | OMe | 2 | NHCO—NHPh |
| cyclobutylmethyl | OH | OH | 2 | NHCO—NHPh |
| cyclobutylmethyl | OH | OMe | 2 | NHCO—NHPh |
| allyl | OH | OH | 2 | NHCO—NHPh |
| allyl | OH | OMe | 2 | NHCO—NHPh |
| H | OH | OH | 2 | NHCO—NHPh |
| H | OH | OMe | 2 | NHCO—NHPh |
| Me | OH | OH | 2 | NHCO—NHPh |
| Me | OH | OMe | 2 | NHCO—NHPh |
| benzyl | OH | OH | 2 | NHCO—NHPh |
| benzyl | OH | OMe | 2 | NHCO—NHPh |
| 2-phenethyl | OH | OH | 2 | NHCO—NHPh |
| 2-phenethyl | OH | OMe | 2 | NHCO—NHPh |
| cyclopropylmethyl | OH | OH | 2 | NHCS—NHPh |
| cyclopropylmethyl | OH | OMe | 2 | NHCS—NHPh |
| cyclobutylmethyl | OH | OH | 2 | NHCS—NHPh |
| cyclobutylmethyl | OH | OMe | 2 | NHCS—NHPh |
| allyl | OH | OH | 2 | NHCS—NHPh |
| allyl | OH | OMe | 2 | NHCS—NHPh |
| H | OH | OH | 2 | NHCS—NHPh |
| H | OH | OMe | 2 | NHCS—NHPh |
| Me | OH | OH | 2 | NHCS—NHPh |
| Me | OH | OMe | 2 | NHCS—NHPh |
| benzyl | OH | OH | 2 | NHCS—NHPh |
| benzyl | OH | OMe | 2 | NHCS—NHPh |
| 2-phenethyl | OH | OH | 2 | NHCS—NHPh |
| 2-phenethyl | OH | OMe | 2 | NHCS—NHPh |
| cyclopropylmethyl | OH | OH | 2 | NHCS—$NHCH_2$Ph |
| cyclopropylmethyl | OH | OMe | 2 | NHCS—$NHCH_2$Ph |
| cyclobutylmethyl | OH | OH | 2 | NHCS—$NHCH_2$Ph |
| cyclobutylmethyl | OH | OMe | 2 | NHCS—$NHCH_2$Ph |
| allyl | OH | OH | 2 | NHCS—$NHCH_2$Ph |
| allyl | OH | OMe | 2 | NHCS—$NHCH_2$Ph |
| H | OH | OH | 2 | NHCS—$NHCH_2$Ph |
| H | OH | OMe | 2 | NHCS—$NHCH_2$Ph |
| Me | OH | OH | 2 | NHCS—$NHCH_2$Ph |
| Me | OH | OMe | 2 | NHCS—$NHCH_2$Ph |
| benzyl | OH | OH | 2 | NHCS—$NHCH_2$Ph |
| benzyl | OH | OMe | 2 | NHCS—$NHCH_2$Ph |
| 2-phenethyl | OH | OH | 2 | NHCS—$NHCH_2$Ph |
| 2-phenethyl | OH | OMe | 2 | NHCS—$NHCH_2$Ph |
| cyclopropylmethyl | OH | OH | 3 | OH |
| cyclopropylmethyl | OH | OMe | 3 | OH |
| cyclobutylmethyl | OH | OH | 3 | OH |
| cyclobutylmethyl | OH | OMe | 3 | OH |
| allyl | OH | OH | 3 | OH |
| allyl | OH | OMe | 3 | OH |
| H | OH | OH | 3 | OH |
| H | OH | OMe | 3 | OH |
| Me | OH | OH | 3 | OH |
| Me | OH | OMe | 3 | OH |
| benzyl | OH | OH | 3 | OH |
| benzyl | OH | OMe | 3 | OH |
| 2-phenethyl | OH | OH | 3 | OH |
| 2-phenethyl | OH | OMe | 3 | OH |
| cyclopropylmethyl | OH | OH | 3 | OMe |
| cyclopropylmethyl | OH | OMe | 3 | OMe |
| cyclobutylmethyl | OH | OH | 3 | OMe |
| cyclobutylmethyl | OH | OMe | 3 | OMe |
| allyl | OH | OH | 3 | OMe |

-continued

| | | | | |
|---|---|---|---|---|
| allyl | OH | OMe | 3 | OMe |
| H | OH | OH | 3 | OMe |
| H | OH | OMe | 3 | OMe |
| Me | OH | OH | 3 | OMe |
| Me | OH | OMe | 3 | OMe |
| benzyl | OH | OH | 3 | OMe |
| benzyl | OH | OMe | 3 | OMe |
| 2-phenethyl | OH | OH | 3 | OMe |
| 2-phenethyl | OH | OMe | 3 | OMe |
| cyclopropylmethyl | OH | OH | 3 | OEt |
| cyclopropylmethyl | OH | OMe | 3 | OEt |
| cyclobutylmethyl | OH | OH | 3 | OEt |
| cyclobutylmethyl | OH | OMe | 3 | OEt |
| allyl | OH | OH | 3 | OEt |
| allyl | OH | OMe | 3 | OEt |
| H | OH | OH | 3 | OEt |
| H | OH | OMe | 3 | OEt |
| Me | OH | OH | 3 | OEt |
| Me | OH | OMe | 3 | OEt |
| benzyl | OH | OH | 3 | OEt |
| benzyl | OH | OMe | 3 | OEt |
| 2-phenethyl | OH | OH | 3 | OEt |
| 2-phenethyl | OH | OMe | 3 | OEt |
| cyclopropylmethyl | OH | OH | 3 | $NH_2$ |
| cyclopropylmethyl | OH | OMe | 3 | $NH_2$ |
| cyclobutylmethyl | OH | OH | 3 | $NH_2$ |
| cyclobutylmethyl | OH | OMe | 3 | $NH_2$ |
| allyl | OH | OH | 3 | $NH_2$ |
| allyl | OH | OMe | 3 | $NH_2$ |
| H | OH | OH | 3 | $NH_2$ |
| H | OH | OMe | 3 | $NH_2$ |
| Me | OH | OH | 3 | $NH_2$ |
| Me | OH | OMe | 3 | $NH_2$ |
| benzyl | OH | OH | 3 | $NH_2$ |
| benzyl | OH | OMe | 3 | $NH_2$ |
| 2-phenethyl | OH | OH | 3 | $NH_2$ |
| 2-phenethyl | OH | OMe | 3 | $NH_2$ |
| cyclopropylmethyl | OH | OH | 3 | $NO_2$ |
| cyclopropylmethyl | OH | OMe | 3 | $NO_2$ |
| cyclobutylmethyl | OH | OH | 3 | $NO_2$ |
| cyclobutylmethyl | OH | OMe | 3 | $NO_2$ |
| allyl | OH | OH | 3 | $NO_2$ |
| allyl | OH | OMe | 3 | $NO_2$ |
| H | OH | OH | 3 | $NO_2$ |
| H | OH | OMe | 3 | $NO_2$ |
| Me | OH | OH | 3 | $NO_2$ |
| Me | OH | OMe | 3 | $NO_2$ |
| benzyl | OH | OH | 3 | $NO_2$ |
| benzyl | OH | OMe | 3 | $NO_2$ |
| 2-phenethyl | OH | OH | 3 | $NO_2$ |
| 2-phenethyl | OH | OMe | 3 | $NO_2$ |
| cyclopropylmethyl | OH | OH | 3 | CN |
| cyclopropylmethyl | OH | OMe | 3 | CN |
| cyclobutylmethyl | OH | OH | 3 | CN |
| cyclobutylmethyl | OH | OMe | 3 | CN |
| allyl | OH | OH | 3 | CN |
| allyl | OH | OMe | 3 | CN |
| H | OH | OH | 3 | CN |
| H | OH | OMe | 3 | CN |
| Me | OH | OH | 3 | CN |
| Me | OH | OMe | 3 | CN |
| benzyl | OH | OH | 3 | CN |
| benzl | OH | OMe | 3 | CN |
| 2-phenethyl | OH | OH | 3 | CN |
| 2-phenethyl | OH | OMe | 3 | CN |
| cyclopropylmethyl | OH | OH | 3 | NCS |
| cyclopropylmethyl | OH | OMe | 3 | NCS |
| cyclobutylmethyl | OH | OH | 3 | NCS |
| cyclobutylmethyl | OH | OMe | 3 | NCS |
| allyl | OH | OH | 3 | NCS |
| allyl | OH | OMe | 3 | NCS |
| H | OH | OH | 3 | NCS |
| H | OH | OMe | 3 | NCS |
| Me | OH | OH | 3 | NCS |
| Me | OH | OMe | 3 | NCS |
| benzyl | OH | OH | 3 | NCS |
| benzyl | OH | OMe | 3 | NCS |
| 2-phenethyl | OH | OH | 3 | NCS |
| 2-phenethyl | OH | OMe | 3 | NCS |
| cyclopropylmethyl | OH | OH | 3 | COOH |
| cyclopropylmethyl | OH | OMe | 3 | COOH |
| cyclobuytlmethyl | OH | OH | 3 | COOH |
| cyclobutylmethyl | OH | OMe | 3 | COOH |
| allyl | OH | OH | 3 | COOH |
| allyl | OH | OMe | 3 | COOH |
| H | OH | OH | 3 | COOH |
| H | OH | OMe | 3 | COOH |
| Me | OH | OH | 3 | COOH |
| Me | OH | OMe | 3 | COOH |
| benzyl | OH | OH | 3 | COOH |
| benzyl | OH | OMe | 3 | COOH |
| 2-phenethyl | OH | OH | 3 | COOH |
| 2-phenethyl | OH | OMe | 3 | COOH |
| cyclopropylmethyl | OH | OH | 3 | COOMe |
| cyclopropylmethyl | OH | OMe | 3 | COOMe |
| cyclobutylmethyl | OH | OH | 3 | COOMe |
| cyclobutylmethyl | OH | OMe | 3 | COOMe |
| allyl | OH | OH | 3 | COOMe |
| allyl | OH | OMe | 3 | COOMe |
| H | OH | OH | 3 | COOMe |
| H | OH | OMe | 3 | COOMe |
| Me | OH | OH | 3 | COOMe |
| Me | OH | OMe | 3 | COOMe |
| benzyl | OH | OH | 3 | COOMe |
| benzyl | OH | OMe | 3 | COOMe |
| 2-phenethyl | OH | OH | 3 | COOMe |
| 2-phenethyl | OH | OMe | 3 | COOMe |
| cyclopropylmethyl | OH | OH | 3 | COOEt |
| cyclopropylmethyl | OH | OMe | 3 | COOEt |
| cyclobutylmethyl | OH | OH | 3 | COOEt |
| cyclobutylmethyl | OH | OMe | 3 | COOEt |
| allyl | OH | OH | 3 | COOEt |
| allyl | OH | OMe | 3 | COOEt |
| H | OH | OH | 3 | COOEt |
| H | OH | OMe | 3 | COOEt |
| Me | OH | OH | 3 | COOEt |
| Me | OH | OMe | 3 | COOEt |
| benzyl | OH | OH | 3 | COOEt |
| benzyl | OH | OMe | 3 | COOet |
| 2-phenethyl | OH | OH | 3 | COOEt |
| 2-phenethyl | OH | OMe | 3 | COOEt |
| cyclopropylmethyl | OH | OH | 3 | NHCHO |
| cyclopropylmethyl | OH | OMe | 3 | NHCHO |
| cyclobutylmethyl | OH | OH | 3 | NHCHO |
| cyclobutylmethyl | OH | OMe | 3 | NHCHO |
| allyl | OH | OH | 3 | NHCHO |
| allyl | OH | OMe | 3 | NHCHO |
| H | OH | OH | 3 | NHCHO |
| H | OH | OMe | 3 | NHCHO |
| Me | OH | OH | 3 | NHCHO |
| Me | OH | OMe | 3 | NHCHO |
| benzyl | OH | OH | 3 | NHCHO |
| benzyl | OH | OMe | 3 | NHCHO |
| 2-phenethyl | OH | OH | 3 | NHCHO |
| 2-phenethyl | OH | OMe | 3 | NHCHO |
| cyclopropylmethyl | OH | OH | 3 | NHCO—Me |
| cyclopropylmethyl | OH | OMe | 3 | NHCO—Me |
| cylcobutylmethyl | OH | OH | 3 | NHCO—Me |
| cyclobutylmethyl | OH | OMe | 3 | NHCO—Me |
| allyl | OH | OH | 3 | NHCO—Me |
| allyl | OH | OMe | 3 | NHCO—Me |
| H | OH | OH | 3 | NHCO—Me |
| H | OH | OMe | 3 | NHCO—Me |
| Me | OH | OH | 3 | NHCO—Me |
| Me | OH | OMe | 3 | NHCO—Me |
| benzyl | OH | OH | 3 | NHCO—Me |
| benzyl | oh | OMe | 3 | NHCO—Me |
| 2-phenethyl | OH | OH | 3 | NHCO—Me |
| 2-phenethyl | OH | OMe | 3 | NHCO—Me |
| cyclopropylmethyl | OH | OH | 3 | NHCO—Ph |
| cyclopropylmethyl | OH | OMe | 3 | NHCO—Ph |
| cyclobutylmethyl | OH | OH | 3 | NHCO—Ph |
| cuclobutylmethyl | OH | OMe | 3 | NHCO—Ph |
| allyl | OH | OH | 3 | NHCO—Ph |
| allyl | OH | OMe | 3 | NHCO—Ph |
| H | OH | OH | 3 | NHCO—Ph |
| H | OH | OMe | 3 | NHCO—Ph |
| Me | OH | OH | 3 | NHCO—Ph |

-continued

| | | | | |
|---|---|---|---|---|
| Me | OH | OMe | 3 | NHCO—Ph |
| benzyl | OH | OH | 3 | NHCO—Ph |
| benzyl | OH | OMe | 3 | NHCO—Ph |
| 2-phenethyl | OH | OH | 3 | NHCO—Ph |
| 2-phenethyl | OH | OMe | 3 | NHCO—Ph |
| cyclopropylmethyl | OH | OH | 3 | NHCO—$(CH_2)_5$Ph |
| cyclopropylmethyl | OH | OMe | 3 | NHCO—$(CH_2)_5$Ph |
| cyclobutylmethyl | OH | OH | 3 | NHCO—$(CH_2)_5$Ph |
| cyclobutylmethyl | OH | OMe | 3 | NHCO—$(CH_2)$Ph |
| allyl | OH | OH | 3 | NHCO—$(CH_2)_5$Ph |
| allyl | OH | OMe | 3 | NHCO—$(CH_2)_5$Ph |
| H | OH | OH | 3 | NHCO—$(CH_2)_5$Ph |
| H | OH | OMe | 3 | NHCO—$(CH_2)_5$Ph |
| Me | OH | OH | 3 | NHCO—$(CH_2)_5$Ph |
| Me | OH | OMe | 3 | NHCO—$(CH_2)_5$Ph |
| benzyl | OH | OH | 3 | NHCO—$(CH_2)_5$Ph |
| benzyl | OH | OMe | 3 | NHCO—$(CH_2)_5$Ph |
| 2-phenethyl | OH | OH | 3 | NHCO—$(CH_2)_5$Ph |
| 2-phenethyl | OH | OMe | 3 | NHCO—$(CH_2)_5$Ph |
| cyclopropylmethyl | OH | OH | 3 | NHCO-cinnamyl |
| cyclopropylmethyl | OH | OMe | 3 | NHCO-cinnamyl |
| cyclobutylmethyl | OH | OH | 3 | NHCO-cinnamyl |
| cyclobutylmethyl | OH | OMe | 3 | NHCO-cinnamyl |
| allyl | OH | OH | 3 | NHCO-cinnamyl |
| allyl | OH | OMe | 3 | NHCO-cinnamyl |
| H | OH | OH | 3 | NHCO-cinnamyl |
| H | OH | OMe | 3 | NHCO-cinnamyl |
| Me | OH | OH | 3 | NHCO-cinnamyl |
| Me | OH | OMe | 3 | NHCO-cinnamyl |
| benzyl | OH | OH | 3 | NHCO-cinnamyl |
| benzyl | OH | OMe | 3 | NHCO-cinnamyl |
| 2-phenethyl | OH | OH | 3 | NHCO-cinnamyl |
| 2-phenethyl | OH | OMe | 3 | NHCO-cinnamyl |
| cyclopropylmethyl | OH | OH | 3 | NHCO—($CF_3$-cinnamyl) |
| cyclopropylmethyl | OH | OMe | 3 | NHCO—($CF_3$-cinnamyl) |
| cyclobutylmethyl | OH | OH | 3 | NHCO—($CF_3$-cinnamyl) |
| cyclobutylmethyl | OH | OMe | 3 | NHCO—($CF_3$-cinnamyl) |
| allyl | OH | OH | 3 | NHCO—($CF_3$-cinnamyl) |
| allyl | OH | OMe | 3 | NHCO—($CF_3$-cinnamyl) |
| H | OH | OH | 3 | NHCO—($CF_3$-cinnamyl) |
| H | OH | OMe | 3 | NHCO—($CF_3$-cinnamyl) |
| Me | OH | OH | 3 | NHCO—($CF_3$-cinnamyl) |
| Me | OH | OMe | 3 | NHCO—($CF_3$-cinnamyl) |
| benzyl | OH | OH | 3 | NHCO—($CF_3$-cinnamyl) |
| benzyl | OH | OMe | 3 | NHCO—($CF_3$-cinnamyl) |
| 2-phenethyl | OH | OH | 3 | NHCO—($CF_3$-cinnamyl) |
| 2-phenethyl | OH | OMe | 3 | NHCO—($CF_3$-cinnamyl) |
| cyclopropylmethyl | OH | OH | 3 | NHCO-pyridyl |
| cyclopropylmethyl | OH | OMe | 3 | NHCO-pyridyl |
| cyclobutylmethyl | OH | OH | 3 | NHCO-pyridyl |
| cyclobutylmethyl | OH | OMe | 3 | NHCO-pyridyl |
| allyl | OH | OH | 3 | NHCO-pyridyl |
| allyl | OH | OMe | 3 | NHCO-pyridyl |
| H | OH | OH | 3 | NHCO-pyridyl |
| H | OH | OMe | 3 | NHCO-pyridyl |
| Me | OH | OH | 3 | NHCO-pyridyl |
| Me | OH | OMe | 3 | NHCO-pyridyl |
| benzyl | OH | OH | 3 | NHCO-pyridyl |
| benzyl | OH | OMe | 3 | NHCO-pyridyl |
| 2-phenethyl | OH | OH | 3 | NHCO-pyridyl |
| 2-phenethyl | OH | OMe | 3 | NHCO-pyridyl |
| cyclopropylmethyl | OH | OH | 3 | NHCO—NHPh |
| cyclopropylmethyl | OH | OMe | 3 | NHCO—NHPh |
| cyclobutylmethyl | OH | OH | 3 | NHCO—NHPh |
| cyclobutylmethyl | OH | OMe | 3 | NHCO—NHPh |
| allyl | OH | OH | 3 | NHCO—NHPh |
| allyl | OH | OMe | 3 | NHCO—NHPh |
| H | OH | OH | 3 | NHCO—NHPh |
| H | OH | OMe | 3 | NHCO—NHPh |
| Me | OH | OH | 3 | NHCO—NHPh |
| Me | OH | OMe | 3 | NHCO—NHPh |
| benzyl | OH | OH | 3 | NHCO—NHPh |
| benzyl | OH | OMe | 3 | NHCO—NHPh |
| 2-phenethyl | OH | OH | 3 | NHCO—NHPh |
| 2-phenethyl | OH | OMe | 3 | NHCO—NHPh |
| cyclopropylmethyl | OH | OH | 3 | NHCS—NHPh |
| cyclopropylmethyl | OH | OMe | 3 | NHCS—NHPh |
| cyclobutylmethyl | OH | OH | 3 | NHCS—NHPh |
| cyclobutylmethyl | OH | OMe | 3 | NHCS—NHPh |
| allyl | OH | OH | 3 | NHCS—NHPh |
| allyl | OH | OMe | 3 | NHCS—NHPh |
| H | OH | OH | 3 | NHCS—NHPh |
| H | OH | OMe | 3 | NHCS—NHPh |
| Me | OH | OH | 3 | NHCS—NHPh |
| Me | OH | OMe | 3 | NHCS—NHPh |
| benzyl | OH | OH | 3 | NHCS—NHPh |
| benzyl | OH | OMe | 3 | NHCS—NHPh |
| 2-phenethyl | OH | OH | 3 | NHCS—nHPh |
| 2-phenethyl | OH | OMe | 3 | NHCS—NHPh |
| cyclopropylmethyl | OH | OH | 3 | NHCS—$NHCH_2$Ph |
| cyclopropylmethyl | OH | OMe | 3 | NHCS—$NHCH_2$Ph |
| cyclobutylmethyl | OH | OH | 3 | NHCS—$NHCH_2$Ph |
| cyclobutylmethyl | OH | OMe | 3 | NHCS—$NHCH_2$Ph |
| allyl | OH | OH | 3 | NHCS—$NHCH_2$Ph |
| allyl | OH | OMe | 3 | NHCS—$NHCH_2$Ph |
| H | OH | OH | 3 | NHCS—$NHCH_2$Ph |
| H | OH | OMe | 3 | NHCS—$NHCH_2$Ph |
| Me | OH | OH | 3 | NHCS—$NHCH_2$Ph |
| Me | OH | OMe | 3 | NHCS—$NHCH_2$Ph |
| benzyl | OH | OH | 3 | NHCS—$NHCH_2$Ph |
| benzyl | OH | OMe | 3 | NHCS—$NHCH_2$Ph |
| 2-phenethyl | OH | OH | 3 | NHCS—$NHCH_2$Ph |
| 2-phenethyl | OH | OMe | 3 | NHCS—$NHCH_2$Ph |
| cyclopropylmethyl | OH | OH | 4 | OH |
| cyclopropylmethyl | OH | OMe | 4 | OH |
| cyclobutylmethyl | OH | OH | 4 | OH |
| cyclobutylmethyl | OH | OMe | 4 | OH |
| allyl | OH | OH | 4 | OH |
| allyl | OH | OMe | 4 | OH |
| H | OH | OH | 4 | OH |
| H | OH | OMe | 4 | OH |
| Me | OH | OH | 4 | OH |
| Me | OH | OMe | 4 | OH |
| benzyl | OH | OH | 4 | OH |
| benzyl | OH | OMe | 4 | OH |
| 2-phenethyl | OH | OH | 4 | OH |
| 2-phenethyl | OH | OMe | 4 | OH |
| cyclopropylmethyl | OH | OH | 4 | OMe |
| cyclopropylmethyl | OH | OMe | 4 | OMe |
| cyclobutylmethyl | OH | OH | 4 | OMe |
| cyclobutylmethyl | OH | OMe | 4 | OMe |
| allyl | OH | OH | 4 | OMe |
| allyl | OH | OMe | 4 | OMe |
| H | OH | OH | 4 | OMe |
| H | OH | OMe | 4 | OMe |
| Me | OH | OH | 4 | OMe |
| Me | OH | OMe | 4 | OMe |
| benzyl | OH | OH | 4 | OMe |
| benzyl | OH | OMe | 4 | OMe |
| 2-phenethyl | OH | OH | 4 | OMe |
| 2-phenethyl | OH | OMe | 4 | OMe |
| cyclopropylmethyl | OH | OH | 4 | OEt |
| cyclopropylmethyl | OH | OMe | 4 | OEt |
| cyclobutylmethyl | OH | OH | 4 | OEt |
| cyclobutylmethyl | OH | OMe | 4 | OEt |
| allyl | OH | OH | 4 | OEt |
| allyl | OH | OMe | 4 | OEt |
| H | OH | OH | 4 | OEt |
| H | OH | OMe | 4 | OEt |
| Me | OH | OH | 4 | OEt |
| ME | OH | OMe | 4 | OEt |
| benzyl | OH | OH | 4 | OEt |
| benzyl | OH | OMe | 4 | OEt |
| 2-phenethyl | OH | OH | 4 | OEt |
| 2-phenethyl | OH | OMe | 4 | OEt |
| cyclopropylmethyl | OH | OH | 4 | $NH_2$ |
| cyclopropylmethyl | OH | OMe | 4 | $NH_2$ |
| cyclobutylmethyl | OH | OH | 4 | $NH_2$ |
| cyclobutylmethyl | OH | OMe | 4 | $NH_2$ |
| allyl | OH | OH | 4 | $NH_2$ |
| allyl | OH | OMe | 4 | $NH_2$ |
| H | OH | OH | 4 | $NH_2$ |
| H | OH | OMe | 4 | $NH_2$ |
| Me | OH | OH | 4 | $NH_2$ |
| Me | OH | OMe | 4 | $NH_2$ |
| benzyl | OH | OH | 4 | $NH_2$ |
| benzyl | OH | OMe | 4 | $NH_2$ |
| 2-phenethyl | OH | OH | 4 | $NH_2$ |

-continued

| | | | | |
|---|---|---|---|---|
| 2-phenethyl | OH | OMe | 4 | NH$_2$ |
| cyclopropylmethyl | OH | OH | 4 | NO$_2$ |
| cyclopropylmethyl | OH | OMe | 4 | NO$_2$ |
| cyclobutylmethyl | OH | OH | 4 | NO$_2$ |
| cyclobutylmethyl | OH | OMe | 4 | NO$_2$ |
| allyl | OH | OH | 4 | NO$_2$ |
| allyl | OH | OMe | 4 | NO$_2$ |
| H | OH | OH | 4 | NO$_2$ |
| H | OH | OMe | 4 | NO$_2$ |
| Me | OH | OH | 4 | NO$_2$ |
| Me | OH | OMe | 4 | NO$_2$ |
| benzyl | OH | OH | 4 | NO$_2$ |
| benzyl | OH | OMe | 4 | NO$_2$ |
| 2-phenethyl | OH | OH | 4 | NO$_2$ |
| 2-phenethyl | OH | OMe | 4 | NO$_2$ |
| cyclopropylmethyl | OH | OH | 4 | CN |
| cyclopropylmethyl | OH | OMe | 4 | CN |
| cyclobutylmethyl | OH | OH | 4 | CN |
| cyclobutylmethyl | OH | OMe | 4 | CN |
| allyl | OH | OH | 4 | CN |
| allyl | OH | OMe | 4 | CN |
| H | OH | OH | 4 | CN |
| H | OH | OMe | 4 | CN |
| Me | OH | OH | 4 | CN |
| Me | OH | OMe | 4 | CN |
| benzyl | OH | OH | 4 | CN |
| benzyl | OH | OMe | 4 | CN |
| 2-phenethyl | OH | OH | 4 | CN |
| 2-phenethyl | OH | OMe | 4 | CN |
| cyclopropylmethyl | OH | OH | 4 | NCS |
| cylopropylmethyl | OH | OMe | 4 | NCS |
| cyclobutylmethyl | OH | OH | 4 | NCS |
| cyclobutylmethyl | OH | OMe | 4 | NCS |
| allyl | OH | OH | 4 | NCS |
| allyl | OH | OMe | 4 | NCS |
| H | OH | OH | 4 | NCS |
| H | OH | OMe | 4 | NCS |
| Me | OH | OH | 4 | NCS |
| Me | OH | OMe | 4 | NCS |
| benzyl | OH | OH | 4 | NCS |
| benzyl | OH | OMe | 4 | NCS |
| 2-phenethyl | OH | OH | 4 | NCS |
| 2-phenethyl | OH | OMe | 4 | NCS |
| cyclopropylmethyl | OH | OH | 4 | COOH |
| cyclopropylmethyl | OH | OMe | 4 | COOH |
| cyclobutylmethyl | OH | OH | 4 | COOH |
| cyclobutylmethyl | OH | OMe | 4 | COOH |
| allyl | OH | OH | 4 | COOH |
| allyl | OH | OMe | 4 | COOH |
| H | OH | OH | 4 | COOH |
| H | OH | OMe | 4 | COOH |
| Me | OH | OH | 4 | COOH |
| Me | OH | OMe | 4 | COOH |
| benzyl | OH | OH | 4 | COOH |
| benzyl | OH | OMe | 4 | COOH |
| 2-phenethyl | OH | OH | 4 | COOH |
| 2-phenethyl | OH | OMe | 4 | COOH |
| cyclopropylmethyl | OH | OH | 4 | COOMe |
| cyclopropylmethyl | OH | OMe | 4 | COOMe |
| cyclobutylmethyl | OH | OH | 4 | COOMe |
| cyclobutylmethyl | OH | OMe | 4 | COOMe |
| allyl | OH | OH | 4 | COOMe |
| allyl | OH | OMe | 4 | COOMe |
| H | OH | OH | 4 | COOMe |
| H | OH | OMe | 4 | COOMe |
| Me | OH | OH | 4 | COOMe |
| Me | OH | OMe | 4 | COOMe |
| benzyl | OH | OH | 4 | COOMe |
| benzyl | OH | OMe | 4 | COOMe |
| 2-phenethyl | OH | OH | 4 | COOMe |
| 2-phenethyl | OH | OMe | 4 | COOMe |
| cyclopropylmethyl | OH | OH | 4 | COOEt |
| cyclopropylmethyl | OH | OMe | 4 | COOEt |
| cyclobutylmethyl | OH | OH | 4 | COOEt |
| cyclobutylmethyl | OH | OMe | 4 | COOEt |
| allyl | OH | OH | 4 | COOEt |
| allyl | OH | OMe | 4 | COOEt |
| H | OH | OH | 4 | COOEt |
| H | OH | OMe | 4 | COOEt |
| Me | OH | OH | 4 | COOEt |
| Me | OH | OMe | 4 | COOEt |
| benzyl | OH | OH | 4 | COOEt |
| benzyl | OH | OMe | 4 | COOEt |
| 2-phenethyl | OH | OH | 4 | COOEt |
| 2-phenethyl | OH | OMe | 4 | COOEt |
| cyclopropylmethyl | OH | OH | 4 | NHCHO |
| cyclopropylmethyl | OH | OMe | 4 | NHCHO |
| cyclobutylmethyl | OH | OH | 4 | NHCHO |
| cyclobutylmethyl | OH | OMe | 4 | NHCHO |
| allyl | OH | OH | 4 | NHCHO |
| allyl | OH | OMe | 4 | NHCHO |
| H | OH | OH | 4 | NHCHO |
| H | OH | OMe | 4 | NHCHO |
| Me | OH | OH | 4 | NHCHO |
| Me | OH | OMe | 4 | NHCHO |
| benzyl | OH | OH | 4 | NHCHO |
| benzyl | OH | OMe | 4 | NHCHO |
| 2-phenethyl | OH | OH | 4 | NHCHO |
| 2-phenethyl | OH | OMe | 4 | NHCHO |
| cyclopropylmethyl | OH | OH | 4 | NHCO—Me |
| cyclopropylmethyl | OH | OMe | 4 | NHCO—Me |
| cyclobutylmethyl | OH | OH | 4 | NHCO—Me |
| cyclobutylmethyl | OH | OMe | 4 | NHCO—Me |
| allyl | OH | OH | 4 | NHCO—Me |
| allyl | OH | OMe | 4 | NHCO—Me |
| H | OH | OH | 4 | NHCO—Me |
| H | OH | OMe | 4 | NHCO—Me |
| Me | OH | OH | 4 | NHCO—Me |
| Me | OH | OMe | 4 | NHCO—Me |
| benzyl | OH | OH | 4 | NHCO—Me |
| benzyl | OH | OMe | 4 | NHCO—Me |
| 2-phenethyl | OH | OH | 4 | NHCO—Me |
| 2-phenethyl | OH | OMe | 4 | NHCO—Me |
| cyclopropylmethyl | OH | OH | 4 | NHCO—Ph |
| cyclopropylmethyl | OH | OMe | 4 | NHCO—Ph |
| cyclobutylmethyl | OH | OH | 4 | NHCO—Ph |
| cyclobutylmethyl | OH | OMe | 4 | NHCO—Ph |
| allyl | OH | OH | 4 | NHCO—Ph |
| allyl | OH | OMe | 4 | NHCO—Ph |
| H | OH | OH | 4 | NHCO—Ph |
| H | OH | OMe | 4 | NHCO—Ph |
| Me | OH | OH | 4 | NHCO—Ph |
| Me | OH | OMe | 4 | NHCO—Ph |
| benzyl | OH | OH | 4 | NHCO—Ph |
| benzyl | OH | OMe | 4 | NHCO—Ph |
| 2-phenethyl | OH | OH | 4 | NHCO—Ph |
| 2-phenethyl | OH | OMe | 4 | NHCO—Ph |
| cyclopropylmethyl | OH | OH | 4 | NHCO—(CH$_2$)$_5$Ph |
| cyclopropylmethyl | OH | OMe | 4 | NHCO—(CH$_2$)$_5$Ph |
| cyclobutylmethyl | OH | OH | 4 | NHCO—(CH$_2$)$_5$Ph |
| cyclobutylmethyl | OH | OMe | 4 | NHCO—(CH$_2$)$_5$Ph |
| allyl | OH | OH | 4 | NHCO—(CH$_2$)$_5$Ph |
| allyl | OH | OMe | 4 | NHCO—(CH$_2$)$_5$Ph |
| H | OH | OH | 4 | NHCO—(CH$_2$)$_5$Ph |
| H | OH | OMe | 4 | NHCO—(CH$_2$)$_5$Ph |
| Me | OH | OH | 4 | NHCO—(CH$_2$)$_5$Ph |
| Me | OH | OMe | 4 | NHCO—(CH$_2$)$_5$Ph |
| benzyl | OH | OH | 4 | NHCO—(CH$_2$)$_5$Ph |
| benzyl | OH | OMe | 4 | NHCO—(CH$_2$)$_5$Ph |
| 2-phenethyl | OH | OH | 4 | NHCO—(CH$_2$)$_5$Ph |
| 2-phenethyl | OH | Ome | 4 | NHCO—(CH$_2$)$_5$Ph |
| cyclopropylmethyl | OH | OH | 4 | NHCO-cinnamyl |
| cyclopropylmethyl | OH | OMe | 4 | NHCO-cinnamyl |
| cyclobutylmethyl | OH | OH | 4 | NHCO-cinnamyl |
| cyclobutylmethyl | OH | OMe | 4 | NHCO-cinnamyl |
| allyl | OH | OH | 4 | NHCO-cinnamyl |
| allyl | OH | OMe | 4 | NCHO-cinnamyl |
| H | OH | OH | 4 | NHCO-cinnamyl |
| H | OH | OMe | 4 | NHCO-cinnamyl |
| Me | OH | OH | 4 | NHCO-cinnamyl |
| Me | OH | OMe | 4 | NHCO-cinnamyl |
| benzyl | OH | OH | 4 | NHCO-cinnamyl |
| benzyl | OH | OMe | 4 | NHCO-cinnamyl |
| 2-phenethyl | OH | OH | 4 | NHCO-cinnamyl |
| 2-phenethyl | OH | OMe | 4 | NHCO-cinnamyl |
| cyclopropylmethyl | OH | OH | 4 | NHCO—(CF$_3$-cinnamyl) |
| cyclopropylmethyl | OH | OME | 4 | NHCO—(CF$_3$-cinnamyl) |

-continued

| R¹ | | | | |
|---|---|---|---|---|
| cyclobutylmethyl | OH | OH | 4 | NHCO—(CF₃-cinnamyl) |
| cyclobutylmethyl | OH | OMe | 4 | NHCO—(CF₃-cinnamyl) |
| allyl | OH | OH | 4 | NHCO—(CF₃-cinnamyl) |
| allyl | OH | OMe | 4 | NHCO—(CF₃-cinnamyl) |
| H | OH | OH | 4 | NHCO—(CF₃-cinnamyl) |
| H | OH | OMe | 4 | NHCO—(CF₃-cinnamyl) |
| Me | OH | OH | 4 | NHCO—(CF₃-cinnamyl) |
| Me | OH | OMe | 4 | NHCO—(CF₃-cinnamyl) |
| benzyl | OH | OH | 4 | NHCO—(CF₃-cinnamyl) |
| benzyl | OH | OMe | 4 | NHCO—(CF₃-cinnamyl) |
| 2-phenethyl | OH | OH | 4 | NHCO—(CF₃-cinnamyl) |
| 2-phenethyl | OH | OMe | 4 | NHCO—(CF₃-cinnamyl) |
| cyclopropylmethyl | OH | OH | 4 | NHCO-pyridyl |
| cyclopropylmethyl | OH | OMe | 4 | NHCO-pyridyl |
| cyclobutylmethyl | OH | OH | 4 | NHCO-pyridyl |
| cyclobutylmethyl | OH | OMe | 4 | NHCO-pyridyl |
| allyl | OH | OH | 4 | NHCO-pyridyl |
| allyl | OH | OMe | 4 | NHCO-pyridyl |
| H | OH | OH | 4 | NHCO-pyridyl |
| H | OH | OMe | 4 | NHCO-pyridyl |
| Me | OH | OH | 4 | NHCO-pyridyl |
| Me | OH | OMe | 4 | NHCO-pyridyl |
| benzyl | OH | OH | 4 | NHCO-pyridyl |
| benzyl | OH | OMe | 4 | NHCO-pyridyl |
| 2-phenethyl | OH | OH | 4 | NHCO-pyridyl |
| 2-phenethyl | OH | OMe | 4 | NHCO-pyridyl |
| cyclopropylmethyl | OH | OH | 4 | NHCO—NHPh |
| cyclopropylmethyl | OH | OMe | 4 | NHCO—NHPh |
| cyclobutylmethyl | OH | OH | 4 | NHCO—NHPh |
| cyclobutylmethyl | OH | OMe | 4 | NHCO—NHPh |
| allyl | OH | OH | 4 | NHCO—NHPh |
| allyl | OH | OMe | 4 | NHCO—NHPh |
| H | OH | OH | 4 | NHCO—NHPh |
| H | OH | OMe | 4 | NHCO—NHPh |
| Me | OH | OH | 4 | NHCO—NHPh |
| Me | OH | OMe | 4 | NHCO—NHPh |
| benzyl | OH | OH | 4 | NHCO—NHPh |
| benzyl | OH | OMe | 4 | NHCO—NHPh |
| 2-phenethyl | OH | OH | 4 | NHCO—NHPh |
| 2-phenethyl | OH | OMe | 4 | NHCO—NHPh |
| cyclopropylmethyl | OH | OH | 4 | NHCS—NHPh |
| cyclopropylmethyl | OH | OMe | 4 | NHCS—NHPh |
| cyclobutylmethyl | OH | OH | 4 | NHCS—NHPh |
| cyclobutylmethyl | OH | OMe | 4 | NHCS—NHPh |
| allyl | OH | OH | 4 | NHCS—NHPh |
| allyl | OH | OMe | 4 | NHCS—NHPh |
| H | OH | OH | 4 | NHCS—NHPh |
| H | OH | OMe | 4 | NHCS—NHPh |
| Me | OH | OH | 4 | NHCS—NHPh |
| Me | OH | OMe | 4 | NHCS—NHPh |
| benzyl | OH | OH | 4 | NHCS—NHPh |
| benzyl | OH | OMe | 4 | NHCS—NHPh |
| 2-phenethyl | OH | OH | 4 | NHCS—NHPh |
| 2-phenethyl | OH | OMe | 4 | NHCS—NHPh |
| cyclopropylmethyl | OH | OH | 4 | NHCS—NHCH₂Ph |
| cyclopropylmethyl | OH | OMe | 4 | NHCS—NHCH₂Ph |
| cyclobutylmethyl | OH | OH | 4 | NHCS—NHCH₂Ph |
| cyclobutylmethyl | OH | OMe | 4 | NHCS—NHCH₂Ph |
| allyl | OH | OH | 4 | NHCS—NHCH₂Ph |
| allyl | OH | OMe | 4 | NHCS—NHCH₂Ph |
| H | OH | OH | 4 | NHCS—NHCH₂Ph |
| H | OH | OMe | 4 | NHCS—NHCH₂Ph |
| Me | OH | OH | 4 | NHCS—NHCH₂Ph |
| Me | OH | OMe | 4 | NHCS—NHCH₂Ph |
| benzyl | OH | OH | 4 | NHCS—NHCH₂Ph |
| benzyl | OH | OMe | 4 | NHCS—NHCH₂Ph |
| 2-phenethyl | OH | OH | 4 | NHCS—NHCH₂Ph |
| 2-phenethyl | OH | OMe | 4 | NHCS—NHCH₂Ph |

-continued

| R¹ | R² | R³ | R⁴ |
|---|---|---|---|
| cyclopropylmethyl | OH | OH | H |
| cyclopropylmethyl | OH | OMe | H |
| cyclobutylmethyl | OH | OH | H |
| cyclobutylmethyl | OH | OMe | H |
| allyl | OH | OH | H |
| allyl | OH | OMe | H |
| H | OH | OH | H |
| H | OH | OMe | H |
| Me | OH | OH | H |
| Me | OH | OMe | OH |
| benzyl | OH | OH | H |
| benzyl | OH | OMe | OH |
| 2-phenethyl | OH | OH | H |
| 2-phenethyl | OH | OMe | H |
| cyclopropylmethyl | OH | OH | Me |
| cyclopropylmethyl | OH | OMe | Me |
| cyclobutylmethyl | OH | OH | Me |
| cyclobutylmethyl | OH | OMe | Me |
| allyl | OH | OH | Me |
| allyl | OH | OMe | Me |
| H | OH | OH | Me |
| H | OH | OMe | ME |
| Me | OH | OH | ME |
| ME | OH | OMe | Me |
| benzyl | OH | OH | Me |
| benzyl | OH | OMe | Me |
| 2-phenethyl | OH | OH | Me |
| 2-phenethyl | OH | OMe | Me |
| cyclopropylmethyl | OH | OH | Et |
| cyclopropylmethyl | OH | OMe | Et |
| cyclobutylmethyl | OH | OH | Et |
| cyclobutylmethyl | OH | OMe | Et |
| allyl | OH | OH | Et |
| allyl | OH | OMe | Et |
| H | OH | OH | Et |
| H | OH | OMe | Et |
| Me | OH | OH | Et |
| Me | OH | OMe | Et |
| benzyl | OH | OH | Et |
| benzyl | OH | OMe | Et |
| 2-phenethyl | OH | OMe | Et |
| cyclopropylmethyl | OH | OH | Bu |
| cyclopropylmethyl | OH | OMe | Bu |
| cyclobutylmethyl | OH | OH | Bu |
| cyclobutylmethyl | OH | OMe | Bu |
| allyl | OH | OH | Bu |
| allyl | OH | OMe | Bu |
| H | OH | OH | Bu |
| H | OH | OMe | Bu |
| Me | OH | OH | Bu |
| Me | OH | OMe | Bu |
| benzyl | OH | OH | Bu |
| benzyl | OH | OMe | Bu |
| 2-phenethyl | OH | OH | Bu |
| 2-phenethyl | OH | OMe | Bu |
| cyclopropylmethyl | OH | OH | PhCH₂ |
| cyclopropylmethyl | OH | OMe | PhCH₂ |
| cyclobutylmethyl | OH | OH | PhCH₂ |
| cyclobutylmethyl | OH | OMe | PhCH₂ |
| allyl | OH | OH | PhCH₂ |
| allyl | OH | OMe | PhCH₂ |
| H | OH | OH | PhCH₂ |

-continued

| | | | |
|---|---|---|---|
| H | OH | OMe | PhCH$_2$ |
| Me | OH | OH | PhCH$_2$ |
| Me | OH | OMe | PhCH$_2$ |
| benzyl | OH | OH | PhCH$_2$ |
| benzyl | OH | OMe | PhCH$_2$ |
| 2-phenethyl | OH | OH | PhCH$_2$ |
| 2-phenethyl | OH | OMe | PhCH$_2$ |
| cyclopropylmethyl | OH | OH | (F—C$_6$H$_4$)CH$_2$ |
| cyclopropylmethyl | OH | OMe | (F—C$_6$H$_4$)CH$_2$ |
| cyclobutylmethyl | OH | OH | (F—C$_6$H$_4$)CH$_2$ |
| cyclobutylmethyl | OH | OMe | (F—C$_6$H$_4$)CH$_2$ |
| allyl | OH | OH | (F—C$_6$H$_4$)CH$_2$ |
| allyl | OH | OMe | (F—C$_6$H$_4$)CH$_2$ |
| H | OH | OH | (F—C$_6$H$_4$)CH$_2$ |
| H | OH | OMe | (F—C$_6$H$_4$)CH$_2$ |
| Me | OH | OH | (F—C$_6$H$_4$)CH$_2$ |
| Me | OH | OMe | (F—C$_6$H$_4$)CH$_2$ |
| benzyl | OH | OH | (F—C$_6$H$_4$)CH$_2$ |
| benzyl | OH | OMe | (F—C$_6$H$_4$)CH$_2$ |
| 2-phenethyl | OH | OH | (F—C$_6$H$_4$)CH$_2$ |
| 2-phenethyl | OH | OMe | (F—C$_6$H$_4$)CH$_2$ |
| cyclopropylmethyl | OH | O | (Br—C$_6$H$_4$)CH$_2$ |
| cyclopropylmethyl | OH | OMe | (Br—C$_6$H$_4$)CH$_2$ |
| cyclobutylmethyl | OH | OH | (Br—C$_6$H$_4$)CH$_2$ |
| cyclobutylmethyl | OH | OMe | (Br—C$_6$H$_4$)CH$_2$ |
| allyl | OH | OH | (Br—C$_6$H$_4$)CH$_2$ |
| allyl | OH | OMe | (Br—C$_9$H$_4$)CH$_2$ |
| H | OH | OH | (Br—C$_9$H$_4$)CH$_2$ |
| H | OH | OMe | (Br—C$_9$H$_4$)CH$_2$ |
| Me | OH | OH | (Br—C$_9$H$_4$)CH$_2$ |
| Me | OH | OMe | (Br—C$_9$H$_4$)CH$_2$ |
| benzyl | OH | OH | (Br—C$_9$H$_4$)CH$_2$ |
| benzyl | OH | OMe | (Br—C$_9$H$_4$)CH$_2$ |
| 2-phenethyl | OH | OH | (Br—C$_9$H$_4$)CH$_2$ |
| 2-phenethyl | OH | OMe | (Br—C$_9$H$_4$)CH$_2$ |
| cyclopropylmethyl | OH | OH | (Me—C$_9$H$_4$)CH$_2$ |
| cyclopropyomethyl | OH | OMe | (Me—C$_9$H$_4$)CH$_2$ |
| cyclobutylmethyl | OH | OH | (Me—C$_9$H$_4$)CH$_2$ |
| cyclobutylmethyl | OH | OMe | (Me—C$_9$H$_4$)CH$_2$ |
| allyl | OH | OH | (Me—C$_9$H$_4$)CH$_2$ |
| allyl | OH | OMe | (Me—C$_9$H$_4$)CH$_2$ |
| H | OH | OH | (Me—C$_9$H$_4$)CH$_2$ |
| H | OH | OMe | (Me—C$_9$H$_4$)CH$_2$ |
| Me | OH | OH | (Me—C$_9$H$_4$)CH$_2$ |
| Me | OH | OMe | (Me—C$_9$H$_4$)CH$_2$ |
| benzyl | OH | OH | (Me—C$_9$H$_4$)CH$_2$ |
| benzyl | OH | OMe | (Me—C$_9$H$_4$)CH$_2$ |
| 2-phenethyl | OH | OH | (Me—C$_9$H$_4$)CH$_2$ |
| 2-phenethyl | OH | OMe | (Me—C$_9$H$_4$)CH$_2$ |
| cyclopropylmethyl | OH | OH | (MeO—C$_6$H$_4$)CH$_2$ |
| cyclopropylmethyl | OH | OMe | (MeO—C$_6$H$_4$)CH$_2$ |
| cyclobutylmethyl | OH | OH | (MeO—C$_6$H$_4$)CH$_2$ |
| cyclobutylmethyl | OH | OMe | (MeO—C$_6$H$_4$)CH$_2$ |
| allyl | OH | OH | (MeO—C$_6$H$_4$)CH$_2$ |
| allyl | OH | OMe | (MeO—C$_6$H$_4$)CH$_2$ |
| H | OH | OH | (MeO—C$_6$H$_4$)CH$_2$ |
| H | OH | OMe | (MeO—C$_6$H$_4$)CH$_2$ |
| Me | OH | OH | (MeO—C$_6$H$_4$)CH$_2$ |
| Me | OH | OMe | (MeO—C$_6$H$_4$)CH$_2$ |
| benzyl | OH | OH | (MeO—C$_6$H$_4$)CH$_2$ |
| benzyl | OH | OMe | (MeO—C$_6$H$_4$)CH$_2$ |
| 2-phenethyl | OH | OH | (MeO—C$_6$H$_4$)CH$_2$ |
| 2-phenethyl | OH | OMe | (MeO—C$_6$H$_4$)CH$_2$ |
| cyclopropylmethyl | OH | OH | (O$_2$N—C$_6$H$_4$)CH$_2$ |
| cyclopropylmethyl | OH | OMe | (O$_2$N—C$_6$H$_4$)CH$_2$ |
| cyclobutylmethyl | OH | OH | (O$_2$N—C$_6$H$_4$)CH$_2$ |
| cyclobutylmethyl | OH | OMe | (O$_2$N—C$_6$H$_4$)CH$_2$ |
| allyl | OH | OH | (O$_2$N—C$_6$H$_4$)CH$_2$ |
| allyl | OH | OMe | (O$_2$N—C$_6$H$_4$)CH$_2$ |
| H | OH | OH | (O$_2$N—C$_6$H$_4$)CH$_2$ |
| H | OH | OMe | (O$_2$N—C$_6$H$_4$)CH$_2$ |
| Me | OH | OH | (O$_2$N—C$_6$H$_4$)CH$_2$ |
| Me | OH | OMe | (O$_2$N—C$_9$H$_4$)CH$_2$ |
| benzyl | OH | OH | (O$_2$N—C$_6$H$_3$)CH$_2$ |
| benzyl | OH | OMe | (O$_2$N—C$_6$H$_4$)CH$_2$ |
| 2-phenethyl | OH | OH | (O$_2$N—C$_6$H$_4$)CH$_2$ |
| 2-phenthethyl | OH | OMe | (O$_2$N—C$_6$H$_4$)CH$_2$ |
| cyclopropylmethyl | OH | OH | (F$_3$C—C$_6$H$_4$)CH$_2$ |
| cyclopropylmethyl | OH | OMe | (F$_3$C—C$_6$H$_4$)CH$_2$ |
| cyclobutylmethyl | OH | OH | (F$_3$C—C$_9$H$_4$)CH$_2$ |
| cyclobutylmethyl | OH | OMe | (F$_3$C—C$_6$H$_4$)CH$_2$ |
| allyl | OH | OH | (F$_3$C—C$_9$H$_4$)CH$_2$ |
| allyl | OH | OMe | (F$_3$C—C$_9$H$_4$)CH$_2$ |
| H | OH | OH | (F$_3$C—C$_9$H$_4$)CH$_2$ |
| H | OH | OMe | (F$_3$C—C$_9$H$_4$)CH$_2$ |
| Me | OH | OH | (F$_3$C—C$_6$H$_4$)CH$_2$ |
| Me | OH | OMe | (F$_3$C—C$_6$H$_4$)CH$_2$ |
| benzyl | OH | OH | (F$_3$C—C$_6$H$_4$)CH$_2$ |
| benzyl | OH | OMe | (F$_3$C—C$_9$H$_4$)CH$_2$ |
| 2-phenethyl | OH | OH | (F$_3$C—C$_9$H$_4$)CH$_2$ |
| 2-phenethyl | OH | OMe | (F$_3$C—C$_9$H$_4$)CH$_2$ |
| cyclopropylmethyl | OH | OH | Ph(CH$_2$)$_2$ |
| cyclopropylmethyl | OH | OMe | Ph(CH$_2$)$_2$ |
| cyclobutylmethyl | OH | OH | Ph(CH$_2$)$_2$ |
| cyclobutylmethyl | OH | OMe | Ph(CH$_2$)$_2$ |
| allyl | OH | OH | Ph(CH$_2$)$_2$ |
| allyl | OH | OMe | Ph(CH$_2$)$_2$ |
| H | OH | OH | Ph(CH$_2$)$_2$ |
| H | OH | OMe | Ph(CH$_2$)$_2$ |
| Me | OH | OH | Ph(CH$_2$)$_2$ |
| Me | OH | OMe | Ph(CH$_2$)$_2$ |
| benzyl | OH | OH | Ph(CH$_2$)$_2$ |
| benzyl | OH | OMe | Ph(CH$_2$)$_2$ |
| 2-phenethyl | OH | OH | Ph(CH$_2$)$_2$ |
| 2-phenethyl | OH | OMe | Ph(CH$_2$)$_2$ |
| cyclopropylmethyl | OH | OH | Ph(CH$_2$)$_3$ |
| cyclopropylmethyl | OH | OMe | Ph(CH$_2$)$_3$ |
| cyclobutylmethyl | OH | OH | Ph(CH$_2$)$_3$ |
| cyclobutylmethyl | OH | OMe | Ph(CH$_2$)$_3$ |
| allyl | OH | OH | Ph(CH$_2$)$_3$ |
| allyl | OH | OMe | Ph(CH$_2$)$_3$ |
| H | OH | OH | Ph(CH$_2$)$_3$ |
| H | OH | OMe | Ph(CH$_2$)$_3$ |
| Me | OH | OH | Ph(CH$_2$)$_3$ |
| Me | OH | OMe | Ph(CH$_2$)$_3$ |
| benzyl | OH | OH | Ph(CH$_2$)$_3$ |
| benzyl | OH | OMe | Ph(CH$_2$)$_3$ |
| 2-phenethyl | OH | OH | Ph(CH$_2$)$_3$ |
| 2-phenethyl | OH | OMe | Ph(CH$_2$)$_3$ |
| cyclopropylmethyl | OH | OH | MeCO |
| cyclopropylmethyl | OH | OMe | MeCO |
| cyclobutylmethyl | OH | OH | MeCO |
| cyclobutylmethyl | OH | OMe | MeCO |
| allyl | OH | OH | MeCO |
| allyl | OH | OMe | MeCO |
| H | OH | OH | MeCO |
| H | OH | OMe | MeCO |
| Me | OH | OH | MeCO |
| Me | OH | OMe | MeCO |
| benzyl | OH | OH | MeCO |
| benzyl | OH | OMe | MeCO |
| 2-phenethyl | OH | OH | MeCO |
| 2-phenethyl | OH | OMe | MeCO |
| cyclopropylmethyl | OH | OH | PhCO |
| cyclopropylmethyl | OH | OMe | PhCO |
| cyclobutylmethyl | OH | OH | PhCO |
| cyclobutylmethyl | OH | OMe | PhCO |
| allyl | OH | OH | PhCO |
| allyl | OH | OMe | PhCO |
| H | OH | OH | PhCO |
| H | OH | OMe | PhCO |
| Me | OH | OH | PhCO |
| Me | OH | OMe | PhCO |
| benzyl | OH | OH | PhCO |
| benzyl | OH | OMe | PhCO |
| 2-phenethyl | OH | OH | PhCO |
| 2-phenethyl | OH | OMe | PhCO |
| cyclopropylmethyl | OH | OH | MeSO$_2$ |
| cyclopropylmethyl | OH | OMe | MeSO$_2$ |
| cyclobutylmethyl | OH | OH | MeSO$_2$ |
| cyclobutylmethyl | OH | OMe | MeSO$_2$ |
| allyl | OH | OH | MeSO$_2$ |
| allyl | OH | OMe | MeSO$_2$ |
| H | OH | OH | MeSO$_2$ |
| H | OH | OMe | MeSO$_2$ |
| Me | OH | OH | MeSO$_2$ |
| Me | OH | OMe | MeSO$_2$ |
| benzyl | OH | OH | MeSO$_2$ |

-continued

| | | | |
|---|---|---|---|
| benzyl | OH | OMe | MeSO$_2$ |
| 2-phenethyl | OH | OH | MeSO$_2$ |
| 2-phenethyl | OH | OMe | MeSO$_2$ |
| cyclopropylmethyl | OH | OH | PhSO$_2$ |
| cyclopropylmethyl | OH | OMe | PhSO$_2$ |
| cyclobutylmethyl | OH | OH | PhSO$_2$ |
| cyclobutylmethyl | OH | OMe | PhSO$_2$ |
| allyl | OH | OH | PhSO$_2$ |
| allyl | OH | OMe | PhSO$_2$ |
| H | OH | OH | PhSO$_2$ |
| H | OH | OMe | PhSO$_2$ |
| Me | OH | OH | PhSO$_2$ |
| Me | OH | OMe | PhSO$_2$ |
| benzyl | OH | OH | PhSO$_2$ |
| benzyl | OH | OMe | PhSO$_2$ |
| 2-phenethyl | OH | OH | PhSO$_2$ |
| 2-phenethyl | OH | OMe | PhSO$_2$ |
| cyclopropylmethyl | OH | OH | (Me—C$_6$H$_4$)SO$_2$ |
| cyclopropylmethyl | OH | OMe | (Me—C$_6$H$_4$)SO$_2$ |
| cyclobutylmethyl | OH | OH | (Me—C$_6$H$_4$)SO$_2$ |
| cyclobutylmethyl | OH | OMe | (Me—C$_6$H$_4$)SO$_2$ |
| allyl | OH | OH | (Me—C$_6$H$_4$)SO$_2$ |
| allyl | OH | OMe | (Me—C$_6$H$_4$)SO$_2$ |
| H | OH | OH | (Me—C$_6$H$_4$)SO$_2$ |
| H | OH | OMe | (Me—C$_6$H$_4$)SO$_2$ |
| Me | OH | OH | (Me—C$_6$H$_4$)SO$_2$ |
| Me | OH | OMe | (Me—C$_6$H$_4$)SO$_2$ |
| benzyl | OH | OH | (Me—C$_6$H$_4$)SO$_2$ |
| benzyl | OH | OMe | (Me—C$_6$H$_4$)SO$_2$ |
| 2-phenethyl | OH | OH | (Me—C$_6$H$_4$)SO$_2$ |
| 2-phenethyl | OH | OMe | (Me—C$_6$H$_4$)SO$_2$ |
| cyclopropylmethyl | OH | OH | PhCH$_2$SO$_2$ |
| cyclopropylmethyl | OH | OMe | PhCH$_2$SO$_2$ |
| cyclobutylmethyl | OH | OH | PhCH$_2$SO$_2$ |
| cyclobutylmethyl | OH | OMe | PhCH$_2$SO$_2$ |
| allyl | OH | OH | PhCH$_2$SO$_2$ |
| allyl | OH | OMe | PhCH$_2$SO$_2$ |
| H | OH | OH | PhCH$_2$SO$_2$ |
| H | OH | OMe | PhCH$_2$SO$_2$ |
| Me | OH | OH | PhCH$_2$SO$_2$ |
| Me | OH | OMe | PhCH$_2$SO$_2$ |
| benzyl | OH | OH | PhCH$_2$SO$_2$ |
| benzyl | OH | OMe | PhCH$_2$SO$_2$ |
| 2-phenethyl | OH | OH | PhCH$_2$SO$_2$ |
| 2-phenethyl | OH | OMe | PhCH$_2$SO$_2$ |

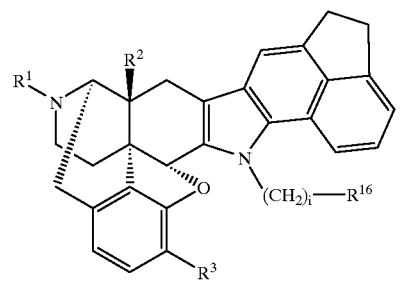

| R$^1$ | R$^2$ | R$^3$ | i | R$^{16}$ |
|---|---|---|---|---|
| cyclopropylmethyl | OH | OH | 2 | OH |
| cyclopropylmethyl | OH | OMe | 2 | OH |
| cyclobutylmethyl | OH | OH | 2 | OH |
| cyclobutylmethyl | OH | OMe | 2 | OH |
| allyl | OH | OH | 2 | OH |
| allyl | OH | OMe | 2 | OH |
| H | OH | OH | 2 | OH |
| H | OMe | OH | 2 | OH |
| Me | OH | OH | 2 | OH |
| Me | OH | OMe | 2 | OH |
| benzyl | OH | OH | 2 | OH |
| benzyl | OH | OMe | 2 | OH |
| 2-phenethyl | OH | OH | 2 | OH |
| 2-phenethyl | OH | OMe | 2 | OH |
| cyclopropylmethyl | OH | OH | 2 | OMe |
| cyclopropylmethyl | OH | OMe | 2 | OMe |

-continued

| | | | | |
|---|---|---|---|---|
| cyclobutylmethyl | OH | OH | 2 | OMe |
| cyclobutylmethyl | OH | OMe | 2 | OMe |
| allyl | OH | OH | 2 | OMe |
| allyl | OH | OMe | 2 | OMe |
| H | OH | OH | 2 | OMe |
| H | OH | OMe | 2 | OMe |
| Me | OH | OH | 2 | OMe |
| Me | OH | OMe | 2 | OMe |
| benzyl | OH | OH | 2 | OMe |
| benzyl | OH | OMe | 2 | OMe |
| 2-phenethyl | OH | OH | 2 | OMe |
| 2-phenethyl | OH | OMe | 2 | OMe |
| cyclopropylmethyl | OH | OH | 2 | OEt |
| cyclopropylmethyl | OH | OMe | 2 | OEt |
| cyclobutylmethyl | OH | OH | 2 | OEt |
| cyclobutylmethyl | OH | OMe | 2 | OEt |
| allyl | OH | OH | 2 | OEt |
| allyl | OH | OMe | 2 | OEt |
| H | OH | OH | 2 | OEt |
| H | OH | OMe | 2 | OEt |
| Me | OH | OH | 2 | OEt |
| Me | OH | OME | 2 | OEt |
| benzyl | OH | OH | 2 | OEt |
| benzyl | OH | OMe | 2 | OEt |
| 2-phenethyl | OH | OH | 2 | OEt |
| 2-phenethyl | OH | OMe | 2 | OEt |
| cyclopropylmethyl | OH | OH | 2 | NH$_2$ |
| cyclopropylmethyl | OH | OMe | 2 | NH$_2$ |
| cyclobutylmethyl | OH | OH | 2 | NH$_2$ |
| cyclobutylmethyl | OH | OMe | 2 | NH$_2$ |
| allyl | OH | OH | 2 | NH$_2$ |
| allyl | OH | OMe | 2 | NH$_2$ |
| H | OH | OH | 2 | NH$_2$ |
| H | OH | OMe | 2 | NH$_2$ |
| Me | OH | OH | 2 | NH$_2$ |
| Me | OH | OMe | 2 | NH$_2$ |
| benzyl | OH | OH | 2 | NH$_2$ |
| benzyl | OH | OMe | 2 | NH$_2$ |
| 2-phenethyl | OH | OH | 2 | NH$_2$ |
| 2-phenethyl | OH | OMe | 2 | NH$_2$ |
| cyclopropylmethyl | OH | OH | 2 | NO$_2$ |
| cyclopropylmethyl | OH | OMe | 2 | NO$_2$ |
| cyclobutylmethyl | OH | OH | 2 | NO$_2$ |
| cyclobutylmethyl | OH | OMe | 2 | NO$_2$ |
| allyl | OH | OH | 2 | NO$_2$ |
| allyl | OH | OMe | 2 | NO$_2$ |
| H | OH | OH | 2 | NO$_2$ |
| H | OH | OMe | 2 | NO$_2$ |
| Me | OH | OH | 2 | NO$_2$ |
| Me | OH | OMe | 2 | NO$_2$ |
| benzyl | OH | OH | 2 | NO$_2$ |
| benzyl | OH | OMe | 2 | NO$_2$ |
| 2-phenethyl | OH | OH | 2 | NO$_2$ |
| 2-phenethyl | OH | OMe | 2 | NO$_2$ |
| cyclopropylmethyl | OH | OH | 2 | CN |
| cyclopropylmethyl | OH | OMe | 2 | CN |
| cyclobutylmethyl | OH | OH | 2 | CN |
| cyclobutylmethyl | OH | OMe | 2 | CN |
| allyl | OH | OH | 2 | CN |
| allyl | OH | OMe | 2 | CN |
| H | OH | OH | 2 | CN |
| H | OH | OMe | 2 | CN |
| Me | OH | OH | 2 | CN |
| Me | OH | OMe | 2 | CN |
| benzyl | OH | OH | 2 | CN |
| benzyl | OH | OMe | 2 | CN |
| 2-phenethyl | OH | OH | 2 | CN |
| 2-phenethyl | OH | OMe | 2 | CN |
| cyclopropylmethyl | OH | OH | 2 | NCS |
| cyclopropylmethyl | OH | OMe | 2 | NCS |
| cyclobutylmethyl | OH | OH | 2 | NCS |
| cyclobutylmethyl | OH | OMe | 2 | NCS |
| allyl | OH | OH | 2 | NCS |
| allyl | OH | OMe | 2 | NCS |
| H | OH | OH | 2 | NCS |
| H | OH | OME | 2 | NCS |
| Me | OH | OH | 2 | NCS |
| Me3 | OH | OMe | 2 | NCS |
| benzyl | OH | OH | 2 | NCS |

| | | | | |
|---|---|---|---|---|
| benzyl | OH | OMe | 2 | NCS |
| 2-phenethyl | OH | OH | 2 | NCS |
| 2-phenethyl | OH | OMe | 2 | NCS |
| cyclopropylmethyl | OH | OH | 2 | COOH |
| cyclopropylmethyl | OH | OMe | 2 | COOH |
| cyclobutylmethyl | OH | OH | 2 | COOH |
| cyclobutylmethyl | OH | OMe | 2 | COOH |
| allyl | OH | OH | 2 | COOH |
| allyl | OH | OMe | 2 | COOH |
| H | OH | OH | 2 | COOH |
| H | OH | OMe | 2 | COOH |
| Me | OH | OH | 2 | COOH |
| Me | OH | OMe | 2 | COOH |
| benzyl | OH | OH | 2 | COOH |
| benzyl | OH | OMe | 2 | COOH |
| 2-phenethyl | OH | OH | 2 | COOH |
| 2-phenethyl | OH | OMe | 2 | COOH |
| cyclopropylmethyl | OH | OH | 2 | COOMe |
| cyclopropylmethyl | OH | OMe | 2 | COOMe |
| cyclobutylmethyl | OH | OH | 2 | COOMe |
| cyclobutylmethyl | OH | OMe | 2 | COOMe |
| allyl | OH | OH | 2 | COOMe |
| allyl | OH | OMe | 2 | COOMe |
| H | OH | OH | 2 | COOMe |
| H | OH | OMe | 2 | COOMe |
| Me | OH | OH | 2 | COOMe |
| Me | OH | OMe | 2 | COOMe |
| benzyl | OH | OH | 2 | COOMe |
| benzyl | OH | OMe | 2 | COOMe |
| 2-phenethyl | OH | OH | 2 | COOMe |
| 2-phenethyl | OH | OMe | 2 | COOMe |
| cyclopropylmethyl | OH | OH | 2 | COOEt |
| cyclopropylmethyl | OH | OMe | 2 | COOEt |
| cyclobutylmethyl | OH | OH | 2 | COOEt |
| cyclobutylmethyl | OH | OMe | 2 | COOEt |
| allyl | OH | OH | 2 | COOEt |
| allyl | OH | OMe | 2 | COOEt |
| H | OH | OH | 2 | COOEt |
| H | OH | OMe | 2 | COOEt |
| Me | OH | OH | 2 | COOEt |
| Me | OH | OMe | 2 | COOEt |
| benzyl | OH | OH | 2 | COOEt |
| benzyl | OH | OMe | 2 | COOEt |
| 2-phenethyl | OH | OH | 2 | COOEt |
| 2-phenethyl | OH | OMe | 2 | COOEt |
| cyclopropylmethyl | OH | OH | 2 | NHCHO |
| cyclopropylmethyl | OH | OMe | 2 | NHCHO |
| cyclobutylmethyl | OH | OH | 2 | NHCHO |
| cyclobutylmethyl | OH | OMe | 2 | NHCHO |
| allyl | OH | OH | 2 | NHCHO |
| allyl | OH | OMe | 2 | NHCHO |
| H | OH | OH | 2 | NHCHO |
| H | OH | OMe | 2 | NHCHO |
| Me | OH | OH | 2 | NHCHO |
| Me | OH | OMe | 2 | NHCHO |
| benzyl | OH | OH | 2 | NHCHO |
| benzyl | OH | OMe | 2 | NHCHO |
| 2-phenethyl | OH | OH | 2 | NHCHO |
| 2-phenethyl | OH | OMe | 2 | NHCHO |
| cyclopropylmethyl | OH | OH | 2 | NHCO—Me |
| cyclopropylmethyl | OH | OMe | 2 | NHCO—Me |
| cyclobutylmethyl | OH | OH | 2 | NHCO—Me |
| cyclobutylmethyl | OH | OMe | 2 | NHCO—Me |
| allyl | OH | OH | 2 | NHCO—Me |
| allyl | OH | OMe | 2 | NHCO—Me |
| H | OH | OH | 2 | NHCO—Me |
| H | OH | OMe | 2 | NHCO—Me |
| Me | OH | OH | 2 | NHCO—Me |
| Me | OH | OMe | 2 | NHCO—Me |
| benzyl | OH | OH | 2 | NHCO—Me |
| benzyl | OH | OMe | 2 | NHCO—Me |
| 2-phenethyl | OH | OH | 2 | NHCO—Me |
| 2-phenethyl | OH | OMe | 2 | NHCO—Me |
| cyclopropylmethyl | OH | OH | 2 | NHCO—Ph |
| cyclopropylmethyl | OH | OMe | 2 | NHCO—Ph |
| cyclobutylmethyl | OH | OH | 2 | NHCO—Ph |
| cyclobutylmethyl | OH | OMe | 2 | NHCO—Ph |
| allyl | OH | OH | 2 | NHCO—Ph |
| allyl | OH | OMe | 2 | NHCO—Ph |
| H | OH | OH | 2 | NHCO—Ph |
| H | OH | OMe | 2 | NHCO—Ph |
| Me | OH | OH | 2 | NHCO—Ph |
| Me | OH | OMe | 2 | NHCO—Ph |
| benzyl | OH | OH | 2 | NHCO—Ph |
| benzyl | OH | OMe | 2 | NHCO—Ph |
| 2-phenethyl | OH | OH | 2 | NHCO—Ph |
| 2-phenethyl | OH | OMe | 2 | NHCO—Ph |
| cyclopropylmethyl | OH | OH | 2 | NHCO—(CH$_2$)$_5$Ph |
| cyclopropylmethyl | OH | OMe | 2 | NHCO—(CH$_2$)$_5$Ph |
| cyclobutylmethyl | OH | OH | 2 | NHCO—(CH$_2$)$_5$Ph |
| cyclobutylmethyl | OH | OMe | 2 | NHCO—(CH$_2$)$_5$Ph |
| allyl | OH | OH | 2 | NHCO—(CH$_2$)$_5$Ph |
| allyl | OH | OMe | 2 | NHCO—(CH$_2$)$_5$Ph |
| H | OH | OH | 2 | NHCO—(CH$_2$)$_5$Ph |
| H | OH | OMe | 2 | NHCO—(CH$_2$)$_5$Ph |
| Me | OH | OH | 2 | NHCO—(CH$_2$)$_5$Ph |
| Me | OH | OMe | 2 | NHCO—(CH$_2$)$_5$Ph |
| benzyl | OH | OH | 2 | NHCO—(CH$_2$)$_5$Ph |
| benzyl | OH | OMe | 2 | NHCO—(CH$_2$)$_5$Ph |
| 2-phenethyl | OH | OH | 2 | NHCO—(CH$_2$)$_5$Ph |
| 2-phenethyl | OH | OMe | 2 | NHCO—(CH$_2$)$_5$Ph |
| cyclopropylmethyl | OH | OH | 2 | NHCO-cinnamyl |
| cyclopropylmethyl | OH | OMe | 2 | NHCO-cinnamyl |
| cyclobutylmethyl | OH | OH | 2 | NHCO-cinnamyl |
| cyclobutylmethyl | OH | OMe | 2 | NHCO-cinnamyl |
| allyl | OH | OH | 2 | NHCO-cinnamyl |
| allyl | OH | OMe | 2 | NHCO-cinnamyl |
| H | OH | OH | 2 | NHCO-cinnamyl |
| H | OH | OMe | 2 | NHCO-cinnamyl |
| Me | OH | OH | 2 | NHCO-cinnamyl |
| Me | OH | OMe | 2 | NHCO-cinnamyl |
| benzyl | OH | OH | 2 | NHCO-cinnamyl |
| benzyl | OH | OMe | 2 | NHCO-cinnamyl |
| 2-phenethyl | OH | OH | 2 | NHCO-cinnamyl |
| 2-phenethyl | OH | OMe | 2 | NHCO-cinnamyl |
| cyclopropylmethyl | OH | OH | 2 | NHCO—(CF$_3$-cinnamyl) |
| cyclopropylmethyl | OH | OMe | 2 | NHCO—(CF$_3$-cinnamyl) |
| cyclobutylmethyl | OH | OH | 2 | NHCO—(CF$_3$-cinnamyl) |
| cyclobutylmethyl | OH | OMe | 2 | NHCO—(CF$_3$-cinnamyl) |
| allyl | OH | OH | 2 | NHCO—(CF$_3$-cinnamyl) |
| allyl | OH | OMe | 2 | NHCO—(CF$_3$-cinnamyl) |
| H | OH | OH | 2 | NHCO—(CF$_3$-cinnamyl) |
| H | OH | OMe | 2 | NHCO—(CF$_3$-cinnamyl) |
| Me | OH | OH | 2 | NHCO—(CF$_3$-cinnamyl) |
| Me | OH | OMe | 2 | NHCO—(CF$_3$-cinnamyl) |
| benzyl | OH | OH | 2 | NHCO—(CF$_3$-cinnamyl) |
| benzyl | OH | OMe | 2 | NHCO—(CF$_3$-cinnamyl) |
| 2-phenethyl | OH | OH | 2 | NHCO—(CF$_3$-cinnamyl) |
| 2-phenethyl | OH | OMe | 2 | NHCO—(CF$_3$-cinnamyl) |
| cyclopropylmethyl | OH | OH | 2 | NHCO-pyridyl |
| cyclopropylmethyl | OH | OMe | 2 | NHCO-pyridyl |
| cyclobutylmethyl | OH | OH | 2 | NHCO-pyridyl |
| cyclobutylmethyl | OH | OMe | 2 | NHCO-pyridyl |
| allyl | OH | OH | 2 | NHCO-pyridyl |
| allyl | OH | OMe | 2 | NHCO-pyridyl |
| H | OH | OH | 2 | NHCO-pyridyl |
| H | OH | OMe | 2 | NHCO-pyridyl |
| Me | OH | OH | 2 | NHCO-pyridyl |
| Me | OH | OMe | 2 | NHCO-pyridyl |
| benzyl | OH | OH | 2 | NHCO-pyridyl |
| benzyl | OH | OMe | 2 | NHCO-pyridyl |
| 2-phenethyl | OH | OH | 2 | NHCO-pyridyl |
| 2-phenethyl | OH | OMe | 2 | NHCO-pyridyl |
| cyclopropylmethyl | OH | OH | 2 | NHCO—NHPh |
| cyclopropylmethyl | OH | OMe | 2 | NHCO—NHPh |
| cyclobutylmethyl | OH | OH | 2 | NHCO—NHPh |
| cyclobutylmethyl | OH | OMe | 2 | NHCO—NHPh |
| allyl | OH | OH | 2 | NHCO—NHPh |
| allyl | OH | OMe | 2 | NHCO—NHPh |
| H | OH | OH | 2 | NHCO—NHPh |
| H | OH | OMe | 2 | NHCO—NHPh |
| Me | OH | OH | 2 | NHCO—NHPh |
| Me | OH | OMe | 2 | NHCO—NHPh |
| benzyl | OH | OH | 2 | NHCO—NHPh |
| benzyl | OH | OMe | 2 | NHCO—NHPh |
| 2-phenethyl | OH | OH | 2 | NHCO—NHPh |
| 2-phenethyl | OH | OMe | 2 | NHCO—NHPh |
| cyclopropylmethyl | OH | OH | 2 | NHCS—NHPh |

-continued

| | | | | |
|---|---|---|---|---|
| cyclopropylmethyl | OH | OMe | 2 | NHCS—NHPh |
| cyclobutylmethyl | OH | OH | 2 | NHCS—NHPh |
| cyclobutylmethyl | OH | OMe | 2 | NHCS—NHPh |
| allyl | OH | OH | 2 | NHCS—NHPh |
| allyl | OH | OMe | 2 | NHCS—NHPh |
| H | OH | OH | 2 | NHCS—NHPh |
| H | OH | OMe | 2 | NHCS—NHPh |
| Me | OH | OH | 2 | NHCS—NHPh |
| Me | OH | OMe | 2 | NHCS—NHPh |
| benzyl | OH | OH | 2 | NHCS—NHPh |
| benzyl | OH | OMe | 2 | NHCS—NHPh |
| 2-phenethyl | OH | OH | 2 | NHCS—NHPh |
| 2-phenethyl | OH | OMe | 2 | NHCS—NHPh |
| cyclopropylmethyl | OH | OH | 2 | NHCS—NHCH$_2$Ph |
| cyclopropylmethyl | OH | OMe | 2 | NHCS—NHCH$_2$Ph |
| cyclobutylmethyl | OH | OH | 2 | NHCS—NHCH$_2$Ph |
| cyclobutylmethyl | OH | OMe | 2 | NHCS—NHCH$_2$Ph |
| allyl | OH | OH | 2 | NHCS—NHCH$_2$Ph |
| allyl | OH | OMe | 2 | NHCS—NHCH$_2$Ph |
| H | OH | OH | 2 | NHCS—NHCH$_2$Ph |
| H | OH | OMe | 2 | NHCS—NHCH$_2$Ph |
| Me | OH | OH | 2 | NHCS—NHCH$_2$Ph |
| Me | OH | OMe | 2 | NHCS—NHCH$_2$Ph |
| benzyl | OH | OH | 2 | NHCS—NHCH$_2$Ph |
| benzyl | OH | OMe | 2 | NHCS—NHCH$_2$Ph |
| 2-phenethyl | OH | OH | 2 | NHCS—NHCH$_2$Ph |
| 2-phenethyl | OH | OMe | 2 | NHCS—NHCH$_2$Ph |
| cyclopropylmethyl | OH | OH | 3 | OH |
| cyclopropylmethyl | OH | OMe | 3 | OH |
| cyclobutylmethyl | OH | OH | 3 | OH |
| cyclobutylmethyl | OH | OMe | 3 | OH |
| allyl | OH | OH | 3 | OH |
| allyl | OH | OMe | 3 | OH |
| H | OH | OH | 3 | OH |
| H | OH | OMe | 3 | OH |
| Me | OH | OH | 3 | OH |
| Me | OH | OMe | 3 | OH |
| benzyl | OH | OH | 3 | OH |
| benzyl | OH | OMe | 3 | OH |
| 2-phenethyl | OH | OH | 3 | OH |
| 2-phenethyl | OH | OMe | 3 | OH |
| cyclopropylmethyl | OH | OH | 3 | OMe |
| cyclopropylmethyl | OH | OMe | 3 | OMe |
| cyclobutylmethyl | OH | OH | 3 | OMe |
| cyclobutylmethyl | OH | OMe | 3 | OMe |
| allyl | OH | OH | 3 | OMe |
| allyl | OH | OMe | 3 | OMe |
| H | OH | OH | 3 | OMe |
| H | OH | OMe | 3 | OMe |
| Me | OH | OH | 3 | OMe |
| Me | OH | OMe | 3 | OMe |
| benzyl | OH | OH | 3 | OMe |
| benzyl | OH | OMe | 3 | OMe |
| 2-phenethyl | OH | OH | 3 | OMe |
| 2-phenethyl | OH | OMe | 3 | OMe |
| cyclopropylmethyl | OH | OH | 3 | OEt |
| cyclopropylmethyl | OH | OMe | 3 | OEt |
| cyclobutylmethyl | OH | OH | 3 | OEt |
| cyclobutylmethyl | OH | OMe | 3 | OEt |
| allyl | OH | OH | 3 | OEt |
| allyl | OH | OMe | 3 | OEt |
| H | OH | OH | 3 | OEt |
| H | OH | OMe | 3 | OEt |
| Me | OH | OH | 3 | OEt |
| Me | OH | OMe | 3 | OEt |
| benzyl | OH | OH | 3 | OEt |
| benzyl | OH | OMe | 3 | OEt |
| 2-phenethyl | OH | OH | 3 | OEt |
| 2-phenethyl | OH | OMe | 3 | OEt |
| cyclopropylmethyl | OH | OH | 3 | NH$_2$ |
| cyclopropylmethyl | OH | OMe | 3 | NH$_2$ |
| cyclobutylmethyl | OH | OH | 3 | NH$_2$ |
| cyclobutylmethyl | OH | OMe | 3 | NH$_2$ |
| allyl | OH | OH | 3 | NH$_2$ |
| allyl | OH | OMe | 3 | NH$_2$ |
| H | OH | OH | 3 | NH$_2$ |
| H | OH | OMe | 3 | NH$_2$ |
| Me | OH | OH | 3 | NH$_2$ |
| Me | OH | OMe | 3 | NH$_2$ |

-continued

| | | | | |
|---|---|---|---|---|
| benzyl | OH | OH | 3 | NH$_2$ |
| benzyl | OH | OMe | 3 | NH$_2$ |
| 2-phenethyl | OH | OH | 3 | NH$_2$ |
| 2-phenethyl | OH | OMe | 3 | NH$_2$ |
| cyclopropylmethyl | OH | OH | 3 | NO$_2$ |
| cyclopropylmethyl | OH | OMe | 3 | NO$_2$ |
| cyclobutylmethyl | OH | OH | 3 | NO$_2$ |
| cyclobutylmethyl | OH | OMe | 3 | NO$_2$ |
| allyl | OH | OH | 3 | NO$_2$ |
| allyl | OH | OMe | 3 | NO$_2$ |
| H | OH | OH | 3 | NO$_2$ |
| H | OH | OMe | 3 | NO$_2$ |
| Me | OH | OH | 3 | NO$_2$ |
| Me | OH | OMe | 3 | NO$_2$ |
| benzyl | OH | OH | 3 | NO$_2$ |
| benzyl | OH | OMe | 3 | NO$_2$ |
| 2-phenethyl | OH | OH | 3 | NO$_2$ |
| 2-phenethyl | OH | OMe | 3 | NO$_2$ |
| cyclopropylmethyl | OH | OH | 3 | CN |
| cyclopropylmethyl | OH | OMe | 3 | CN |
| cyclobutylmethyl | OH | OH | 3 | CN |
| cyclobutylmethyl | OH | OMe | 3 | CN |
| allyl | OH | OH | 3 | CN |
| allyl | OH | OMe | 3 | CN |
| H | OH | OH | 3 | CN |
| H | OH | OMe | 3 | CN |
| Me | OH | OH | 3 | CN |
| Me | OH | OMe | 3 | CN |
| benzyl | OH | OH | 3 | CN |
| benzyl | OH | OMe | 3 | CN |
| 2-phenethyl | OH | OH | 3 | CN |
| 2-phenethyl | OH | OMe | 3 | CN |
| cyclopropylmethyl | OH | OH | 3 | NCS |
| cyclopropylmethyl | OH | OMe | 3 | NCS |
| cyclobutylmethyl | OH | OH | 3 | NCS |
| cyclobutylmethyl | OH | OMe | 3 | NCS |
| allyl | OH | OH | 3 | NCS |
| allyl | OH | OMe | 3 | NCS |
| H | OH | OH | 3 | NCS |
| H | OH | OMe | 3 | NCS |
| Me | OH | OH | 3 | NCS |
| ME | OH | OMe | 3 | NCS |
| benzyl | OH | OH | 3 | NCS |
| benzyl | OH | OMe | 3 | NCS |
| 2-phenethyl | OH | OH | 3 | NCS |
| 2-phenethyl | OH | OMe | 3 | NCS |
| cyclopropylmethyl | OH | OH | 3 | COOH |
| cyclopropylmethyl | OH | OMe | 3 | COOH |
| cyclobutylmethyl | OH | OH | 3 | COOH |
| cyclobutylmethyl | OH | OMe | 3 | COOH |
| allyl | OH | OH | 3 | COOH |
| allyl | OH | OMe | 3 | COOH |
| H | OH | OH | 3 | COOH |
| H | OH | OMe | 3 | COOH |
| Me | OH | OH | 3 | COOH |
| Me | OH | OMe | 3 | COOH |
| benzyl | OH | OH | 3 | COOH |
| benzyl | OH | OMe | 3 | COOH |
| 2-phenethyl | OH | OH | 3 | COOH |
| 2-phenethyl | OH | OMe | 3 | COOH |
| cyclopropylmethyl | OH | OH | 3 | COOMe |
| cyclopropylmethyl | OH | OMe | 3 | COOMe |
| cyclobutylmethyl | OH | OH | 3 | COOMe |
| cyclobutylmethyl | OH | OMe | 3 | COOMe |
| allyl | OH | OH | 3 | COOMe |
| allyl | OH | OMe | 3 | COOMe |
| H | OH | OH | 3 | COOMe |
| H | OH | OMe | 3 | COOMe |
| Me | OH | OH | 3 | COOMe |
| Me | OH | OMe | 3 | COOMe |
| benzyl | OH | OH | 3 | COOMe |
| benzyl | OH | OMe | 3 | COOMe |
| 2-phenethyl | OH | OH | 3 | COOMe |
| 2-phenethyl | OH | OMe | 3 | COOMe |
| cyclopropylmethyl | OH | OH | 3 | COOEt |
| cyclopropylmethyl | OH | OMe | 3 | COOEt |
| cyclobutylmethyl | OH | OH | 3 | COOEt |
| cyclobutylmethyl | OH | OMe | 3 | COOEt |
| allyl | OH | OH | 3 | COOEt |

-continued

| | | | | |
|---|---|---|---|---|
| allyl | OH | OMe | 3 | COOEt |
| H | OH | OH | 3 | COOEt |
| H | OH | OMe | 3 | COOEt |
| Me | OH | OH | 3 | COOEt |
| Me | OH | OMe | 3 | COOEt |
| benzyl | OH | OH | 3 | COOEt |
| benzyl | OH | OMe | 3 | COOEt |
| 2-phenethyl | OH | OH | 3 | COOEt |
| 2-phenethyl | OH | OMe | 3 | COOEt |
| cyclopropylmethyl | OH | OH | 3 | NHCHO |
| cyclopropylmethyl | OH | OMe | 3 | NHCHO |
| cyclobutylmethyl | OH | OH | 3 | NHCHO |
| cyclobutylmethyl | OH | OMe | 3 | NHCHO |
| allyl | OH | OH | 3 | NHCHO |
| allyl | OH | OMe | 3 | NHCHO |
| H | OH | OH | 3 | NHCHO |
| H | OH | OMe | 3 | NHCHO |
| Me | OH | OH | 3 | NHCHO |
| Me | OH | OMe | 3 | NHCHO |
| benzyl | OH | OH | 3 | NHCHO |
| benzyl | OH | OMe | 3 | NHCHO |
| 2-phenethyl | OH | OH | 3 | NHCHO |
| 2-phenethyl | OH | OMe | 3 | NHCHO |
| cyclopropylmethyl | OH | OH | 3 | NHCO—Me |
| cyclopropylmethyl | OH | OMe | 3 | NHCO—Me |
| cyclobutylmethyl | OH | OH | 3 | NHCO—Me |
| cyclobutylmethyl | OH | OMe | 3 | NHCO—Me |
| allyl | OH | OH | 3 | NHCO—Me |
| allyl | OH | OMe | 3 | NHCO—Me |
| H | OH | OH | 3 | NHCO—Me |
| H | OH | OMe | 3 | NHCO—Me |
| Me | OH | OH | 3 | NHCO—Me |
| Me | OH | OMe | 3 | NHCO—Me |
| benzyl | OH | OH | 3 | NHCO—Me |
| benzyl | OH | OMe | 3 | NHCO—Me |
| 2-phenethyl | OH | OH | 3 | NHCO—Me |
| 2-phenethyl | OH | OMe | 3 | NHCO—Me |
| cyclopropylmethyl | OH | OH | 3 | NHCO—Ph |
| cyclopropylmethyl | OH | OMe | 3 | NHCO—Ph |
| cyclobutylmethyl | OH | OH | 3 | NHCO—Ph |
| cyclobutylmethyl | OH | OMe | 3 | NHCO—Ph |
| allyl | OH | OH | 3 | NHCO—Ph |
| allyl | OH | OMe | 3 | NHCO—Ph |
| H | OH | OH | 3 | NHCO—Ph |
| H | OH | OMe | 3 | NHCO—Ph |
| Me | OH | OH | 3 | NHCO—Ph |
| Me | OH | OMe | 3 | NHCO—Ph |
| benzyl | OH | OH | 3 | NHCO—Ph |
| benzyl | OH | OMe | 3 | NHCO—Ph |
| 2-phenethyl | OH | OH | 3 | NHCO—Ph |
| 2-phenethyl | OH | OMe | 3 | NHCO—Ph |
| cyclopropylmethyl | OH | OH | 3 | NHCO—(CH$_2$)$_5$Ph |
| cyclopropylmethyl | OH | OMe | 3 | NHCO—(CH$_2$)$_5$Ph |
| cyclobutylmethyl | OH | OH | 3 | NHCO—(CH$_2$)$_5$Ph |
| cyclobutylmethyl | OH | OMe | 3 | NHCO—(CH$_2$)$_5$Ph |
| allyl | OH | OH | 3 | NHCO—(CH$_2$)$_5$Ph |
| allyl | OH | OMe | 3 | NHCO—(CH$_2$)$_5$Ph |
| H | OH | OH | 3 | NHCO—(CH$_2$)$_5$Ph |
| H | OH | OMe | 3 | NHCO—(CH$_2$)$_5$Ph |
| Me | OH | OH | 3 | NHCO—(CH$_2$)$_5$Ph |
| Me | OH | OMe | 3 | NHCO—(CH$_2$)$_5$Ph |
| benzyl | OH | OH | 3 | NHCO—(CH$_2$)$_5$Ph |
| benzyl | OH | OMe | 3 | NHCO—(CH$_2$)$_5$Ph |
| 2-phenethyl | OH | OH | 3 | NHCO—(CH$_2$)$_5$Ph |
| 2-phenethyl | OH | OMe | 3 | NHCO—(CH$_2$)$_5$Ph |
| cyclopropylmethyl | OH | OH | 3 | NHCO-cinnamyl |
| cyclopropylmethyl | OH | OMe | 3 | NHCO-cinnamyl |
| cylcobutylmethyl | OH | OH | 3 | NHCO-cinnamyl |
| cyclobutylmethyl | OH | OMe | 3 | NHCO-cinnamyl |
| allyl | OH | OH | 3 | NHCO-cinnamyl |
| allyl | OH | OMe | 3 | NHCO-cinnamyl |
| H | OH | OH | 3 | NHCO-cinnamyl |
| H | OH | OMe | 3 | NHCO-cinnamyl |
| Me | OH | OH | 3 | NHCO-cinnamyl |
| Me | OH | OMe | 3 | NHCO-cinnamyl |
| benzyl | OH | OH | 3 | NHCO-cinnamyl |
| benzyl | OH | OMe | 3 | NHCO-cinnamyl |
| 2-phenethyl | OH | OH | 3 | NHCO-cinnamyl |
| 2-phenethyl | OH | OMe | 3 | NHCO-cinnamyl |
| cyclopropylmethyl | OH | OH | 3 | NHCO—(CF$_2$-cinnamyl) |
| cyclopropylmethyl | OH | OMe | 3 | NHCO—(CF$_2$-cinnamyl) |
| cylcobutylmethyl | OH | OH | 3 | NHCO—(CF$_2$-cinnamyl) |
| cyclobutylmethyl | OH | OMe | 3 | NHCO—(CF$_2$-cinnamyl) |
| allyl | OH | OH | 3 | NHCO—(CF$_2$-cinnamyl) |
| allyl | OH | OMe | 3 | NHCO—(CF$_2$-cinnamyl) |
| H | OH | OH | 3 | NHCO—(CF$_2$-cinnamyl) |
| H | OH | OMe | 3 | NHCO—(CF$_2$-cinnamyl) |
| Me | OH | OH | 3 | NHCO—(CF$_2$-cinnamyl) |
| Me | OH | OMe | 3 | NHCO—(CF$_2$-cinnamyl) |
| benzyl | OH | OH | 3 | NHCO—(CF$_2$-cinnamyl) |
| benzyl | OH | OMe | 3 | NHCO—(CF$_2$-cinnamyl) |
| 2-phenethyl | OH | OH | 3 | NHCO—(CF$_2$-cinnamyl) |
| 2-phenethyl | OH | OMe | 3 | NHCO—(CF$_2$-cinnamyl) |
| cyclopropylmethyl | OH | OH | 3 | NHCO-pyridyl |
| cyclobutylmethyl | OH | OH | 3 | NHCO-pyridyl |
| cyclobutylemthyl | OH | OMe | 3 | NHCO-pyridyl |
| allyl | OH | OH | 3 | NHCO-pyridyl |
| allyl | OH | OMe | 3 | NHCO-pyridyl |
| H | OH | OH | 3 | NHCO-pyridyl |
| H | OH | OMe | 3 | NHCO-pyridyl |
| Me | OH | OH | 3 | NHCO-pyridyl |
| Me | OH | OMe | 3 | NHCO-pyridyl |
| benzyl | OH | OH | 3 | NHCO-pyridyl |
| benzyl | OH | OMe | 3 | NHCO-pyridyl |
| 2-phenethyl | OH | OH | 3 | NHCO-pyridyl |
| 2-phenethyl | OH | OMe | 3 | NHCO-pyridyl |
| cyclopropylmethyl | OH | OH | 3 | NHCO—NHPh |
| cyclopropylmethyl | OH | OMe | 3 | NHCO—NHPh |
| cyclobutylmethyl | OH | OH | 3 | NHCO—NHPh |
| cyclobutylmethyl | OH | OMe | 3 | NHCO—NHPh |
| allyl | OH | OH | 3 | NHCO—NHPh |
| allyl | OH | OMe | 3 | NHCO—NHPh |
| H | OH | OH | 3 | NHCO—NHPh |
| H | OH | OMe | 3 | NHCO—NHPh |
| Me | OH | OH | 3 | NHCO—NHPh |
| Me | OH | OMe | 3 | NHCO—NHPh |
| benzyl | OH | OH | 3 | NHCO—NHPh |
| benzyl | OH | OMe | 3 | NHCO—NHPh |
| 2-phenethyl | OH | OH | 3 | NHCO—NHPh |
| 2-phenethyl | OH | OMe | 3 | NHCO—NHPh |
| cyclopropylmethyl | OH | OH | 3 | NHCS—NHPh |
| cyclopropylmethyl | OH | OMe | 3 | NHCS—NHPh |
| cyclobutylmethyl | OH | OH | 3 | NHCS—NHPh |
| cyclobutylmethyl | OH | OMe | 3 | NHCS—NHPh |
| allyl | OH | OH | 3 | NHCS—NHPh |
| allyl | OH | OMe | 3 | NHCS—NHPh |
| H | OH | OH | 3 | NHCS—NHPh |
| H | OH | OMe | 3 | NHCS—NHPh |
| Me | OH | OH | 3 | NHCS—NHPh |
| Me | OH | OMe | 3 | NHCS—NHPh |
| benzyl | OH | OH | 3 | NHCS—NHPh |
| benzyl | OH | OMe | 3 | NCHS—NHPh |
| 2-phenethyl | OH | OH | 3 | NHCS—NHPh |
| 2-phenethyl | OH | OMe | 3 | NHCS—NHPh |
| cyclopropylmethyl | OH | OH | 3 | NHCS—NHCH$_2$Ph |
| cyclopropylmethyl | OH | OMe | 3 | NHCS—NHCH$_2$Ph |
| cyclobutylmethyl | OH | OH | 3 | NHCS—NHCH$_2$Ph |
| cyclobutylmethyl | OH | OMe | 3 | NHCS—NHCH$_2$Ph |
| allyl | OH | OH | 3 | NHCS—NHCH$_2$Ph |
| allyl | OH | OMe | 3 | NHCS—NHCH$_2$Ph |
| H | OH | OH | 3 | NHCS—NHCH$_2$Ph |
| H | OH | OMe | 3 | NHCS—NHCH$_2$Ph |
| Me | OH | OH | 3 | NHCS—NHCH$_2$Ph |
| Me | OH | OMe | 3 | NHCS—NHCH$_2$Ph |
| benzyl | OH | OH | 3 | NHCS—NHCH$_2$Ph |
| benzyl | OH | OMe | 3 | NHCS—NHCH$_2$Ph |
| 2-phenethyl | OH | OH | 3 | NHCS—NHCH$_2$Ph |
| 2-phenethyl | OH | OMe | 3 | NHCS—NHCH$_2$Ph |
| cyclopropylmethyl | OH | OH | 4 | OH |
| cyclopropylmethyl | OH | OMe | 4 | OH |
| cyclobutylmethyl | OH | OH | 4 | OH |
| cyclobutylmethyl | OH | OMe | 4 | OH |
| allyl | OH | OH | 4 | OH |
| allyl | OH | OMe | 4 | OH |
| H | OH | OH | 4 | OH |
| H | OH | OMe | 4 | OH |
| Me | OH | OH | 4 | OH |

-continued

| | | | | |
|---|---|---|---|---|
| Me | OH | OMe | 4 | OH |
| benzyl | OH | OH | 4 | OH |
| benzyl | OH | OMe | 4 | OH |
| 2-phenethyl | OH | OH | 4 | OH |
| 2-phenethyl | OH | OMe | 4 | OH |
| cyclopropylmethyl | OH | OH | 4 | OMe |
| cyclopropylmethyl | OH | OMe | 4 | OMe |
| cyclobutylmethyl | OH | OH | 4 | OMe |
| cyclobutylmethyl | OH | OMe | 4 | OMe |
| allyl | OH | OH | 4 | OMe |
| allyl | OH | OMe | 4 | OMe |
| H | OH | OH | 4 | OMe |
| H | OH | OMe | 4 | OMe |
| Me | OH | OH | 4 | OMe |
| Me | OH | OMe | 4 | OMe |
| benzyl | OH | OH | 4 | OMe |
| benzyl | OH | OMe | 4 | OMe |
| 2-phenethyl | OH | OH | 4 | OMe |
| 2-phenethyl | OH | OMe | 4 | OMe |
| cyclopropylmethyl | OH | OH | 4 | OEt |
| cyclopropylmethyl | OH | OMe | 4 | OEt |
| cyclobutylmethyl | OH | OH | 4 | OEt |
| cyclobutylmethyl | OH | OMe | 4 | OEt |
| allyl | OH | OH | 4 | OEt |
| allyl | OH | OMe | 4 | OEt |
| H | OH | OH | 4 | OEt |
| H | OH | OMe | 4 | OEt |
| Me | OH | OH | 4 | OEt |
| Me | OH | OMe | 4 | OEt |
| benzyl | OH | OH | 4 | OEt |
| benzyl | OH | OMe | 4 | OEt |
| 2-phenethyl | OH | OH | 4 | OEt |
| 2-phenethyl | OH | OMe | 4 | OEt |
| cyclopropylmethyl | OH | OH | 4 | $NH_2$ |
| cyclopropylmethyl | OH | OMe | 4 | $NH_2$ |
| cyclobutylmethyl | OH | OH | 4 | $NH_2$ |
| cyclobutylmethyl | OH | OMe | 4 | $NH_2$ |
| allyl | OH | OH | 4 | $NH_2$ |
| allyl | OH | OMe | 4 | $NH_2$ |
| H | OH | OH | 4 | $NH_2$ |
| H | OH | OMe | 4 | $NH_2$ |
| Me | OH | OH | 4 | $NH_2$ |
| Me | OH | OMe | 4 | $NH_2$ |
| benzyl | OH | OH | 4 | $NH_2$ |
| benzyl | OH | OMe | 4 | $NH_2$ |
| 2-phenethyl | OH | OH | 4 | $NH_2$ |
| 2-phenethyl | OH | OMe | 4 | $NH_2$ |
| cyclopropylmethyl | OH | OH | 4 | $NO_2$ |
| cyclopropylmethyl | OH | OME | 4 | $NO_2$ |
| cyclobutylmethyl | OH | OH | 4 | $NO_2$ |
| cyclobutylmethyl | OH | OMe | 4 | $NO_2$ |
| allyl | OH | OH | 4 | $NO_2$ |
| allyl | OH | OMe | 4 | $NO_2$ |
| H | OH | OH | 4 | $NO_2$ |
| H | OH | OMe | 4 | $NO_2$ |
| Me | OH | OH | 4 | $NO_2$ |
| Me | OH | OMe | 4 | $NO_2$ |
| benzyl | OH | OH | 4 | $NO_2$ |
| benzyl | OH | OMe | 4 | $NO_2$ |
| 2-phenethyl | OH | OH | 4 | $NO_2$ |
| 2-phenethyl | OH | OMe | 4 | $NO_2$ |
| cyclopropylmethyl | OH | OH | 4 | CN |
| cyclopropylmethyl | OH | OMe | 4 | CN |
| cyclobutylmethyl | OH | OH | 4 | CN |
| cyclobutylmethyl | OH | OMe | 4 | CN |
| allyl | OH | OH | 4 | CN |
| allyl | OH | OMe | 4 | CN |
| H | OH | OH | 4 | CN |
| H | OH | OMe | 4 | CN |
| Me | OH | OH | 4 | CN |
| Me | OH | OMe | 4 | CN |
| benzyl | OH | OH | 4 | CN |
| benzyl | OH | OMe | 4 | CN |
| 2-phenethyl | OH | OH | 4 | CN |
| 2-phenethyl | OH | OMe | 4 | CN |
| cyclopropylmethyl | OH | OH | 4 | NCS |
| cyclopropylmethyl | OH | OMe | 4 | NCS |
| cyclobutylmethyl | OH | OH | 4 | NCS |
| cyclobutylmethyl | OH | OMe | 4 | NCS |

-continued

| | | | | |
|---|---|---|---|---|
| allyl | OH | OH | 4 | NCS |
| allyl | OH | OMe | 4 | NCS |
| H | OH | OH | 4 | NCS |
| H | OH | OMe | 4 | NCS |
| Me | OH | OH | 4 | NCS |
| Me | OH | OMe | 4 | NCS |
| benzyl | OH | OH | 4 | NCS |
| benzyl | OH | OMe | 4 | NCS |
| 2-phenethyl | OH | OH | 4 | NCS |
| 2-phenethyl | OH | OMe | 4 | NCS |
| cyclopropylmethyl | OH | OH | 4 | COOH |
| cyclopropylmethyl | OH | OMe | 4 | COOH |
| cyclobutylmethyl | OH | OH | 4 | COOH |
| cyclobutylmethyl | OH | OMe | 4 | COOH |
| allyl | OH | OH | 4 | COOH |
| allyl | OH | OMe | 4 | COOH |
| H | OH | OH | 4 | COOH |
| H | OH | OMe | 4 | COOH |
| Me | OH | OH | 4 | COOH |
| Me | OH | OMe | 4 | COOH |
| benzyl | OH | OH | 4 | COOH |
| benzyl | OH | OMe | 4 | COOH |
| 2-phenethyl | OH | OH | 4 | COOH |
| 2-phenethyl | OH | OMe | 4 | COOH |
| cyclopropylmethyl | OH | OH | 4 | COOMe |
| cyclopropylmethyl | OH | OMe | 4 | COOMe |
| cyclobutylmethyl | OH | OH | 4 | COOMe |
| cyclobutylmethyl | OH | OMe | 4 | COOMe |
| allyl | OH | OH | 4 | COOMe |
| allyl | OH | OMe | 4 | COOMe |
| H | OH | OH | 4 | COOMe |
| H | OH | OMe | 4 | COOMe |
| Me | OH | OH | 4 | COOMe |
| Me | OH | OMe | 4 | COOMe |
| benzyl | OH | OH | 4 | COOMe |
| benzyl | OH | OMe | 4 | COOMe |
| 2-phenethyl | OH | OH | 4 | COOMe |
| 2-phenethyl | OH | OMe | 4 | COOMe |
| cyclopropylmethyl | OH | OH | 4 | COOEt |
| cyclopropylmethyl | OH | OMe | 4 | COOEt |
| cyclobutylmethyl | OH | OH | 4 | COOEt |
| cyclobutylmethyl | OH | OMe | 4 | COOEt |
| allyl | OH | OH | 4 | COOEt |
| allyl | OH | OMe | 4 | COOEt |
| H | OH | OH | 4 | COOEt |
| H | OH | OMe | 4 | COOEt |
| Me | OH | OH | 4 | COOEt |
| Me | OH | OMe | 4 | COOEt |
| benzyl | OH | OH | 4 | COOEt |
| benzyl | OH | OMe | 4 | COOEt |
| 2-phenethyl | OH | OH | 4 | COOEt |
| 2-phenethyl | OH | OMe | 4 | COOEt |
| cyclopropylmethyl | OH | OH | 4 | NHCHO |
| cyclopropylmethyl | OH | OMe | 4 | NHCHO |
| cyclobutylmethyl | OH | OH | 4 | NHCHO |
| cyclobutylmethyl | OH | OMe | 4 | NHCHO |
| allyl | OH | OH | 4 | NHCHO |
| allyl | OH | OMe | 4 | NHCHO |
| H | OH | OH | 4 | NHCHO |
| H | OH | OMe | 4 | NHCHO |
| Me | OH | OH | 4 | NHCHO |
| Me | OH | OMe | 4 | NHCHO |
| benzyl | OH | OH | 4 | NHCHO |
| benzyl | OH | OMe | 4 | NHCHO |
| 2-phenethyl | OH | OH | 4 | NHCHO |
| 2-phenethyl | OH | OMe | 4 | NHCHO |
| cyclopropylmethyl | OH | OH | 4 | NHCO—Me |
| cyclopropylmethyl | OH | OMe | 4 | NHCO—Me |
| cyclobutylmethyl | OH | OH | 4 | NHCO—Me |
| cyclobutylmethyl | OH | OMe | 4 | NHCO—Me |
| allyl | OH | OH | 4 | NHCO—Me |
| allyl | OH | OMe | 4 | NHCO—Me |
| H | OH | OH | 4 | NHCO—Me |
| H | OH | OMe | 4 | NHCO—Me |
| Me | OH | OH | 4 | NHCO—Me |
| Me | OH | OMe | 4 | NHCO—Me |
| benzyl | OH | OH | 4 | NHCO—Me |
| benzyl | OH | OMe | 4 | NHCO—Me |
| 2-phenethyl | OH | OH | 4 | NHCO—Me |

-continued

| | | | | |
|---|---|---|---|---|
| 2-phenethyl | OH | OMe | 4 | NHCO—Me |
| cyclopropylmethyl | OH | OH | 4 | NHCO—Ph |
| cyclopropylmethyl | OH | OMe | 4 | NHCO—Ph |
| cyclobutylmethyl | OH | OH | 4 | NHCO—Ph |
| cyclobutylmethyl | OH | OMe | 4 | NHCO—Ph |
| allyl | OH | OH | 4 | NHCO—Ph |
| allyl | OH | OMe | 4 | NHCO—Ph |
| H | OH | OH | 4 | NHCO—Ph |
| H | OH | OMe | 4 | NHCO—Ph |
| Me | OH | OH | 4 | NHCO—Ph |
| Me | OH | OMe | 4 | NHCO—Ph |
| H | OH | OH | 4 | NHCO—Ph |
| H | OH | OMe | 4 | NHCO—Ph |
| Me | OH | OH | 4 | NHCO—Ph |
| Me | OH | OMe | 4 | NHCO—Ph |
| benzyl | OH | OH | 4 | NHCO—Ph |
| benzyl | OH | OMe | 4 | NHCO—Ph |
| 2-phenethyl | OH | OH | 4 | NHCO—Ph |
| 2-phenethyl | OH | OMe | 4 | NHCO—Ph |
| cyclopropylmethyl | OH | OH | 4 | NHCO—$(CH_2)_5$Ph |
| cyclopropylmethyl | OH | OMe | 4 | NHCO—$(CH_2)_5$Ph |
| cyclobutylmethyl | OH | OH | 4 | NHCO—$(CH_2)_5$Ph |
| cyclobutylmethyl | OH | OMe | 4 | NHCO—$(CH_2)_5$Ph |
| allyl | OH | OH | 4 | NHCO—$(CH_2)_5$Ph |
| allyl | OH | OMe | 4 | NHCO—$(CH_2)_5$Ph |
| H | OH | OH | 4 | NHCO—$(CH_2)_5$Ph |
| H | OH | OMe | 4 | NHCO—$(CH_2)_5$Ph |
| Me | OH | OH | 4 | NHCO—$(CH_2)_5$Ph |
| Me | OH | OMe | 4 | NHCO—$(CH_2)_5$Ph |
| benzyl | OH | OH | 4 | NHCO—$(CH_2)_5$Ph |
| benzyl | OH | OMe | 4 | NHCO—$(CH_2)_5$Ph |
| 2-phenethyl | OH | OH | 4 | NHCO—$(CH_2)_5$Ph |
| 2-phenethyl | OH | OMe | 4 | NHCO—$(CH_2)_5$Ph |
| cyclopropylmethyl | OH | OMe | 4 | NHCO-cinnamyl |
| cyclopropylmethyl | OH | OMe | 4 | NHCO-cinnamyl |
| cyclobutylmethyl | OH | OH | 4 | NHCO-cinnamyl |
| cyclobutylmethyl | OH | OMe | 4 | NHCO-cinnamyl |
| allyl | OH | OH | 4 | NHCO-cinnamyl |
| allyl | OH | OMe | 4 | NHCO-cinnamyl |
| H | OH | OH | 4 | NHCO-cinnamyl |
| H | OH | OMe | 4 | NHCO-cinnamyl |
| benzyl | OH | OH | 4 | NHCO-cinnamyl |
| benzyl | OH | OMe | 4 | NHCO-cinnamyl |
| 2-phenethyl | OH | OH | 4 | NHCO-cinnamyl |
| 2-phenethyl | OH | OMe | 4 | NHCO-cinnamyl |
| cyclopropylmethyl | OH | OH | 4 | NHCO—($CF_3$-cinnamyl) |
| cyclopropylmethyl | OH | OMe | 4 | NHCO—($CF_3$-cinnamyl) |
| cyclobutylmethyl | OH | OH | 4 | NHCO—($CF_3$-cinnamyl) |
| cyclobutylmethyl | OH | OMe | 4 | NHCO—($CF_3$-cinnamyl) |
| allyl | OH | OH | 4 | NHCO—($CF_3$-cinnamyl) |
| allyl | OH | OMe | 4 | NHCO—($CF_3$-cinnamyl) |
| H | OH | OH | 4 | NHCO—($CF_3$-cinnamyl) |
| H | OH | OMe | 4 | NHCO—($CF_3$-cinnamyl) |
| Me | OH | OH | 4 | NHCO—($CF_3$-cinnamyl) |
| Me | OH | OMe | 4 | NHCO—($CF_3$-cinnamyl) |
| benzyl | OH | OH | 4 | NHCO—($CF_3$-cinnamyl) |
| benzyl | OH | OMe | 4 | NHCO—($CF_3$-cinnamyl) |
| 2-phenethyl | OH | OH | 4 | NHCO—($CF_3$-cinnamyl) |
| 2-phenethyl | OH | OMe | 4 | NHCO—($CF_3$-cinnamyl) |
| cyclopropylmethyl | OH | OH | 4 | NHCO-pyridyl |
| cyclopropylmethyl | OH | OMe | 4 | NHCO-pyridyl |
| cyclobutylmethyl | OH | OH | 4 | NHCO-pyridyl |
| cyclobutylmethyl | OH | OMe | 4 | NHCO-pyridyl |
| allyl | OH | OH | 4 | NHCO-pyridyl |
| allyl | OH | OMe | 4 | NHCO-pyridyl |
| H | OH | OH | 4 | NHCO-pyridyl |
| H | OH | OMe | 4 | NHCO-pyridyl |
| Me | OH | OH | 4 | NHCO-pyridyl |
| Me | OH | OMe | 4 | NHCO-pyridyl |
| benzyl | OH | OH | 4 | NHCO-pyridyl |
| benzyl | OH | OMe | 4 | NHCO-pyridyl |
| 2-phenethyl | OH | OH | 4 | NHCO-pyridyl |
| 2-phenethyl | OH | OMe | 4 | NHCO-pyridyl |
| cyclopropylmethyl | OH | OH | 4 | NHCO—NHPh |
| cyclopropylmethyl | OH | OMe | 4 | NHCO—NHPh |
| cyclobutylmethyl | OH | OH | 4 | NHCO—NHPh |
| cyclobutylmethyl | OH | OMe | 4 | NHCO—NHPh |
| allyl | OH | OH | 4 | NHCO—NHPh |
| allyl | OH | OMe | 4 | NHCO—NHPh |

-continued

| | | | | |
|---|---|---|---|---|
| H | OH | OH | 4 | NHCO—NHPh |
| H | OH | OMe | 4 | NHCO—NHPh |
| Me | OH | OH | 4 | NHCO—NHPh |
| Me | OH | OMe | 4 | NHCO—NHPh |
| benzyl | OH | OH | 4 | NHCO—NHPh |
| benzyl | OH | OMe | 4 | NHCO—NHPh |
| 2-phenethyl | OH | OH | 4 | NHCO—NHPh |
| 2-phenethyl | OH | OMe | 4 | NHCO—NHPh |
| cyclopropylmethyl | OH | OH | 4 | NHCS—NHPh |
| cyclopropylmethyl | OH | OMe | 4 | NHCS—NHPh |
| cyclobutylmethyl | OH | OH | 4 | NHCS—NHPh |
| cyclobutylmethyl | OH | OMe | 4 | NHCS—NHPh |
| allyl | OH | OH | 4 | NHCS—NHPh |
| allyl | OH | OMe | 4 | NHCS—NHPh |
| H | OH | OH | 4 | NHCS—NHPh |
| H | OH | OMe | 4 | NHCS—NHPh |
| Me | OH | OH | 4 | NHCS—NHPh |
| Me | OH | OMe | 4 | NHCS—NHPh |
| benzyl | OH | OH | 4 | NHCS—NHPh |
| benzyl | OH | OMe | 4 | NHCS—NHPh |
| 2-phenethyl | OH | OH | 4 | NHCS—NHPh |
| 2-phenethyl | OH | OMe | 4 | NHCS—NHPh |
| cyclopropylmethyl | OH | OH | 4 | NHCS—NHCH$_2$Ph |
| cyclopropylmethyl | OH | OMe | 4 | NHCS—NHCH$_2$Ph |
| cyclobutylmethyl | OH | OH | 4 | NHCS—NHCH$_2$Ph |
| cyclobutylmethyl | OH | OMe | 4 | NHCS—NHCH$_2$Ph |
| allyl | OH | OH | 4 | NHCS—NHCH$_2$Ph |
| allyl | OH | OMe | 4 | NHCS—NHCH$_2$Ph |
| H | OH | OH | 4 | NHCS—NHCH$_2$Ph |
| H | OH | OMe | 4 | NHCS—NHCH$_2$Ph |
| Me | OH | OH | 4 | NHCS—NHCH$_2$Ph |
| Me | OH | OMe | 4 | NHCS—NHCH$_2$Ph |
| benzyl | OH | OH | 4 | NHCS—NHCH$_2$Ph |
| benzyl | OH | OMe | 4 | NHCS—NHCH$_2$Ph |
| 2-phenethyl | OH | OH | 4 | NHCS—NHCH$_2$Ph |
| 2-phenethyl | OH | OMe | 4 | NHCS—NHCH$_2$Ph |

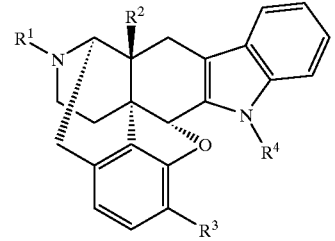

| $R^1$ | $R^2$ | $R^3$ | $R^4$ |
|---|---|---|---|
| cyclopropylmethyl | OH | OH | H |
| cyclobutylmethyl | OH | OH | H |
| allyl | OH | OH | H |
| H | OH | OH | H |
| Me | OH | OH | H |
| benzyl | OH | OH | H |
| 2-phenethyl | OH | OH | H |
| cyclopropylmethyl | OH | OH | Me |
| cyclobutylmethyl | OH | OH | Me |
| allyl | OH | OH | Me |
| H | OH | OH | Me |
| Me | OH | OH | Me |
| benzyl | OH | OH | Me |
| 2-phenethyl | OH | OH | Me |
| cyclopropylmethyl | OH | OH | Bu |
| cylcobutylmethyl | OH | OH | Bu |
| allyl | OH | OH | Bu |
| H | OH | OH | Bu |
| Me | OH | OH | Bu |
| Me | OH | OH | Bu |
| benzyl | OH | OH | Bu |
| 2-phenethyl | OH | OH | Bu |
| cyclopropylmethyl | OH | OH | PhCH$_2$ |
| cyclobutylmethyl | OH | OH | PhCH$_2$ |
| allyl | OH | OH | PhCH$_2$ |
| H | OH | OH | PhCH$_2$ |
| Me | OH | OH | PhCH$_2$ |

-continued

| | | | |
|---|---|---|---|
| benzyl | OH | OH | PhCH$_2$ |
| 2-phenethyl | OH | OH | PhCH$_2$ |
| cyclopropylmethyl | OH | OH | (F—C$_6$H$_4$)CH$_2$ |
| cyclobutylmethyl | OH | OH | (F—C$_6$H$_4$)CH$_2$ |
| allyl | OH | OH | (F—C$_6$H$_4$)CH$_2$ |
| H | OH | OH | (F—C$_6$H$_4$)CH$_2$ |
| Me | OH | OH | (F—C$_6$H$_4$)CH$_2$ |
| benzyl | OH | OH | (F—C$_6$H$_4$)CH$_2$ |
| 2-phenethyl | OH | OH | (F—C$_6$H$_4$)CH$_2$ |
| cyclopropylmethyl | OH | OH | (Cl—C$_6$H$_4$)CH$_2$ |
| cyclobutylmethyl | OH | OH | (Cl—C$_6$H$_4$)CH$_2$ |
| allyl | OH | OH | (Cl—C$_6$H$_4$)CH$_2$ |
| H | OH | OH | (Cl—C$_6$H$_4$)CH$_2$ |
| Me | OH | OH | (Cl—C$_6$H$_4$)CH$_2$ |
| benzyl | OH | OH | (Cl—C$_6$H$_4$)CH$_2$ |
| 2-phenethyl | OH | OH | (Cl—C$_6$H$_4$)CH$_2$ |
| cyclopropylmethyl | OH | OH | (Br—C$_6$H$_4$)CH$_2$ |
| cyclobutylmethyl | OH | OH | (Br—C$_6$H$_4$)CH$_2$ |
| allyl | OH | OH | (Br—C$_6$H$_4$)CH$_2$ |
| H | OH | OH | (Br—C$_6$H$_4$)CH$_2$ |
| Me | OH | OH | (Br—C$_6$H$_4$)CH$_2$ |
| benzyl | OH | OH | (Br—C$_6$H$_4$)CH$_2$ |
| 2-phenethyl | OH | OH | (Br—C$_6$H$_4$)CH$_2$ |
| cyclopropylmethyl | OH | OH | (Me—C$_6$H$_4$)CH$_3$ |
| cyclobutylmethyl | OH | OH | (Me—C$_9$H$_4$)CH$_3$ |
| allyl | OH | OH | (Me—C$_9$H$_4$)CH$_3$ |
| H | OH | OH | (Me—C$_9$H$_4$)CH$_3$ |
| Me | OH | OH | (Me—C$_9$H$_4$)CH$_3$ |
| benzyl | OH | OH | (Me—C$_9$H$_4$)CH$_3$ |
| 2-phenethyl | OH | OH | (Me—C$_9$H$_4$)CH$_3$ |
| cyclopropylmethyl | OH | OH | (MeO—C$_9$H$_4$)CH$_2$ |
| cyclobutylmethyl | OH | OH | (MeO—C$_6$H$_4$)CH$_2$ |
| allyl | OH | OH | (MeO—C$_6$H$_4$)CH$_2$ |
| H | OH | OH | (MeO—C$_6$H$_4$)CH$_2$ |
| Me | OH | OH | (MeO—C$_9$H$_4$)CH$_2$ |
| benzyl | OH | OH | (MeO—C$_9$H$_4$)CH$_2$ |
| 2-phenethyl | OH | OH | (MeO—C$_9$H$_4$)CH$_2$ |
| cylopropylmethyl | OH | OH | (F$_3$C—C$_9$H$_4$)CH$_2$ |
| cyclobutylmethyl | OH | OH | (F$_3$C—C$_9$H$_4$)CH$_2$ |
| allyl | OH | OH | (F$_3$C—C$_9$H$_4$)CH$_2$ |
| H | OH | OH | (F$_3$C—C$_9$H$_4$)CH$_2$ |
| Me | OH | OH | (F$_3$C—C$_9$H$_4$)CH$_2$ |
| benzyl | OH | OH | (F$_3$C—C$_6$H$_4$)CH$_2$ |
| 2-phenethyl | OH | OH | (F$_3$C—C$_6$H$_4$)CH$_2$ |
| cyclopropylmethyl | OH | OH | (O$_2$N—C$_6$H$_4$)CH$_2$ |
| cyclobutylmethyl | OH | OH | (O$_2$N—C$_6$H$_4$)CH$_2$ |
| allyl | OH | OH | (O$_2$N—C$_6$H$_4$)CH$_2$ |
| H | OH | OH | (O$_2$N—C$_6$H$_4$)CH$_2$ |
| Me | OH | OH | (O$_2$N—C$_6$H$_4$)CH$_2$ |
| benzyl | OH | OH | (O$_2$N—C$_6$H$_4$)CH$_2$ |
| 2-phenethyl | OH | OH | (O$_2$N—C$_6$H$_4$)CH$_2$ |
| cyclopropylmethyl | OH | OH | Ph(CH$_2$)$_2$ |
| cyclobutylmethyl | OH | OH | Ph(CH$_2$)$_2$ |
| allyl | OH | OH | Ph(CH$_2$)$_2$ |
| Me | OH | OH | Ph(CH$_2$)$_2$ |
| benzyl | OH | OH | Ph(CH$_2$)$_2$ |
| 2-phenethyl | OH | OH | Ph(CH$_2$)$_2$ |
| cyclopropylmethyl | OH | OH | Ph(CH$_2$)$_3$ |
| cylobutylmethyl | OH | OH | Ph(CH$_2$)$_3$ |
| allyl | OH | OH | Ph(CH$_2$)$_3$ |
| H | OH | OH | Ph(CH$_2$)$_3$ |
| Me | OH | OH | Ph(CH$_2$)$_3$ |
| benzyl | OH | OH | Ph(CH$_2$)$_3$ |
| 2-phenethyl | OH | OH | Ph(CH$_2$)$_3$ |
| cyclopropylmethyl | OH | OH | PhCO |
| cyclobutylmethyl | OH | OH | PhCO |
| allyl | OH | OH | PhCO |
| H | OH | OH | PhCO |
| Me | OH | OH | PhCO |
| benzyl | OH | OH | PhCO |
| 2-phenethyl | OH | OH | PhCO |
| cyclopropylmethyl | OH | OH | MeSO$_2$ |
| cyclobutylmethyl | OH | OH | MeSO$_2$ |
| allyl | OH | OH | MeSO$_2$ |
| H | OH | OH | MeSO$_2$ |
| Me | OH | OH | MeSO$_2$ |
| benzyl | OH | OH | MeSO$_2$ |
| d2-phenethyl | OH | OH | MeOS$_2$ |
| cyclopropylmethyl | OH | OH | PhSO$_2$ |
| cyclobutylmethyl | OH | OH | PhSO$_2$ |
| allyl | OH | OH | PhSO$_2$ |
| H | OH | OH | PhSO$_2$ |
| Me | OH | OH | PhSO$_2$ |
| benzyl | OH | OH | PhSO$_2$ |
| 2-phenethyl | OH | OH | PhSO$_2$ |

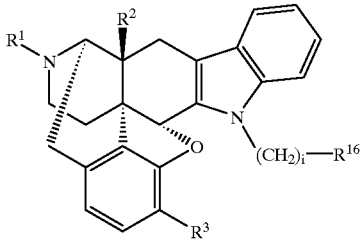

| R$^1$ | R$^2$ | R$^3$ | i | R$^{16}$ |
|---|---|---|---|---|
| cyclopropylmethyl | OH | OH | 2 | OH |
| cyclobutylmethyl | OH | OH | 2 | OH |
| allyl | OH | OH | 2 | OH |
| H | OH | OH | 2 | OH |
| M | OH | OH | 2 | OH |
| benzyl | OH | OH | 2 | OH |
| 2-phenethyl | OH | OH | 2 | OH |
| cyclopropylmethyl | OH | OH | 2 | OMe |
| cyclobutylmethyl | OH | OH | 2 | OMe |
| allyl | OH | OH | 2 | OMe |
| H | OH | OH | 2 | OMe |
| Me | OH | OH | 2 | OMe |
| benzyl | OH | OH | 2 | OMe |
| 2-phenethyl | OH | OH | 2 | OMe |
| cyclopropylmethyl | OH | OH | 2 | OEt |
| cyclobutylmethyl | OH | OH | 2 | OEt |
| allyl | OH | OH | 2 | OEt |
| H | OH | OH | 2 | OEt |
| Me | OH | OH | 2 | OEt |
| benzyl | OH | OH | 2 | OEt |
| 2-phenethyl | OH | OH | 2 | OEt |
| cyclopropylmethyl | OH | OH | 2 | NH$_2$ |
| cyclobutylmethyl | OH | OH | 2 | NH$_2$ |
| allyl | OH | OH | 2 | NH$_2$ |
| H | OH | OH | 2 | NH$_2$ |
| Me | OH | OH | 2 | NH$_2$ |
| benzyl | OH | OH | 2 | NH$_2$ |
| 2-phenethyl | OH | OH | 2 | NH$_2$ |
| cyclopropylmethyl | OH | OH | 2 | NO$_2$ |
| cyclobutylmethyl | OH | OH | 2 | NO$_2$ |
| allyl | OH | OH | 2 | NO$_2$ |
| H | OH | OH | 2 | NO$_2$ |
| Me | OH | OH | 2 | NO$_2$ |
| benzyl | OH | OH | 2 | NO$_2$ |
| 2-phenethyl | OH | OH | 2 | NO$_2$ |
| cyclopropylmethyl | OH | OH | 2 | CN |
| cyclobutylmethyl | OH | OH | 2 | CN |
| allyl | OH | OH | 2 | CN |
| H | OH | OH | 2 | CN |
| Me | OH | OH | 2 | CN |
| benzyl | OH | OH | 2 | CN |
| 2-phenethyl | OH | OH | 2 | CN |
| cyclopropylmethyl | OH | OH | 2 | NCS |
| cyclobutylmethyl | OH | OH | 2 | NCS |
| allyl | OH | OH | 2 | NCS |
| H | OH | OH | 2 | NCS |
| Me | OH | OH | 2 | NCS |
| benzyl | OH | OH | 2 | NCS |
| 2-phenethyl | OH | OH | 2 | NCS |
| cyclopropylmethyl | OH | OH | 2 | COOH |
| cyclobutylmethyl | OH | OH | 2 | COOH |
| allyl | OH | OH | 2 | OCOH |
| H | OH | OH | 2 | OCOH |
| Me | OH | OH | 2 | COOH |
| benzyl | OH | OH | 2 | COOH |
| 2-phenethyl | OH | OH | 2 | COOH |
| cyclopropylmethyl | OH | OH | 2 | COOMe |

-continued

| | | | | |
|---|---|---|---|---|
| cyclobutylmethyl | OH | OH | 2 | COOMe |
| allyl | OH | OH | 2 | COOMe |
| H | OH | OH | 2 | COOMe |
| Me | OH | OH | 2 | COOMe |
| benzyl | OH | OH | 2 | COOMe |
| 2-phenethyl | OH | OH | 2 | COOMe |
| cyclopropylmethyl | OH | OH | 2 | COOEt |
| cyclobutylmethyl | OH | OH | 2 | COOEt |
| allyl | OH | OH | 2 | COOEt |
| H | OH | OH | 2 | COOEt |
| Me | OH | OH | 2 | COOEt |
| benzyl | OH | OH | 2 | COOEt |
| 2-phenethyl | OH | OH | 2 | COOEt |
| cyclopropylmetnyl | OH | OH | 2 | NHCHO |
| cyclobutylmethyl | OH | OH | 2 | NHCHO |
| allyl | OH | OH | 2 | NHCHO |
| H | OH | OH | 2 | NHCHO |
| Me | OH | OH | 2 | NHCHO |
| benzyl | OH | OH | 2 | NHCHO |
| 2-phenethyl | OH | OH | 2 | NHCHO |
| cylopropylmethyl | OH | OH | 2 | NHCO—Me |
| cyclobutylmethyl | OH | OH | 2 | NHCO—Me |
| allyl | OH | OH | 2 | NHCO—Me |
| H | OH | OH | 2 | NHCO—Me |
| benzyl | OH | OH | 2 | NHCO—Me |
| 2-phenethyl | OH | OH | 2 | NHCO—Me |
| cyclopropylmethyl | OH | OH | 2 | NHCO—Ph |
| cyclobutylmethyl | OH | OH | 2 | NHCO—Ph |
| allyl | OH | OH | 2 | NHCO—Ph |
| H | OH | OH | 2 | NHCO—Ph |
| Me | OH | OH | 2 | NHCO—Ph |
| benzyl | OH | OH | 2 | NHCO—Ph |
| 2-phenethyl | OH | OH | 2 | NHCO—Ph |
| cyclopropylmethyl | OH | OH | 2 | NHCO—(CH$_2$)$_5$Ph |
| cyclobutylmethyl | OH | OH | 2 | NHCO—(CH$_2$)$_5$Ph |
| allyl | OH | OH | 2 | NHCO—(CH$_2$)$_5$Ph |
| H | OH | OH | 2 | NHCO—(CH$_2$)$_5$Ph |
| Me | OH | OH | 2 | NHCO—(CH$_2$)$_5$Ph |
| benzyl | OH | OH | 2 | NHCO—(CH$_2$)$_5$Ph |
| 2-phenethyl | OH | OH | 2 | NHCO—(CH$_2$)$_5$Ph |
| cyclopropylmethyl | OH | OH | 2 | NHCO-cinnamyl |
| cyclobutylmethyl | OH | OH | 2 | NHCO-cinnamyl |
| allyl | OH | OH | 2 | NHCO-cinnamyl |
| H | OH | OH | 2 | NHCO-cinnamyl |
| Me | OH | OH | 2 | NHCO-cinnamyl |
| benzyl | OH | OH | 2 | NHCO-cinnamyl |
| 2-phenethyl | OH | OH | 2 | NHCO-cinnamyl |
| cyclopropylmethyl | OH | OH | 2 | NHCO—(CF$_3$-cinnamyl) |
| cyclobutylmethyl | OH | OH | 2 | NHCO—(CF$_3$-cinnamyl) |
| allyl | OH | OH | 2 | NHCO—(CF$_3$-cinnamyl) |
| H | OH | OH | 2 | NHCO—(CF$_3$-cinnamyl) |
| Me | OH | OH | 2 | NHCO—(CF$_3$-cinnamyl) |
| benzyl | OH | OH | 2 | NHCO—(CF$_3$-cinnamyl) |
| 2-phenethyl | OH | OH | 2 | NHCO—(CF$_3$-cinnamyl) |
| cyclopropylmethyl | OH | OH | 2 | NHCO-pyridyl |
| cyclobutylmethyl | OH | OH | 2 | NHCO-pyridyl |
| allyl | OH | OH | 2 | NHCO-pyridyl |
| H | OH | OH | 2 | NHCO-pyridyl |
| Me | OH | OH | 2 | NHCO-pyridyl |
| benzyl | OH | OH | 2 | NHCO-pyridyl |
| 2-phenethyl | OH | OH | 2 | NHCO-pyridyl |
| cyclopropylmethyl | OH | OH | 2 | NHCO—NHPh |
| cyclobutylmethyl | OH | OH | 2 | NHCO—NHPh |
| allyl | OH | OH | 2 | NHCO—NHPh |
| H | OH | OH | 2 | NHCO—NHPh |
| Me | OH | OH | 2 | NHCO—NHPh |
| benzyl | OH | OH | 2 | NHCO—NHPh |
| 2-phenethyl | OH | OH | 2 | NHCO—NHPh |
| cyclopropylmethyl | OH | OH | 2 | NHCS—NHPh |
| cyclobutylmethyl | OH | OH | 2 | NHCS—NHPh |
| allyl | OH | OH | 2 | NHCS—NHPh |
| H | OH | OH | 2 | NHCS—NHPh |
| Me | OH | OH | 2 | NHCS—NHPh |
| benzyl | OH | OH | 2 | NHCS—NHPh |
| 2-phenethyl | OH | OH | 2 | NHCS—NHPh |
| cyclopropylmethyl | OH | OH | 2 | NHCS—NHCH$_2$Ph |
| cyclobutylmethyl | OH | OH | 2 | NHCS—NHCH$_2$Ph |
| allyl | OH | OH | 2 | NHCS—NHCH$_2$Ph |
| H | OH | OH | 2 | NHCS—NHCH$_2$Ph |
| Me | OH | OH | 2 | NHCS—NHCH$_2$Ph |
| benzyl | OH | OH | 2 | NHCS—NHCH$_2$Ph |
| 2-phenethyl | OH | OH | 2 | NHCS—NHCH$_2$Ph |
| cyclopropylmethyl | OH | OH | 3 | OH |
| cyclobutylmethyl | OH | OH | 3 | OH |
| allyl | OH | OH | 3 | OH |
| H | OH | OH | 3 | OH |
| Me | OH | OH | 3 | OH |
| benzyl | OH | OH | 3 | OH |
| 2-phenethl | OH | OH | 3 | OH |
| cyclopropylmethyl | OH | OH | 3 | OMe |
| cyclobutylmethyl | OH | OH | 3 | OMe |
| allyl | OH | OH | 3 | OMe |
| H | OH | OH | 3 | OMe |
| Me | OH | OH | 3 | OMe |
| benzyl | OH | OH | 3 | OMe |
| 2-phenethyl | OH | OH | 3 | OMe |
| cyclopropylmethyl | OH | OH | 3 | OEt |
| cyclobutylmethyl | OH | OH | 3 | OEt |
| allyl | OH | OH | 3 | OEt |
| H | OH | OH | 3 | OEt |
| Me | OH | OH | 3 | OEt |
| benzyl | OH | OH | 3 | OEt |
| 2-phenethyl | OH | OH | 3 | OEt |
| cyclopropylmethyl | OH | OH | 3 | NH$_2$ |
| cyclobutylmethyl | OH | OH | 3 | NH$_2$ |
| allyl | OH | OH | 3 | NH$_2$ |
| H | OH | OH | 3 | NH$_2$ |
| Me | OH | OH | 3 | NH$_2$ |
| benzyl | OH | OH | 3 | NH$_2$ |
| 2-phenethyl | OH | OH | 3 | NH$_3$ |
| cyclopropylmethyl | OH | OH | 3 | NO$_2$ |
| cyclobutylmethyl | OH | OH | 3 | NO$_2$ |
| allyl | OH | OH | 3 | NO$_2$ |
| H | OH | OH | 3 | NO$_2$ |
| Me | OH | OH | 3 | NO$_2$ |
| benzyl | OH | OH | 3 | NO$_2$ |
| 2-phenethyl | OH | OH | 3 | NO$_2$ |
| cyclopropylmethyl | OH | OH | 3 | CN |
| allyl | OH | OH | 3 | CN |
| H | OH | OH | 3 | CN |
| Me | OH | OH | 3 | CN |
| benzyl | OH | OH | 3 | CN |
| 2-phenethyl | OH | OH | 3 | CN |
| cyclopropylmethyl | OH | OH | 3 | NCS |
| cyclobutylmethyl | OH | OH | 3 | NCS |
| allyl | OH | OH | 3 | NCS |
| H | OH | OH | 3 | NCS |
| Me | OH | OH | 3 | NCS |
| benzyl | OH | OH | 3 | NCS |
| 2-phenethyl | OH | OH | 3 | NCS |
| cyclopropylmethyl | OH | OH | 3 | COOH |
| cyclobutylmethyl | OH | OH | 3 | COOH |
| allyl | OH | OH | 3 | COOH |
| H | OH | OH | 3 | COOH |
| Me | OH | OH | 3 | COOH |
| benzyl | OH | OH | 3 | COOH |
| 2-phenethyl | OH | OH | 3 | COOH |
| cyclopropylmethyl | OH | OH | 3 | COOMe |
| cyclobutylmethyl | OH | OH | 3 | COOMe |
| allyl | OH | OH | 3 | COOMe |
| H | OH | OH | 3 | COOMe |
| Me | OH | OH | 3 | COOMe |
| benzyl | OH | OH | 3 | COOMe |
| 2-phenethyl | OH | OH | 3 | COOMe |
| cyclopropylmethyl | OH | OH | 3 | COOEt |
| cyclobutylmethyl | OH | OH | 3 | COOEt |
| allyl | OH | OH | 3 | COOEt |
| H | OH | OH | 3 | COOEt |
| Me | OH | OH | 3 | COOEt |
| benzyl | OH | OH | 3 | COOEt |
| 2-phenethyl | OH | OH | 3 | COOEt |
| cyclopropylmethyl | OH | OH | 3 | NHCHO |
| cyclobutylmethyl | OH | OH | 3 | NHCHO |
| allyl | OH | OH | 3 | NHCHO |
| H | OH | OH | 3 | NHCHO |
| Me | OH | OH | 3 | NHCHO |
| benzyl | OH | OH | 3 | NHCHO |
| 2-phenethyl | OH | OH | 3 | NHCHO |

-continued

| | | | | |
|---|---|---|---|---|
| cyclopropylmethyl | OH | OH | 3 | NHCO—Me |
| cyclobutylmethyl | OH | OH | 3 | NHCO—Me |
| allyl | OH | OH | 3 | NHCO—Me |
| H | OH | OH | 3 | NHCO—Me |
| Me | OH | OH | 3 | NHCO—Me |
| benzyl | OH | OH | 3 | NHCO—Me |
| 2-phenethyl | OH | OH | 3 | NHCO—Me |
| cyclopropylmethyl | OH | OH | 3 | NHCO—Ph |
| cyclobutylmethyl | OH | OH | 3 | NHCO—Ph |
| allyl | OH | OH | 3 | NHCO—Ph |
| H | OH | OH | 3 | NHCO—Ph |
| Me | OH | OH | 3 | NHCO—Ph |
| benzyl | OH | OH | 3 | NHCO—Ph |
| 2-phenethyl | OH | OH | 3 | NHCO—Ph |
| cyclopropylmethyl | OH | OH | 3 | NHCO—(CH$_2$)$_5$Ph |
| cyclobutylmethyl | OH | OH | 3 | NHCO—(CH$_2$)$_5$Ph |
| allyl | OH | OH | 3 | NHCO—(CH$_2$)$_5$Ph |
| H | OH | OH | 3 | NHCO—(CH$_2$)$_5$Ph |
| Me | OH | OH | 3 | NHCO—(CH$_2$)$_5$Ph |
| benzyl | OH | OH | 3 | NHCO—(CH$_2$)$_5$Ph |
| 2-phenethyl | OH | OH | 3 | NHCO—(CH$_2$)$_5$Ph |
| cyclopropylmethyl | OH | OH | 3 | NHCO-cinnamyl |
| cyclobutylmethyl | OH | OH | 3 | NHCO-cinnamyl |
| allyl | OH | OH | 3 | NHCO-cinnamyl |
| H | OH | OH | 3 | NHCO-cinnamyl |
| Me | OH | OH | 3 | NHCO-cinnamyl |
| benzyl | OH | OH | 3 | NHCO-cinnamyl |
| 2-phenethyl | OH | OH | 3 | NHCO-cinnamyl |
| cyclopropylethyl | OH | OH | 3 | NHCO—(CF$_3$-cinnamyl) |
| cyclobutylmethyl | OH | OH | 3 | NHCO—(CF$_3$-cinnamyl) |
| allyl | OH | OH | 3 | NHCO—(CF$_3$-cinnamyl) |
| H | OH | OH | 3 | NHCO—(CF$_3$-cinnamyl) |
| Me | OH | OH | 3 | NHCO—(CF$_3$-cinnamyl) |
| benzyl | OH | OH | 3 | NHCO—(CF$_3$-cinnamyl) |
| 2-phenethyl | OH | OH | 3 | NHCO—(CF$_3$-cinnamyl) |
| cyclopropylmethyl | OH | OH | 3 | NHCO-pyridyl |
| cyclobutylmethyl | OH | OH | 3 | NHCO-pyridyl |
| allyl | OH | OH | 3 | NHCO-pyridyl |
| H | OH | OH | 3 | NHCO-pyridyl |
| Me | OH | OH | 3 | NHCO-pyridyl |
| benzyl | OH | OH | 3 | NHCO-pyridyl |
| 2-phenethyl | OH | OH | 3 | NHCO-pyridyl |
| cyclopropylmethyl | OH | OH | 3 | NHCO—NHPh |
| cyclobutylmethyl | OH | OH | 3 | NHCO—NHPh |
| allyl | OH | OH | 3 | NHCO—NHPh |
| H | OH | OH | 3 | NHCO—NHPh |
| Me | OH | OH | 3 | NHCO—NHPh |
| benzyl | OH | OH | 3 | NHCO—NHPh |
| 2-phenethyl | OH | OH | 3 | NHCO—NHPh |
| cyclopropylmethyl | OH | OH | 3 | NHCS—NHPh |
| cyclobutylmethyl | OH | OH | 3 | NHCS—NHPh |
| allyl | OH | OH | 3 | NHCS—NHPh |
| H | OH | OH | 3 | NHCS—NHPh |
| Me | OH | OH | 3 | NHCS—NHPh |
| benzyl | OH | OH | 3 | NHCS—NHPh |
| 2-phenethyl | OH | OH | 3 | NHCS—NHPh |
| cyclopropylmethyl | OH | OH | 3 | NHCS—NHCH$_2$Ph |
| cyclobutylmethyl | OH | OH | 3 | NHCS—NHCH$_2$Ph |
| allyl | OH | OH | 3 | NHCS—NHCH$_2$Ph |
| H | OH | OH | 3 | NHCS—NHCH$_2$Ph |
| Me | OH | OH | 3 | NHCS—NHCH$_2$Ph |
| benzyl | OH | OH | 3 | NHCS—NHCH$_2$Ph |
| 2-phenethyl | OH | OH | 3 | NHCS—NHCH$_2$Ph |
| cyclopropylmethyl | OH | OH | 4 | OH |
| cyclobutylmethyl | OH | OH | 4 | OH |
| allyl | OH | OH | 4 | OH |
| H | OH | OH | 4 | OH |
| Me | OH | OH | 4 | OH |
| benzyl | OH | OH | 4 | OH |
| 2-phenethyl | OH | OH | 4 | OH |
| cyclopropylmethyl | OH | OH | 4 | OMe |
| cyclopropylmethyl | OH | OH | 4 | OMe |
| cyclobutylmethyl | OH | OH | 4 | OMe |
| allyl | OH | OH | 4 | OMe |
| H | OH | OH | 4 | OMe |
| Me | OH | OH | 4 | OMe |
| benzyl | OH | OH | 4 | OMe |
| 2-phenethyl | OH | OH | 4 | OMe |
| cyclopropylmethyl | OH | OH | 4 | OEt |
| cyclobutylmethyl | OH | OH | 4 | OEt |
| allyl | OH | OH | 4 | OEt |
| H | OH | OH | 4 | OEt |
| Me | OH | OH | 4 | OEt |
| benzyl | OH | OH | 4 | OEt |
| 2-phenethyl | OH | OH | 4 | OEt |
| cyclopropylmethyl | OH | OH | 4 | NH$_2$ |
| cyclobutylmethyl | OH | OH | 4 | NH$_2$ |
| allyl | OH | OH | 4 | NH$_2$ |
| H | OH | OH | 4 | NH$_2$ |
| Me | OH | OH | 4 | NH$_2$ |
| benzyl | OH | OH | 4 | NH$_2$ |
| 2-phenethyl | OH | OH | 4 | NH$_2$ |
| cyclopropylmethyl | OH | OH | 4 | NO$_2$ |
| cyclobutylmethyl | OH | OH | 4 | NO$_2$ |
| allyl | OH | OH | 4 | NO$_2$ |
| H | OH | OH | 4 | NO$_2$ |
| Me | OH | OH | 4 | NO$_2$ |
| benzyl | OH | OH | 4 | NO$_2$ |
| 2-phenethyl | OH | OH | 4 | NO$_2$ |
| cyclopropylmethyl | OH | OH | 4 | CN |
| cyclobutylmethyl | OH | OH | 4 | CN |
| allyl | OH | OH | 4 | CN |
| H | OH | OH | 4 | CN |
| Me | OH | OH | 4 | CN |
| benzyl | OH | OH | 4 | CN |
| 2-phenethyl | OH | OH | 4 | CN |
| cyclopropylmethyl | OH | OH | 4 | NCS |
| cyclobutylmethyl | OH | OH | 4 | NCS |
| allyl | OH | OH | 4 | NCS |
| H | OH | OH | 4 | NCS |
| H | OH | OH | 4 | NCS |
| Me | OH | OH | 4 | NCS |
| benzyl | OH | OH | 4 | NCS |
| 2-phenethyl | OH | OH | 4 | NCS |
| cyclopropylmethyl | OH | OH | 4 | COOH |
| cyclobutylmethyl | OH | OH | 4 | COOH |
| allyl | OH | OH | 4 | COOH |
| H | OH | OH | 4 | COOH |
| H | OH | OH | 4 | COOH |
| Me | OH | OH | 4 | OCOH |
| benzyl | OH | OH | 4 | COOH |
| 2-phenethyl | OH | OH | 4 | COOH |
| cyclopropylmethyl | OH | OH | 4 | OCOMe |
| cyclobutylmethyl | OH | OH | 4 | COOMe |
| allyl | OH | OH | 4 | COOMe |
| H | OH | OH | 4 | COOMe |
| Me | OH | OH | 4 | COOMe |
| benzyl | OH | OH | 4 | COOMe |
| 2-phenethyl | OH | OH | 4 | COOMe |
| cyclopropylmethyl | OH | OH | 4 | COOEt |
| cyclobutylmethyl | OH | OH | 4 | COOEt |
| allyl | OH | OH | 4 | COOEt |
| H | OH | OH | 4 | COOEt |
| Me | OH | OH | 4 | COOEt |
| benzyl | OH | OH | 4 | COOEt |
| 2-phenethyl | OH | OH | 4 | COOEt |
| cyclopropylmethyl | OH | OH | 4 | NHCHO |
| cyclobutylmethyl | OH | OH | 4 | NHCHO |
| allyl | OH | OH | 4 | NHCHO |
| H | OH | OH | 4 | NHCHO |
| Me | OH | OH | 4 | NHCHO |
| benzyl | OH | OH | 4 | NHCHO |
| 2-phenethyl | OH | OH | 4 | NHCHO |
| cyclopropylmethyl | OH | OH | 4 | NHCO—Me |
| cyclobutylmethyl | OH | OH | 4 | NHCO—Me |
| allyl | OH | OH | 4 | NHCO—Me |
| H | OH | OH | 4 | NHCO—Me |
| Me | OH | OH | 4 | NHCO—Me |
| benzyl | OH | OH | 4 | NHCO—Me |
| 2-phenethyl | OH | OH | 4 | NHCO—Me |
| cyclopropylmethyl | OH | OH | 4 | NHCO—Ph |
| cyclobutylmethyl | OH | OH | 4 | NHCO—Ph |
| allyl | OH | OH | 4 | NHCO—Ph |
| H | OH | OH | 4 | NHCO—Ph |
| Me | OH | OH | 4 | NHCO—Ph |
| benzyl | OH | OH | 4 | NHCO—Ph |
| 2-phenethyl | OH | OH | 4 | NHCO—Ph |
| cyclopropylmethyl | OH | OH | 4 | NHCO—(CH$_2$)$_5$Ph |

-continued

| R¹ | R² | R³ | | R⁵ |
|---|---|---|---|---|
| cyclobutylmethyl | OH | OH | 4 | NHCO—(CH₂)₅Ph |
| allyl | OH | OH | 4 | NHCO—(CH₂)₅Ph |
| H | OH | OH | 4 | NHCO—(CH₂)₅Ph |
| Me | OH | OH | 4 | NHCO—(CH₂)₅Ph |
| benzyl | OH | OH | 4 | NHCO—(CH₂)₅Ph |
| 2-phenethyl | OH | OH | 4 | NHCO—(CH₂)₅Ph |
| cyclopropylmethyl | OH | OH | 4 | NHCO-cinnamyl |
| cyclobutylmethyl | OH | OH | 4 | NHCO-cinnamyl |
| allyl | OH | OH | 4 | NHCO-cinnamyl |
| H | OH | OH | 4 | NHCO-cinnamyl |
| Me | OH | OH | 4 | NHCO-cinnamyl |
| benzyl | OH | OH | 4 | NHCO-cinnamyl |
| 2-phenethyl | OH | OH | 4 | NHCO-cinnamyl |
| cyclopropylmethyl | OH | OH | 4 | NHCO—(CF₃-cinnamyl) |
| cyclobutylmethyl | OH | OH | 4 | NHCO—(CF₃-cinnamyl) |
| allyl | OH | OH | 4 | NHCO—(CF₃-cinnamyl) |
| H | OH | OH | 4 | NHCO—(CF₃-cinnamyl) |
| Me | OH | OH | 4 | NHCO—(CF₃-cinnamyl) |
| benzyl | OH | OH | 4 | NHCO—(CF₃-cinnamyl) |
| 2-phenethyl | OH | OH | 4 | NHCO—(CF₃-cinnamyl) |
| cyclopropylmethyl | OH | OH | 4 | NHCO-pyridyl |
| cyclobutylmethyl | OH | OH | 4 | NHCO-pyridyl |
| allyl | OH | OH | 4 | NHCO-pyridyl |
| H | OH | OH | 4 | NHCO-pyridyl |
| Me | OH | OH | 4 | NHCO-pyridyl |
| benzyl | OH | OH | 4 | NHCO-pyridyl |
| 2-phenethyl | OH | OH | 4 | NHCO-pyridyl |
| cyclopropylmethyl | OH | OH | 4 | NHCO—NHPh |
| cyclobutylmethyl | OH | OH | 4 | NHCO—NHPh |
| allyl | OH | OH | 4 | NHCO—NHPh |
| H | OH | OH | 4 | NHCO—NHPh |
| Me | OH | OH | 4 | NHCO—NHPh |
| benzyl | OH | OH | 4 | NHCO—NHPh |
| 2-phenethyl | OH | OH | 4 | NHCO—NHPh |
| cyclopropylmethyl | OH | OH | 4 | NHCS—NHPh |
| cyclobutylmethyl | OH | OH | 4 | NHCS—NHPh |
| allyl | OH | OH | 4 | NHCS—NHPh |
| H | OH | OH | 4 | NHCS—NHPh |
| Me | OH | OH | 4 | NHCS—NHPh |
| benzyl | OH | OH | 4 | NHCS—NHPh |
| 2-phenethyl | OH | OH | 4 | NHCS—NHPh |
| cyclopropylmethyl | OH | OH | 4 | NHCS—NHCH₂Ph |
| cyclobutylmethyl | OH | OH | 4 | NHCS—NHCH₂Ph |
| allyl | OH | OH | 4 | NHCS—NHCH₂Ph |
| H | OH | OH | 4 | NHCS—NHCH₂Ph |
| Me | OH | OH | 4 | NHCS—NHCH₂Ph |
| benzyl | OH | OH | 4 | NHCS—NHCH₂Ph |
| 2-phenethyl | OH | OH | 4 | NHCS—NHCH₂Ph |
| cyclopropylmethyl | OH | OMe | 3 | OH |
| cyclopropylmethyl | OH | OMe | 3 | OMe |
| cyclopropylmethyl | OH | OMe | 3 | NH₂ |
| cyclopropylmethyl | OH | OMe | 3 | CN |
| cyclopropylmethyl | OH | OMe | 3 | NCS |
| cyclopropylmethyl | OH | OMe | 3 | COOH |
| cyclopropylmethyl | OH | OMe | 3 | COOMe |
| cyclopropylmethyl | OH | OMe | 3 | NHCHO |
| cyclopropylmethyl | OH | OMe | 3 | NHCH—Ph |
| cyclopropylmethyl | OH | OMe | 3 | NHCO—(CH₂)₅Ph |
| cyclopropylmethyl | OH | OMe | 3 | NHCO—(CF₃-cinnamyl) |
| cyclopropylmethyl | OH | OMe | 3 | NHCO-pyridyl |
| cyclopropylmethyl | OH | OMe | 3 | NHCO—NHPh |
| cyclopropylmethyl | OH | OMe | 3 | NHCS—NHPh |
| cyclopropylmethyl | OH | OMe | 4 | OH |
| cyclopropylmethyl | OH | OMe | 4 | OMe |
| cyclopropylmethyl | OH | OMe | 4 | NH₂ |
| cyclopropylmethyl | OH | OMe | 4 | CN |
| cyclopropylmethyl | OH | OMe | 4 | NCS |
| cyclopropylmethyl | OH | OMe | 4 | COOH |
| cyclopropylmethyl | OH | OMe | 4 | COOMe |
| cyclopropylmethyl | OH | OMe | 4 | NHCHO |
| cyclopropylmethyl | OH | OMe | 4 | NHCO—Ph |
| cyclopropylmethyl | OH | OMe | 4 | NHCO—(CH₂)₅Ph |
| cyclopropylmethyl | OH | OMe | 4 | NHCO—(CF₃-cinnamyl) |
| cyclopropylmethyl | OH | OMe | 4 | NHCO-pyridyl |
| cyclopropylmethyl | OH | OMe | 4 | NHCO—NHPh |
| cyclopropylmethyl | OH | OMe | 4 | NHCS—NHPh |

-continued

| R¹ | R² | R³ | R⁴ |
|---|---|---|---|
| cyclopropylmethyl | OH | OH | H |
| cyclobutylmethyl | OH | OH | H |
| allyl | OH | OH | H |
| H | OH | OH | H |
| benzyl | OH | OH | H |
| 2-phenethyl | OH | OH | H |
| cyclopropylmethyl | OH | OH | Me |
| cyclobutylmethyl | OH | OH | Me |
| allyl | OH | OH | Me |
| H | OH | OH | Me |
| Me | OH | OH | Me |
| benzyl | OH | OH | Me |
| 2-phenethyl | OH | OH | Me |
| cyclopropylmethyl | OH | OH | Bu |
| cyclobutylmethyl | OH | OH | Bu |
| allyl | OH | OH | Bu |
| H | OH | OH | Bu |
| Me | OH | OH | Bu |
| benzyl | OH | OH | Bu |
| 2-phenethyl | OH | OH | Bu |
| cyclopropylmethyl | OH | OH | PhCH₂ |
| cyclobutylmethyl | OH | OH | PhCH₂ |
| allyl | OH | OH | PhCH₂ |
| H | OH | OH | PhCH₂ |
| Me | OH | OH | PhCH₂ |
| benzyl | OH | OH | PhCH₂ |
| 2-phenethyl | OH | OH | PhCH₂ |
| cyclopropylmethyl | OH | OH | (F—C₆H₄)CH₂ |
| cyclobutylmethyl | OH | OH | (F—C₆H₄)CH₂ |
| allyl | OH | OH | (F—C₆H₄)CH₂ |
| H | OH | OH | (F—C₆H₄)CH₂ |
| Me | OH | OH | (F—C₆H₄)CH₂ |
| benzyl | OH | OH | (F—C₆H₄)CH₂ |
| 2-phenethyl | OH | OH | (F—C₆H₄)CH₂ |
| cyclopropylmethyl | OH | OH | (Cl—C₆H₄)CH₂ |
| cyclobutylmethyl | OH | OH | (Cl—C₆H₄)CH₂ |
| allyl | OH | OH | (Cl—C₆H₄)CH₂ |
| H | OH | OH | (Cl—C₆H₄)CH₂ |
| Me | OH | OH | (Cl—C₆H₄)CH₂ |
| benzyl | OH | OH | (Cl—C₆H₄)CH₂ |
| 2-phenethyl | OH | OH | (Cl—C₆H₄)CH₂ |
| cyclopropylmethyl | OH | OH | (Br—C₆H₄)CH₂ |
| cyclobutylmethyl | OH | OH | (Br—C₆H₄)CH₂ |
| allyl | OH | OH | (Br—C₉H₄)CH₂ |
| H | OH | OH | (Br—C₉H₄)CH₂ |
| Me | OH | OH | (Be—C₆H₄)CH₂ |
| benzyl | OH | OH | (Br—C₆H₄)CH₂ |
| 2-phenethyl | OH | OH | (Br—C₆H₄)CH₂ |
| cyclopropylmethyl | OH | OH | (Me—C₆H₄)CH₂ |
| cyclobutylmethyl | OH | OH | (Me—C₉H₄)CH₂ |
| allyl | OH | OH | (Me—C₉H₄)CH₂ |
| H | OH | OH | (Me—C₉H₄)CH₂ |
| Me | OH | OH | (Me—C₉H₄)CH₂ |
| benzyl | OH | OH | (Me—C₉H₄)CH₂ |
| 2-phenethyl | OH | OH | (Me—C₉H₄)CH₂ |
| cyclopropylmethyl | OH | OH | (MeO—C₆H₄)CH₂ |
| cyclobutylmethyl | OH | OH | (MeO—C₆H₄)CH₂ |
| allyl | OH | OH | (MeO—C₆H₄)CH₂ |
| H | OH | OH | (MeO—C₆H₄)CH₂ |
| Me | OH | OH | (MeO—C₅H₄)CH₂ |
| benzyl | OH | OH | (MeO—C₆H₄)CH₂ |
| 2-phenethyl | OH | OH | (MeO—C₆H₄)CH₂ |
| cyclopropylmethyl | OH | OH | (F₃C—C₆H₄)CH₂ |
| cyclobutylmethyl | OH | OH | (F₃C—C₆H₄)CH₂ |

-continued

| R¹ | R² | R³ | R¹⁶ |
|---|---|---|---|
| allyl | OH | OH | (F₃C—C₆H₄)CH₂ |
| H | OH | OH | (F₃C—C₆H₄)CH₂ |
| Me | OH | OH | (F₃C—C₆H₄)CH₂ |
| benzyl | OH | OH | (F₃C—C₆H₄)CH₂ |
| 2-phenethyl | OH | OH | (F₃C—C₆H₄)CH₂ |
| cyclopropylmethyl | OH | OH | (O₂N—C₆H₄)CH₂ |
| cyclobutylmethyl | OH | OH | (O₂N—C₆H₄)CH₂ |
| allyl | OH | OH | (O₂N—C₆H₄)CH₂ |
| H | OH | OH | (O₂N—C₅H₆)CH₂ |
| Me | OH | OH | (O₂N—C₆H₄)CH₂ |
| benzyl | OH | OH | (O₂N—C₆H₄)CH₂ |
| 2-phenethyl | OH | OH | (O₂N—C₆H₄)CH₂ |
| cyclopropylmethyl | OH | OH | Ph(CH₂)₂ |
| cyclobutylmethyl | OH | OH | Ph(CH₂)₂ |
| allyl | OH | OH | Ph(CH₂)₂ |
| H | OH | OH | Ph(CH₂)₂ |
| Me | OH | OH | Ph(CH₂)₂ |
| benzyl | OH | OH | Ph(CH₂)₂ |
| 2-phenethyl | OH | OH | Ph(CH₂)₂ |
| cyclopropylmethyl | OH | OH | Ph(CH₂)₃ |
| cyclobutylmethyl | OH | OH | Ph(CH₂)₃ |
| allyl | OH | OH | Ph(CH₂)₃ |
| H | OH | OH | Ph(CH₂)₃ |
| Me | OH | OH | Ph(CH₂)₃ |
| benzyl | OH | OH | Ph(CH₂)₃ |
| 2-phenethyl | OH | OH | Ph(CH₂)₃ |
| cyclopropylmethyl | OH | OH | PhCO |
| cyclobutylmethyl | OH | OH | PhCO |
| allyl | OH | OH | PhCO |
| H | OH | OH | PhCO |
| Me | OH | OH | PhCO |
| benzyl | OH | OH | PhCO |
| 2-phenethyl | OH | OH | PhCO |
| cyclopropylmethyl | OH | OH | MeSO₂ |
| cyclobutylmethyl | OH | OH | MeSO₂ |
| allyl | OH | OH | MeSO₂ |
| H | OH | OH | MeSO₂ |
| Me | OH | OH | MeSO₂ |
| benzyl | OH | OH | MeSO₂ |
| 2-phenethyl | OH | OH | MeSO₂ |
| cyclopropylmethyl | OH | OH | PhSO₂ |
| cyclobutylmethyl | OH | OH | PhSO₂ |
| allyl | OH | OH | PhSO₂ |
| H | OH | OH | PhSO₂ |
| Me | OH | OH | PhSO₂ |
| benzyl | OH | OH | PhSO₂ |
| 2-phenethyl | OH | OH | PhSO₂ |

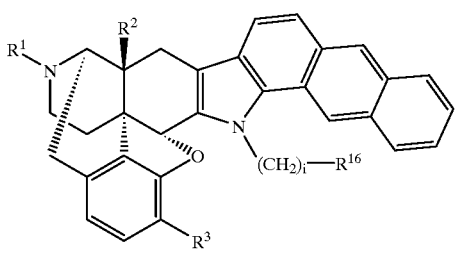

| R¹ | R² | R³ | i | R¹⁶ |
|---|---|---|---|---|
| cyclopropylmethyl | OH | OH | 2 | OH |
| cyclobutylmethyl | OH | OH | 2 | OH |
| allyl | OH | OH | 2 | OH |
| H | OH | OH | 2 | OH |
| Me | OH | OH | 2 | OH |
| benzyl | OH | OH | 2 | OH |
| 2-phenethyl | OH | OH | 2 | OH |
| cyclopropylmethyl | OH | OH | 2 | OMe |
| cylobutylmethyl | OH | OH | 2 | OMe |
| allyl | OH | OH | 2 | OMe |
| H | OH | OH | 2 | OMe |
| Me | OH | OH | 2 | OMe |
| benzyl | OH | OH | 2 | OMe |
| 2-phenethyl | OH | OH | 2 | OMe |
| cyclopropylmethyl | OH | OH | 2 | OEt |
| cyclobutylmethyl | OH | OH | 2 | OEt |
| allyl | OH | OH | 2 | OEt |
| H | OH | OH | 2 | OEt |
| Me | OH | OH | 2 | OEt |
| benzyl | OH | OH | 2 | OEt |
| 2-phenethyl | OH | OH | 2 | OEt |
| cyclopropylmethyl | OH | OH | 2 | NH₂ |
| cyclobutylmethyl | OH | OH | 2 | NH₂ |
| allyl | OH | OH | 2 | NH₂ |
| H | OH | OH | 2 | NH₂ |
| Me | OH | OH | 2 | NH₂ |
| benzyl | OH | OH | 2 | NH₂ |
| 2-phenethyl | OH | OH | 2 | NH₂ |
| cyclopropylmethyl | OH | OH | 2 | NO₂ |
| cyclobutylmethyl | OH | OH | 2 | NO₂ |
| allyl | OH | OH | 2 | NO₂ |
| H | OH | OH | 2 | NO₂ |
| Me | OH | OH | 2 | NO₂ |
| benzyl | OH | OH | 2 | NO₂ |
| 2-phenethyl | OH | OH | 2 | NO₂ |
| cyclopropylmethyl | OH | OH | 2 | CN |
| cyclobutylmethyl | OH | OH | 2 | CN |
| allyl | OH | OH | 2 | CN |
| H | OH | OH | 2 | CN |
| Me | OH | OH | 2 | CN |
| benzyl | OH | OH | 2 | CN |
| 2-phenethyl | OH | OH | 2 | CN |
| cyclopropylmethyl | OH | OH | 2 | NCS |
| cyclobutylmethyl | OH | OH | 2 | NCS |
| allyl | OH | OH | 2 | NCS |
| H | OH | OH | 2 | NCS |
| Me | OH | OH | 2 | NCS |
| benzyl | OH | OH | 2 | NCS |
| 2-phenethyl | OH | OH | 2 | NCS |
| cyclopropylmethyl | OH | OH | 2 | COOH |
| cyclobutylmethyl | OH | OH | 2 | COOH |
| allyl | OH | OH | 2 | COOH |
| H | OH | OH | 2 | COOH |
| Me | OH | OH | 2 | COOH |
| benzyl | OH | OH | 2 | COOH |
| 2-phenethyl | OH | OH | 2 | COOH |
| cyclopropylmethyl | OH | OH | 2 | COOMe |
| cyclobutylmethyl | OH | OH | 2 | COOMe |
| allyl | OH | OH | 2 | COOMe |
| H | OH | OH | 2 | COOMe |
| Me | OH | OH | 2 | COOMe |
| benzyl | OH | OH | 2 | COOMe |
| 2-phenethyl | OH | OH | 2 | COOMe |
| cyclopropylmethyl | OH | OH | 2 | COOEt |
| cyclobutylmethyl | OH | OH | 2 | COOEt |
| allyl | OH | OH | 2 | COOEt |
| H | OH | OH | 2 | COOEt |
| Me | OH | OH | 2 | COOEt |
| benzyl | OH | OH | 2 | COOEt |
| 2-phenethyl | OH | OH | 2 | COOEt |
| cyclopropylmethyl | OH | OH | 2 | NHCHO |
| cyclobutylmethyl | OH | OH | 2 | NHCHO |
| allyl | OH | OH | 2 | NHCHO |
| H | OH | OH | 2 | NHCHO |
| Me | OH | OH | 2 | NHCHO |
| benzyl | OH | OH | 2 | NHCHO |
| 2-phenethyl | OH | OH | 2 | NHCHO |
| cyclopropylmethyl | OH | OH | 2 | NHCO—Me |
| cyclobutylmethyl | OH | OH | 2 | NHCO—Me |
| allyl | OH | OH | 2 | NHCO—Me |
| H | OH | OH | 2 | NHCO—Me |
| Me | OH | OH | 2 | NHCO—Me |
| benzyl | OH | OH | 2 | NHCO—Me |
| 2-phenethyl | OH | OH | 2 | NHCO—Me |
| cyclopropylmethyl | OH | OH | 2 | NHCO—Ph |
| cyclobutylmethyl | OH | OH | 2 | NHCO—Ph |
| allyl | OH | OH | 2 | NHCO—Ph |
| H | OH | OH | 2 | NHCO—Ph |
| Me | OH | OH | 2 | NHCO—Ph |
| benzyl | OH | OH | 2 | NHCO—Ph |
| 2-phenethyl | OH | OH | 2 | NHCO—Ph |
| cyclopropylmethyl | OH | OH | 2 | NHCO—(CH₂)₅Ph |
| cyclobutylmethyl | OH | OH | 2 | NHCO—(CH₂)₅Ph |
| allyl | OH | OH | 2 | NHCO—(CH₂)₅Ph |
| H | OH | OH | 2 | NHCO—(CH₂)₅Ph |

-continued

| | | | | |
|---|---|---|---|---|
| Me | OH | OH | 2 | NHCO—(CH$_2$)$_5$Ph |
| benzyl | OH | OH | 2 | NHCO—(CH$_2$)$_5$Ph |
| 2-phenethyl | OH | OH | 2 | NHCO—(CH$_2$)$_5$Ph |
| cyclopropyomethyl | OH | OH | 2 | NHCO-cinnamyl |
| cyclobutylmethyl | OH | OH | 2 | NHCO-cinnamyl |
| allyl | OH | OH | 2 | NHCO-cinnamyl |
| H | OH | OH | 2 | NHCO-cinnamyl |
| Me | OH | OH | 2 | NHCO-cinnamyl |
| benzyl | OH | OH | 2 | NHCO-cinnamyl |
| 2-phenethyl | OH | OH | 2 | NHCO-cinnamyl |
| cyclopropylmethyl | OH | OH | 2 | NHCO—(CF$_3$-cinnamyl) |
| cyclobutylmethyl | OH | OH | 2 | NHCO—(CF$_3$-cinnamyl) |
| allyl | OH | OH | 2 | NHCO—(CF$_3$-cinnamyl) |
| H | OH | OH | 2 | NHCO—(CF$_3$-cinnamyl) |
| Me | OH | OH | 2 | NHCO—(CF$_3$-cinnamyl) |
| benzyl | OH | OH | 2 | NHCO—(CF$_3$-cinnamyl) |
| 2-phenethyl | OH | OH | 2 | NHCO—(CF$_3$-cinnamyl) |
| cyclopropylmethyl | OH | OH | 2 | NHCO-pyridyl |
| cyclobutylmethyl | OH | OH | 2 | NHCO-pyridyl |
| allyl | OH | OH | 2 | NHCO-pyridyl |
| H | OH | OH | 2 | NHCO-pyridyl |
| Me | OH | OH | 2 | NHCO-pyridyl |
| benzyl | OH | OH | 2 | NHCO-pyridyl |
| 2-phenethyl | OH | OH | 2 | NHCO-pyridyl |
| cyclopropylmethyl | OH | OH | 2 | NHCO—NHPh |
| cyclobutylmethyl | OH | OH | 2 | NHCO—NHPh |
| allyl | OH | OH | 2 | NHCO—NHPh |
| H | OH | OH | 2 | NHCO—NHPh |
| Me | OH | OH | 2 | NHCO—NHPh |
| benzyl | OH | OH | 2 | NHCO—NHPh |
| 2-phenethyl | OH | OH | 2 | NHCO—NHPh |
| cyclopropylmethyl | OH | OH | 2 | NHCS—NHPh |
| cyclobutylmethyl | OH | OH | 2 | NHCS—NHPh |
| allyl | OH | OH | 2 | NHCS—NHPh |
| H | OH | OH | 2 | NHCS—NHPh |
| Me | OH | OH | 2 | NHCS—NHPh |
| benzyl | OH | OH | 2 | NHCS—NHPh |
| 2-phenethyl | OH | OH | 2 | NHCS—NHPh |
| cyclopropylmethyl | OH | OH | 2 | NHCS—NHCHPh |
| cyclobutylmethyl | OH | OH | 2 | NHCS—NHCH$_2$Ph |
| allyl | OH | OH | 2 | NHCS—NHCH$_2$Ph |
| H | OH | OH | 2 | NHCS—NHCH$_2$Ph |
| Me | OH | OH | 2 | NHCS—NHCH$_2$Ph |
| benzyl | OH | OH | 2 | NHCS—NHCH$_2$Ph |
| 2-phenethyl | OH | OH | 2 | NHCS—NHCH$_2$Ph |
| cyclopropylmethyl | OH | OH | 3 | OH |
| cyclobutylmethyl | OH | OH | 3 | OH |
| allyl | OH | OH | 3 | OH |
| H | OH | OH | 3 | OH |
| Me | OH | OH | 3 | OH |
| benzyl | OH | OH | 3 | OH |
| 2-phenethyl | OH | OH | 3 | OH |
| cyclopropylmethyl | OH | OH | 3 | OMe |
| cyclobutylmethyl | OH | OH | 3 | OMe |
| allyl | OH | OH | 3 | OMe |
| H | OH | OH | 3 | OMe |
| Me | OH | OH | 3 | OMe |
| benzyl | OH | OH | 3 | OMe |
| 2-phenethyl | OH | OH | 3 | OMe |
| cyclopropylmethyl | OH | OH | 3 | OEt |
| cyclobutylmethyl | OH | OH | 3 | OEt |
| allyl | OH | OH | 3 | OEt |
| H | OH | OH | 3 | OEt |
| Me | OH | OH | 3 | OEt |
| benzyl | OH | OH | 3 | OEt |
| 2-phenethyl | OH | OH | 3 | OEt |
| cyclopropylmethyl | OH | OH | 3 | NH$_2$ |
| cyclobutylmethyl | OH | OH | 3 | NH$_2$ |
| allyl | OH | OH | 3 | NH$_2$ |
| H | OH | OH | 3 | NH$_2$ |
| Me | OH | OH | 3 | NH$_2$ |
| benzyl | OH | OH | 3 | NH$_2$ |
| 2-phenethyl | OH | OH | 3 | NH$_2$ |
| cyclopropylmethyl | OH | OH | 3 | NO$_2$ |
| cyclobutylmethyl | OH | OH | 3 | NO$_2$ |
| allyl | OH | OH | 3 | NO$_2$ |
| H | OH | OH | 3 | NO$_2$ |
| Me | OH | OH | 3 | NO$_2$ |
| benzyl | OH | OH | 3 | NO$_2$ |
| 2-phenethyl | OH | OH | 3 | NO$_2$ |
| cyclopropylmethyl | OH | OH | 3 | CN |
| cyclobutylmethyl | OH | OH | 3 | CN |
| allyl | OH | OH | 3 | CN |
| H | OH | OH | 3 | CN |
| Me | OH | OH | 3 | CN |
| benzyl | OH | OH | 3 | CN |
| 2-phenethyl | OH | OH | 3 | CN |
| cyclopropylmethyl | OH | OH | 3 | NCS |
| cyclobutylmethyl | OH | OH | 3 | NCS |
| allyl | OH | OH | 3 | NCS |
| H | OH | OH | 3 | NCS |
| Me | OH | OH | 3 | NCS |
| benzyl | OH | OH | 3 | NCS |
| 2-phenethyl | OH | OH | 3 | NCS |
| cyclopropylmethyl | OH | OH | 3 | COOH |
| cyclobutylmethyl | OH | OH | 3 | COOH |
| allyl | OH | OH | 3 | COOH |
| H | OH | OH | 3 | COOH |
| Me | OH | OH | 3 | COOH |
| benzyl | OH | OH | 3 | COOH |
| 2-phenethyl | OH | OH | 3 | COOH |
| cyclopropylmethyl | OH | OH | 3 | COOMe |
| cyclobutylmethyl | OH | OH | 3 | COOMe |
| allyl | OH | OH | 3 | COOMe |
| H | OH | OH | 3 | COOMe |
| Me | OH | OH | 3 | COOMe |
| benzyl | OH | OH | 3 | COOMe |
| 2-phenethyl | OH | OH | 3 | COOMe |
| cyclopropylmethyl | OH | OH | 3 | COOEt |
| cyclobutylmethyl | OH | OH | 3 | COOEt |
| allyl | OH | OH | 3 | COOEt |
| H | OH | OH | 3 | COOEt |
| Me | OH | OH | 3 | COOEt |
| benzyl | OH | OH | 3 | COOEt |
| 2-phenethyl | OH | OH | 3 | COOEt |
| cyclopropylmethyl | OH | OH | 3 | NHCHO |
| cyclobutylmethyl | OH | OH | 3 | NHCHO |
| allyl | OH | OH | 3 | NHCHO |
| H | OH | OH | 3 | NHCHO |
| Me | OH | OH | 3 | NHCHO |
| benzyl | OH | OH | 3 | NHCHO |
| 2-phenethyl | OH | OH | 3 | NHCHO |
| cyclopropylmethyl | OH | OH | 3 | NHCO—Me |
| cyclobutylmethyl | OH | OH | 3 | NHCO—Me |
| allyl | OH | OH | 3 | NHCO—Me |
| H | OH | OH | 3 | NHCO—Me |
| Me | OH | OH | 3 | NHCO—Me |
| benzyl | OH | OH | 3 | NHCO—Me |
| 2-phenethyl | OH | OH | 3 | NHCO—Me |
| cyclopropylmethyl | OH | OH | 3 | NHCO—Ph |
| cyclobutylmethyl | OH | OH | 3 | NHCO—Ph |
| allyl | OH | OH | 3 | NHCO—Ph |
| H | OH | OH | 3 | NHCO—Ph |
| Me | OH | OH | 3 | NHCO—Ph |
| benzyl | OH | OH | 3 | NHCO—Ph |
| 2-phenethyl | OH | OH | 3 | NHCO—Ph |
| cyclopropylmethyl | OH | OH | 3 | NHCO—(CH$_2$)$_5$Ph |
| cyclobutylmethyl | OH | OH | 3 | NHCO—(CH$_2$)$_5$Ph |
| allyl | OH | OH | 3 | NHCO—(CH$_2$)$_5$Ph |
| H | OH | OH | 3 | NHCO—(CH$_2$)$_5$Ph |
| Me | OH | OH | 3 | NHCO—(CH$_2$)$_5$Ph |
| benzyl | OH | OH | 3 | NHCO—(CH$_2$)$_5$Ph |
| 2-phenethyl | OH | OH | 3 | NHCO—(CH$_2$)$_5$Ph |
| cyclopropylmethyl | OH | OH | 3 | NHCO-cinnamyl |
| cyclobutylmethyl | OH | OH | 3 | NHCO-cinnamyl |
| allyl | OH | OH | 3 | NHCO-cinnamyl |
| H | OH | OH | 3 | NHCO-cinnamyl |
| Me | OH | OH | 3 | NHCO-cinnamyl |
| benzyl | OH | OH | 3 | NHCO-cinnamyl |
| 2-phenethyl | OH | OH | 3 | NHCO-cinnamyl |
| cyclopropylmethyl | OH | OH | 3 | NHCO—(CF$_3$-cinnamyl) |
| cylcobutylmethyl | OH | OH | 3 | NHCO—(CF$_3$-cinnamyl) |
| allyl | OH | OH | 3 | NHCO—(CF$_3$-cinnamyl) |
| H | OH | OH | 3 | NHCO—(CF$_3$-cinnamyl) |
| Me | OH | OH | 3 | NHCO—(CF$_3$-cinnamyl) |
| benzyl | OH | OH | 3 | NHCO—(CF$_3$-cinnamyl) |
| 2-phenethyl | OH | OH | 3 | NHCO—(CF$_3$-cinnamyl) |
| cyclopropylmethyl | OH | OH | 3 | NHCO-pyridyl |

-continued

| | | | | |
|---|---|---|---|---|
| cyclobutylemthyl | OH | OH | 3 | NHCO-pyridyl |
| allyl | OH | OH | 3 | NHCO-pyridyl |
| H | OH | OH | 3 | NHCO-pyridyl |
| Me | OH | OH | 3 | NHCO-pyridyl |
| benzyl | OH | OH | 3 | NHCO-pyridyl |
| 2-phenethyl | OH | OH | 3 | NHCO-pyridyl |
| cyclopropylmethyl | OH | OH | 3 | NHCO—NHPh |
| cyclobutylmethyl | OH | OH | 3 | NHCO—NHPh |
| allyl | OH | OH | 3 | NHCO—NHPh |
| H | OH | OH | 3 | NHCO—NHPh |
| Me | OH | OH | 3 | NHCO—NHPh |
| benzyl | OH | OH | 3 | NHCO—NHPh |
| 2-phenethyl | OH | OH | 3 | NHCO—NHPh |
| cyclopropylmethyl | OH | OH | 3 | NHCS—NHPh |
| cyclobutylmethyl | OH | OH | 3 | NHCS—NHPh |
| allyl | OH | OH | 3 | NHCS—NHPh |
| H | OH | OH | 3 | NHCS—NHPh |
| Me | OH | OH | 3 | NHCS—NHPh |
| benzyl | OH | OH | 3 | NHCS—NHPh |
| 2-phenethyl | OH | OH | 3 | NHCS—NHPh |
| cyclopropylmethyl | OH | OH | 3 | NHCS—NHCH$_2$Ph |
| cyclobutylmethyl | OH | OH | 3 | NHCS—NHCH$_2$Ph |
| allyl | OH | OH | 3 | NHCS—NHCH$_2$Ph |
| H | OH | OH | 3 | NHCS—NHCH$_2$Ph |
| Me | OH | OH | 3 | NHCS—NHCH$_2$Ph |
| benzyl | OH | OH | 3 | NHCS—NHCH$_2$Ph |
| 2-phenethyl | OH | OH | 3 | NHCS—NHCH$_2$Ph |
| cyclopropylmethyl | OH | OH | 4 | OH |
| cyclobutylmethyl | OH | OH | 4 | OH |
| allyl | OH | OH | 4 | OH |
| H | OH | OH | 4 | OH |
| Me | OH | OH | 4 | OH |
| benzyl | OH | OH | 4 | OH |
| 2-phenethyl | OH | OH | 4 | OH |
| cyclopropylmethyl | OH | OH | 4 | OMe |
| cyclobutylmethyl | OH | OH | 4 | OMe |
| allyl | OH | OH | 4 | OMe |
| H | OH | OH | 4 | OMe |
| Me | OH | OH | 4 | OMe |
| benzyl | OH | OH | 4 | OMe |
| 2-phenethyl | OH | OH | 4 | OMe |
| cyclopropylmethyl | OH | OH | 4 | OEt |
| cyclobutylmethyl | OH | OH | 4 | OEt |
| allyl | OH | OH | 4 | OEt |
| H | OH | OH | 4 | OEt |
| Me | OH | OH | 4 | OEt |
| benzyl | OH | OH | 4 | OEt |
| 2-phenethyl | OH | OH | 4 | OEt |
| cyclopropylmethyl | OH | OH | 4 | NH$_2$ |
| cyclobutylmethyl | OH | OH | 4 | NH$_2$ |
| allyl | OH | OH | 4 | NH$_2$ |
| H | OH | OH | 4 | NH$_2$ |
| Me | OH | OH | 4 | NH$_2$ |
| benzyl | OH | OH | 4 | NH$_2$ |
| 2-phenethyl | OH | OH | 4 | NH$_2$ |
| cyclopropylmethyl | OH | OH | 4 | NO$_2$ |
| cyclobutylmethyl | OH | OH | 4 | NO$_2$ |
| allyl | OH | OH | 4 | NO$_2$ |
| H | OH | OH | 4 | NO$_2$ |
| Me | OH | OH | 4 | NO$_2$ |
| benzyl | OH | OH | 4 | NO$_2$ |
| 2-phenethyl | OH | OH | 4 | NO$_2$ |
| cyclopropylmethyl | OH | OH | 4 | CN |
| cyclobutylmethyl | OH | OH | 4 | CN |
| allyl | OH | OH | 4 | CN |
| H | OH | OH | 4 | CN |
| Me | OH | OH | 4 | CN |
| benzyl | OH | OH | 4 | CN |
| 2-phenethyl | OH | OH | 4 | CN |
| cyclopropylmethyl | OH | OH | 4 | NCS |
| cyclobutylmethyl | OH | OH | 4 | NCS |
| allyl | OH | OH | 4 | NCS |
| H | OH | OH | 4 | NCS |
| Me | OH | OH | 4 | NCS |
| benzyl | OH | OH | 4 | NCS |
| 2-phenethyl | OH | OH | 4 | NCS |
| cyclopropylmethyl | OH | OH | 4 | COOH |
| cyclobutylmethyl | OH | OH | 4 | COOH |
| allyl | OH | OH | 4 | COOH |
| H | OH | OH | 4 | COOH |
| Me | OH | OH | 4 | COOH |
| benzyl | OH | OH | 4 | COOH |
| 2-phenethyl | OH | OH | 4 | COOH |
| cyclopropylmethyl | OH | OH | 4 | COOMe |
| cyclobutylmethyl | OH | OH | 4 | COOMe |
| allyl | OH | OH | 4 | COOMe |
| H | OH | OH | 4 | COOMe |
| Me | OH | OH | 4 | COOMe |
| benzyl | OH | OH | 4 | COOMe |
| 2-phenethyl | OH | OH | 4 | COOMe |
| cyclopropylmethyl | OH | OH | 4 | COOEt |
| cyclobutylmethyl | OH | OH | 4 | COOEt |
| allyl | OH | OH | 4 | COOEt |
| H | OH | OH | 4 | COOEt |
| Me | OH | OH | 4 | COOEt |
| benzyl | OH | OH | 4 | COOEt |
| 2-phenethyl | OH | OH | 4 | COOEt |
| cyclopropylmethyl | OH | OH | 4 | NHCHO |
| cyclobutylmethyl | OH | OH | 4 | NHCHO |
| allyl | OH | OH | 4 | NHCHO |
| H | OH | OH | 4 | NHCHO |
| Me | OH | OH | 4 | NHCHO |
| benzyl | OH | OH | 4 | NHCHO |
| 2-phenethyl | OH | OH | 4 | NHCHO |
| cyclopropylmethyl | OH | OH | 4 | NHCO—Me |
| cyclobutylmethyl | OH | OH | 4 | NHCO—Me |
| allyl | OH | OH | 4 | NHCO—Me |
| H | OH | OH | 4 | NHCO—Me |
| Me | OH | OH | 4 | NHCO—Me |
| benzyl | OH | OH | 4 | NHCO—Me |
| 2-phenethyl | OH | OH | 4 | NHCO—Me |
| cyclopropylmethyl | OH | OH | 4 | NHCO—Ph |
| cyclobutylmethyl | OH | OH | 4 | NHCO—Ph |
| allyl | OH | OH | 4 | NHCO—Ph |
| H | OH | OH | 4 | NHCO—Ph |
| Me | OH | OH | 4 | NHCO—Ph |
| benzyl | OH | OH | 4 | NHCO—Ph |
| 2-phenethyl | OH | OH | 4 | NHCO—Ph |
| cyclopropylmethyl | OH | OH | 4 | NHCO—(CH$_2$)$_5$Ph |
| cyclobutylmethyl | OH | OH | 4 | NHCO—(CH$_2$)$_5$Ph |
| allyl | OH | OH | 4 | NHCO—(CH$_2$)$_5$Ph |
| H | OH | OH | 4 | NHCO—(CH$_2$)$_5$Ph |
| Me | OH | OH | 4 | NHCO—(CH$_2$)$_5$Ph |
| benzyl | OH | OH | 4 | NHCO—(CH$_2$)$_5$Ph |
| 2-phenethyl | OH | OH | 4 | NHCO—(CH$_2$)$_5$Ph |
| cylopropylmethyl | OH | OH | 4 | NHCO-cinnamyl |
| cyclobutylmethyl | OH | OH | 4 | NHCO-cinnamyl |
| allyl | OH | OH | 4 | NHCO-cinnamyl |
| H | OH | OH | 4 | NHCO-cinnamyl |
| Me | OH | OH | 4 | NHCO-cinnamyl |
| benzyl | OH | OH | 4 | NHCO-cinnamyl |
| 2-phenethyl | OH | OH | 4 | NHCO-cinnamyl |
| cyclopropylmethyl | OH | OH | 4 | NHCO—(CF$_3$-cinnamyl) |
| cyclobutylmethyl | OH | OH | 4 | NHCO—(CF$_3$-cinnamyl) |
| allyl | OH | OH | 4 | NHCO—(CF$_3$-cinnamyl) |
| H | OH | OH | 4 | NHCO—(CF$_3$-cinnamyl) |
| Me | OH | OH | 4 | NHCO—(CF$_3$-cinnamyl) |
| benzyl | OH | OH | 4 | NHCO—(CF$_3$-cinnamyl) |
| 2-phenethyl | OH | OH | 4 | NHCO—(CF$_3$-cinnamyl) |
| cyclopropylmethyl | OH | OH | 4 | NHCO-pyridyl |
| cyclobutylmethyl | OH | OH | 4 | NHCO-pyridyl |
| allyl | OH | OH | 4 | NHCO-pyridyl |
| H | OH | OH | 4 | NHCO-pyridyl |
| Me | OH | OH | 4 | NHCO-pyridyl |
| benzyl | OH | OH | 4 | NHCO-pyridyl |
| 2-phenethyl | OH | OH | 4 | NHCO-pyridyl |
| cyclopropylmethyl | OH | OH | 4 | NHCO—NHPh |
| cyclobutylmethyl | OH | OH | 4 | NHCO—NHPh |
| allyl | OH | OH | 4 | NHCO—NHPh |
| H | OH | OH | 4 | NHCO—NHPh |
| Me | OH | OH | 4 | NHCO—NHPh |
| benzyl | OH | OH | 4 | NHCO—NHPh |
| 2-phenethyl | OH | OH | 4 | NHCO—NHPh |
| cyclopropylmethyl | OH | OH | 4 | NHCS—NHPh |
| cyclobutylmethyl | OH | OH | 4 | NHCS—NHPh |
| allyl | OH | OH | 4 | NHCS—NHPh |
| H | OH | OH | 4 | NHCS—NHPh |
| Me | OH | OH | 4 | NHCS—NHPh |

-continued

| R1 | | | | |
|---|---|---|---|---|
| benzyl | OH | OH | 4 | NHCS—NHPh |
| 2-phenethyl | OH | OH | 4 | NHCS—NHPh |
| cyclopropylmethyl | OH | OH | 4 | NHCS—NHCH$_2$Ph |
| cyclobutylmethyl | OH | OH | 4 | NHCS—NHCH$_2$Ph |
| allyl | OH | OH | 4 | NHCS—NHCH$_2$Ph |
| H | OH | OH | 4 | NHCS—NHCH$_2$Ph |
| Me | OH | OH | 4 | NHCS—NHCH$_2$Ph |
| benzyl | OH | OH | 4 | NHCS—NHCH$_2$Ph |
| 2-phenethyl | OH | OH | 4 | NHCS—NHCH$_2$Ph |
| cyclopropylmethyl | OH | OMe | 3 | OH |
| cyclopropylmethyl | OH | OMe | 3 | OMe |
| cyclopropylmethyl | OH | OMe | 3 | NH$_2$ |
| cyclopropylmethyl | OH | OMe | 3 | CN |
| cyclopropylmethyl | OH | OMe | 3 | NCS |
| cyclopropylmethyl | OH | OMe | 3 | COOH |
| cyclopropylmethyl | OH | OMe | 3 | NHCHO |
| cyclopropylmethyl | OH | OMe | 3 | NHCO—Ph |
| cyclopropylmethyl | OH | OMe | 3 | NHCO—(CH$_2$)$_5$Ph |
| cyclopropylmethyl | OH | OMe | 3 | NHCO—(CF$_3$-cinnamyl) |
| cyclopropylmethyl | OH | OMe | 3 | NHCO-pyridyl |
| cyclopropylmethyl | OH | OMe | 3 | NHCO—NHPh |
| cyclopropylmethyl | OH | OMe | 3 | NHCS—NHPh |
| cyclopropylmethyl | OH | OMe | 4 | OH |
| cyclopropylmethyl | OH | OMe | 4 | OMe |
| cyclopropylmethyl | OH | OMe | 4 | NH$_2$ |
| cyclopropylmethyl | OH | OMe | 4 | CN |
| cyclopropylmethyl | OH | OMe | 4 | NCS |
| cyclopropylmethyl | OH | OMe | 4 | OCOH |
| cyclopropylmethyl | OH | OMe | 4 | COOMe |
| cyclopropylmethyl | OH | OMe | 4 | NHCHO |
| cyclopropylmethyl | OH | OMe | 4 | NHCO—Ph |
| cyclopropylmethyl | OH | OMe | 4 | NHCO—(CH$_2$)$_5$Ph |
| cyclopropylmethyl | OH | OMe | 4 | NHCO-pyridyl |
| cyclopropylmethyl | OH | OMe | 4 | NHCO—NHPh |
| cyclopropylmethyl | OH | OMe | 4 | NHCS—NHPh |

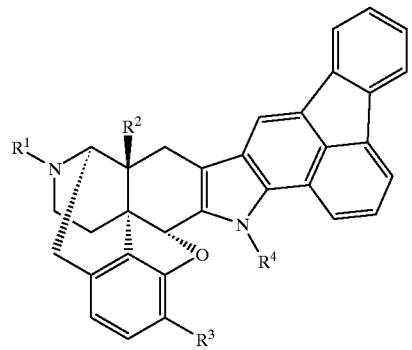

| R1 | R2 | R3 | R4 |
|---|---|---|---|
| cyclopropylmethyl | OH | OH | H |
| cyclobutylmethyl | OH | OH | H |
| allyl | OH | OH | H |
| H | OH | OH | H |
| Me | OH | OH | H |
| benzyl | OH | OH | H |
| 2-phenethyl | OH | OH | H |
| cyclopropylmethyl | OH | OH | Me |
| cyclobutylmethyl | OH | OH | Me |
| allyl | OH | OH | Me |
| H | OH | OH | Me |
| Me | OH | OH | Me |
| benzyl | OH | OH | Me |
| 2-phenethyl | OH | OH | Me |
| cyclopropylmethyl | OH | OH | Bu |
| cyclobutylmethyl | OH | OH | Bu |
| allyl | OH | OH | Bu |
| H | OH | OH | Bu |
| Me | OH | OH | Bu |
| benzyl | OH | OH | Bu |
| 2-phenethyl | OH | OH | Bu |
| cyclopropylmethyl | OH | OH | PhCH$_2$ |
| cyclobutylmethyl | OH | OH | PhCH$_2$ |
| allyl | OH | OH | PhCH$_2$ |
| H | OH | OH | PhCH$_2$ |
| Me | OH | OH | PhCH$_2$ |
| benzyl | OH | OH | PhCH$_2$ |
| 2-phenethyl | OH | OH | PhCH$_2$ |
| cyclopropylmethyl | OH | OH | (F—C$_6$H$_4$)CH$_2$ |
| cyclobutylmethyl | OH | OH | (F—C$_6$H$_4$)CH$_2$ |
| allyl | OH | OH | (F—C$_6$H$_4$)CH$_2$ |
| H | OH | OH | (F—C$_6$H$_4$)CH$_2$ |
| Me | OH | OH | (F—C$_6$H$_4$)CH$_2$ |
| benzyl | OH | OH | (F—C$_6$H$_4$)CH$_2$ |
| 2-phenethyl | OH | OH | (F—C$_6$H$_4$)CH$_2$ |
| cyclopropylmethyl | OH | OH | (Cl—C$_6$H$_4$)CH$_2$ |
| cyclobutylmethyl | OH | OH | (Cl—C$_6$H$_4$)CH$_2$ |
| allyl | OH | OH | (Cl—C$_6$H$_4$)CH$_2$ |
| H | OH | OH | (Cl—C$_6$H$_4$)CH$_2$ |
| Me | OH | OH | (Cl—C$_6$H$_4$)CH$_2$ |
| benzyl | OH | OH | (Cl—C$_6$H$_4$)CH$_2$ |
| 2-phenethyl | OH | OH | (Cl—C$_6$H$_4$)CH$_2$ |
| cyclopropylmethyl | OH | OH | (Br—C$_9$H$_4$)CH$_2$ |
| cyclobutylmethyl | OH | OH | (Br—C$_9$H$_4$)CH$_2$ |
| allyl | OH | OH | (Br—C$_9$H$_4$)CH$_2$ |
| H | OH | OH | (Br—C$_9$H$_4$)CH$_2$ |
| Me | OH | OH | (Br—C$_9$H$_4$)CH$_2$ |
| benzyl | OH | OH | (Br—C$_9$H$_4$)CH$_2$ |
| 2-phenethyl | OH | OH | (Br—C$_9$H$_4$)CH$_2$ |
| cyclopropylmethyl | OH | OH | (Me—C$_9$H$_4$)CH$_2$ |
| cyclobutylmethyl | OH | OH | (Me—C$_9$H$_4$)CH$_2$ |
| allyl | OH | OH | (Me—C$_9$H$_4$)CH$_2$ |
| H | OH | OH | (Me—C$_9$H$_4$)CH$_2$ |
| Me | OH | OH | (Me—C$_9$H$_4$)CH$_2$ |
| benzyl | OH | OH | (Me—C$_9$H$_4$)CH$_2$ |
| 2-phenethyl | OH | OH | (Me—C$_9$H$_4$)CH$_2$ |
| cyclopropylmethyl | OH | OH | (MeO—C$_6$H$_4$)CH$_2$ |
| cyclobutylmethyl | OH | OH | (MeO—C$_9$H$_4$)CH$_2$ |
| allyl | OH | OH | (MeO—C$_9$H$_4$)CH$_2$ |
| H | OH | OH | (MeO—C$_9$H$_4$)CH$_2$ |
| Me | OH | OH | (MeO—C$_6$H$_4$)CH$_2$ |
| benzyl | OH | OH | (MeO—C$_6$H$_4$)CH$_2$ |
| 2-phenethyl | OH | OH | (MeO—C$_6$H$_4$)CH$_2$ |
| cyclopropylmethyl | OH | OH | (F$_3$C—C$_6$H$_4$)CH$_2$ |
| cyclobutylmethyl | OH | OH | (F$_3$C—C$_6$H$_4$)CH$_2$ |
| allyl | OH | OH | (F$_3$C—C$_6$H$_4$)CH$_2$ |
| H | OH | OH | (F$_3$C—C$_9$H$_4$)CH$_2$ |
| Me | OH | OH | (F$_3$C—C$_6$H$_4$)CH$_2$ |
| benzyl | OH | OH | (F$_3$C—C$_6$H$_4$)CH$_2$ |
| 2-phenethyl | OH | OH | (F$_3$C—C$_6$H$_4$)CH$_2$ |
| cyclopropylmethyl | OH | OH | (O$_2$N—C$_6$H$_4$)CH$_2$ |
| cyclobutylmethyl | OH | OH | (O$_2$N—C$_6$H$_4$)CH$_2$ |
| allyl | OH | OH | (O$_2$N—C$_6$H$_4$)CH$_2$ |
| H | OH | OH | (O$_2$N—C$_6$H$_4$)CH$_2$ |
| Me | OH | OH | (O$_2$N—C$_6$H$_4$)CH$_2$ |
| benzyl | OH | OH | (O$_2$N—C$_6$H$_4$)CH$_2$ |
| 2-phenethyl | OH | OH | (O$_2$N—C$_6$H$_4$)CH$_2$ |
| cyclopropylmethyl | OH | OH | Ph(CH$_2$)$_2$ |
| cyclobutylmethyl | OH | OH | Ph(CH$_2$)$_2$ |
| allyl | OH | OH | Ph(CH$_2$)$_2$ |
| H | OH | OH | Ph(CH$_2$)$_2$ |
| Me | OH | OH | Ph(CH$_2$)$_2$ |
| benzyl | OH | OH | Ph(CH$_2$)$_2$ |
| 2-phenethyl | OH | OH | Ph(CH$_2$)$_2$ |
| cyclopropylmethyl | OH | OH | Ph(CH$_2$)$_3$ |
| cyclobutylmethyl | OH | OH | Ph(CH$_2$)$_3$ |
| allyl | OH | OH | Ph(CH$_2$)$_3$ |
| H | OH | OH | Ph(CH$_2$)$_3$ |
| Me | OH | OH | Ph(CH$_2$)$_3$ |
| benzyl | OH | OH | Ph(CH$_2$)$_3$ |
| 2-phenethyl | OH | OH | Ph(CH$_2$)$_3$ |
| cyclopropylmethyl | OH | OH | PhCO |
| cyclobutylmethyl | OH | OH | phCO |
| allyl | OH | OH | PhCO |
| H | OH | OH | PhCO |
| Me | OH | OH | PhCO |
| benzyl | OH | OH | PhCO |
| 2-phenethyl | OH | OH | PhCO |
| cyclopropylmethyl | OH | OH | MeSO$_2$ |
| cyclobutylmethyl | OH | OH | MeSO$_2$ |
| allyl | OH | OH | MeSO$_2$ |
| H | OH | OH | MeSO$_2$ |

-continued

| R¹ | | | R¹⁶ |
|---|---|---|---|
| Me | OH | OH | MeSO₂ |
| benzyl | OH | OH | MeSO₂ |
| 2-phenethyl | OH | OH | MeSO₂ |
| cyclopropylmethyl | OH | OH | PhSO₂ |
| cyclobutylmethyl | OH | OH | PhSO₂ |
| allyl | OH | OH | PhSO₂ |
| H | OH | OH | PhSO₂ |
| Me | OH | OH | PhSO₂ |
| benzyl | OH | OH | PhSO₂ |
| 2-phenethyl | OH | OH | PhSO₂ |

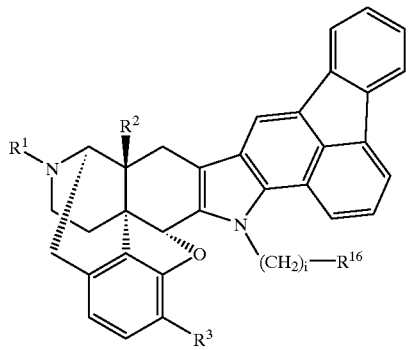

| R¹ | R² | R³ | i | R¹⁶ |
|---|---|---|---|---|
| cyclopropylmethyl | OH | OH | 2 | OH |
| cyclobutylmethyl | OH | OH | 2 | OH |
| allyl | OH | OH | 2 | OH |
| H | OH | OH | 2 | OH |
| Me | OH | OH | 2 | OH |
| benzyl | OH | OH | 2 | OH |
| 2-phenethyl | OH | OH | 2 | OH |
| cyclopropylmethyl | OH | OH | 2 | OMe |
| cyclobutylmethyl | OH | OH | 2 | OMe |
| allyl | OH | OH | 2 | OMe |
| H | OH | OH | 2 | OMe |
| Me | OH | OH | 2 | OMe |
| benzyl | OH | OH | 2 | OMe |
| 2-phenethyl | OH | OH | 2 | OMe |
| cyclopropylmethyl | OH | OH | 2 | OEt |
| cyclobutylmethyl | OH | OH | 2 | OEt |
| allyl | OH | OH | 2 | OEt |
| H | OH | OH | 2 | OEt |
| Me | OH | OH | 2 | OEt |
| benzyl | OH | OH | 2 | OEt |
| 2-phenethyl | OH | OH | 2 | OEt |
| cyclopropylmethyl | OH | OH | 2 | NH₂ |
| cyclobutylmethyl | OH | OH | 2 | NH₂ |
| allyl | OH | OH | 2 | NH₂ |
| H | OH | OH | 2 | NH₂ |
| Me | OH | OH | 2 | NH₂ |
| benzyl | OH | OH | 2 | NH₂ |
| 2-phenethyl | OH | OH | 2 | NH₂ |
| cyclopropylmethyl | OH | OH | 2 | NO₂ |
| cyclobutylmethyl | OH | OH | 2 | NO₂ |
| allyl | OH | OH | 2 | NO₂ |
| H | OH | OH | 2 | NO₂ |
| Me | OH | OH | 2 | NO₂ |
| benzyl | OH | OH | 2 | NO₂ |
| 2-phenethyl | OH | OH | 2 | NO₂ |
| cyclopropylmethyl | OH | OH | 2 | CN |
| cyclobutylmethyl | OH | OH | 2 | CN |
| allyl | OH | OH | 2 | CN |
| H | OH | OH | 2 | CN |
| Me | OH | OH | 2 | CN |
| benzyl | OH | OH | 2 | CN |
| 2-phenethyl | OH | OH | 2 | CN |
| cyclopropylmethyl | OH | OH | 2 | NCS |
| cyclobutylmethyl | OH | OH | 2 | NCS |
| allyl | OH | OH | 2 | NCS |
| H | OH | OH | 2 | NCS |
| Me | OH | OH | 2 | NCS |
| benzyl | OH | OH | 2 | NCS |
| 2-phenethyl | OH | OH | 2 | NCS |
| cyclopropylmethyl | OH | OH | 2 | COOH |
| cyclobutylmethyl | OH | OH | 2 | COOH |
| allyl | OH | OH | 2 | COOH |
| H | OH | OH | 2 | OCOH |
| Me | OH | OH | 2 | OCOH |
| benzyl | OH | OH | 2 | OCOH |
| 2-phenethyl | OH | OH | 2 | COOH |
| cyclopropylmethyl | OH | OH | 2 | COOMe |
| cyclobutylmethyl | OH | OH | 2 | COOMe |
| allyl | OH | OH | 2 | COOMe |
| H | OH | OH | 2 | COOMe |
| Me | OH | OH | 2 | COOMe |
| benzyl | OH | OH | 2 | COOMe |
| 2-phenethyl | OH | OH | 2 | COOEt |
| cyclopropylmethyl | OH | OH | 2 | COOEt |
| cyclobutylmethyl | OH | OH | 2 | COOEt |
| allyl | OH | OH | 2 | COOEt |
| H | OH | OH | 2 | COOEt |
| Me | OH | OH | 2 | COOEt |
| benzyl | OH | OH | 2 | COOEt |
| 2-phenethyl | OH | OH | 2 | COOEt |
| cyclopropylmethyl | OH | OH | 2 | NHCHO |
| cyclobutylmethyl | OH | OH | 2 | NHCHO |
| allyl | OH | OH | 2 | NHCHO |
| H | OH | OH | 2 | NHCHO |
| Me | OH | OH | 2 | NHCHO |
| benzyl | OH | OH | 2 | NHCHO |
| 2-phenethyl | OH | OH | 2 | NHCHO |
| cyclopropylmethyl | OH | OH | 2 | NHCO—Me |
| cyclobutylmethyl | OH | OH | 2 | NHCO—Me |
| allyl | OH | OH | 2 | NHCO—Me |
| H | OH | OH | 2 | NHCO—Me |
| Me | OH | OH | 2 | NHCO—Me |
| benzyl | OH | OH | 2 | NHCO—Me |
| 2-phenethyl | OH | OH | 2 | NHCO—Me |
| cyclopropylmethyl | OH | OH | 2 | NHCO—Ph |
| cyclobutylmethyl | OH | OH | 2 | NHCO—Ph |
| allyl | OH | OH | 2 | NHCO—Ph |
| H | OH | OH | 2 | NHCO—Ph |
| Me | OH | OH | 2 | NHCO—Ph |
| benzyl | OH | OH | 2 | NHCO—Ph |
| 2-phenethyl | OH | OH | 2 | NHCO—Ph |
| cyclopropylmethyl | OH | OH | 2 | NHCO—(CH₂)₅Ph |
| cyclobutylmethyl | OH | OH | 2 | NHCO—(CH₂)₅Ph |
| allyl | OH | OH | 2 | NHCO—(CH₂)₅Ph |
| H | OH | OH | 2 | NHCO—(CH₂)₅Ph |
| Me | OH | OH | 2 | NHCO—(CH₂)₅Ph |
| benzyl | OH | OH | 2 | NHCO—(CH₂)₅Ph |
| 2-phenethyl | OH | OH | 2 | NHCO—(CH₂)₅Ph |
| cyclopropylmethyl | OH | OH | 2 | NHCO-cinnamyl |
| cyclobutylmethyl | OH | OH | 2 | NHCO-cinnamyl |
| allyl | OH | OH | 2 | NHCO-cinnamyl |
| H | OH | OH | 2 | NHCO-cinnamyl |
| Me | OH | OH | 2 | NHCO-cinnamyl |
| benzyl | OH | OH | 2 | NHCO-cinnamyl |
| 2-phenethyl | OH | OH | 2 | NHCO-cinnamyl |
| cyclopropylmethyl | OH | OH | 2 | NHCO—(CF₃-cinnamyl) |
| cyclobutylmethyl | OH | OH | 2 | NHCO—(CF₃-cinnamyl) |
| allyl | OH | OH | 2 | NHCO—(CF₃-cinnamyl) |
| H | OH | OH | 2 | NHCO—(CF₃-cinnamyl) |
| Me | OH | OH | 2 | NHCO—(CF₃-cinnamyl) |
| benzyl | OH | OH | 2 | NHCO—(CF₃-cinnamyl) |
| 2-phenethyl | OH | OH | 2 | NHCO—(CF₃-cinnamyl) |
| cyclopropylmethyl | OH | OH | 2 | NHCO-pyridyl |
| cyclobutylmethyl | OH | OH | 2 | NHCO-pyridyl |
| allyl | OH | OH | 2 | NHCO-pyridyl |
| H | OH | OH | 2 | NCHO-pyridyl |
| Me | OH | OH | 2 | NHCO-pyridyl |
| benzyl | OH | OH | 2 | NHCO-pyridyl |
| 2-phenethyl | OH | OH | 2 | NHCO-pyridyl |
| cyclopropylmethyl | OH | OH | 2 | NHCO—NHPh |
| cyclobutylmethyl | OH | OH | 2 | NHCO—NHPh |
| allyl | OH | OH | 2 | NHCO—NHPh |
| H | OH | OH | 2 | NHCO—NHPh |
| Me | OH | OH | 2 | NHCO—NHPh |
| benzyl | OH | OH | 2 | NHCO—NHPh |
| 2-phenethyl | OH | OH | 2 | NHCO—NHPh |
| cyclopropylmethyl | OH | OH | 2 | NHCS—NHPh |

-continued

| | | | | |
|---|---|---|---|---|
| cyclobutylmethyl | OH | OH | 2 | NHCS—NHPh |
| allyl | OH | OH | 2 | NHCS—NHPh |
| H | OH | OH | 2 | NHCS—NHPh |
| Me | OH | OH | 2 | NHCS—NHPh |
| benzyl | OH | OH | 2 | NHCS—NHPh |
| 2-phenethyl | OH | OH | 2 | NHCS—NHPh |
| cyclopropylmethyl | OH | OH | 2 | NHCS—NHCH$_2$Ph |
| cyclobutylmethyl | OH | OH | 2 | NHCS—NHCH$_2$Ph |
| allyl | OH | OH | 2 | NHCS—NHCH$_2$Ph |
| H | OH | OH | 2 | NHCS—NHCH$_2$Ph |
| Me | OH | OH | 2 | NHCS—NHCH$_2$Ph |
| benzyl | OH | OH | 2 | NHCS—NHCH$_2$Ph |
| 2-phenethyl | OH | OH | 2 | NHCS—NHCH$_2$Ph |
| cyclopropylmethyl | OH | OH | 3 | OH |
| cyclobutylmethyl | OH | OH | 3 | OH |
| H | OH | OH | 3 | OH |
| Me | OH | OH | 3 | OH |
| benzyl | OH | OH | 3 | OH |
| 2-phenethyl | OH | OH | 3 | OH |
| cyclopropylmethyl | OH | OH | 3 | OMe |
| cyclobutylmethyl | OH | OH | 3 | OMe |
| allyl | OH | OH | 3 | OMe |
| H | OH | OH | 3 | OMe |
| Me | OH | OH | 3 | OMe |
| benzyl | OH | OH | 3 | OMe |
| 2-phenethyl | OH | OH | 3 | OMe |
| cyclopropylmethyl | OH | OH | 3 | OEt |
| cyclobutylmethyl | OH | OH | 3 | OEt |
| allyl | OH | OH | 3 | OEt |
| H | OH | OH | 3 | OEt |
| Me | OH | OH | 3 | OEt |
| benzyl | OH | OH | 3 | OEt |
| 2-phenethyl | OH | OH | 3 | OEt |
| cyclopropylmethyl | OH | OH | 3 | NH$_2$ |
| cyclobutylmethyl | OH | OH | 3 | NH$_2$ |
| allyl | OH | OH | 3 | NH$_2$ |
| H | OH | OH | 3 | NH$_2$ |
| Me | OH | OH | 3 | NH$_2$ |
| benzyl | OH | OH | 3 | NH$_2$ |
| 2-phenethyl | OH | OH | 3 | NH$_2$ |
| cyclopropylmethyl | OH | OH | 3 | NO$_2$ |
| cyclobutylmethyl | OH | OH | 3 | NO$_2$ |
| allyl | OH | OH | 3 | NO$_2$ |
| H | OH | OH | 3 | NO$_2$ |
| Me | OH | OH | 3 | NO$_2$ |
| benzyl | OH | OH | 3 | NO$_2$ |
| 2-phenethyl | OH | OH | 3 | NO$_2$ |
| cyclopropylmethyl | OH | OH | 3 | CN |
| cyclobutylmethyl | OH | OH | 3 | CN |
| allyl | OH | OH | 3 | CN |
| H | OH | OH | 3 | CN |
| Me | OH | OH | 3 | CN |
| benzyl | OH | OH | 3 | CN |
| 2-phenethyl | OH | OH | 3 | CN |
| cyclopropylmethyl | OH | OH | 3 | NCS |
| cyclobutylmethyl | OH | OH | 3 | NCS |
| allyl | OH | OH | 3 | NCS |
| H | OH | OH | 3 | NCS |
| Me | OH | OH | 3 | NCS |
| benzyl | OH | OH | 3 | NCS |
| 2-phenethyl | OH | OH | 3 | NCS |
| cyclopropylmethyl | OH | OH | 3 | COOH |
| cyclobutylmethyl | OH | OH | 3 | COOH |
| allyl | OH | OH | 3 | COOH |
| H | OH | OH | 3 | COOH |
| Me | OH | OH | 3 | COOH |
| benzyl | OH | OH | 3 | COOH |
| 2-phenethyl | OH | OH | 3 | COOH |
| cyclopropylmethyl | OH | OH | 3 | COOMe |
| cyclobutylmethyl | OH | OH | 3 | COOMe |
| allyl | OH | OH | 3 | COOMe |
| H | OH | OH | 3 | COOMe |
| Me | OH | OH | 3 | COOMe |
| benzyl | OH | OH | 3 | COOMe |
| 2-phenethyl | OH | OH | 3 | COOMe |
| cyclopropylmethyl | OH | OH | 3 | COOEt |
| cyclobutylmethyl | OH | OH | 3 | COOEt |
| allyl | OH | OH | 3 | COOEt |
| H | OH | OH | 3 | COOEt |
| Me | OH | OH | 3 | COOMe |
| benzyl | OH | OH | 3 | COOMe |
| 2-phenethyl | OH | OH | 3 | COOMe |
| cyclopropylmethyl | OH | OH | 3 | COOEt |
| cyclobutylmethyl | OH | OH | 3 | COOEt |
| allyl | OH | OH | 3 | COOEt |
| H | OH | OH | 3 | COOEt |
| Me | OH | OH | 3 | COOEt |
| benzyl | OH | OH | 3 | COOEt |
| 2-phenethyl | OH | OH | 3 | COOEt |
| cyclopropylmethyl | OH | OH | 3 | NHCHO |
| cyclobutylmethyl | OH | OH | 3 | NHCHO |
| allyl | OH | OH | 3 | NHCHO |
| H | OH | OH | 3 | NHCHO |
| Me | OH | OH | 3 | NHCHO |
| benzyl | OH | OH | 3 | NHCHO |
| 2-phenethyl | OH | OH | 3 | NHCHO |
| cyclopropylmethyl | OH | OH | 3 | NHCO—Me |
| cyclobutylmethyl | OH | OH | 3 | NHCO—Me |
| allyl | OH | OH | 3 | NHCO—Me |
| H | OH | OH | 3 | NHCO—Me |
| Me | OH | OH | 3 | NHCO—Me |
| benzyl | OH | OH | 3 | NHCO—Me |
| 2-phenethyl | OH | OH | 3 | NHCO—Me |
| cyclopropylmethyl | OH | OH | 3 | NHCO—Ph |
| cyclobutylmethyl | OH | OH | 3 | NHCO—Ph |
| allyl | OH | OH | 3 | NHCO—Ph |
| H | OH | OH | 3 | NHCO—Ph |
| Me | OH | OH | 3 | NHCO—Ph |
| benzyl | OH | OH | 3 | NHCO—Ph |
| 2-phenethyl | OH | OH | 3 | NHCO—Ph |
| cyclopropylmethyl | OH | OH | 3 | NHCO—(CH$_2$)$_5$Ph |
| cyclobutylmethyl | OH | OH | 3 | NHCO—(CH$_2$)$_5$Ph |
| allyl | OH | OH | 3 | NHCO—(CH$_2$)$_5$Ph |
| H | OH | OH | 3 | NHCO—(CH$_2$)$_5$Ph |
| Me | OH | OH | 3 | NHCO—(CH$_2$)$_5$Ph |
| benzyl | OH | OH | 3 | NHCO—(CH$_2$)$_5$Ph |
| 2-phenethyl | OH | OH | 3 | NHCO—(CH$_2$)$_{Ph}$ |
| cyclopropylmethyl | OH | OH | 3 | NHCO-cinnamyl |
| cyclobutylmethyl | OH | OH | 3 | NHCO-cinnamyl |
| allyl | OH | OH | 3 | NHCO-cinnamyl |
| H | OH | OH | 3 | NHCO-cinnamyl |
| Me | OH | OH | 3 | NHCO-cinnamyl |
| benzyl | OH | OH | 3 | NHCO-cinnamyl |
| 2-phenethyl | OH | OH | 3 | NHCO-cinnamyl |
| cyclopropylmethyl | OH | OH | 3 | NHCO—(CF$_3$-cinnamyl) |
| cyclobutylmethyl | OH | OH | 3 | NHCO—(CF$_3$-cinnamyl) |
| allyl | OH | OH | 3 | NHCO—(CF$_3$-cinnamyl) |
| H | OH | OH | 3 | NHCO—(CF$_3$-cinnamyl) |
| Me | OH | OH | 3 | NHCO—(CF$_3$-cinnamyl) |
| benzyl | OH | OH | 3 | NHCO—(CF$_3$-cinnamyl) |
| 2-phenethyl | OH | OH | 3 | NHCO—(CF$_3$-cinnamyl) |
| cyclopropylmethyl | OH | OH | 3 | NHCO-pyridyl |
| cyclobutylmethyl | OH | OH | 3 | NHCO-pyridyl |
| allyl | OH | OH | 3 | NHCO-pyridyl |
| H | OH | OH | 3 | NHCO-pyridyl |
| Me | OH | OH | 3 | NHCO-pyridyl |
| benzyl | OH | OH | 3 | NHCO-pyridyl |
| 2-phenethyl | OH | OH | 3 | NHCO-pyridyl |
| cyclopropylmethyl | OH | OH | 3 | NHCO—NHPh |
| cyclobutylmethyl | OH | OH | 3 | NHCO—NHph |
| allyl | OH | OH | 3 | NHCO—NHPh |
| H | OH | OH | 3 | NHCO—NHPh |
| Me | OH | OH | 3 | NHCO—NHPh |
| benzyl | OH | OH | 3 | NHCO—NHPh |
| 2-phenethyl | OH | OH | 3 | NHCO—NHPh |
| cyclopropylmethyl | OH | OH | 3 | NHCS—NHPh |
| cyclobutylmethyl | OH | OH | 3 | NHCS—NHPh |
| allyl | OH | OH | 3 | NHCS—NHPh |
| H | OH | OH | 3 | NHCS—NHPh |
| Me | OH | OH | 3 | NHCS—NHPh |
| benzyl | OH | OH | 3 | NHCS—NHPh |
| 2-phenethyl | OH | OH | 3 | NHCS—NHPh |
| cyclopropylmethyl | OH | OH | 3 | NHCS—NHCH$_2$Ph |
| cyclobutylmethyl | OH | OH | 3 | NHCS—NHCH$_2$Ph |
| allyl | OH | OH | 3 | NHCS—NHCH$_2$Ph |
| H | OH | OH | 3 | NHCS—NHCH$_2$Ph |
| Me | OH | OH | 3 | NHCS—NHCH$_2$Ph |
| benzyl | OH | OH | 3 | NHCS—NHCH$_2$Ph |

-continued

| | | | | |
|---|---|---|---|---|
| 2-phenethyl | OH | OH | 3 | NHCS—NHCH$_2$Ph |
| cyclopropylmethyl | OH | OH | 4 | OH |
| cyclobutylmethyl | OH | OH | 4 | OH |
| allyl | OH | OH | 4 | OH |
| H | OH | OH | 4 | OH |
| Me | OH | OH | 4 | OH |
| benzyl | OH | OH | 4 | OH |
| 2-phenethyl | OH | OH | 4 | OH |
| cyclopropylmethyl | OH | OH | 4 | OMe |
| cyclobutylmethyl | OH | OH | 4 | OMe |
| allyl | OH | OH | 4 | OMe |
| H | OH | OH | 4 | OMe |
| Me | OH | OH | 4 | OMe |
| benzyl | OH | OH | 4 | OMe |
| 2-phenethyl | OH | OH | 4 | OMe |
| cyclopropylmethyl | OH | OH | 4 | OEt |
| cyclobutylmethyl | OH | OH | 4 | OEt |
| allyl | OH | OH | 4 | OEt |
| H | OH | OH | 4 | OEt |
| Me | OH | OH | 4 | OEt |
| benzyl | OH | OH | 4 | OEt |
| 2-phenethyl | OH | OH | 4 | OEt |
| cyclopropylmethyl | OH | OH | 4 | NH$_2$ |
| cyclobutylmethyl | OH | OH | 4 | NH$_2$ |
| allyl | OH | OH | 4 | NH$_2$ |
| H | OH | OH | 4 | NH$_2$ |
| Me | OH | OH | 4 | NH$_2$ |
| benzyl | OH | OH | 4 | NH$_2$ |
| 2-phenethyl | OH | OH | 4 | NH$_2$ |
| cyclopropylmethyl | OH | OH | 4 | NO$_2$ |
| cyclobutylmethyl | OH | OH | 4 | NO$_2$ |
| allyl | OH | OH | 4 | NO$_2$ |
| H | OH | OH | 4 | NO$_2$ |
| Me | OH | OH | 4 | NO$_2$ |
| benzyl | OH | OH | 4 | NO$_2$ |
| 2-phenethyl | OH | OH | 4 | NO$_2$ |
| cyclopropylmethyl | OH | OH | 4 | CN |
| cyclobutylmethyl | OH | OH | 4 | CN |
| allyl | OH | OH | 4 | CN |
| H | OH | OH | 4 | CN |
| Me | OH | OH | 4 | CN |
| benzyl | OH | OH | 4 | CN |
| 2-phenethyl | OH | OH | 4 | CN |
| cyclopropylmethyl | OH | OH | 4 | NCS |
| cyclobutylmethyl | OH | OH | 4 | NCS |
| allyl | OH | OH | 4 | NCS |
| H | OH | OH | 4 | NCS |
| Me | OH | OH | 4 | NCS |
| benzyl | OH | OH | 4 | NCS |
| 2-phenethyl | OH | OH | 4 | NCS |
| cyclopropylmethyl | OH | OH | 4 | COOH |
| cyclobutylmethyl | OH | OH | 4 | COOH |
| allyl | OH | OH | 4 | COOH |
| H | OH | OH | 4 | COOH |
| Me | OH | OH | 4 | COOH |
| benzyl | OH | OH | 4 | COOH |
| 2-phenethyl | OH | OH | 4 | COOH |
| cyclopropylmethyl | OH | OH | 4 | COOMe |
| cyclobutylmethyl | OH | OH | 4 | COOMe |
| allyl | OH | OH | 4 | COOMe |
| H | OH | OH | 4 | COOMe |
| Me | OH | OH | 4 | COOMe |
| benzyl | OH | OH | 4 | COOMe |
| 2-phenethyl | OH | OH | 4 | COOMe |
| cyclopropylmethyl | OH | OH | 4 | COOEt |
| cyclobutylmethyl | OH | OH | 4 | COOEt |
| allyl | OH | OH | 4 | COOEt |
| H | OH | OH | 4 | COOEt |
| Me | OH | OH | 4 | COOEt |
| benzyl | OH | OH | 4 | COOEt |
| 2-phenethyl | OH | OH | 4 | COOEt |
| cyclopropylmethyl | OH | OH | 4 | NHCHO |
| cyclobutylmethyl | OH | OH | 4 | NHCHO |
| allyl | OH | OH | 4 | NHCHO |
| H | OH | OH | 4 | NHCHO |
| Me | OH | OH | 4 | NHCHO |
| benzyl | OH | OH | 4 | NHCHO |
| 2-phenethyl | OH | OH | 4 | NHCHO |
| cyclopropylmethyl | OH | OH | 4 | NHCO—Me |
| cyclobutylmethyl | OH | OH | 4 | NHCO—Me |
| allyl | OH | OH | 4 | NHCO—Me |
| H | OH | OH | 4 | NHCO—Me |
| Me | OH | OH | 4 | NHCO—Me |
| benzyl | OH | OH | 4 | NHCO—Me |
| 2-phenethyl | OH | OH | 4 | NHCO—Me |
| cyclopropylmethyl | OH | OH | 4 | NHCO—Ph |
| cyclobutylmethyl | OH | OH | 4 | NHCO—Ph |
| allyl | OH | OH | 4 | NHCO—Ph |
| H | OH | OH | 4 | NHCO—Ph |
| Me | OH | OH | 4 | NHCO—Ph |
| benzyl | OH | OH | 4 | NHCO—Ph |
| 2-phenethyl | OH | OH | 4 | NHCO—Ph |
| cyclopropylmethyl | OH | OH | 4 | NHCO—(CH$_2$)$_5$Ph |
| cyclobutylmethyl | OH | OH | 4 | NHCO—(CH$_2$)$_5$Ph |
| allyl | OH | OH | 4 | NHCO—(CH$_2$)$_5$Ph |
| H | OH | OH | 4 | NHCO—(CH$_2$)$_5$Ph |
| Me | OH | OH | 4 | NHCO—(CH$_2$)$_5$Ph |
| benzyl | OH | OH | 4 | NHCO—(CH$_2$)$_5$Ph |
| 2-phenethyl | OH | OH | 4 | NHCO—(CH$_2$)$_5$Ph |
| cycloropylmethyl | OH | OH | 4 | NHCO-cinnamyl |
| cyclobutylmethyl | OH | OH | 4 | NHCO-cinnamyl |
| allyl | OH | OH | 4 | NHCO-cinnamyl |
| H | OH | OH | 4 | NHCO-cinnamyl |
| Me | OH | OH | 4 | NCHO-cinnamyl |
| benzyl | OH | OH | 4 | NHCO-cinnamyl |
| 2-phenethyl | OH | OH | 4 | NHCO-cinnamyl |
| cyclopropylmethyl | OH | OH | 4 | NHCO—(CF$_3$-cinnamyl) |
| cyclobutylmethyl | OH | OH | 4 | NHCO—(CF$_3$-cinnamyl) |
| allyl | OH | OH | 4 | NHCO—(CF$_3$-cinnamyl) |
| H | OH | OH | 4 | NHCO—(CF$_3$-cinnamyl) |
| Me | OH | OH | 4 | NHCO—(CF$_3$-cinnamyl) |
| benzyl | OH | OH | 4 | NHCO—(CF$_3$-cinnamyl) |
| 2-phenethyl | OH | OH | 4 | NHCO—(CF$_3$-cinnamyl) |
| cyclopropylmethyl | OH | OH | 4 | NHCO-pyridyl |
| cyclobutylmethyl | OH | OH | 4 | NHCO-pyridyl |
| allyl | OH | OH | 4 | NHCO-pyridyl |
| H | OH | OH | 4 | NHCO-pyridyl |
| Me | OH | OH | 4 | NHCO-pyridyl |
| benzyl | OH | OH | 4 | NHCO-pyridyl |
| 2-phenethyl | OH | OH | 4 | NHCO-pyridyl |
| cyclopropylmethyl | OH | OH | 4 | NHCO—NHPh |
| cyclobutylmethyl | OH | OH | 4 | NHCO—NHPh |
| allyl | OH | OH | 4 | NHCO—NHPh |
| H | OH | OH | 4 | NHCO—NHPh |
| Me | OH | OH | 4 | NHCO—NHPh |
| benzyl | OH | OH | 4 | NHCO—NHPh |
| 2-phenethyl | OH | OH | 4 | NHCO—NHPh |
| cyclopropylmethyl | OH | OH | 4 | NHCS—NHPh |
| cyclobutylmethyl | OH | OH | 4 | NHCS—NHPh |
| allyl | OH | OH | 4 | NHCS—NHPh |
| H | OH | OH | 4 | NHCS—NHPh |
| Me | OH | OH | 4 | NHCS—NHPh |
| benzyl | OH | OH | 4 | NHCS—NHPh |
| 2-phenethyl | OH | OH | 4 | NHCS—NHPh |
| cyclopropylmethyl | OH | OH | 4 | NHCS—NHCH$_2$Ph |
| cyclobutylmethyl | OH | OH | 4 | NHCS—NHCH$_2$Ph |
| allyl | OH | OH | 4 | NHCS—NHCH$_2$Ph |
| H | OH | OH | 4 | NHCS—NHCH$_2$Ph |
| Me | OH | OH | 4 | NHCS—NHCH$_2$Ph |
| benzyl | OH | OH | 4 | NHCS—NHCH$_2$Ph |
| 2-phenethyl | OH | OH | 4 | NHCS—NHCH$_2$Ph |
| cyclopropylmethyl | OH | OMe | 3 | OH |
| cyclopropylmethyl | OH | OMe | 3 | OMe |
| cyclopropylmethyl | OH | OMe | 3 | NH$_2$ |
| cyclopropylmethyl | OH | OMe | 3 | CN |
| cyclopropylmethyl | OH | OMe | 3 | NCS |
| cyclopropylmethyl | OH | OMe | 3 | COOH |
| cyclopropylmethyl | OH | OMe | 3 | COOMe |
| cyclopropylmethyl | OH | OMe | 3 | NHCHO |
| cyclopropylmethyl | OH | OMe | 3 | NHCO—Ph |
| cyclopropylmethyl | OH | OMe | 3 | NHCO—(Ch$_2$)$_5$Ph |
| cyclopropylmethyl | OH | OMe | 3 | NHCO—(CF$_3$-cinnamyl) |
| cyclopropylmethyl | OH | OMe | 3 | NHCO-pyridyl |
| cyclopropylmethyl | OH | OMe | 3 | NHCO—NHPh |
| cyclopropylmethyl | OH | OMe | 3 | NHCS—NHPh |
| cyclopropylmethyl | OH | OMe | 4 | OH |
| cyclopropylmethyl | OH | OMe | 4 | OMe |
| cyclopropylmethyl | OH | OMe | 4 | NH$_2$ |
| cyclopropylmethyl | OH | OMe | 4 | CN |

-continued

| | | | | |
|---|---|---|---|---|
| cyclopropylmethyl | OH | OMe | 4 | NCS |
| cyclopropylmethyl | OH | OMe | 4 | COOH |
| cyclopropylmethyl | OH | OMe | 4 | COOMe |
| cyclopropylmethyl | OH | OMe | 4 | NHCHO |
| cyclopropylmethyl | OH | OMe | 4 | NHCO—Ph |
| cyclopropylmethyl | OH | OMe | 4 | NHCO—(CH$_3$)$_2$Ph |
| cyclopropylmethyl | OH | OMe | 4 | NHCO—(CF$_3$-cinnamyl) |
| cyclopropylmethyl | OH | OMe | 4 | NHCO-pyridyl |
| cyclopropylmethyl | OH | OMe | 4 | NHCO—NHPh |
| cyclopropylmethyl | OH | OMe | 4 | NHCS—NHPh |

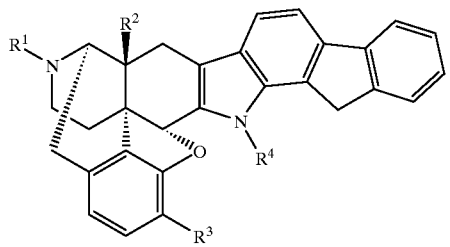

| R$^1$ | R$^2$ | R$^3$ | R$^4$ |
|---|---|---|---|
| cyclopropylmethyl | OH | OH | H |
| cyclobutylmethyl | OH | OH | H |
| allyl | OH | OH | H |
| H | OH | OH | H |
| Me | OH | OH | H |
| benzyl | OH | OH | H |
| 2-phenethyl | OH | OH | H |
| cyclopropylmelthyl | OH | OH | Me |
| cyclobutylmethyl | OH | OH | Me |
| allyl | OH | OH | Me |
| H | OH | OH | Me |
| Me | OH | OH | Me |
| benzyl | OH | OH | Me |
| 2-phenethyl | OH | OH | Me |
| cyclopropylmethyl | OH | OH | Bu |
| cyclobutylmethyl | OH | OH | Bu |
| allyl | OH | OH | Br |
| H | OH | OH | Bu |
| Me | OH | OH | Bu |
| benzyl | OH | OH | Bu |
| 2-phenethyl | OH | OH | Bu |
| cyclopropylmethyl | OH | OH | (F—C$_6$H$_4$)CH$_2$ |
| cyclobutylmethyl | OH | OH | (F—C$_6$H$_4$)CH$_2$ |
| allyl | OH | OH | (F—C$_6$H$_4$)CH$_2$ |
| H | OH | OH | (F—C$_6$H$_4$)CH$_2$ |
| Me | OH | OH | (F—C$_6$H$_4$)CH$_2$ |
| benzyl | OH | OH | (F—C$_6$H$_4$)CH$_2$ |
| 2-phenethyl | OH | OH | (F—C$_6$H$_4$)CH$_2$ |
| cyclopropylmethyl | OH | OH | (Cl—C$_6$H$_4$)CH$_2$ |
| cyclobutylmethyl | OH | OH | (Cl—C$_6$H$_4$)CH$_2$ |
| allyl | OH | OH | (Cl—C$_6$H$_4$)CH$_2$ |
| H | OH | OH | (Cl—C$_6$H$_4$)CH$_2$ |
| Me | OH | OH | (Cl—C$_6$H$_4$)CH$_2$ |
| benzyl | OH | OH | (Cl—C$_6$H$_4$)CH$_2$ |
| 2-phenethyl | OH | OH | (Cl—C$_6$H$_4$)CH$_2$ |
| cyclopropylmethyl | OH | OH | (Br—C$_5$H)CH$_2$ |
| cyclobutylmethyl | OH | OH | (Br—C$_6$H$_4$)CH$_2$ |
| allyl | OH | OH | (Br—C$_6$H$_4$)CH$_2$ |
| H | OH | OH | (Br—C$_6$H$_4$)CH$_2$ |
| Me | OH | OH | (Br—C$_6$H$_4$)CH$_2$ |
| benzyl | OH | OH | (Br—C$_6$H$_4$)CH$_2$ |
| 2-phenethyl | OH | OH | (Br—C$_6$H$_4$)CH$_2$ |
| cyclopropylmethyl | OH | OH | (Me—C$_9$H$_4$)CH$_2$ |
| cyclobutylmethyl | OH | OH | (Me—C$_6$H$_4$)CH$_2$ |
| allyl | OH | OH | (Me—CH$_4$)CH$_2$ |
| H | OH | OH | (Me—C$_9$H$_4$)CH$_2$ |
| Me | OH | OH | (Me—C$_9$H$_4$)CH$_2$ |
| benzyl | OH | OH | (Me—C$_9$H$_4$)CH$_2$ |
| 2-phenethyl | OH | OH | (Me—C$_9$H$_4$)CH$_2$ |
| cyclopropylmethyl | OH | OH | (MeO—C$_5$H$_4$)CH$_2$ |
| cyclobutylmethyl | OH | OH | (MeO—C$_6$H$_4$)CH$_2$ |
| allyl | OH | OH | (MeO—C$_6$H$_4$)CH$_2$ |
| H | OH | OH | (MeO—C$_6$H$_4$)CH$_2$ |

-continued

| | | | |
|---|---|---|---|
| Me | OH | OH | (MeO—C$_6$H$_4$)CH$_2$ |
| benzyl | OH | OH | (MeO—C$_6$H$_4$)CH$_2$ |
| 2-phenethyl | OH | OH | (MeO—C$_6$H$_4$)CH$_2$ |
| cyclopropylmethyl | OH | OH | (F$_3$C—C$_5$H$_4$)CH$_2$ |
| cyclobutylmethyl | OH | OH | (F$_3$C—C$_6$H$_4$)CH$_2$ |
| allyl | OH | OH | (F$_3$C—C$_6$H$_4$)CH$_2$ |
| H | OH | OH | (F$_3$C—C$_6$H$_4$)CH$_2$ |
| Me | OH | OH | (F$_3$C—C$_6$H$_4$)CH$_2$ |
| benzyl | OH | OH | (F$_3$C—C$_6$H$_4$)CH$_2$ |
| 2-phenethyl | OH | OH | (F$_3$C—C$_6$H$_4$)CH$_2$ |
| cyclopropylmethyl | OH | OH | (O$_2$N—C$_6$H$_4$)CH$_2$ |
| cyclobutylmethyl | OH | OH | (O$_2$N—C$_6$H$_4$)CH$_2$ |
| allyl | OH | OH | (O$_2$N—C$_6$H$_4$)CH$_2$ |
| H | OH | OH | (O$_2$N—C$_6$H$_4$)CH$_2$ |
| Me | OH | OH | (O$_2$N—C$_6$H$_4$)CH$_2$ |
| benzyl | OH | OH | (O$_2$N—C$_6$H$_4$)CH$_2$ |
| 2-phenethyl | OH | OH | (O$_2$N—C$_6$H$_4$)CH$_2$ |
| cyclopropylmethyl | OH | OH | Ph(CH$_2$)$_2$ |
| cyclobutylmethyl | OH | OH | Ph(CH$_2$)$_2$ |
| allyl | OH | OH | Ph(CH$_2$)$_2$ |
| H | OH | OH | Ph(CH$_2$)$_2$ |
| Me | OH | OH | Ph(CH$_2$)$_2$ |
| benzyl | OH | OH | Ph(CH$_2$)$_2$ |
| 2-phenethyl | OH | OH | Ph(CH$_2$)$_2$ |
| cyclopropylmethyl | OH | OH | Ph(CH$_2$)$_3$ |
| cyclobutylmethyl | OH | OH | Ph(CH$_2$)$_3$ |
| allyl | OH | OH | Ph(CH$_2$)$_3$ |
| H | OH | OH | Ph(CH$_2$)$_3$ |
| Me | OH | OH | Ph(CH$_2$)$_3$ |
| benzyl | OH | OH | Ph(CH$_2$)$_3$ |
| 2-phenethyl | OH | OH | Ph(CH$_2$)$_3$ |
| cyclopropylmethyl | OH | OH | PhCO |
| cyclobutylmethyl | OH | OH | PhCO |
| allyl | OH | OH | PhCO |
| H | OH | OH | PhCO |
| Me | OH | OH | PhCO |
| benzyl | OH | OH | PhCO |
| cyclopropylmethyl | OH | OH | MeSO$_2$ |
| cyclobutylmethyl | OH | OH | MeSO$_2$ |
| allyl | OH | OH | MeSO$_2$ |
| H | OH | OH | MeSO$_2$ |
| Me | OH | OH | MeSO$_2$ |
| benzyl | OH | OH | MeSO$_2$ |
| 2-phenethyl | OH | OH | MeSO$_2$ |
| cyclopropylmethyl | OH | OH | PhSO$_2$ |
| cyclobutylmethyl | OH | OH | PhSO$_2$ |
| allyl | OH | OH | PhSO$_2$ |
| H | OH | OH | PhSO$_2$ |
| Me | OH | OH | PhSO$_2$ |
| benzyl | OH | OH | PhSO$_2$ |
| 2-phenethyl | OH | OH | PhSO$_2$ |

| R$^1$ | R$^2$ | R$^3$ | i | R$^{16}$ |
|---|---|---|---|---|
| cyclopropylmethyl | OH | OH | 2 | OH |
| cyclobutylmethyl | OH | OH | 2 | OH |
| allyl | OH | OH | 2 | OH |
| H | OH | OH | 2 | OH |
| Me | OH | OH | 2 | OH |
| benzyl | OH | OH | 2 | OH |
| 2-phenethyl | OH | OH | 2 | OH |
| cyclopropylmethyl | OH | OH | 2 | OMe |
| cyclobutylmethyl | OH | OH | 2 | OMe |
| allyl | OH | OH | 2 | OMe |
| H | OH | OH | 2 | OMe |
| Me | OH | OH | 2 | OMe |

-continued

| | | | | |
|---|---|---|---|---|
| benzyl | OH | OH | 2 | OMe |
| 2-phenethyl | OH | OH | 2 | OMe |
| cyclopropylmethyl | OH | OH | 2 | OEt |
| cyclobutylmethyl | OH | OH | 2 | OEt |
| allyl | OH | OH | 2 | OEt |
| H | OH | OH | 2 | OEt |
| Me | OH | OH | 2 | OEt |
| benzyl | OH | OH | 2 | OEt |
| 2-phenethyl | OH | OH | 2 | OEt |
| cyclopropylmethyl | OH | OH | 2 | $NH_2$ |
| cyclobutylmethyl | OH | OH | 2 | $NH_2$ |
| allyl | OH | OH | 2 | $NH_2$ |
| H | OH | OH | 2 | $NH_2$ |
| Me | OH | OH | 2 | $NH_2$ |
| benzyl | OH | OH | 2 | $NH_2$ |
| 2-phenethyl | OH | OH | 2 | $NO_2$ |
| cyclopropylmethyl | OH | OH | 2 | CN |
| cyclobutylmethyl | OH | OH | 2 | CN |
| allyl | OH | OH | 2 | CN |
| H | OH | OH | 2 | CN |
| Me | OH | OH | 2 | CN |
| benzyl | OH | OH | 2 | CN |
| 2-phenethyl | OH | OH | 2 | CN |
| cyclopropylmethyl | OH | OH | 2 | NCS |
| cyclobutylmethyl | OH | OH | 2 | NCS |
| allyl | OH | OH | 2 | NCS |
| H | OH | OH | 2 | NCS |
| Me | OH | OH | 2 | NCS |
| benzyl | OH | OH | 2 | NCS |
| 2-phenethyl | OH | OH | 2 | NCS |
| cyclopropylmethyl | OH | OH | 2 | COOH |
| cyclobutylmethyl | OH | OH | 2 | COOH |
| allyl | OH | OH | 2 | OCOH |
| H | OH | OH | 2 | COOH |
| Me | OH | OH | 2 | COOH |
| benzyl | OH | OH | 2 | COOH |
| 2-phenethyl | OH | OH | 2 | COOH |
| cyclopropylmethyl | OH | OH | 2 | COOMe |
| cyclobutylmethyl | OH | OH | 2 | COOMe |
| allyl | OH | OH | 2 | COOMe |
| H | OH | OH | 2 | COOMe |
| Me | OH | OH | 2 | COOMe |
| benzyl | OH | OH | 2 | COOMe |
| 2-phenethyl | OH | OH | 2 | COOMe |
| cyclopropylmethyl | OH | OH | 2 | COOEt |
| cyclobutylmethyl | OH | OH | 2 | COOEt |
| allyl | OH | OH | 2 | COOEt |
| H | OH | OH | 2 | COOEt |
| Me | OH | OH | 2 | COOEt |
| benzyl | OH | OH | 2 | COOEt |
| 2-phenethyl | OH | OH | 2 | COOEt |
| cyclopropylmethyl | OH | OH | 2 | NHCHO |
| cyclobutylmethyl | OH | OH | 2 | NHCHO |
| allyl | OH | OH | 2 | NHCHO |
| H | OH | OH | 2 | NHCHO |
| Me | OH | OH | 2 | NHCHO |
| benzyl | OH | OH | 2 | NHCHO |
| 2-phenethyl | OH | OH | 2 | NHCHO |
| cyclopropylmethyl | OH | OH | 2 | NHCO—Me |
| cyclobutylmethyl | OH | OH | 2 | NHCO—Me |
| allyl | OH | OH | 2 | NHCO—Me |
| H | OH | OH | 2 | NHCO—Me |
| Me | OH | OH | 2 | NHCO—Me |
| benzyl | OH | OH | 2 | NHCO—Me |
| 2-phenethyl | OH | OH | 2 | NHCO—Me |
| cyclopropylmethyl | OH | OH | 2 | NHCO—$(CH_2)_5$Ph |
| cyclobutylmethyl | OH | OH | 2 | NHCO—$(CH_2)_5$Ph |
| allyl | OH | OH | 2 | NHCO—$(CH_2)_5$Ph |
| H | OH | OH | 2 | NHCO—$(CH_2)_5$Ph |
| Me | OH | OH | 2 | NHCO—$(CH_2)_5$Ph |
| benzyl | OH | OH | 2 | NHCO—$(CH_2)_5$Ph |
| 2-phenethyl | OH | OH | 2 | NHCO—$(CH_2)_5$Ph |
| cyclopropylmethyl | OH | OH | 2 | NHCO-cinnamyl |
| cyclobutylmethyl | OH | OH | 2 | NHCO-cinnamyl |
| allyl | OH | OH | 2 | NHCO-cinnamyl |
| H | OH | OH | 2 | NHCO-cinnamyl |
| Me | OH | OH | 2 | NHCO-cinnamyl |
| benzyl | OH | OH | 2 | NHCO-cinnamyl |
| 2-phenethyl | OH | OH | 2 | NHCO-cinnamyl |
| cyclopropylmethyl | OH | OH | 2 | NHCO—($CF_3$-cinnamyl) |
| cyclobutylmethyl | OH | OH | 2 | NHCO—($CF_3$-cinnamyl) |
| allyl | OH | OH | 2 | NHCO—($CF_3$-cinnamyl) |
| H | OH | OH | 2 | NHCO—($CF_3$-cinnamyl) |
| Me | OH | OH | 2 | NHCO—($CF_3$-cinnamyl) |
| benzyl | OH | OH | 2 | NHCO—($CF_3$-cinnamyl) |
| 2-phenethyl | OH | OH | 2 | NHCO—($CF_3$-cinnamyl) |
| cyclopropylmethyl | OH | OH | 2 | NHCO-pyridyl |
| cyclobutylmethyl | OH | OH | 2 | NHCO-pyridyl |
| allyl | OH | OH | 2 | NHCO-pyridyl |
| H | OH | OH | 2 | NHCO-pyridyl |
| Me | OH | OH | 2 | NHCO-pyridyl |
| benzyl | OH | OH | 2 | NHCO-pyridyl |
| 2-phenethyl | OH | OH | 2 | NHCO-pyridyl |
| cyclopropylmethyl | OH | OH | 2 | NHCO—NHPh |
| cyclobutylmethyl | OH | OH | 2 | NHCO—NHPh |
| allyl | OH | OH | 2 | NHCO—NHPh |
| H | OH | OH | 2 | NHCO—NHPh |
| Me | OH | OH | 2 | NHCO—NHPh |
| benzyl | OH | OH | 2 | NHCO—NHPh |
| 2-phenethyl | OH | OH | 2 | NHCO—NHPh |
| cyclopropylmethyl | OH | OH | 2 | NHCS—NHPh |
| cyclobutylmethyl | OH | OH | 2 | NHCS—NHPh |
| allyl | OH | OH | 2 | NHCS—NHPh |
| H | OH | OH | 2 | NHCS—NHPh |
| Me | OH | OH | 2 | NHCS—NHPh |
| benzyl | OH | OH | 2 | NHCS—NHPh |
| 2-phenethyl | OH | OH | 2 | NHCS—NHPh |
| cyclopropylmethyl | OH | OH | 2 | NHCS—$NHCH_2$Ph |
| cyclobutylmethyl | OH | OH | 2 | NHCS—$NHCH_2$Ph |
| allyl | OH | OH | 2 | NHCS—$NHCH_2$Ph |
| H | OH | OH | 2 | NHCS—$NHCH_2$Ph |
| Me | OH | OH | 2 | NHCS—$NHCH_2$Ph |
| benzyl | OH | OH | 2 | NHCS—$NHCH_2$Ph |
| 2-phenethyl | OH | OH | 2 | NHCS—$NHCH_2$Ph |
| cyclopropylmethyl | OH | OH | 3 | OH |
| cyclobutylmethyl | OH | OH | 3 | OH |
| allyl | OH | OH | 3 | OH |
| H | OH | OH | 3 | OH |
| Me | OH | OH | 3 | OH |
| benzyl | OH | OH | 3 | OH |
| 2-phenethyl | OH | OH | 3 | OH |
| cyclopropylmethyl | OH | OH | 3 | OMe |
| cyclobutylmethyl | OH | OH | 3 | OMe |
| allyl | OH | OH | 3 | OMe |
| H | OH | OH | 3 | OMe |
| Me | OH | OH | 3 | OMe |
| benzyl | OH | OH | 3 | OMe |
| 2-phenethyl | OH | OH | 3 | OMe |
| cyclopropylmethyl | OH | OH | 3 | OEt |
| cyclobutylmethyl | OH | OH | 3 | OEt |
| allyl | OH | OH | 3 | OEt |
| H | OH | OH | 3 | OEt |
| Me | OH | OH | 3 | OEt |
| benzyl | OH | OH | 3 | OEt |
| 2-phenethyl | OH | OH | 3 | OEt |
| cyclopropylmethyl | OH | OH | 3 | $NH_2$ |
| cyclobutylmethyl | OH | OH | 3 | $NH_2$ |
| allyl | OH | OH | 3 | $NH_2$ |
| H | OH | OH | 3 | $NH_2$ |
| Me | OH | OH | 3 | $NH_2$ |
| benzyl | OH | OH | 3 | $NH_2$ |
| 2-phenethyl | OH | OH | 3 | $NH_2$ |
| cyclopropylmethyl | OH | OH | 3 | $NO_2$ |
| cyclobutylmethyl | OH | OH | 3 | $NO_2$ |
| allyl | OH | OH | 3 | $NO_2$ |
| H | OH | OH | 3 | $NO_2$ |
| Me | OH | OH | 3 | $NO_2$ |
| benzyl | OH | OH | 3 | $NO_2$ |
| 2-phenethyl | OH | OH | 3 | $NO_2$ |
| cyclopropylmethyl | OH | OH | 3 | CN |
| cyclobutylmethyl | OH | OH | 3 | CN |
| allyl | OH | OH | 3 | CN |
| H | OH | OH | 3 | CN |
| Me | OH | OH | 3 | CN |
| benzyl | OH | OH | 3 | CN |
| 2-phenethyl | OH | OH | 3 | CN |
| cyclopropylmethyl | OH | OH | 3 | NCS |

-continued

| | | | | |
|---|---|---|---|---|
| cyclobutylmethyl | OH | OH | 3 | NCS |
| allyl | OH | OH | 3 | NCS |
| H | OH | OH | 3 | NCS |
| Me | OH | OH | 3 | NCS |
| benzyl | OH | OH | 3 | NCS |
| 2-phenethyl | OH | OH | 3 | NCS |
| cyclopropylmethyl | OH | OH | 3 | COOH |
| cyclobutylmethyl | OH | OH | 3 | COOH |
| allyl | OH | OH | 3 | COOH |
| H | OH | OH | 3 | COOH |
| Me | OH | OH | 3 | COOH |
| benzyl | OH | OH | 3 | COOH |
| 2-phenethyl | OH | OH | 3 | COOH |
| cyclopropylmethyl | OH | OH | 3 | COOMe |
| cyclobutylmethyl | OH | OH | 3 | COOMe |
| allyl | OH | OH | 3 | COOMe |
| H | OH | OH | 3 | COOMe |
| Me | OH | OH | 3 | COOMe |
| benzyl | OH | OH | 3 | COOMe |
| 2-phenethyl | OH | OH | 3 | COOMe |
| cyclopropylmethyl | OH | OH | 3 | COOEt |
| cyclobutylmethyl | OH | OH | 3 | COOEt |
| allyl | OH | OH | 3 | COOEt |
| H | OH | OH | 3 | COOEt |
| Me | OH | OH | 3 | COOEt |
| benzyl | OH | OH | 3 | COOEt |
| 2-phenethyl | OH | OH | 3 | COOEt |
| cyclopropylmethyl | OH | OH | 3 | NHCHO |
| cyclobutylmethyl | OH | OH | 3 | NHCHO |
| allyl | OH | OH | 3 | NHCHO |
| H | OH | OH | 3 | NHCHO |
| Me | OH | OH | 3 | NHCHO |
| benzyl | OH | OH | 3 | NHCHO |
| 2-phenethyl | OH | OH | 3 | NHCHO |
| cylcopropylmethyl | OH | OH | 3 | NHCO—Me |
| cyclobutylmethyl | OH | OH | 3 | NHCO—Me |
| allyl | OH | OH | 3 | NHCO—Me |
| H | OH | OH | 3 | NHCO—Me |
| Me | OH | OH | 3 | NHCO—Me |
| benzyl | OH | OH | 3 | NHCO—Me |
| 2-phenethyl | OH | OH | 3 | NHCO—Me |
| cyclopropylmethyl | OH | OH | 3 | NHCO—Ph |
| cyclobutylmethyl | OH | OH | 3 | NHCO—Ph |
| allyl | OH | OH | 3 | NHCO—Ph |
| H | OH | OH | 3 | NHCO—Ph |
| Me | OH | OH | 3 | NHCO—Ph |
| benzyl | OH | OH | 3 | NHCO—Ph |
| 2-phenethyl | OH | OH | 3 | NHCO—Ph |
| cyclopropylmethyl | OH | OH | 3 | NHCO—$(CH_2)_5$Ph |
| cyclobutylmethyl | OH | OH | 3 | NHCO—$(CH_2)_5$Ph |
| allyl | OH | OH | 3 | NHCO—$(CH_2)_5$Ph |
| H | OH | OH | 3 | NHCO—$(CH_2)_5$Ph |
| Me | OH | OH | 3 | NHCO—$(CH_2)_5$Ph |
| benzyl | OH | OH | 3 | NHCO—$(CH_2)_5$Ph |
| 2-phenethyl | OH | OH | 3 | NHCO—$(CH_2)_5$Ph |
| cyclopropylmethyl | OH | OH | 3 | NHCO-cinnamyl |
| cyclobutylmethyl | OH | OH | 3 | NHCO-cinnamyl |
| allyl | OH | OH | 3 | NHCO-cinnamyl |
| H | OH | OH | 3 | NHCO-cinnamyl |
| Me | OH | OH | 3 | NHCO-cinnamyl |
| benzyl | OH | OH | 3 | NHCO-cinnamyl |
| 2-phenethyl | OH | OH | 3 | NHCO-cinnamyl |
| cyclopropylmethyl | OH | OH | 3 | NHCO—($CF_3$-cinnamyl) |
| cyclobutylmethyl | OH | OH | 3 | NHCO—($CF_3$-cinnamyl) |
| allyl | OH | OH | 3 | NHCO—($CF_3$-cinnamyl) |
| H | OH | OH | 3 | NHCO—($CF_3$-cinnamyl) |
| Me | OH | OH | 3 | NHCO—($CF_3$-cinnamyl) |
| benzyl | OH | OH | 3 | NHCO—($CF_3$-cinnamyl) |
| 2-phenethyl | OH | OH | 3 | NHCO—($CF_3$-cinnamyl) |
| cyclopropylmethyl | OH | OH | 3 | NHCO-pyridyl |
| cyclobutylmethyl | OH | OH | 3 | NHCO-pyridyl |
| allyl | OH | OH | 3 | NHCO-pyridyl |
| H | OH | OH | 3 | NHCO-pyridyl |
| Me | OH | OH | 3 | NHCO-pyridyl |
| benzyl | OH | OH | 3 | NHCO-pyridyl |
| 2-phenethyl | OH | OH | 3 | NHCO-pyridyl |
| cyclopropylmethyl | OH | OH | 3 | NHCO—NHPh |
| cyclobutylmethyl | OH | OH | 3 | NHCO—NHPh |
| allyl | OH | OH | 3 | NHCO—NHPh |
| H | OH | OH | 3 | NHCO—NHPh |
| Me | OH | OH | 3 | NHCO—NHPh |
| benzyl | OH | OH | 3 | NHCO—NHPh |
| 2-phenethyl | OH | OH | 3 | NHCO—NHPh |
| cyclopropylmethyl | OH | OH | 3 | NHCS—NHPh |
| cyclobutylmethyl | OH | OH | 3 | NHCS—NHPh |
| allyl | OH | OH | 3 | NHCS—NHPh |
| H | OH | OH | 3 | NHCS—NHPh |
| Me | OH | OH | 3 | NHCS—NHPh |
| benzyl | OH | OH | 3 | NHCS—NHPh |
| 2-phenethyl | OH | OH | 3 | NHCS—NHPh |
| cyclopropylmethyl | OH | OH | 3 | NHCS—NHCH$_2$Ph |
| cyclobutylmethyl | OH | OH | 3 | NHCS—NHCH$_2$Ph |
| allyl | OH | OH | 3 | NHCS—NHCH$_2$Ph |
| H | OH | OH | 3 | NHCS—NHCH$_2$Ph |
| Me | OH | OH | 3 | NHCS—NHCH$_2$Ph |
| benzyl | OH | OH | 3 | NHCS—NHCH$_2$Ph |
| 2-phenethyl | OH | OH | 3 | NHCS—NHCH$_2$Ph |
| cyclopropylmethyl | OH | OH | 4 | OH |
| cyclobutylmethyl | OH | OH | 4 | OH |
| allyl | OH | OH | 4 | OH |
| H | OH | OH | 4 | OH |
| Me | OH | OH | 4 | OH |
| benzyl | OH | OH | 4 | OH |
| 2-phenethyl | OH | OH | 4 | OH |
| cyclopropylmethyl | OH | OH | 4 | OMe |
| cyclobutylmethyl | OH | OH | 4 | OMe |
| allyl | OH | OH | 4 | OMe |
| H | OH | OH | 4 | OMe |
| Me | OH | OH | 4 | OMe |
| benzyl | OH | OH | 4 | OMe |
| 2-phenethyl | OH | OH | 4 | OMe |
| cyclopropylmethyl | OH | OH | 4 | OEt |
| cyclobutylmethyl | OH | OH | 4 | OEt |
| allyl | OH | OH | 4 | OEt |
| H | OH | OH | 4 | OEt |
| Me | OH | OH | 4 | OEt |
| benzyl | OH | OH | 4 | OEt |
| 2-phenethyl | OH | OH | 4 | OEt |
| cyclopropylmethyl | OH | OH | 4 | NH$_2$ |
| cyclobutylmethyl | OH | OH | 4 | NH$_2$ |
| allyl | OH | OH | 4 | NH$_2$ |
| H | OH | OH | 4 | NH$_2$ |
| Me | OH | OH | 4 | NH$_2$ |
| benzyl | OH | OH | 4 | NH$_2$ |
| 2-phenethyl | OH | OH | 4 | NH$_2$ |
| cyclopropylmethyl | OH | OH | 4 | NO$_2$ |
| cyclobutylmethyl | OH | OH | 4 | NO$_2$ |
| allyl | OH | OH | 4 | NO$_2$ |
| H | OH | OH | 4 | NO$_2$ |
| Me | OH | OH | 4 | NO$_2$ |
| benzyl | OH | OH | 4 | NO$_2$ |
| 2-phenethyl | OH | OH | 4 | NO$_2$ |
| cyclopropylmethyl | OH | OH | 4 | CN |
| cyclobutylemthyl | OH | OH | 4 | CN |
| allyl | OH | OH | 4 | CN |
| H | OH | OH | 4 | CN |
| Me | OH | OH | 4 | CN |
| benzyl | OH | OH | 4 | CN |
| 2-phenethyl | OH | OH | 4 | CN |
| cyclopropylmethyl | OH | OH | 4 | NCS |
| cyclobutylmethyl | OH | OH | 4 | NCS |
| allyl | OH | OH | 4 | NCS |
| H | OH | OH | 4 | NCS |
| Me | OH | OH | 4 | NCS |
| benzyl | OH | OH | 4 | NCS |
| 2-phenethyl | OH | OH | 4 | NCS |
| cyclopropylmethyl | OH | OH | 4 | COOH |
| cyclobutylmethyl | OH | OH | 4 | COOH |
| allyl | OH | OH | 4 | COOH |
| H | OH | OH | 4 | COOH |
| Me | OH | OH | 4 | COOH |
| benzyl | OH | OH | 4 | COOH |
| 2-phenethyl | OH | OH | 4 | COOH |
| cyclopropylmethyl | OH | OH | 4 | COOMe |
| cyclobutylmethyl | OH | OH | 4 | COOMe |
| allyl | OH | OH | 4 | COOMe |
| H | OH | OH | 4 | COOMe |
| Me | OH | OH | 4 | COOMe |

-continued

| R¹ | | | | R⁵ |
|---|---|---|---|---|
| benzyl | OH | OH | 4 | COOMe |
| 2-phenethyl | OH | OH | 4 | COOMe |
| cyclopropylmethyl | OH | OH | 4 | COOEt |
| cyclobutylmethyl | OH | OH | 4 | COOEt |
| allyl | OH | OH | 4 | COOEt |
| H | OH | OH | 4 | COOEt |
| Me | OH | OH | 4 | COOEt |
| benzyl | OH | OH | 4 | COOEt |
| 2-phenethyl | OH | OH | 4 | COOEt |
| cyclopropylmethyl | OH | OH | 4 | NHCHO |
| cyclobutylmethyl | OH | OH | 4 | NHCHO |
| allyl | OH | OH | 4 | NHCHO |
| H | OH | OH | 4 | NHCHO |
| Me | OH | OH | 4 | NHCHO |
| benzyl | OH | OH | 4 | NHCHO |
| 2-phenethyl | OH | OH | 4 | NHCHO |
| cyclopropylmethyl | OH | OH | 4 | NHCO—Me |
| cyclobutylmethyl | OH | OH | 4 | NHCO—Me |
| allyl | OH | OH | 4 | NHCO—Me |
| H | OH | OH | 4 | NHCO—Me |
| Me | OH | OH | 4 | NHCO—Me |
| benzyl | OH | OH | 4 | NHCO—Me |
| 2-phenethyl | OH | OH | 4 | NHCO—Me |
| cyclopropylmethyl | OH | OH | 4 | NHCO—Ph |
| cyclobutylmethyl | OH | OH | 4 | NHCO—Ph |
| allyl | OH | OH | 4 | NHCO—Ph |
| H | OH | OH | 4 | NHCO—Ph |
| Me | OH | OH | 4 | NHCO—Ph |
| benzyl | OH | OH | 4 | NHCO—Ph |
| 2-phenethyl | OH | OH | 4 | NHCO—Ph |
| cyclopropylmethyl | OH | OH | 4 | NHCO—(CH$_2$)$_5$Ph |
| cyclobutylmethyl | OH | OH | 4 | NHCO—(CH$_2$)$_5$Ph |
| allyl | OH | OH | 4 | NHCO—(CH$_2$)$_5$Ph |
| H | OH | OH | 4 | NHCO—(CH$_2$)$_5$Ph |
| Me | OH | OH | 4 | NHCO—(CH$_2$)$_5$Ph |
| benzyl | OH | OH | 4 | NHCO—(CH$_2$)$_5$Ph |
| 2-phenethyl | OH | OH | 5 | NHCO—(CH$_2$)$_5$Ph |
| cyclopropylmethyl | OH | OH | 4 | NHCO-cinnamyl |
| cyclobutylmethyl | OH | OH | 4 | NHCO-cinnamyl |
| allyl | OH | OH | 4 | NHCO-cinnamyl |
| H | OH | OH | 4 | NHCO-cinnamyl |
| Me | OH | OH | 4 | NHCO-cinnamyl |
| benzyl | OH | OH | 4 | NHCO-cinnamyl |
| 2-phenethyl | OH | OH | 4 | NHCO-cinnamyl |
| cyclopropylmethyl | OH | OH | 4 | NHCO—(CF$_3$-cinnamyl) |
| cyclobutylmethyl | OH | OH | 4 | NHCO—(CF$_3$-cinnamyl) |
| allyl | OH | OH | 4 | NHCO—(CF$_3$-cinnamyl) |
| H | OH | OH | 4 | NHCO—(CF$_3$-cinnamyl) |
| Me | OH | OH | 4 | NHCO—(CF$_3$-cinnamyl) |
| benzyl | OH | OH | 4 | NHCO—(CF$_3$-cinnamyl) |
| 2-phenethyl | OH | OH | 4 | NHCO—(CF$_3$-cinnamyl) |
| cyclopropylmethyl | OH | OH | 4 | NHCO-pyridyl |
| cyclobutylmethyl | OH | OH | 4 | NHCO-pyridyl |
| allyl | OH | OH | 4 | NHCO-pyridyl |
| H | OH | OH | 4 | NHCO-pyridyl |
| Me | OH | OH | 4 | NHCO-pyridyl |
| benzyl | OH | OH | 4 | NHCO-pyridyl |
| 2-phenethyl | OH | OH | 4 | NHCO-pyridyl |
| cyclopropylmethyl | OH | OH | 4 | NHCO—NHPh |
| cyclobutylmethyl | OH | OH | 4 | NHCO—NHPh |
| allyl | OH | OH | 4 | NHCO—NHPh |
| H | OH | OH | 4 | NHCO—NHPh |
| Me | OH | OH | 4 | NHCO—NHPh |
| benzyl | OH | OH | 4 | NHCO—NHPh |
| 2-phenethyl | OH | OH | 4 | NHCO—NHPh |
| cyclopropylmethyl | OH | OH | 4 | NHCS—NHPh |
| cyclobutylmethyl | OH | OH | 4 | NHCS—NHPh |
| allyl | OH | OH | 4 | NHCS—NHPh |
| H | OH | OH | 4 | NHCS—NHPh |
| Me | OH | OH | 4 | NHCS—NHPh |
| benzyl | OH | OH | 4 | NHCS—NHPh |
| 2-phenethyl | OH | OH | 4 | NHCS—NHPh |
| cyclopropylmethyl | OH | OH | 4 | NHCS—NHCH$_2$Ph |
| cyclobutylmethyl | OH | OH | 4 | NHCS—NHCH$_2$Ph |
| allyl | OH | OH | 4 | NHCS—NHCH$_2$Ph |
| H | OH | OH | 4 | NHCS—NHCH$_2$Ph |
| Me | OH | OH | 4 | NHCS—NHCH$_2$Ph |
| benzyl | OH | OH | 4 | NHCS—NHCH$_2$Ph |
| 2-phenethyl | OH | OH | 4 | NHCS—NHCH$_2$Ph |
| cyclopropylmethyl | OH | OMe | 3 | OH |
| cyclopropylmethyl | OH | OMe | 3 | OMe |
| cyclopropylmethyl | OH | OMe | 3 | NH$_2$ |
| cyclopropylmethyl | OH | OMe | 3 | CN |
| cyclopropylmethyl | OH | OMe | 3 | NCS |
| cyclopropylmethyl | OH | OMe | 3 | COOH |
| cyclopropylmethyl | OH | OMe | 3 | COOMe |
| cyclopropylmethyl | OH | OMe | 3 | NHCHO |
| cyclopropylmethyl | OH | OMe | 3 | NHCO—Ph |
| cyclopropylmethyl | OH | OMe | 3 | NHCO—(CH$_2$)$_5$Ph |
| cyclopropylmethyl | OH | OMe | 3 | NHCO—(CF$_3$-cinnamyl) |
| cyclopropylmethyl | OH | OMe | 3 | NHCO-pyridyl |
| cyclopropylmethyl | OH | OMe | 3 | NHCO—NHPh |
| cyclopropylmethyl | OH | OMe | 3 | NHCS—NHPh |
| cyclopropylmethyl | OH | OMe | 3 | OH |
| cyclopropylmethyl | OH | OMe | 3 | OMe |
| cyclopropylmethyl | OH | OMe | 3 | NH$_2$ |
| cyclopropylmethyl | OH | OMe | 3 | CN |
| cyclopropylmethyl | OH | OMe | 3 | NCS |
| cyclopropylmethyl | OH | OMe | 3 | COOH |
| cyclopropylmethyl | OH | OMe | 3 | COOMe |
| cyclopropylmethyl | OH | OMe | 3 | NHCHO |
| cyclopropylmethyl | OH | OMe | 3 | NHCO—Ph |
| cyclopropylmethyl | OH | OMe | 3 | NHCO—(CH$_2$)$_5$Ph |
| cyclopropylmethyl | OH | OMe | 3 | NHCO—(CF$_3$-cinnamyl) |
| cyclopropylmethyl | OH | OMe | 3 | NHCO-pyridyl |
| cyclopropylmethyl | OH | OMe | 3 | NHCO—NHPh |
| cyclopropylmethyl | OH | OMe | 3 | NHCS—NHPh |

| R¹ | R² | R³ | R⁴ |
|---|---|---|---|
| cyclopropylmethyl | OH | OH | H |
| cyclobutylmethyl | OH | OH | H |
| allyl | OH | OH | H |
| H | OH | OH | H |
| Me | OH | OH | H |
| benzyl | OH | OH | H |
| 2-phenethyl | OH | OH | H |
| cyclopropylmethyl | OH | OH | Me |
| cyclobutylmethyl | OH | OH | Me |
| allyl | OH | OH | Me |
| H | OH | OH | Me |
| Me | OH | OH | Me |
| benzyl | OH | OH | Me |
| 2-phenethyl | OH | OH | Me |
| cyclopropylmethyl | OH | OH | Bu |
| cyclobutylmethyl | OH | OH | Bu |
| allyl | OH | OH | Bu |
| H | OH | OH | Bu |
| Me | OH | OH | Bu |
| benzyl | OH | OH | Bu |
| 2-phenethyl | OH | OH | Bu |
| cyclopropylmethyl | OH | OH | PhCH$_2$ |
| cyclobutylmethyl | OH | OH | PhCH$_2$ |
| allyl | OH | OH | PhCH$_2$ |
| H | OH | OH | PhCH$_2$ |
| Me | OH | OH | PhCH$_2$ |
| benzyl | OH | OH | PhCH$_2$ |
| 2-phenethyl | OH | OH | PhCH$_2$ |
| cyclopropylmethyl | OH | OH | (F—C$_6$H$_4$)CH$_2$ |
| cyclobutylmethyl | OH | OH | (F—C$_6$H$_4$)CH$_2$ |
| allyl | OH | OH | (F—C$_6$H$_4$)CH$_2$ |
| H | OH | OH | (F—C$_6$H$_4$)CH$_2$ |
| Me | OH | OH | (F—C$_6$H$_4$)CH$_2$ |
| benzyl | OH | OH | (F—C$_6$H$_4$)CH$_2$ |
| 2-phenethyl | OH | OH | (F—C$_6$H$_4$)CH$_2$ |

-continued

| | R¹ | R² | R³ |
|---|---|---|---|
| cyclopropylmethyl | OH | OH | (Cl—C₆H₄)CH₂ |
| cyclobutylmethyl | OH | OH | (Cl—C₆H₄)CH₂ |
| allyl | OH | OH | (Cl—C₆H₄)CH₂ |
| H | OH | OH | (Cl—C₆H₄)CH₂ |
| Me | OH | OH | (Cl—C₆H₄)CH₂ |
| benzyl | OH | OH | (Cl—C₆H₄)CH₂ |
| 2-phenethyl | OH | OH | (Cl—C₆H₄)CH₂ |
| cyclopropylmethyl | OH | OH | (Br—C₆H₄)CH₂ |
| cyclobutylmethyl | OH | OH | (Br—C₆H₄)CH₂ |
| allyl | OH | OH | (Br—C₆H₄)CH₂ |
| H | OH | OH | (Br—C₆H₄)CH₂ |
| Me | OH | OH | (Br—C₆H₄)CH₂ |
| benzyl | OH | OH | (Br—C₆H₄)CH₂ |
| 2-phenethyl | OH | OH | (Br—C₉H₄)CH₂ |
| cyclopropylmethyl | OH | OH | (Me—C₆H₄)CH₂ |
| cyclobutylmethyl | OH | OH | (Me—C₆H₄)CH₂ |
| allyl | OH | OH | (Me—C₉H₄)CH₂ |
| H | OH | OH | (Me—C₆H₄)CH₂ |
| Me | OH | OH | (Me—C₆H₄)CH₂ |
| benzyl | OH | OH | (Me—C₉H₄)CH₂ |
| 2-phenethyl | OH | OH | (Me—C₉H₄)CH₂ |
| cyclopropylmethyl | OH | OH | (MeO—C₆H₄)CH₂ |
| cyclobutylmethyl | OH | OH | (MeO—C₆H₄)CH₂ |
| allyl | OH | OH | (MeO—C₉H₄)CH₂ |
| H | OH | OH | (MeO—C₉H₄)CH₂ |
| Me | OH | OH | (MeO—C₉H₄)CH₂ |
| benzyl | OH | OH | (MeO—C₉H₄)CH₂ |
| 2-phenethyl | OH | OH | (MeO—C₉H₄)CH₂ |
| cyclopropylmethyl | OH | OH | (F₃C—C₆H₄)CH₂ |
| cylcobutylmethyl | OH | OH | (F₃C—C₆H₄)CH₂ |
| allyl | OH | OH | (F₃C—C₆H₄)CH₂ |
| H | OH | OH | (F₃C—C₆H₄)CH₂ |
| Me | OH | OH | (F₃C—C₆H₄)CH₂ |
| benzyl | OH | OH | (F₃C—C₆H₄)CH₂ |
| 2-phenethyl | OH | OH | (F₃C—C₆H₄)CH₂ |
| cyclopropylmethyl | OH | OH | (O₂N—C₆H₄)CH₂ |
| cyclobutylmethyl | OH | OH | (O₂N—C₆H₄)CH₂ |
| allyl | OH | OH | (O₂N—C₆H₄)CH₂ |
| H | OH | OH | (O₂N—C₆H₄)CH₂ |
| Me | OH | OH | (O₂N—C₆H₄)CH₂ |
| benzyl | OH | OH | (O₂N—C₆H₄)CH₂ |
| 2-phenethyl | OH | OH | (O₂N—C₆H₄)CH₂ |
| cyclopropylmethyl | OH | OH | Ph(CH₂)₂ |
| cyclobutylmethyl | OH | OH | Ph(CH₂)₂ |
| allyl | OH | OH | Ph(CH₂)₂ |
| H | OH | OH | Ph(CH₂)₂ |
| Me | OH | OH | Ph(CH₂)₂ |
| benzyl | OH | OH | Ph(CH₂)₂ |
| 2-phenethyl | OH | OH | Ph(CH₂)₂ |
| cyclopropylmethyl | OH | OH | Ph(CH₂)₃ |
| cyclobutylmethyl | OH | OH | Ph(CH₂)₃ |
| allyl | OH | OH | Ph(CH₂)₃ |
| H | OH | OH | Ph(CH₂)₃ |
| Me | OH | OH | Ph(CH₂)₃ |
| benzyl | OH | OH | Ph(CH₂)₃ |
| 2-phenethyl | OH | OH | Ph(CH₂)₃ |
| cyclopropylmethyl | OH | OH | PhCO |
| cyclobutylmethyl | OH | OH | PhCO |
| allyl | OH | OH | PhCO |
| H | OH | OH | PhCO |
| Me | OH | OH | PhCO |
| benzyl | OH | OH | PhCO |
| 2-phenethyl | OH | OH | PhCO |
| cyclopropylmethyl | OH | OH | MeSO₂ |
| cyclobutylmethyl | OH | OH | MeSO₂ |
| allyl | OH | OH | MeSO₂ |
| H | OH | OH | MeSO₂ |
| Me | OH | OH | MeSO₂ |
| benzyl | OH | OH | MeSO₂ |
| 2-phenethyl | OH | OH | MeSO₂ |
| cyclopropylmethyl | OH | OH | PhSO₃ |
| cyclobutylmethyl | OH | OH | PhSO₃ |
| allyl | OH | OH | PhSO₃ |
| H | OH | OH | PhSO₃ |
| Me | OH | OH | PhSO₃ |
| benzyl | OH | OH | PhSO₃ |
| 2-phenethyl | OH | OH | PhSO₃ |

-continued

| R¹ | R² | R³ | i | R¹⁶ |
|---|---|---|---|---|
| cyclopropylmethyl | OH | OH | 2 | OH |
| cyclobutylmethyl | OH | OH | 2 | OH |
| allyl | OH | OH | 2 | OH |
| H | OH | OH | 2 | OH |
| Me | OH | OH | 2 | OH |
| benzyl | OH | OH | 2 | OH |
| 2-phenethyl | OH | OH | 2 | OH |
| cyclopropylmethyl | OH | OH | 2 | OMe |
| cyclobutylmethyl | OH | OH | 2 | OMe |
| allyl | OH | OH | 2 | OMe |
| H | OH | OH | 2 | OMe |
| Me | OH | OH | 2 | OMe |
| benzyl | OH | OH | 2 | OMe |
| 2-phenethyl | OH | OH | 2 | OMe |
| cyclopropylmethyl | OH | OH | 2 | OEt |
| cyclobutylmethyl | OH | OH | 2 | OEt |
| allyl | OH | OH | 2 | OEt |
| H | OH | OH | 2 | OEt |
| Me | OH | OH | 2 | OEt |
| benzyl | OH | OH | 2 | OEt |
| 2-phenethyl | OH | OH | 2 | OEt |
| cyclopropylmethyl | OH | OH | 2 | NH₂ |
| cyclobutylmethyl | OH | OH | 2 | NH₂ |
| allyl | OH | OH | 2 | NH₂ |
| H | OH | OH | 2 | NH₂ |
| Me | OH | OH | 2 | NH₂ |
| benzyl | OH | OH | 2 | NH₂ |
| 2-phenethyl | OH | OH | 2 | NH₂ |
| cyclopropylmethyl | OH | OH | 2 | NO₂ |
| cyclobutylmethyl | OH | OH | 2 | NO₂ |
| allyl | OH | OH | 2 | NO₂ |
| H | OH | OH | 2 | NO₂ |
| Me | OH | OH | 2 | NO₂ |
| benzyl | OH | OH | 2 | NO₂ |
| 2-phenethyl | OH | OH | 2 | NO₂ |
| cyclopropylmethyl | OH | OH | 2 | CN |
| cyclobutylmethyl | OH | OH | 2 | CN |
| allyl | OH | OH | 2 | CN |
| H | OH | OH | 2 | CN |
| Me | OH | OH | 2 | CN |
| benzyl | OH | OH | 2 | CN |
| 2-phenethyl | OH | OH | 2 | CN |
| cyclopropylmethyyl | OH | OH | 2 | NCS |
| cyclobutylmethyl | OH | OH | 2 | NCS |
| allyl | OH | OH | 2 | NCS |
| H | OH | OH | 2 | NCS |
| Me | OH | OH | 2 | NCS |
| benzyl | OH | OH | 2 | NCS |
| 2-phenethyl | OH | OH | 2 | NCS |
| cyclopropylmethyl | OH | OH | 2 | COOH |
| cyclobutylmethyl | OH | OH | 2 | COOH |
| allyl | OH | OH | 2 | COOH |
| H | OH | OH | 2 | COOH |
| Me | OH | OH | 2 | COOH |
| benzyl | OH | OH | 2 | COOH |
| 2-phenethyl | OH | OH | 2 | COOH |
| cyclopropylmethyl | OH | OH | 2 | COOMe |
| cyclobutylmethyl | OH | OH | 2 | COOMe |
| allyl | OH | OH | 2 | COOMe |
| H | OH | OH | 2 | COOMe |
| Me | OH | OH | 2 | COOMe |
| benzyl | OH | OH | 2 | COOMe |
| 2-phenethyl | OH | OH | 2 | COOMe |
| cyclopropylmethyl | OH | OH | 2 | COOEt |

| | | | | |
|---|---|---|---|---|
| cyclobutylmethyl | OH | OH | 2 | COOEt |
| allyl | OH | OH | 2 | COOEt |
| H | OH | OH | 2 | COOEt |
| Me | OH | OH | 2 | COOEt |
| benzyl | OH | OH | 2 | COOEt |
| 2-phenethyl | OH | OH | 2 | COOEt |
| cyclopropylmethyl | OH | OH | 2 | NHCHO |
| cyclobutylmethyl | OH | OH | 2 | NHCHO |
| allyl | OH | OH | 2 | NHCHO |
| H | OH | OH | 2 | NHCHO |
| Me | OH | OH | 2 | NHCHO |
| benzyl | OH | OH | 2 | NHCHO |
| 2-phenethyl | OH | OH | 2 | NHCHO |
| cyclopropylmethyl | OH | OH | 2 | NHCO—Me |
| cyclobutylmethyl | OH | OH | 2 | NHCO—Me |
| allyl | OH | OH | 2 | NHCO—Me |
| H | OH | OH | 2 | NHCO—Me |
| Me | OH | OH | 2 | NHCO—Me |
| benzyl | OH | OH | 2 | NHCO—Me |
| 2-phenethyl | OH | OH | 2 | NHCO—Me |
| cyclopropylmethyl | OH | OH | 2 | NHCO—Ph |
| cyclobutylmethyl | OH | OH | 2 | NHCO—Ph |
| allyl | OH | OH | 2 | NHCO—Ph |
| H | OH | OH | 2 | NHCO—Ph |
| Me | OH | OH | 2 | NHCO—Ph |
| benzyl | OH | OH | 2 | NHCO—Ph |
| cyclopropylmethyl | OH | OH | 2 | NHCO—$(CH_2)_4$Ph |
| cyclobutylmethyl | OH | OH | 2 | NHCO—$(CH_2)_5$Ph |
| allyl | OH | OH | 2 | NHCO—$(CH_2)_5$Ph |
| H | OH | OH | 2 | NHCO—$(CH_2)_5$Ph |
| Me | OH | OH | 2 | NHCO—$(CH_2)_5$Ph |
| benzyl | OH | OH | 2 | NHCO—$(CH_2)_5$Ph |
| 2-phenethyl | OH | OH | 2 | NHCO—$(CH_2)_5$Ph |
| cyclopropylmethyl | OH | OH | 2 | NHCO-cinnamyl |
| cyclobutylmethyl | OH | OH | 2 | NHCO-cinnamyl |
| allyl | OH | OH | 2 | NHCO-cinnamyl |
| H | OH | OH | 2 | NHCO-cinnamyl |
| Me | OH | OH | 2 | NHCO-cinnamyl |
| benzyl | OH | OH | 2 | NHCO-cinnamyl |
| 2-phenethyl | OH | OH | 2 | NHCO-cinnamyl |
| cyclopropylmethyl | OH | OH | 2 | NHCO—($CF_3$-cinnamyl) |
| cyclobutylmethyl | OH | OH | 2 | NHCO—($CF_3$-cinnamyl) |
| allyl | OH | OH | 2 | NHCO—($CF_3$-cinnamyl) |
| H | OH | OH | 2 | NHCO—($CF_3$-cinnamyl) |
| Me | OH | OH | 2 | NHCO—($CF_3$-cinnamyl) |
| benzyl | OH | OH | 2 | NHCO—($CF_3$-cinnamyl) |
| 2-phenethyl | OH | OH | 2 | NHCO—($CF_3$-cinnamyl) |
| cyclopropylmethyl | OH | OH | 2 | NHCO-pyridyl |
| cyclobutylmethyl | OH | OH | 2 | NHCO-pyridyl |
| allyl | OH | OH | 2 | NHCO-pyridyl |
| H | OH | OH | 2 | NHCO-pyridyl |
| Me | OH | OH | 2 | NHCO-pyridyl |
| benzyl | OH | OH | 2 | NHCO-pyridyl |
| 2-phenethyl | OH | OH | 2 | NHCO-pyridyl |
| cyclopropylmethyl | OH | OH | 2 | NHCO—NHPh |
| cyclobutylmethyl | OH | OH | 2 | NHCO—NHPh |
| allyl | OH | OH | 2 | NHCO—NHPh |
| H | OH | OH | 2 | NHCO—NHPh |
| Me | OH | OH | 2 | NHCO—NHPh |
| 2-phenethyl | OH | OH | 2 | NHCO—NHPh |
| cyclopropylmethyl | OH | OH | 2 | NHCS—NHPh |
| cyclobutylmethyl | OH | OH | 2 | NHCS—NHPh |
| allyl | OH | OH | 2 | NHCS—NHPh |
| H | OH | OH | 2 | NHCS—NHPh |
| Me | OH | OH | 2 | NHCS—NHPh |
| benzyl | OH | OH | 2 | NHCS—NHPh |
| 2-phenethyl | OH | OH | 2 | NHCS—NHPh |
| cyclopropylmethyl | OH | OH | 2 | NHCS—$NHCH_2$Ph |
| cyclobutylmethyl | OH | OH | 2 | NHCS—$NHCH_2$Ph |
| allyl | OH | OH | 2 | NHCS—$NHCH_2$Ph |
| H | OH | OH | 2 | NHCS—$NHCH_2$Ph |
| Me | OH | OH | 2 | NHCS—$NHCH_2$Ph |
| benzyl | OH | OH | 2 | NHCS—$NHCH_2$Ph |
| 2-phenethyl | OH | OH | 2 | NHCS—$NHCH_2$Ph |
| cyclopropylmethyl | OH | OH | 3 | OH |
| cyclobutylmethyl | OH | OH | 3 | OH |
| allyl | OH | OH | 3 | OH |
| H | OH | OH | 3 | OH |
| Me | OH | OH | 3 | OH |
| benzyl | OH | OH | 3 | OH |
| 2-phenethyl | OH | OH | 3 | OH |
| cyclopropylmethyl | OH | OH | 3 | OMe |
| cyclobutylmethyl | OH | OH | 3 | OMe |
| allyl | OH | OH | 3 | OMe |
| H | OH | OH | 3 | OMe |
| Me | OH | OH | 3 | OMe |
| benzyl | OH | OH | 3 | OMe |
| 2-phenethyl | OH | OH | 3 | OMe |
| cyclopropylmethyl | OH | OH | 3 | OEt |
| cyclobutylmethyl | OH | OH | 3 | OEt |
| allyl | OH | OH | 3 | OEt |
| H | OH | OH | 3 | OEt |
| Me | OH | OH | 3 | OEt |
| benzyl | OH | OH | 3 | OEt |
| 2-phenethyl | OH | OH | 3 | OEt |
| cyclopropylmethyl | OH | OH | 3 | $NH_2$ |
| cyclobutylmethyl | OH | OH | 3 | $NH_2$ |
| allyl | OH | OH | 3 | $NH_3$ |
| H | OH | OH | 3 | $NH_2$ |
| Me | OH | OH | 3 | $NH_2$ |
| benzyl | OH | OH | 3 | $NH_2$ |
| 2-phenethyl | OH | OH | 3 | $NH_2$ |
| cyclopropylmethyl | OH | OH | 3 | $NO_2$ |
| cyclobutylmethyl | OH | OH | 3 | $NO_2$ |
| allyl | OH | OH | 3 | $NO_2$ |
| H | OH | OH | 3 | $NO_2$ |
| Me | OH | OH | 3 | $NO_2$ |
| benzyl | OH | OH | 3 | $NO_2$ |
| 2-phenethyl | OH | OH | 3 | $NO_2$ |
| cyclopropylmethyl | OH | OH | 3 | CN |
| cyclobutylmethyl | OH | OH | 3 | CN |
| allyl | OH | OH | 3 | CN |
| H | OH | OH | 3 | CN |
| Me | OH | OH | 3 | CN |
| benzyl | OH | OH | 3 | CN |
| 2-phenethyl | OH | OH | 3 | CN |
| cyclopropylmethyl | OH | OH | 3 | NCS |
| cyclobutylmethyl | OH | OH | 3 | NCS |
| allyl | OH | OH | 3 | NCS |
| H | OH | OH | 3 | NCS |
| Me | OH | OH | 3 | NCS |
| benzyl | OH | OH | 3 | NCS |
| 2-phenethyl | OH | OH | 3 | NCS |
| cyclopropylmethyl | OH | OH | 3 | COOH |
| cyclobutylmethyl | OH | OH | 3 | COOH |
| allyl | OH | OH | 3 | COOH |
| H | OH | OH | 3 | COOH |
| Me | OH | OH | 3 | COOH |
| benzyl | OH | OH | 3 | COOH |
| 2-phenethyl | OH | OH | 3 | COOH |
| cyclopropylmethyl | OH | OH | 3 | COOMe |
| cyclobutylmethyl | OH | OH | 3 | COOMe |
| allyl | OH | OH | 3 | COOMe |
| H | OH | OH | 3 | COOMe |
| Me | OH | OH | 3 | COOMe |
| benzyl | OH | OH | 3 | COOMe |
| 2-phenethyl | OH | OH | 3 | COOMe |
| cyclopropylmethyl | OH | OH | 3 | COOEt |
| cyclobutylmethyl | OH | OH | 3 | COOEt |
| allyl | OH | OH | 3 | COOEt |
| H | OH | OH | 3 | COOEt |
| Me | OH | OH | 3 | COOEt |
| benzyl | OH | OH | 3 | COOEt |
| 2-phenethyl | OH | OH | 3 | COOEt |
| cyclopropylmethyl | OH | OH | 3 | NHCHO |
| cyclobutylmethyl | OH | OH | 3 | NHCHO |
| allyl | OH | OH | 3 | NHCHO |
| H | OH | OH | 3 | NHCHO |
| Me | OH | OH | 3 | NHCHO |
| benzyl | OH | OH | 3 | NHCHO |
| 2-phenethyl | OH | OH | 3 | NHCHO |
| cyclopropylmethyl | OH | OH | 3 | NHCO—Me |
| cyclobutylmethyl | OH | OH | 3 | NHCO—Me |
| allyl | OH | OH | 3 | NHCO—Me |
| H | OH | OH | 3 | NHCO—Me |
| Me | OH | OH | 3 | NHCO—Me |
| benzyl | OH | OH | 3 | NHCO—Me |

-continued

| | | | | |
|---|---|---|---|---|
| 2-phenethyl | OH | OH | 3 | NHCO—Me |
| cyclopropylmethyl | OH | OH | 3 | NHCO—Ph |
| cyclobutylmethyl | OH | OH | 3 | NHCO—Ph |
| allyl | OH | OH | 3 | NHCO—Ph |
| H | OH | OH | 3 | NHCO—Ph |
| Me | OH | OH | 3 | NHCO—Ph |
| benzyl | OH | OH | 3 | NHCO—Ph |
| 2-phenethyl | OH | OH | 3 | NHCO—Ph |
| cyclopropylmethyl | OH | OH | 3 | NHCO—$(CH_2)_5$Ph |
| cyclobutylmethyl | OH | OH | 3 | NHCO—$(CH_2)_5$Ph |
| allyl | OH | OH | 3 | NHCO—$(CH_2)_5$Ph |
| H | OH | OH | 3 | NHCO—$(CH_2)_5$Ph |
| Me | OH | OH | 3 | NHCO—$(CH_2)_5$Ph |
| benzyl | OH | OH | 3 | NHCO—$(CH_2)_5$Ph |
| 2-phenethyl | OH | OH | 3 | NHCO—$(CH_2)_5$Ph |
| cyclopropylmethyl | OH | OH | 3 | NHCO-cinnamyl |
| cyclobutylmethyl | OH | OH | 3 | NHCO-cinnamyl |
| allyl | OH | OH | 3 | NHCO-cinnamyl |
| H | OH | OH | 3 | NCHO-cinnamyl |
| Me | OH | OH | 3 | NHCO-cinnamyl |
| benzyl | OH | OH | 3 | NHCO-cinnamyl |
| 2-phenethyl | OH | OH | 3 | NHCO-cinnamyl |
| cyclopropylmethyl | OH | OH | 3 | NHCO—($CF_3$-cinnamyl) |
| cyclobutylmethyl | OH | OH | 3 | NHCO—($CF_3$-cinnamyl) |
| allyl | OH | OH | 3 | NHCO—($CF_3$-cinnamyl) |
| H | OH | OH | 3 | NHCO—($CF_3$-cinnamyl) |
| Me | OH | OH | 3 | NHCO—($CF_3$-cinnamyl) |
| benzyl | OH | OH | 3 | NHCO—($CF_3$-cinnamyl) |
| 2-phenethyl | OH | OH | 3 | NHCO—($CF_3$-cinnamyl) |
| cyclopropylmethyl | OH | OH | 3 | NHCO-pyridyl |
| cyclobutylmethyl | OH | OH | 3 | NHCO-pyridyl |
| allyl | OH | OH | 3 | NHCO-pyridyl |
| H | OH | OH | 3 | NHCO-pyridyl |
| Me | OH | OH | 3 | NHCO-pyridyl |
| benzyl | OH | OH | 3 | NHCO-pyridyl |
| 2-phenethyl | OH | OH | 3 | NHCO-pyridyl |
| cyclopropylmethyl | OH | OH | 3 | NHCO—NHPh |
| cyclobutylmethyl | OH | OH | 3 | NHCO—NHPh |
| allyl | OH | OH | 3 | NHCO—NHPh |
| H | OH | OH | 3 | NHCO—NHPh |
| Me | OH | OH | 3 | NHCO—NHPh |
| benzyl | OH | OH | 3 | NHCO—NHPh |
| 2-phenethyl | OH | OH | 3 | NHCO—NHPh |
| cyclopropylmethyl | OH | OH | 3 | NHCS—NHPh |
| cyclobutylmethyl | OH | OH | 3 | NHCS—NHPh |
| allyl | OH | OH | 3 | NHCS—NHPh |
| H | OH | OH | 3 | NHCS—NHPh |
| Me | OH | OH | 3 | NHCS—NHPh |
| benzyl | OH | OH | 3 | NHCS—NHPh |
| 2-phenethyl | OH | OH | 3 | NHCS—NHPh |
| cyclopropylmethyl | OH | OH | 3 | NHCS—NHCH$_2$Ph |
| cyclobutylmethyl | OH | OH | 3 | NHCS—NHCH$_2$Ph |
| allyl | OH | OH | 3 | NHCS—NHCH$_2$Ph |
| H | OH | OH | 3 | NHCS—NHCH$_2$Ph |
| Me | OH | OH | 3 | NHCS—NHCH$_2$Ph |
| benzyl | OH | OH | 3 | NHCS—NHCH$_2$Ph |
| 2-phenethyl | OH | OH | 3 | NHCS—NHCH$_2$Ph |
| cyclopropylmethyl | OH | OH | 4 | OH |
| cyclobutylmethyl | OH | OH | 4 | OH |
| allyl | OH | OH | 4 | OH |
| H | OH | OH | 4 | OH |
| Me | OH | OH | 4 | OH |
| benzyl | OH | OH | 4 | OH |
| 2-phenethyl | OH | OH | 4 | OH |
| cyclopropylmethyl | OH | OH | 4 | OMe |
| cyclobutylmethyl | OH | OH | 4 | OMe |
| allyl | OH | OH | 4 | OMe |
| H | OH | OH | 4 | OMe |
| Me | OH | OH | 4 | OMe |
| benzyl | OH | OH | 4 | OMe |
| 2-phenethyl | OH | OH | 4 | OMe |
| cyclopropylmethyl | OH | OH | 4 | OEt |
| cyclobutylmethyl | OH | OH | 4 | OEt |
| allyl | OH | OH | 4 | OEt |
| H | OH | OH | 4 | OEt |
| Me | OH | OH | 4 | OEt |
| benzyl | OH | OH | 4 | OEt |
| 2-phenethyl | OH | OH | 4 | OEt |
| cyclopropylmethyl | OH | OH | 4 | NH$_2$ |
| cyclobutylmethyl | OH | OH | 4 | NH$_2$ |
| allyl | OH | OH | 4 | NH$_2$ |
| H | OH | OH | 4 | NH$_2$ |
| Me | OH | OH | 4 | NH$_2$ |
| benzyl | OH | OH | 4 | NH$_2$ |
| 2-phenethyl | OH | OH | 4 | NO$_2$ |
| cyclopropylmethyl | OH | OH | 4 | NO$_2$ |
| cyclobutylmethyl | OH | OH | 4 | NO$_2$ |
| allyl | OH | OH | 4 | NO$_2$ |
| H | OH | OH | 4 | NO$_2$ |
| Me | OH | OH | 4 | NO$_2$ |
| benzyl | OH | OH | 4 | NO$_2$ |
| 2-phenethyl | OH | OH | 4 | NO$_2$ |
| cyclopropylmethyl | OH | OH | 4 | CN |
| cyclobutylmethyl | OH | OH | 4 | CN |
| allyl | OH | OH | 4 | CN |
| H | OH | OH | 4 | CN |
| Me | OH | OH | 4 | CN |
| benzyl | OH | OH | 4 | CN |
| 2-phenethyl | OH | OH | 4 | CN |
| cyclopropylmethyl | OH | OH | 4 | NCS |
| cyclobutylmethyl | OH | OH | 4 | NCS |
| allyl | OH | OH | 4 | NCS |
| H | OH | OH | 4 | NCS |
| Me | OH | OH | 4 | NCS |
| benzyl | OH | OH | 4 | NCS |
| 2-phenethyl | OH | OH | 4 | NCS |
| cyclopropylmethyl | OH | OH | 4 | COOH |
| cyclobutylmethyl | OH | OH | 4 | COOH |
| allyl | OH | OH | 4 | COOH |
| H | OH | OH | 4 | COOH |
| Me | OH | OH | 4 | COOH |
| benzyl | OH | OH | 4 | COOH |
| 2-phenethyl | OH | OH | 4 | COOH |
| cyclopropylmethyl | OH | OH | 4 | COOMe |
| cyclobutylmethyl | OH | OH | 4 | COOMe |
| allyl | OH | OH | 4 | COOMe |
| H | OH | OH | 4 | COOMe |
| Me | OH | OH | 4 | COOMe |
| benzyl | OH | OH | 4 | COOMe |
| 2-phenethyl | OH | OH | 4 | COOMe |
| cyclopropylmethyl | OH | OH | 4 | COOEt |
| cyclobutylmethyl | OH | OH | 4 | COOEt |
| allyl | OH | OH | 4 | COOEt |
| H | OH | OH | 5 | COOEt |
| Me | OH | OH | 4 | COOEt |
| benzyl | OH | OH | 4 | COOEt |
| 2-phenethyl | OH | OH | 4 | COOEt |
| cyclopropylmethyl | OH | OH | 4 | NHCHO |
| cyclobutylmethyl | OH | OH | 4 | NHCHO |
| allyl | OH | OH | 4 | NHCHO |
| H | OH | OH | 4 | NHCHO |
| Me | OH | OH | 4 | NHCHO |
| benzyl | OH | OH | 4 | NHCHO |
| 2-phenethyl | OH | OH | 4 | NHCHO |
| cyclopropylmethyl | OH | OH | 4 | NHCO—Me |
| cyclobutylmethyl | OH | OH | 4 | NHCO—Me |
| allyl | OH | OH | 4 | NHCO—Me |
| H | OH | OH | 4 | NHCO—Me |
| Me | OH | OH | 4 | NHCO—Me |
| benzyl | OH | OH | 4 | NHCO—Me |
| 2-phenethyl | OH | OH | 4 | NHCO—Me |
| cyclopropylmethyl | OH | OH | 4 | NHCO—Ph |
| cyclobutylmethyl | OH | OH | 4 | NHCO—Ph |
| allyl | OH | OH | 4 | NHCO—Ph |
| H | OH | OH | 4 | NHCO—Ph |
| Me | OH | OH | 4 | NHCO—Ph |
| benzyl | OH | OH | 4 | NHCO—Ph |
| 2-phenethyl | OH | OH | 4 | NHCO—Ph |
| cyclopropylmethyl | OH | OH | 4 | NHCO—$(CH_2)_5$Ph |
| cyclobutylmethyl | OH | OH | 4 | NHCO—$(CH_2)_5$Ph |
| allyl | OH | OH | 4 | NHCO—$(CH_2)_5$Ph |
| H | OH | OH | 4 | NHCO—$(CH_2)_5$Ph |
| Me | OH | OH | 4 | NHCO—$(CH_2)_5$Ph |
| benzyl | OH | OH | 4 | NHCO—$(CH_2)_5$Ph |
| 2-phenethyl | OH | OH | 4 | NHCO—$(CH_2)_5$Ph |
| cyclopropylmethyl | OH | OH | 4 | NHCO-cinnamyl |
| cyclobutylmethyl | OH | OH | 4 | NHCO-cinnamyl |
| allyl | OH | OH | 4 | NHCO-cinnamyl |

-continued

| | | | | |
|---|---|---|---|---|
| H | OH | OH | 4 | NHCO-cinnamyl |
| Me | OH | OH | 4 | NHCO-cinnamyl |
| benzyl | OH | OH | 4 | NHCO-cinnamyl |
| 2-phenethyl | OH | OH | 4 | NHCO-cinnamyl |
| cyloproylmethyl | OH | OH | 4 | NHCO—(CF$_3$-cinnamyl) |
| cyclobutylmethyl | OH | OH | 4 | NHCO—(CF$_3$-cinnamyl) |
| allyl | OH | OH | 4 | NHCO—(CF$_3$-cinnamyl) |
| H | OH | OH | 4 | NHCO—(CF$_3$-cinnamyl) |
| Me | OH | OH | 4 | NHCO—(CF$_3$-cinnamyl) |
| benzyl | OH | OH | 4 | NHCO—(CF$_3$-cinnamyl) |
| 2-phenethyl | OH | OH | 4 | NHCO—(CF$_3$-cinnamyl) |
| cylcopropylmethyl | OH | OH | 4 | NHCO-pyridyl |
| cyclobutylmethyl | OH | OH | 4 | NHCO-pyridyl |
| allyl | OH | OH | 4 | NHCO-pyridyl |
| H | OH | OH | 4 | NHCO-pyridyl |
| Me | OH | OH | 4 | NHCO-pyridyl |
| benzyl | OH | OH | 4 | NHCO-pyridyl |
| 2-phenethyl | OH | OH | 4 | NHCO-pyridyl |
| cyclopropylmethyl | OH | OH | 4 | NHCO—NHPh |
| cyclobutylmethyl | OH | OH | 4 | NHCO—NHPh |
| allyl | OH | OH | 4 | NHCO—NHPh |
| H | OH | OH | 4 | NHCO—NHPh |
| Me | OH | OH | 4 | NHCO—NHPh |
| benzyl | OH | OH | 4 | NHCO—NHPh |
| 2-phenethyl | OH | OH | 4 | NHCO—NHPh |
| cyclopropylmethyl | OH | OH | 4 | NHCS—NHPh |
| cyclobutylmethyl | OH | OH | 4 | NHCS—NHPh |
| allyl | OH | OH | 4 | NHCS—NHPh |
| H | OH | OH | 4 | NHCS—NHPh |
| Me | OH | OH | 4 | NHCS—NHPh |
| benzyl | OH | OH | 4 | NHCS—NHPh |
| 2-phenethyl | OH | OH | 4 | NHCS—NHPh |
| cyclopropylmethyl | OH | OH | 4 | NHCS—NHCH$_2$Ph |
| cyclobutylmethyl | OH | OH | 4 | NHCS—NHCH$_2$Ph |
| allyl | OH | OH | 4 | NHCS—NHCH$_2$Ph |
| H | OH | OH | 4 | NHCS—NHCH$_2$Ph |
| Me | OH | OH | 4 | NHCS—NHCH$_2$Ph |
| benzyl | OH | OH | 4 | NHCS—NHCH$_2$Ph |
| 2-phenethyl | OH | OH | 4 | NHCS—NHCH$_2$Ph |
| cyclopropylmethyl | OH | OMe | 3 | OH |
| cyclopropylmethyl | OH | OMe | 3 | OMe |
| cyclopropylmethyl | OH | OMe | 3 | NH$_2$ |
| cyclopropylmethyl | OH | OMe | 3 | CN |
| cyclopropylmethyl | OH | OMe | 3 | NCS |
| cyclopropylmethyl | OH | OMe | 3 | COOH |
| cyclopropylmethyl | OH | OMe | 3 | COOMe |
| cyclopropylmethyl | OH | OMe | 3 | NHCHO |
| cyclopropylmethyl | OH | OMe | 3 | NHCO—Ph |
| cyclopropylmethyl | OH | OMe | 3 | NHCO—(CH$_2$)$_5$Ph |
| cyclopropylmethyl | OH | OMe | 3 | NHCO—(CF$_3$-cinnamyl) |
| cyclopropylmethyl | OH | OMe | 3 | NHCO-pyridyl |
| cyclopropylmethyl | OH | OMe | 3 | NHCO—NHPh |
| cyclopropylmethyl | OH | OMe | 3 | NHCS—NHPh |
| cyclopropylmethyl | OH | OMe | 4 | OH |
| cyclopropylmethyl | OH | OMe | 4 | OMe |
| cyclopropylmethyl | OH | OMe | 4 | NH$_2$ |
| cyclopropylmethyl | OH | OMe | 4 | CN |
| cyclopropylmethyl | OH | OMe | 4 | NCS |
| cyclopropylmethyl | OH | OMe | 4 | COOH |
| cyclopropylmethyl | OH | OMe | 4 | COOMe |
| cyclopropylmethyl | OH | OMe | 4 | NHCHO |
| cyclopropylmethyl | OH | OMe | 4 | NHCO—Ph |
| cyclopropylmethyl | OH | OMe | 4 | NHCO—(CH$_2$)$_5$Ph |
| cyclopropylmethyl | OH | OMe | 4 | NHCO—(CF$_3$-cinnamyl) |
| cyclopropylmethyl | OH | OMe | 4 | NHCO-pyridyl |
| cyclopropylmethyl | OH | OMe | 4 | NHCO—NHPh |
| cyclopropylmethyl | OH | OMe | 4 | NHCS—NHPh |

-continued

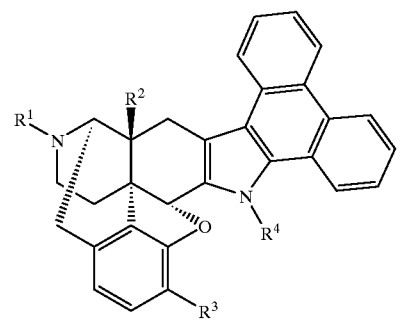

| $R^1$ | $R^2$ | $R^3$ | $R^4$ |
|---|---|---|---|
| cyclopropylmethyl | OH | OH | H |
| cylcobutylmethyl | OH | OH | H |
| allyl | OH | OH | H |
| H | OH | OH | H |
| Me | OH | OH | H |
| benzyl | OH | OH | H |
| 2-phenethyl | OH | OH | H |
| cyclopropylmethyl | OH | OH | Me |
| cyclobutylmethyl | OH | OH | Me |
| allyl | OH | OH | Me |
| H | OH | OH | Me |
| Me | OH | OH | Me |
| benzyl | OH | OH | Me |
| 2-phenethyl | OH | OH | Me |
| cyclopropylmethyl | OH | OH | Bu |
| cyclobutylmethyl | OH | OH | Bu |
| allyl | OH | OH | Bu |
| H | OH | OH | Bu |
| Me | OH | OH | Bu |
| benzyl | OH | OH | Bu |
| 2-phenethyl | OH | OH | Bu |
| cyclopropylmethyl | OH | OH | PhCH$_2$ |
| cyclobutylmethyl | OH | OH | PhCH$_2$ |
| allyl | OH | OH | PhCH$_2$ |
| H | OH | OH | PhCH$_2$ |
| Me | OH | OH | PhCH$_2$ |
| benzyl | OH | OH | PhCH$_2$ |
| 2-phenethyl | OH | OH | PhCH$_2$ |
| cyclopropylmethyl | OH | OH | (F—C$_6$H$_4$)CH$_2$ |
| cyclobutylmethyl | OH | OH | (F—C$_6$H$_4$)CH$_2$ |
| allyl | OH | OH | (F—C$_6$H$_4$)CH$_2$ |
| H | OH | OH | (F—C$_6$H$_4$)CH$_2$ |
| Me | OH | OH | (F—C$_6$H$_4$)CH$_2$ |
| benzyl | OH | OH | (F—C$_6$H$_4$)CH$_2$ |
| 2-phenethyl | OH | OH | (F—C$_6$H$_4$)CH$_2$ |
| cyclopropylmethyl | OH | OH | (Cl—C$_6$H$_4$)CH$_2$ |
| cyclobutylmethyl | OH | OH | (Cl—C$_6$H$_4$)CH$_2$ |
| allyl | OH | OH | (Cl—C$_6$H$_4$)CH$_2$ |
| H | OH | OH | (Cl—C$_6$H$_4$)CH$_2$ |
| Me | OH | OH | (Cl—C$_6$H$_4$)CH$_2$ |
| benzyl | OH | OH | (Cl—C$_6$H$_4$)CH$_2$ |
| 2-phenethyl | OH | OH | (Cl—C$_6$H$_4$)CH$_2$ |
| cyclopropylmethyl | OH | OH | (Br—C$_6$H$_4$)CH$_2$ |
| cyclobutylmethyl | OH | OH | (Br—C$_6$H$_4$)CH$_2$ |
| allyl | OH | OH | (Br—C$_6$H$_4$)CH$_2$ |
| H | OH | OH | (Br—C$_9$H$_4$)CH$_2$ |
| Me | OH | OH | (Br—C$_6$H$_4$)CH$_2$ |
| benzyl | OH | OH | (Br—C$_6$H$_4$)CH$_2$ |
| 2-phenethyl | OH | OH | (Br—C$_6$H$_4$)CH$_2$ |
| cyclopropylmethyl | OH | OH | (Me—C$_9$H$_4$)CH$_2$ |
| cyclobutylmethyl | OH | OH | (Me—C$_9$H$_4$)CH$_2$ |
| allyl | OH | OH | (Me—C$_9$H$_4$)CH$_2$ |
| H | OH | OH | (Me—C$_9$H$_4$)CH$_2$ |
| Me | OH | OH | (Me—C$_9$H$_4$)CH$_2$ |
| benzyl | OH | OH | (Me—C$_9$H$_4$)CH$_2$ |
| 2-phenethyl | OH | OH | (Me—C$_9$H$_4$)CH$_2$ |
| cyclopropylmethyl | OH | OH | (MeO—C$_9$H$_4$)CH$_2$ |
| cyclobutylmethyl | OH | OH | (MeO—C$_9$H$_4$)CH$_2$ |
| allyl | OH | OH | (MeO—C$_6$H$_4$)CH$_2$ |
| H | OH | OH | (MeO—C$_6$H$_4$)CH$_2$ |

-continued

| R1 | R2 | R3 | R16 |
|---|---|---|---|
| Me | OH | OH | (MeO—C9H4)CH2 |
| benzyl | OH | OH | (MeO—C9H4)CH2 |
| 2-phenethyl | OH | OH | (MeO—C6H4)CH2 |
| cyclopropylmethyl | OH | OH | (F3C—C9H4)CH2 |
| cyclobutylmethyl | OH | OH | (F3C—C9H4)CH2 |
| allyl | OH | OH | (F3C—C9H4)CH2 |
| H | OH | OH | (F3C—C9H4)CH2 |
| Me | OH | OH | (F3C—C9H4)CH2 |
| benzyl | OH | OH | (F3C—C9H4)CH2 |
| 2-phenethyl | OH | OH | (F3C—C9H4)CH2 |
| cylcopropylmethyl | OH | OH | (O2N—C5H4)CH2 |
| cyclobutylmethyl | OH | OH | (O2N—C6H4)CH2 |
| allyl | OH | OH | (O2N—C6H4)CH2 |
| H | OH | OH | (O2N—C6H4)CH2 |
| Me | OH | OH | (O2N—C9H4)CH2 |
| benzyl | OH | OH | (O2N—C6H4)CH2 |
| 2-phenethyl | OH | OH | (O2N—C6H4)CH2 |
| cyclopropylmethyl | OH | OH | Ph(CH2)2 |
| cyclobutylmethyl | OH | OH | Ph(CH2)2 |
| allyl | OH | OH | Ph(CH2)2 |
| H | OH | OH | Ph(CH2)2 |
| Me | OH | OH | Ph(CH2)2 |
| benzyl | OH | OH | Ph(CH2)2 |
| 2-phenethyl | OH | OH | Ph(CH2)2 |
| cyclopropylmethyl | OH | OH | Ph(CH2)3 |
| cyclobutylmethyl | OH | OH | Ph(CH2)3 |
| allyl | OH | OH | Ph(CH2)3 |
| H | OH | OH | Ph(CH2)3 |
| Me | OH | OH | Ph(CH2)3 |
| benzyl | OH | OH | Ph(CH2)3 |
| 2-phenethyl | OH | OH | Ph(CH2)3 |
| cyclopropylmethyl | OH | OH | PhCO |
| cyclobutylmethyl | OH | OH | PhCO |
| allyl | OH | OH | PhCO |
| H | OH | OH | PhCO |
| Me | OH | OH | PhCO |
| benzyl | OH | OH | PhCO |
| 2-phenethyl | OH | OH | PhCO |
| cyclopropylmethyl | OH | OH | MeSO2 |
| cyclobutylmethyl | OH | OH | MeSO2 |
| allyl | OH | OH | MeOS2 |
| H | OH | OH | MeSO2 |
| Me | OH | OH | MeSO2 |
| benzyl | OH | OH | MeSO2 |
| 2-phenethyl | OH | OH | MeSO2 |
| cyclopropylmethyl | OH | OH | PhSO2 |
| cyclobutylmethyl | OH | OH | PhSO2 |
| allyl | OH | OH | PhSO2 |
| H | OH | OH | PhSO2 |
| Me | OH | OH | PhSO2 |
| benzyl | OH | OH | PhSO2 |
| 2-phenethyl | OH | OH | PhSO2 |

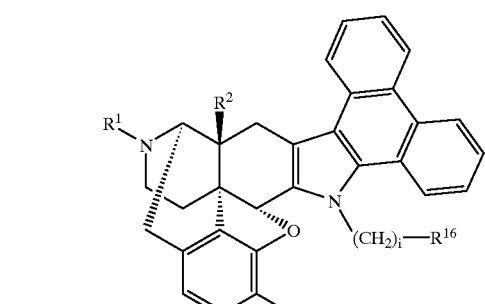

| R1 | R2 | R3 | i | R16 |
|---|---|---|---|---|
| cyclopropylmethyl | OH | OH | 2 | OH |
| cyclobutylmethyl | OH | OH | 2 | OH |
| allyl | OH | OH | 2 | OH |
| H | OH | OH | 2 | OH |
| Me | OH | OH | 2 | OH |
| benzyl | OH | OH | 2 | OH |
| 2-phenethyl | OH | OH | 2 | OH |

-continued

| R1 | R2 | R3 | i | R16 |
|---|---|---|---|---|
| cyclopropylmethyl | OH | OH | 2 | OMe |
| cyclobutylmethyl | OH | OH | 2 | OMe |
| allyl | OH | OH | 2 | OMe |
| H | OH | OH | 2 | OMe |
| Me | OH | OH | 2 | OMe |
| benzyl | OH | OH | 2 | OMe |
| 2-phenethyl | OH | OH | 2 | OMe |
| cyclopropylmethyl | OH | OH | 2 | OEt |
| cyclobutylmethyl | OH | OH | 2 | OEt |
| allyl | OH | OH | 2 | OEt |
| H | OH | OH | 2 | OEt |
| Me | OH | OH | 2 | OEt |
| benzyl | OH | OH | 2 | OEt |
| 2-phenethyl | OH | OH | 2 | OEt |
| cyclopropylmethyl | OH | OH | 2 | NH2 |
| cyclobutylmethyl | OH | OH | 2 | NH2 |
| allyl | OH | OH | 2 | NH2 |
| H | OH | OH | 2 | NH2 |
| Me | OH | OH | 2 | NH2 |
| benzyl | OH | OH | 2 | NH2 |
| 2-phenethyl | OH | OH | 2 | NH2 |
| cyclopropylmethyl | OH | OH | 2 | NO2 |
| cyclobutylmethyl | OH | OH | 2 | NO2 |
| allyl | OH | OH | 2 | NO2 |
| H | OH | OH | 2 | NO2 |
| Me | OH | OH | 2 | NO2 |
| benzyl | OH | OH | 2 | NO2 |
| 2-phenethyl | OH | OH | 2 | NO2 |
| cyclopropylmethyl | OH | OH | 2 | CN |
| cyclobutylmethyl | OH | OH | 2 | CN |
| allyl | OH | OH | 2 | CN |
| H | OH | OH | 2 | CN |
| Me | OH | OH | 2 | CN |
| benzyl | OH | OH | 2 | CN |
| 2-phenethyl | OH | OH | 2 | CN |
| cyclopropylmethyl | OH | OH | 2 | NCS |
| cyclobutylmethyl | OH | OH | 2 | NCS |
| allyl | OH | OH | 2 | NCS |
| H | OH | OH | 2 | NCS |
| Me | OH | OH | 2 | NCS |
| benzyl | OH | OH | 2 | NCS |
| 2-phenethyl | OH | OH | 2 | NCS |
| cyclopropylmethyl | OH | OH | 2 | COOH |
| cyclobutylmethyl | OH | OH | 2 | COOH |
| allyl | OH | OH | 2 | COOH |
| H | OH | OH | 2 | COOH |
| Me | OH | OH | 2 | COOH |
| benzyl | OH | OH | 2 | COOH |
| 2-phenethyl | OH | OH | 2 | COOH |
| cyclopropylmethyl | OH | OH | 2 | COOMe |
| cyclobutylmethyl | OH | OH | 2 | COOMe |
| allyl | OH | OH | 2 | COOMe |
| H | OH | OH | 2 | COOMe |
| Me | OH | OH | 2 | COOMe |
| benzyl | OH | OH | 2 | COOMe |
| 2-phenethyl | OH | OH | 2 | COOMe |
| cyclopropylmethyl | OH | OH | 2 | COOEt |
| cyclobutylmethyl | OH | OH | 2 | COOEt |
| allyl | OH | OH | 2 | COOEt |
| H | OH | OH | 2 | COOEt |
| Me | OH | OH | 2 | COOEt |
| benzyl | OH | OH | 2 | COOEt |
| 2-phenethyl | OH | OH | 2 | COOEt |
| cyclopropylmethyl | OH | OH | 2 | NHCHO |
| cyclobutylmethyl | OH | OH | 2 | NHCHO |
| allyl | OH | OH | 2 | NHCHO |
| H | OH | OH | 2 | NHCHO |
| Me | OH | OH | 2 | NHCHO |
| benzyl | OH | OH | 2 | NHCHO |
| 2-phenethyl | OH | OH | 2 | NHCHO |
| cyclopropylmethyl | OH | OH | 2 | NHCO—Me |
| cyclobutylmethyl | OH | OH | 2 | NHCO—Me |
| allyl | OH | OH | 2 | NHCO—Me |
| H | OH | OH | 2 | NHCO—Me |
| Me | OH | OH | 2 | NHCO—Me |
| benzyl | OH | OH | 2 | NHCO—Me |
| 2-phenethyl | OH | OH | 2 | NHCO—Me |
| cyclopropylmethyl | OH | OH | 2 | NHCO—Ph |
| cyclobutylmethyl | OH | OH | 2 | NHCO—Ph |

| | | | | |
|---|---|---|---|---|
| allyl | OH | OH | 2 | NHCO—Ph |
| H | OH | OH | 2 | NHCO—Ph |
| Me | OH | OH | 2 | NHCO—Ph |
| benzyl | OH | OH | 2 | NHCO—Ph |
| 2-phenethyl | OH | OH | 2 | NHCO—Ph |
| cyclopropylmethyl | OH | OH | 2 | NHCO—(CH$_2$)$_5$Ph |
| cyclobutylmethyl | OH | OH | 2 | NHCO—(CH$_2$)$_5$Ph |
| allyl | OH | OH | 2 | NHCO—(CH$_2$)$_5$Ph |
| H | OH | OH | 2 | NHCO—(CH$_2$)$_5$Ph |
| Me | OH | OH | 2 | NHCO—(CH$_2$)$_5$Ph |
| benzyl | OH | OH | 2 | NHCO—(CH$_2$)$_5$Ph |
| 2-phenethyl | OH | OH | 2 | NHCO—(CH$_2$)$_5$Ph |
| cyclopropylmethyl | OH | OH | 2 | NHCO-cinnamyl |
| cyclobutylmethyl | OH | OH | 2 | NHCO-cinnamyl |
| allyl | OH | OH | 2 | NHCO-cinnamyl |
| H | OH | OH | 2 | NHCO-cinnamyl |
| Me | OH | OH | 2 | NCHO-cinnamyl |
| benzyl | OH | OH | 2 | NHCO-cinnamyl |
| 2-phenethyl | OH | OH | 2 | NHCO-cinnamyl |
| cylcopropylmethyl | OH | OH | 2 | NHCO—(CF$_3$-cinnamyl) |
| cyclobutylmethyl | OH | OH | 2 | NHCO—CF$_3$-cinnamyl) |
| allyl | OH | OH | 2 | NHCO—(CF$_3$-cinnamyl) |
| H | OH | OH | 2 | NHCO—(CF$_3$-cinnamyl) |
| Me | OH | OH | 2 | NHCO—(CF$_3$-cinnamyl) |
| benzyl | OH | OH | 2 | NHCO—(CF$_3$-cinnamyl) |
| 2-phenethyl | OH | OH | 2 | NHCO—(CF$_3$-cinnamyl) |
| cyclopropylmethyl | OH | OH | 2 | NHCO-pyridyl |
| cylcobutylmethyl | OH | OH | 2 | NHCO-pyridyl |
| allyl | OH | OH | 2 | NHCO-pyridyl |
| H | OH | OH | 2 | NHCO-pyridyl |
| Me | OH | OH | 2 | NHCO-pyridyl |
| benzyl | OH | OH | 2 | NHOC-pyridyl |
| 2-phenethyl | OH | OH | 2 | NHCO-pyridyl |
| cyclopropylmethyl | OH | OH | 2 | NHCO—NHPh |
| cyclobutylmethyl | OH | OH | 2 | NHCO—NHPh |
| allyl | OH | OH | 2 | NHCO—NHPh |
| H | OH | OH | 2 | NHCO—NHPh |
| Me | OH | OH | 2 | NHCO—NHPh |
| benzyl | OH | OH | 2 | NHCO—NHPh |
| 2-phenethyl | OH | OH | 2 | NHCO—NHPh |
| cyclopropylmethyl | OH | OH | 2 | NHCS—NHPh |
| cyclobutylmethyl | OH | OH | 2 | NHCS—NHPh |
| allyl | OH | OH | 2 | NHCS—NHPh |
| H | OH | OH | 2 | NHCS—NHPh |
| Me | OH | OH | 2 | NHCS—NHPh |
| benzyl | OH | OH | 2 | NHCS—NHPh |
| 2-phenethyl | OH | OH | 2 | NHCS—NHPh |
| cyclopropylmethyl | OH | OH | 2 | NHCS—NHCH$_2$Ph |
| cyclobutylmethyl | OH | OH | 2 | NHCS—NHCH$_2$Ph |
| allyl | OH | OH | 2 | NHCS—NHCH$_2$Ph |
| H | OH | OH | 2 | NHCS—NHCH$_2$Ph |
| Me | OH | OH | 2 | NHCS—NHCH$_2$Ph |
| benzyl | OH | OH | 2 | NHCS—NHCH$_2$Ph |
| 2-phenethyl | OH | OH | 2 | NHCS—NHCH$_2$Ph |
| cyclopropylmethyl | OH | OH | 2 | OH |
| cyclobutylmethyl | OH | OH | 3 | OH |
| allyl | OH | OH | 3 | OH |
| H | OH | OH | 3 | OH |
| Me | OH | OH | 3 | OH |
| benzyl | OH | OH | 3 | OH |
| 2-phenethyl | OH | OH | 3 | OH |
| cylcopropylmethyl | OH | OH | 3 | OEt |
| cyclobutylmethyl | OH | OH | 3 | OEt |
| allyl | OH | OH | 3 | OEt |
| H | OH | OH | 3 | OEt |
| Me | OH | OH | 3 | OEt |
| benzyl | OH | OH | 3 | OEt |
| 2-phenethyl | OH | OH | 3 | OEt |
| cyclopropylmethyl | OH | OH | 3 | NH$_2$ |
| cyclobutylmethyl | OH | OH | 3 | NH$_2$ |
| allyl | OH | OH | 3 | NH$_2$ |
| H | OH | OH | 3 | NH$_2$ |
| Me | OH | OH | 3 | NH$_2$ |
| benzyl | OH | OH | 3 | NH$_2$ |
| 2-phenethyl | OH | OH | 3 | NH$_2$ |
| cyclopropylmethyl | OH | OH | 3 | NO$_2$ |
| cyclobutylmethyl | OH | OH | 3 | NO$_2$ |
| allyl | OH | OH | 3 | NO$_2$ |
| H | OH | OH | 3 | NO$_2$ |
| Me | OH | OH | 3 | NO$_2$ |
| benzyl | OH | OH | 3 | NO$_2$ |
| 2-phenethyl | OH | OH | 3 | NO$_2$ |
| cyclopropylmethyl | OH | OH | 3 | CN |
| cylcobutylmethyl | OH | OH | 3 | CN |
| allyl | OH | OH | 3 | CN |
| H | OH | OH | 3 | CN |
| Me | OH | OH | 3 | CN |
| benzyl | OH | OH | 3 | CN |
| 2-phenethyl | OH | OH | 3 | CN |
| cyclopropylmethyl | OH | OH | 3 | NCS |
| cyclobutylmethyl | OH | OH | 3 | NCS |
| allyl | OH | OH | 3 | NCS |
| H | OH | OH | 3 | NCS |
| Me | OH | OH | 3 | NCS |
| benzyl | OH | OH | 3 | NCS |
| 2-phenethyl | OH | OH | 3 | NCS |
| cyclopropylmethyl | OH | OH | 3 | COOH |
| cyclobutylmethyl | OH | OH | 3 | COOH |
| allyl | OH | OH | 3 | COOH |
| H | OH | OH | 3 | COOH |
| Me | OH | OH | 3 | COOH |
| benzyl | OH | OH | 3 | COOH |
| 2-phenethyl | OH | OH | 3 | COOH |
| cyclopropylmethyl | OH | OH | 3 | COOMe |
| cyclobutylmethyl | OH | OH | 3 | COOMe |
| allyl | OH | OH | 3 | COOMe |
| H | OH | OH | 3 | COOMe |
| Me | OH | OH | 3 | COOMe |
| benzyl | OH | OH | 3 | COOMe |
| 2-phenethyl | OH | OH | 3 | COOMe |
| cyclopropylmethyl | OH | OH | 3 | COOEt |
| cyclobutylmethyl | OH | OH | 3 | COOEt |
| allyl | OH | OH | 3 | COOEt |
| H | OH | OH | 3 | COOEt |
| Me | OH | OH | 3 | COOEt |
| benzyl | OH | OH | 3 | COOEt |
| 2-phenethyl | OH | OH | 3 | COOEt |
| cyclopropylmethyl | OH | OH | 3 | NHCHO |
| cyclobutylmethyl | OH | OH | 3 | NHCHO |
| allyl | OH | OH | 3 | NHCHO |
| H | OH | OH | 3 | NHCHO |
| Me | OH | OH | 3 | NHCHO |
| benzyl | OH | OH | 3 | NHCHO |
| 2-phenethyl | OH | OH | 3 | NHCHO |
| cyclopropylmethyl | OH | OH | 3 | NHCO—Me |
| cyclobutylmethyl | OH | OH | 3 | NHCO—Me |
| allyl | OH | OH | 3 | NHCO—Me |
| H | OH | OH | 3 | NHCO—Me |
| Me | OH | OH | 3 | NHCO—Me |
| benzyl | OH | OH | 3 | NHCO—Me |
| 2-phenethyl | OH | OH | 3 | NHCO—Me |
| cyclopropylmethyl | OH | OH | 3 | NHCO—Ph |
| cyclobutylmethyl | OH | OH | 3 | NHCO—Ph |
| allyl | OH | OH | 3 | NHCO—Ph |
| H | OH | OH | 3 | NHCO—Ph |
| Me | OH | OH | 3 | NHCO—Ph |
| benzyl | OH | OH | 3 | NHCO—Ph |
| 2-phenethyl | OH | OH | 3 | NHCO—Ph |
| cyclopropylmethyl | OH | OH | 3 | NHCO—(CH$_2$)$_5$Ph |
| cyclobutylmethyl | OH | OH | 3 | NHCO—(CH$_2$)$_5$Ph |
| allyl | OH | OH | 3 | NHCO—(CH$_2$)$_5$Ph |
| H | OH | OH | 3 | NHCO—(CH$_2$)$_5$Ph |
| Me | OH | OH | 3 | NHCO—(CH$_2$)$_5$Ph |
| benzyl | OH | OH | 3 | NHCO—(CH$_2$)$_5$Ph |
| 2-phenethyl | OH | OH | 3 | NHOC—(CH$_2$)$_5$Ph |
| cyclopropylmethyl | OH | OH | 3 | NHCO-cinnamyl |
| cylcobutylmethyl | OH | OH | 3 | NHCO-cinnamyl |
| allyl | OH | OH | 3 | NHCO-cinnamyl |
| H | OH | OH | 3 | NHCO-cinnamyl |
| Me | OH | OH | 3 | NHCO-cinnamyl |
| benzyl | OH | OH | 3 | NHCO-cinnamyl |
| 2-phenethyl | OH | OH | 3 | NHCO-cinnamyl |
| cyclopropylmethyl | OH | OH | 3 | NHCO—(CF$_3$-cinnamyl) |
| cylcobutylmethyl | OH | OH | 3 | NHCO—(CF$_3$-cinnamyl) |
| allyl | OH | OH | 3 | NHCO—(CF$_3$-cinnamyl) |
| H | OH | OH | 3 | NHCO—(CF$_3$-cinnamyl) |
| Me | OH | OH | 3 | NHCO—(CF$_3$-cinnamyl) |
| benzyl | OH | OH | 3 | NHCO—(CF$_3$-cinnamyl) |

| | | | | | | | | | |
|---|---|---|---|---|---|---|---|---|---|
| 2-phenethyl | OH | OH | 3 | NHCO—(CF₃-cinnamyl) | H | OH | OH | 4 | COOEt |
| cyclopropylmethyl | OH | OH | 3 | NHCO-pyridyl | Me | OH | OH | 4 | COOEt |
| cyclobutylmethyl | OH | OH | 3 | NHCO-pyridyl | benzyl | OH | OH | 4 | COOEt |
| allyl | OH | OH | 3 | NHCO-pyridyl | 2-phenethyl | OH | OH | 4 | COOEt |
| H | OH | OH | 3 | NHCO-pyridyl | cyclopropylmethyl | OH | OH | 4 | NHCHO |
| Me | OH | OH | 3 | NHCO-pyridyl | cyclobutylmethyl | OH | OH | 4 | NHCHO |
| benzyl | OH | OH | 3 | NHCO-pyridyl | allyl | OH | OH | 4 | NHCHO |
| 2-phenethyl | OH | OH | 3 | NHCO-pyridyl | H | OH | OH | 4 | NHCHO |
| cylcopropylmethyl | OH | OH | 3 | NHCO—NHPh | Me | OH | OH | 4 | NHCHO |
| cyclobutylmethyl | OH | OH | 3 | NHCO—NHPh | benzyl | OH | OH | 4 | NHCHO |
| allyl | OH | OH | 3 | NHCO—NHPh | 2-phenethyl | OH | OH | 4 | NHCHO |
| H | OH | OH | 3 | NHCO—NHPh | cylopropylmethyl | OH | OH | 4 | NHCO—Me |
| Me | OH | OH | 3 | NHCO—NHPh | cyclobutylmethyl | OH | OH | 4 | NHCO—Me |
| benzyl | OH | OH | 3 | NHCO—NHPh | allyl | OH | OH | 4 | NHCO—Me |
| 2-phenethyl | OH | OH | 3 | NHCO—NHPh | H | OH | OH | 4 | NHCO—Me |
| cyclopropylmethyl | OH | OH | 3 | NHCS—NHPh | Me | OH | OH | 4 | NHCO—Me |
| cyclobutylmethyl | OH | OH | 3 | NHCS—NHCH₂Ph | benzyl | OH | OH | 4 | NHCO—Me |
| allyl | OH | OH | 3 | NHCS—NHCH₂Ph | 2-phenethyl | OH | OH | 4 | NHCO—Me |
| H | OH | OH | 3 | NHCS—NHCH₂Ph | cyclopropylmethyl | OH | OH | 4 | NHOC—Ph |
| Me | OH | OH | 3 | NHCS—NHCH₂Ph | cyclobutylmethyl | OH | OH | 4 | NHCO—Ph |
| benzyl | OH | OH | 3 | NHCS—NHCH₂Ph | allyl | OH | OH | 4 | NHCO—Ph |
| 2-phenethyl | OH | OH | 3 | NHCS—NHCH₂Ph | H | OH | OH | 4 | NHCO—Ph |
| cyclopropylmethyl | OH | OH | 4 | OH | Me | OH | OH | 4 | NHCO—Ph |
| cyclobutylmethyl | OH | OH | 4 | OH | benzyl | OH | OH | 4 | NHCO—Ph |
| allyl | OH | OH | 4 | OH | 2-phenethyl | OH | OH | 4 | NHCO—Ph |
| H | OH | OH | 4 | OH | cyclopropylmethyl | OH | OH | 4 | NHCO—(CH₂)₅Ph |
| Me | OH | OH | 4 | OH | cyclobutylmethyl | OH | OH | 4 | NHCO—(CH₂)₅Ph |
| benzyl | OH | OH | 4 | OH | allyl | OH | OH | 4 | NHCO—(CH₂)₅Ph |
| 2-phenethyl | OH | OH | 4 | OH | H | OH | OH | 4 | NHCO—(CH₂)₅Ph |
| cyclopropylmethyl | OH | OH | 4 | OMe | Me | OH | OH | 4 | NHCO—(CH₂)₅Ph |
| cyclobutylmethyl | OH | OH | 4 | OMe | benzyl | OH | OH | 4 | NHCO—(CH₂)₅Ph |
| allyl | OH | OH | 4 | OMe | 2-phenethyl | OH | OH | 4 | NHCO—(CH₂)₅Ph |
| H | OH | OH | 4 | OMe | cyclopropylmethyl | OH | OH | 4 | NHCO-cinnamyl |
| Me | OH | OH | 4 | OMe | cylcobutylmethyl | OH | OH | 4 | NHCO-cinnamyl |
| benzyl | OH | OH | 4 | OMe | allyl | OH | OH | 4 | NHCO-cinnamyl |
| 2-phenethyl | OH | OH | 4 | OMe | H | OH | OH | 4 | NHCO-cinnamyl |
| cyclopropylmethyl | OH | OH | 4 | OEt | Me | OH | OH | 4 | NHCO-cinnamyl |
| cyclobutylmethyl | OH | OH | 4 | OEt | benzyl | OH | OH | 4 | NHCO-cinnamyl |
| allyl | OH | OH | 4 | OEt | 2-phenethyl | OH | OH | 4 | NHCO-cinnamyl |
| H | OH | OH | 4 | OEt | cyclopropylmethyl | OH | OH | 4 | NHCO—(CF₃-cinnamyl) |
| Me | OH | OH | 4 | OEt | cylcobutylmethyl | OH | OH | 4 | NHCO—(CF₃-cinnamyl) |
| benzyl | OH | OH | 4 | OEt | allyl | OH | OH | 4 | NHCO—(CF₃-cinnamyl) |
| 2-phenethyl | OH | OH | 4 | OEt | H | OH | OH | 4 | NHCO—(CF₃-cinnamyl) |
| cyclopropylmethyl | OH | OH | 4 | NH₂ | Me | OH | OH | 4 | NHCO—(CF₃-cinnamyl) |
| cyclobutylmethyl | OH | OH | 4 | NH₂ | benzyl | OH | OH | 4 | NHCO—(CF₃-cinnamyl) |
| allyl | OH | OH | 4 | NH₂ | 2-phenethyl | OH | OH | 4 | NHCO—(CF₃-cinnamyl) |
| H | OH | OH | 4 | NH₂ | cyclopropylmethyl | OH | OH | 4 | NHCO-pyridyl |
| 2-phenethyl | OH | OH | 4 | NH₂ | cyclobutylmethyl | OH | OH | 4 | NHCO-pyridyl |
| cyclopropylmethyl | OH | OH | 4 | CN | allyl | OH | OH | 4 | NHCO-pyridyl |
| cyclobutylmethyl | OH | OH | 4 | CN | H | OH | OH | 4 | NHCO-pyridyl |
| allyl | OH | OH | 4 | CN | Me | OH | OH | 4 | NHCO-pyridyl |
| H | OH | OH | 4 | CN | benzyl | OH | OH | 4 | NHCO-pyridyl |
| Me | OH | OH | 4 | CN | 2-phenethyl | OH | OH | 4 | NHCO-pyridyl |
| benzyl | OH | OH | 4 | CN | cyclopropylmethyl | OH | OH | 4 | NHCO—NHPh |
| 2-phenethyl | OH | OH | 4 | CN | cyclobutylmethyl | OH | OH | 4 | NHCO—NHPh |
| cyclopropylmethyl | OH | OH | 4 | NCS | allyl | OH | OH | 4 | NHCO—NHPh |
| cyclobutylmethyl | OH | OH | 4 | NCS | H | OH | OH | 4 | NHCO—NHPh |
| allyl | OH | OH | 4 | NCS | Me | OH | OH | 4 | NHCO—NHPh |
| H | OH | OH | 4 | NCS | benzyl | OH | OH | 4 | NHCO—NHPh |
| Me | OH | OH | 4 | NCS | 2-phenethyl | OH | OH | 4 | NHCO—NHPh |
| benzyl | OH | OH | 4 | NCS | cyclopropylmethyl | OH | OH | 4 | NHCS—NHPh |
| 2-phenethyl | OH | OH | 4 | NCS | cyclobutylmethyl | OH | OH | 4 | NHCS—NHPh |
| cyclopropylmethyl | OH | OH | 4 | COOH | allyl | OH | OH | 4 | NHCS—NHPh |
| cyclobutylmethyl | OH | OH | 4 | COOH | H | OH | OH | 4 | NHCS—NHPh |
| allyl | OH | OH | 4 | COOH | Me | OH | OH | 4 | NHCS—NHPh |
| H | OH | OH | 4 | COOH | benzyl | OH | OH | 4 | NHCS—NHPh |
| Me | OH | OH | 4 | COOH | 2-phenethyl | OH | OH | 4 | NHCS—NHPh |
| benzyl | OH | OH | 4 | COOH | cyclopropylmethyl | OH | OH | 4 | NHCS—NHCH₂Ph |
| 2-phenethyl | OH | OH | 4 | COOH | cyclobutylmethyl | OH | OH | 4 | NHCS—NHCH₂Ph |
| cyclopropylmethyl | OH | OH | 4 | COOMe | allyl | OH | OH | 4 | NHCS—NHCH₂Ph |
| cyclobutylmethyl | OH | OH | 4 | COOMe | H | OH | OH | 4 | NHCS—NHCH₂Ph |
| allyl | OH | OH | 4 | COOMe | Me | OH | OH | 4 | NHCS—NHCH₂Ph |
| H | OH | OH | 4 | COOMe | benzyl | OH | OH | 4 | NHCS—NHCH₂Ph |
| Me | OH | OH | 4 | COOMe | 2-phenethyl | OH | OH | 4 | NHCS—NHCH₂Ph |
| benzyl | OH | OH | 4 | COOMe | cyclopropylmethyl | OH | OMe | 3 | OH |
| 2-phenethyl | OH | OH | 4 | COOMe | cyclopropylmethyl | OH | OMe | 3 | OMe |
| cyclopropylmethyl | OH | OH | 4 | COOEt | cyclopropylmethyl | OH | OMe | 3 | NH₂ |
| cyclobutylemthyl | OH | OH | 4 | COOEt | cyclopropylmethyl | OH | OMe | 3 | CN |
| allyl | OH | OH | 4 | COOEt | cyclopropylmethyl | OH | OMe | 3 | NCS |

| | | | | |
|---|---|---|---|---|
| cyclopropylmethyl | OH | OMe | 3 | COOH |
| cyclopropylmethyl | OH | OMe | 3 | COOMe |
| cyclopropylmethyl | OH | OMe | 3 | NHCHO |
| cyclopropylmethyl | OH | OMe | 3 | NHCO—Ph |
| cyclopropylmethyl | OH | OMe | 3 | NHCO—(CH$_2$)$_5$Ph |
| cyclopropylmethyl | OH | OMe | 3 | NHCO—(CF$_3$-cinnamyl) |
| cylcopropylmethyl | OH | OMe | 3 | NHCO-pyridyl |
| cyclopropylmethyl | OH | OMe | 3 | NHCO—NHPh |
| cylcopropylmethyl | OH | OMe | 3 | NHCS—NHPh |
| cyclopropylmethyl | OH | OMe | 4 | OH |
| cyclopropylmethyl | OH | OMe | 4 | OMe |
| cyclopropylmethyl | OH | OMe | 4 | NH$_2$ |
| cyclopropylmethyl | OH | OMe | 4 | CN |
| cyclopropylmethyl | OH | OMe | 4 | NCS |
| cyclopropylmethyl | OH | OMe | 4 | COOH |
| cyclopropylmethyl | OH | OMe | 4 | COOMe |
| cyclopropylmethyl | OH | OMe | 4 | NHCHO |
| cyclopropylmethyl | OH | OMe | 4 | NHCO—Ph |
| cyclopropylmethyl | OH | OMe | 4 | NHCO—(CH$_2$)$_5$Ph |
| cyclopropylmethyl | OH | OMe | 4 | NHCO—(CF$_3$-cinnamyl) |
| cyclopropylmethyl | OH | OMe | 4 | NHCO-pyridyl |
| cyclopropylmethyl | OH | OMe | 4 | NHCO—NHPh |
| cyclopropylmethyl | OH | OMe | 4 | NHCS—NHPh |

The compounds represented by formula (I) of the present invention are generally produced by indole synthesis reaction using a ketone compound represented by formula (V) and a phenylhydrazine derivative presented by formula (VI), as shown by Scheme 1.

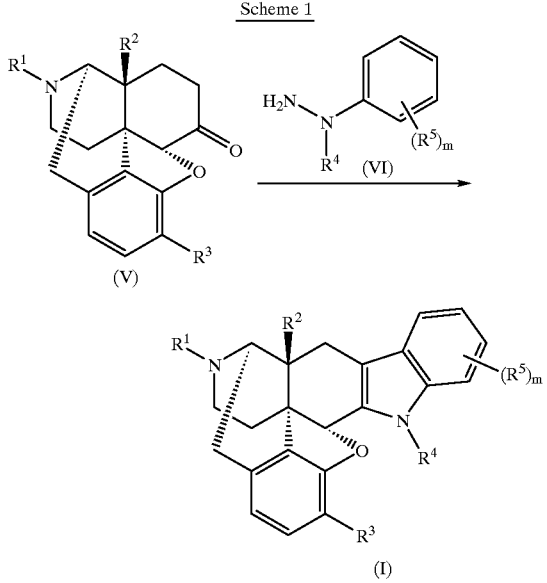

Scheme 1

Some of the compounds of formula (I) of the present invention produced by the above method are disclosed in U.S. Pat. No. 4,816,586 or International Patent Publication No. WO94/14445, and the production method disclosed in these publications can be used. Compounds of formula (I) which are not disclosed in these publications can be produced by a similar method, as described below.

Of ketone compounds represented by formula (V), compounds in which both of $R^2$ and $R^3$ are hydroxy, and $R^1$ is hydrogen, methyl, allyl and cyclopropylmethyl are generally known as noroxymorphone, oxymorphone, naloxone, and nartrexone, respectively, and a compound in which $R^2$ is hydroxy, $R^3$ is methoxy, and $R^1$ is hydrogen is generally known as noroxycodone. These compounds can be used without any change. Ketone compounds (V) in which $R^1$ is a group other than the above are can be prepared from noroxymorphone or noroxycodone in which $R^1$ is hydrogen by using the method disclosed in the document [J. Med. Chem., Vol. 35, 4329 (1992).] or the like. Specifically, such ketone compounds can be prepared by alkylation reaction using alkyl halide $R^1$-$X^1$ (wherein $X^1$ represents chloro, bromo, iodo, or p-toluenesulfonyloxy) in the presence of an appropriate base, as shown by the formula on the upper right of Scheme 2. The compounds of formula (I) can be produced by indole synthesis reaction using the thus-obtained ketone compounds represented by formula (V).

Alternatively, compounds (I) of the present invention can also be produced by any one of methods (1), (2) and (3) below using compounds of the present invention ($R^2$, $R^3$, $R^4$, $R^5$ and m are defined as the same as the above) represented by formula (I') in which $R^1$ is hydrogen obtained by indole synthesis reaction using the above ketone compounds (V').

In other words, as shown by the formula on the lower left of Scheme 2, the compounds (I) of the present invention can also be produced from the ketone compounds (wherein $R^2$ and $R^3$ are defined as the same as the above) represented by formula (V') in which $R^1$ is hydrogen, by a method (1) of alkylation reaction using an alkyl halide $R^1$-$X^1$ (wherein $X^1$ is defined as the same as the above) in the presence of an appropriate base, a method (2) of reductive amination using an appropriate aldehyde $R^{1'}$-CHO (wherein $R^{1'}$ represents a group obtained by removing a methylen terminal from $R^1$) and a reducing agent such as sodium cyanoborohydride, sodium triacetoxyborohydride, or the like, or hydrogenation reaction, or a method (3) comprising amidation using an appropriate acid chloride R2'-CO—Cl (wherein R1' is defined as the same as the above) according to a general method, and then reduction of the amide using a reducing agent such as lithium aluminum hydride or borane, or the like.

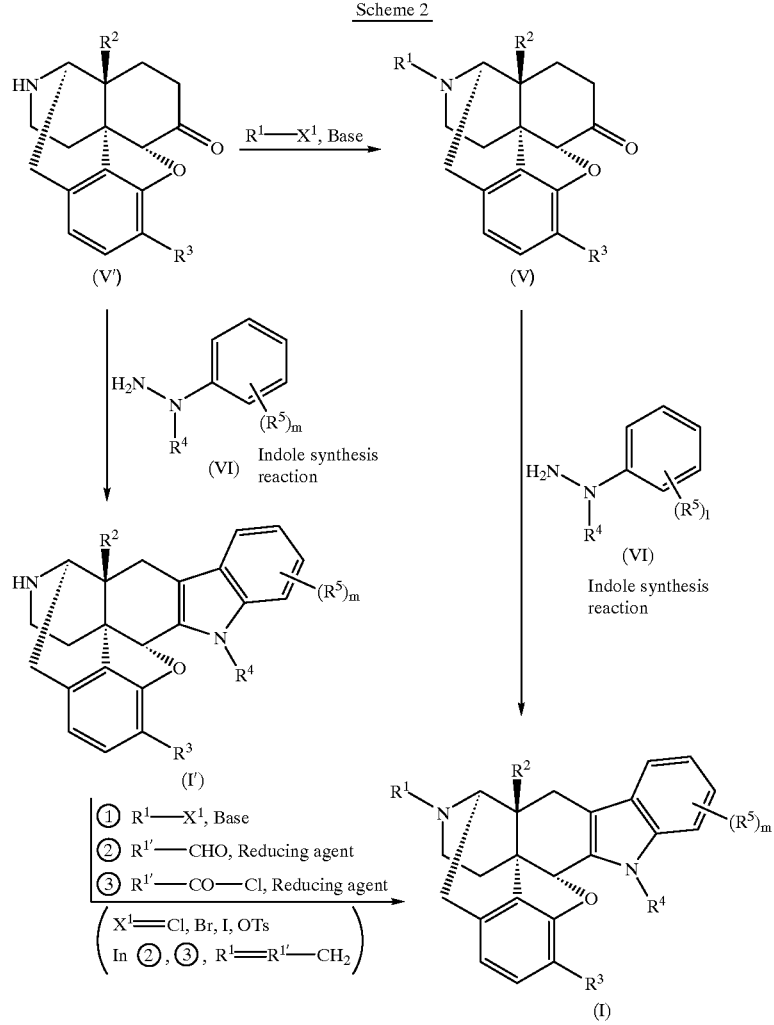

In the present invention, indole synthesis reaction can generally be effected in the presence of an appropriate acid according to demand in an appropriate solvent. Examples of the solvent include alcoholic solvents such as methanol, ethanol, and the like; organic carboxylic acid solvents such as formic acid, acetic acid, propionic acid, and the like; polar aprotic solvents such as DMF, DMSO, and the like; hydrocarbon solvents such as benzene, toluene, and the like. Particularly, alcoholic solvents and organic acid solvents are preferably used, and the use of ethanol or acetic acid produces sufficiently satisfactory results. Examples of acids include a wide range of acids such as inorganic acids such as hydrochloric acid, sulfuric acid, nitric acid, phosphoric acid, and the like; organic carboxylic acids such as formic acid, acetic acid, propionic acid, and the like; organic sulfonic acids such as methanesulfonic acid, p-toluenesulfonic acid, camphorsulfonic acid, and the like; Lewis acids such as zinc chloride, phosphorus trichloride, and the like. Of these acids, hydrochloric acid, sulfuric acid, phosphoric acid, formic acid, acetic acid, propionic acid, methanesulfonic acid, p-toluenesulfonic acid, camphorsulfonic acid, and zinc chloride are proferably used, and particulary hydrochloric acid, sulfuric acid, methanesulfonic acid, and acetic acid which can also be used as a solvent are preferable.

Of the compounds represented by formula (I) used in the present invention, compounds represented by formula (Ia) in which $R^4$ is hydrogen ($R^1$, $R^2$, $R^3$, $R^5$ and m are defined as the same as the above) are produced by using phenylhydrazine derivatives represented by formula (VIa) in which $R^4$ is hydrogen, as shown by Scheme 3.

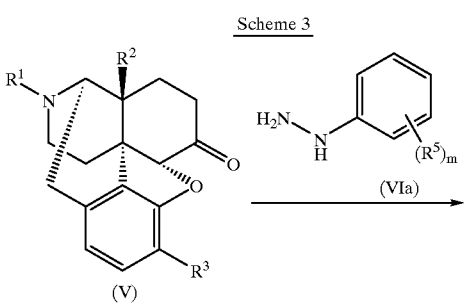

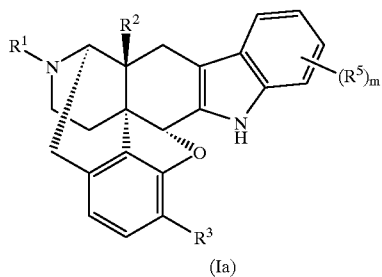

(Ia)

Commerically available phenylhydrazine derivatives (VIa) can be used in this method without any treatment, but the phenylhydrazine derivatives can also be prepared from corresponding nitrobenzene derivatives (VII) ($R^5$ and m are defined as the same as the above) or aniline derivatives (VIII) ($R^5$ and m are defined as the same as the above).

The nitrobenzene derivatives (VII) are generally led to aniline derivatives (VIII) by hydrogenation reaction or general reduction of nitro groups using a metal hydride reducing agent, a metal, a metal halide or the like.

As the method of preparing the phenylhydrazine derivatives (VIa) from the aniline derivatives (VIII), a method is generally used in which the aniline derivatives are diazotized by reaction with a nitrite such as sodium nitrite under acidic conditions of hydrochloric acid, sulfuric acid, acetic acid, or the like, followed by reduction with tin chloride, iron chloride, tin, iron, zinc, sodium sulfite, sodium thiosulfate, or the like under the similar acidic conditions to the above, as shown by the lower formula (a) in Scheme 4. The phenylhydrazine derivatives can also be prepared by the method disclosed in the document [Synthesis, 1 (1977)], which uses an amination agent such as o-mesitylenesulfonylhydroxylamine or the like, as shown by the lower formula (b) in Scheme 3.

The phenylhydrazine derivatives (VIa) can also be prepared from halogenated benzene derivatives (IX) (wherein $X^2$ represents chloro or bromo, and $R^5$ and m are defined as the same as the above), as shown in Scheme 5.

Scheme 5

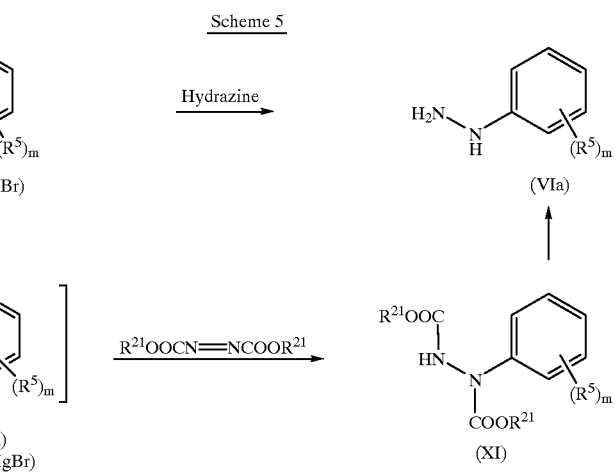

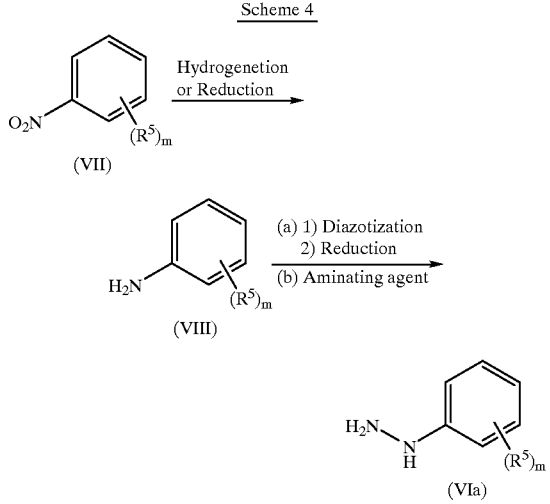

An example of this method is a method in which chlorinated benezene derivatives (IX, $X^2$=Cl) are converted directly to hydrazine derivatives by using hydrazine or a hydrate thereof in a solvent such alcohol such as ethanol, water or a solvent mixture thereof. Another method is the method disclosed in the document [Tetrahedron Lett., Vol. 28, 4933 (1987)] in which brominated benzene derivatives (IX, $X^2$=Br) are generally converted to phenyllithium derivatives (Xa) (wherein M represents Li) or Grignard derivatives (Xb) (wherein M represents MgBr), and reacted with dialkyl azodicarboxylate to form bis(alkoxycarbonyl) phenylhydrazine derivatives (XI) (wherein $R^{21}$ represents alkyl having a carbon number of 1 to 5), followed by hydrolysis to obtain phenylhydrazine derivatives (VIa). Here, the fully satisfied result can be obtained when the dialkyl azodicarboxylate in which $R^{21}$ is ethyl is used. Although bis(alkoxycarbonyl)phenylhydrazine derivatives (XI) can be hydrolyzed under either of acidic or basic conditions, hydrolysis is preferably effected under acidic conditions, and acidic conditions of hydrochloric acid are preferably used. In carrying out this method, bis (alkoxycarbonyl)phenylhydrazine derivatives (XI) can be used directly in indole synthesis reaction effected under acidic conditions in the same manner as phenylhydrazine derivatives (VIa).

The preparation method is appropriately selected from the above several methods of preparing phenylhydrazine derivatives (VIa) in accordance with availability, reactivity, reaction sensitivity of substituent $R^5$ of the starting materials.

Of the compounds represented by formula (I) of the present invention, compounds ($R^1$, $R^2$, $R^3$, $R^5$, and m are defined as the same as the above) represented by formula (Ib) in which $R^4$ is a substituent $R^{4b}$ representing alkyl having a carbon number of 1 to 8 or aralkyl having a carbon number of 7 to 13 (which may be subsituted by at least one substituent $R^{15'}$ which represents fluoro, chloro, bromo, iodo, nitro, alkyl having a carbon number of 1 to 5, alkoxy having a carbon number of 1 to 5, trifluoromethyl, trifluoromethoxy, or cyano) can be prepared by alkylation of nitrogen of the indole rings of compounds represented by formula (Ia) in which $R^4$ is hydrogen, by using an alkylation agent $R^{4b}$-$X^3$ (wherein $X^3$ represents chloro, bromo, iodo, methanesulfonyloxy, trifluoromethanesulfonyloxy, benzenesulfonyloxy, or p-toluenesulfonyloxy) under usual basic conditions to introduce the substituent $R^{4b}$.

Scheme 6

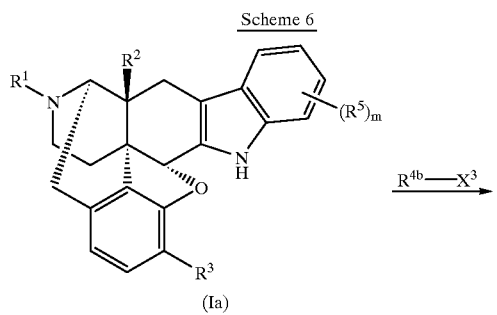

(Ia)

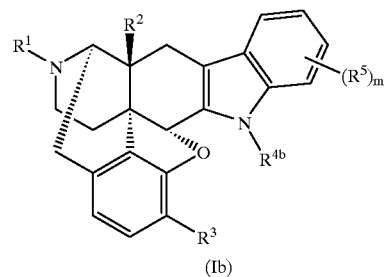

(Ib)

As the alkylation agent $R^{4b}$-$X^3$ used in this method, an agent in which $X^3$ is chloro, bromo, iodo or p-toluenesulfonyloxy is preferably used. As the base, sodium hydroxide, potassium hydroxide, sodium alkoxide, potassium alkoxide, sodium hydride, potassium hydride, butyllithium, and the like can be used. As the solvent, hydrocarbon solvents such as benzene, toluene, and the like; halogenated hydrocarbon solvents such as dichloromethane, dichloroethane, and the like; ether solvents such as diethyl ether, THF, DME, dioxane, and the like, alcohol solvents such as a methanol, ethanol, and the like; polar aprotic solvents such as DMF, DMSO, and the like can be used. Preferred combinations of these bases and solvents include conditions using a phase transfer catalyst such as tetrabutylammonium hydrogensulfate, tetrabutylammonium bromide, or the like, and if required, crown ether, in a two-layer solvent system comprising an aqueous solution of sodium hydroxide or potassium hydroxide, and benzene, toluene, or dichloromethane, conditions using powdered sodium hydroxide or potassium hydroxide in a solvent of DMF or DMSO, and conditions using sodium hydride in a solvent of THF, DMF, DMSO, or the like.

Compounds represented by formula (Ib) can also be produced by indole synthesis reaction using ketone compounds represented by formula (V), and phenylhydrazine derivatives substituted by $R^{4b}$ and represented by formula (VIb1), (VIb2) or (VIb3), as shown in Scheme 7.

Scheme 7

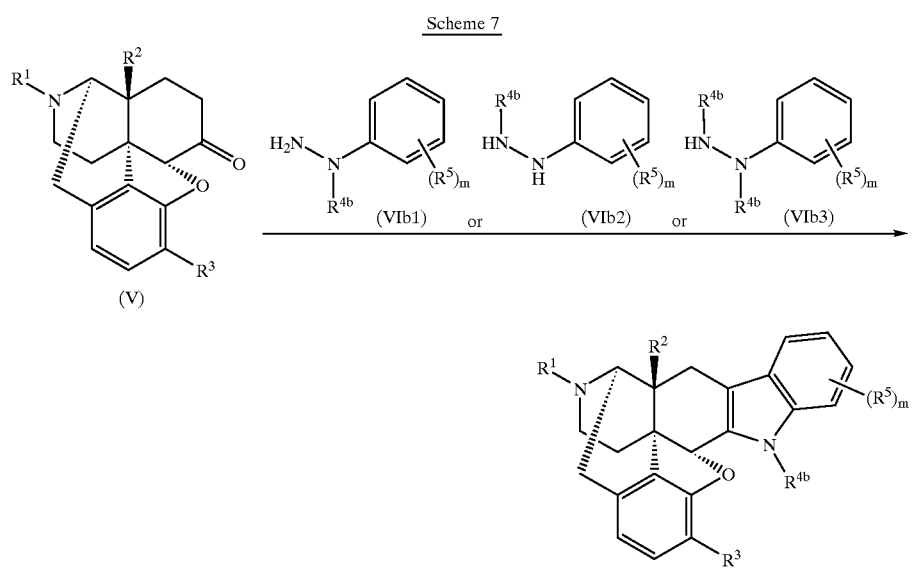

Of the compounds represented by formula (I) of the present invention, compounds represented by formula (Ic) ($R^1$, $R^2$, $R^3$, $R^5$ and m are defined as the same as the above) in which $R^4$ is substituent $R^{4c}$ representing alkanoyl having a carbon number of 1 to 5, arylcarbonyl having a carbon number of 7 to 13 (which may be subsituted by at least one substituent $R^{15'}$ defined as the same as the above), alkysulfonyl having a carbon number of 1 to 5, arylsulfonyl having a carbon number of 6 to 12 (which may be substituted by at least one substituent $R^{15'}$ defined as the same as the above), or aralkylsulfonyl having a carbon number of 7 to 13 (which may be substituted by at least one substituent $R^{15'}$ defined as the same as the above), can be produced by acylation or sulfonylation of nitrogen of the indole rings of the compounds used in the present invention and represented by formula (Ia) in which $R^4$ is hydrogen, by using acid chloride, sulfonic acid chloride $R^{4c}$-Cl, acid anhydride or sulfonic acid anhydride $R^{4c}$-O—$R^{4c}$ under basic conditions to introduce substitutent $R^{4c}$, as shown by Scheme 8.

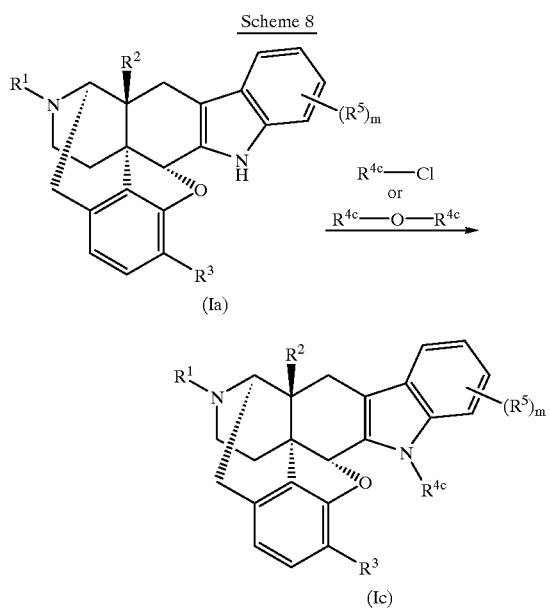

(Ia)

(Ic)

Acylation or sulfonylation reaction can generally be effected by using acid chloride or sulfonic acid chloride $R^{4c}$-Cl under the same conditions of alkylation reaction for introducing substituent $R^{4b}$ shown by the above scheme 6. Particularly, it is preferable to use the conditions using a phase transfer catalyst such as tetrabutylammonium hydrogensulfate, tetrabutylammonium bromide, or the like in a two-layer solvent system comprising an aqueous solution of sodium hydroxide or potassium hydroxide, and benzene, toluene, or dichloromethane, the conditions using powdered sodium hydroxide or potassium hydroxide in a solvent of DMF or DMSO, or the conditions using sodium hydride in a solvent of THF, DMF, DMSO, or the like.

Of the compounds represented by formula (I) of the present invention, compounds represented by formula (Id) ($R^1$, $R^2$, $R^3$, $R^5$ and m are defined as the same as the above) in which $R^4$ is $R^{4d}$ representing $(CH_2)_i$-$R^{16}$ (i is defined as the same as the above) wherein $R^{16}$ is $OR^7$, $NR^7R^{7'}$, or cyano (R7 and R7' are defined as the same as the above) can be produced by introducing the subsituent $R^{4d}$ into the indole ring nitrogen of the compounds used in the present invention and represented by formula (Ia) wherein $R^4$ is hydrogen, by using an alkylation agent $R^{4d}$-$X^3$ ($X^3$ is defined as the same as the above) under basic conditions, for example, as shown by Scheme 9.

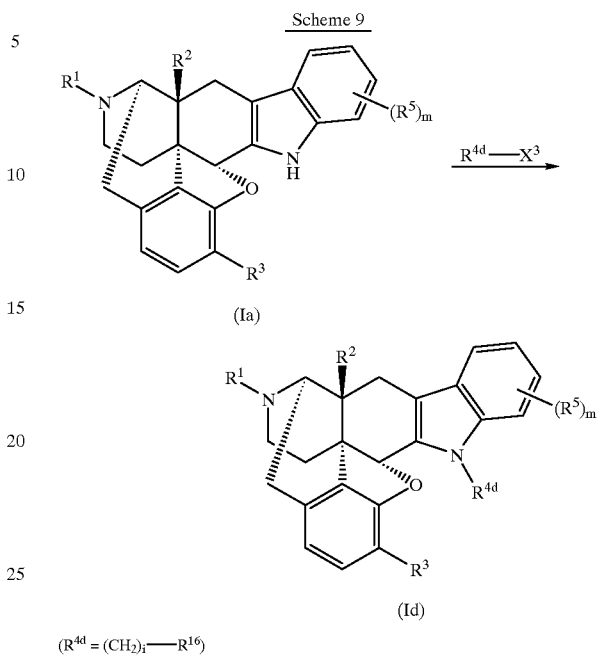

(Ia)

(Id)

($R^{4d} = (CH_2)_i$—$R^{16}$)

The introduction of this substituent can be carried out by using an alkylation agent $R^{4d}$-$X^3$ in which $X^3$ is generally chloro, bromo, iodo, or p-toluenesulfonyloxy under the same conditions as alkylation reaction for introducing the substituent $R^{4b}$ shown in the above scheme 6. Particularly, it is preferable to use the conditions using a phase transfer catalyst such as tetrabutylammonium hydrogensulfate, tetrabutylammonium bromide, or the like in a two-layer solvent system comprising an aqueous solution of sodium hydroxide or potassium hydroxide, and benzene, toluene, or dichloromethane, or the conditions using powdered sodium hydroxide or potassium hydroxide in a solvent of DMF or DMSO.

Of the compounds represented by formula (Id), compounds in which $R^{16}$ is $OR^7$, and particularly $R^7$ is hydrogen can also be produced by demethylation of the methyl groups of compounds in which $R^7$ is methyl, by a method using boron tribromide [Document: Tetrahedron, vol. 24, 2289 (1968)] or boron trichloride in a solvent such as dichloromethane, chloroform or 1,2-dichloroethane, a method using thioalkoxide, particularly sodium thioethoxide [Document: Tetrahedron Lett., 1327 (1970)], or the like.

Of the compounds represented by formula (Id), compounds in which $R^{4d}$ is $(CH_2)_i$-$R^{16}$ (i is defined as the same as the above) wherein $R^{16}$ is $NR^7R^{7'}$, and particularly, both $R^7$ and $R^{7'}$ are hydrogen are defined as the following formula (Id1) ($R^1$, $R^2$, $R^3$, $R^5$ and m are defined as the same as above).

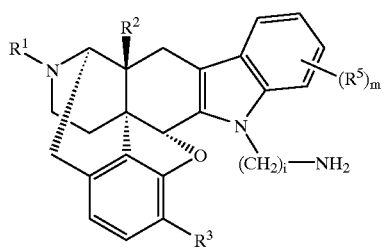

(Id1)

Besides the above production method, particularly, compounds represented by formula (Id1') in which i is an integer of 3 to 5 can also be produced by indole synthesis reaction of ketone compounds of formula (V) using cyclic hydrazine compounds (i represents an integer of 3 to 5, and $R^5$ and m are defined as the same as the above) represented by formula (VId1) which can be prepared by the method disclosed in the document [J. Pharm. Sci., Vol. 68, 377 (1979), Tetrahedron, Vol, 29, 4045 (1973)], for example, as shown by Scheme 10.

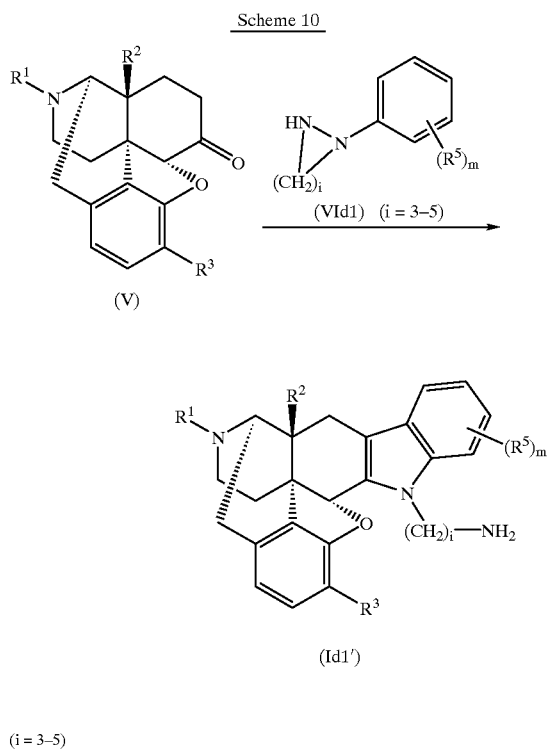

Of the compounds represented by formula (I) of the present invention, compounds (Y represents O or S, and $R^1$, $R^2$, $R^3$, $R^5$ and m are defined as the same as the above) represented by formula (Ie) in which $R^4$ is $R^{4e}$ representing $(CH_2)_i$-$R^{16}$ (i is defined as the same as the above) wherein $R^{16}$ is isocyanato or isothiocyanato can be produced by converting compounds represented by formula (Id1) to isocyanate or thioisocyanate, for example, as shown by Scheme 11.

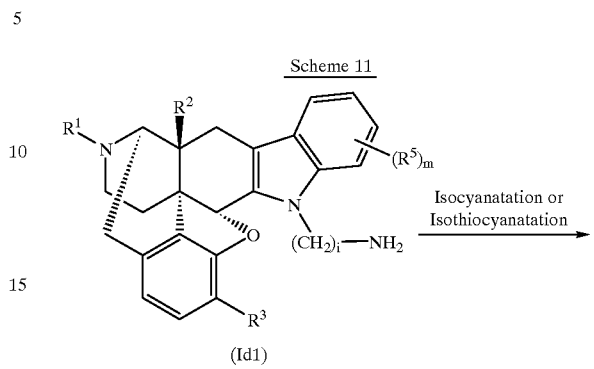

(Y = O, S)

Conversion to isocyanate can be carried out by using phosgene or triphosgene in a solvent such as benzene, toluene, pyridine, ethanol, dichloromethane, chloroform or the like in accordance with an ordinary method. Conversion to isothiocyanate can be carried out by a method using thiophosgene in a solvent such as benzene, toluene, dichloromethane, chloroform, or acetone, or a two-layer solvent system comprising a basic aqueous solution of sodium hydroxide, sodium bicarbonate, or the like, and dichloromethane, chloroform, or the like, or a method using di(2-pyridyl) thionocarbonate in dichloromethane [Tetrahedron Lett., Vol. 26, 1661 (1985)].

Of the compounds represented by formula (I) of the present invention, compounds represented by formula (If1), (If2), (If3) and (If4) ($R^1$, $R^2$, $R^3$, $R^5$ and m are defined as the same as the above) wherein $R^4$ is $(CH_2)_i$-$R^{16}$ (i is defined as the same as the above) wherein $R^{16}$ is $NR^7(C=O)$—$R^9$, $NR^7(C=Y)NHR^9$, $NR^7(C=Y)O$—$R^9$ and $NR^7CHO$ ($R^7$, $R^9$ and Y are defined as the same as the above), respectively, can be produced by condensation of compounds represented by formula (Id2) with carboxylic acid chloride $R^9$—CO—Cl, carboxylic acid anhydride $(R^9$—$CO)_2O$, carboxylic acid $R^9$—COOH, isocyanate $R^9$—NCO, isothiocyanato $R^9$—NCS, chloroformate ester $R^9O$—CO—Cl, chlorothionoformate ester $R^9O$—CS—Cl, formic acid, formate ester, or the like, for example, as shown in Scheme 12.

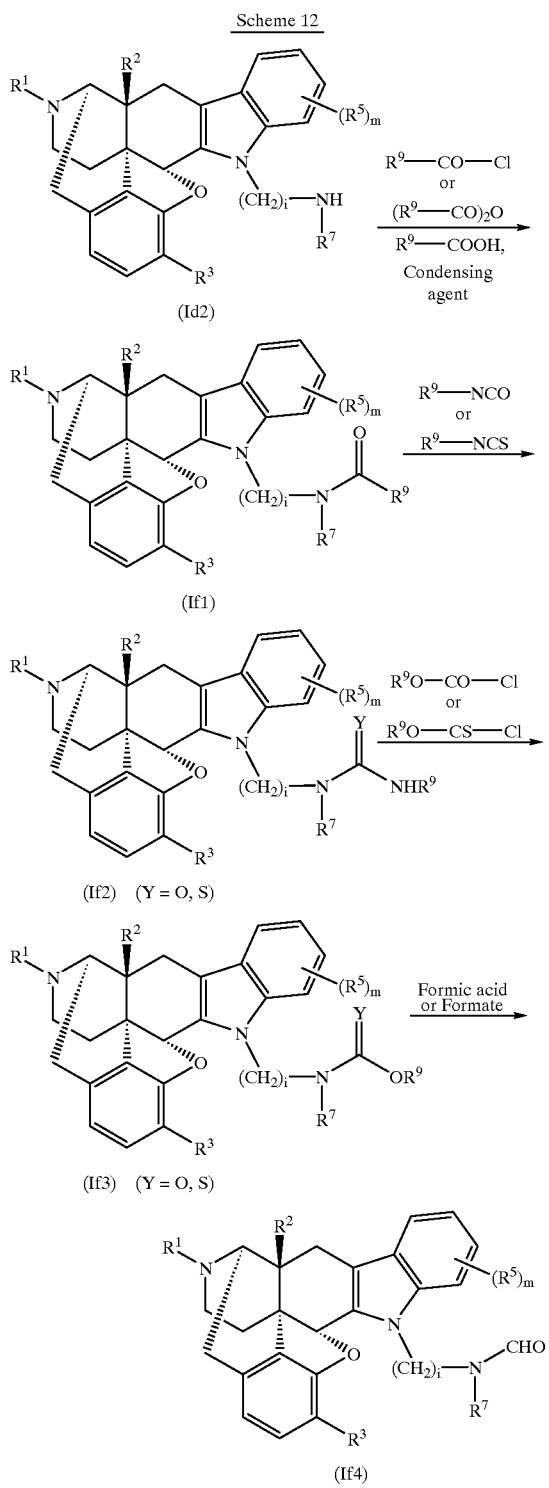

Scheme 12

(Id2) → (If1) → (If2) (Y = O, S) → (If3) (Y = O, S) → (If4)

Condensation with carboxylic acid chloride R⁹—CO—Cl, carboxylic acid anhydride (R⁹—CO)₂O, chloroformate ester R⁹O—CO—Cl or chlorothionoformate ester R⁹O—CS—Cl can be carried out by using, as a base, a tertiary amine such as triethylamine, diisopropylethylamine, proton sponge, or the like, an organic base such as pyridine, dimethylaminopyridine, imidazole, or the like, an inorganic base such as potassium carbonate, sodium carbonate, sodium bicarbonate, sodium hydroxide, potassium hydroxide, or the like in a solvent such as a halogenated hydrocarbon solvent such as dichloromethane, chloroform, carbon tetrachloride, 1,2-dichloroethane, or the like; an ether solvent such as an ether, THF, DME, dioxane, or the like; pyridine, water, or a solvent mixture thereof. Particularly, in the case of carboxylic acid chloride, chloroformate ester or chlorothionoformate ester, conditions using triethylamine in dichloromethane or chloroform, or conditions using potassium carbonate, sodium carbonate or sodium bicarbonate in a THF-water solvent mixture are preferably used. In the use of carboxylic acid anhydride, conditions using pyridine as both a base and a solvent are preferably used.

Condensation with carboxylic acid R9—COOH can generally be carried out by using any one of general known condensation agents. Particularly, condensation agents such as N,N'-dicyclohexylcarbodiimide (abbreviated to "DCC" hereinafter), 1,1'-carbonyldiimidazole (abbreviated to "CDI" hereinafter), bis-(2-oxo-3-oxazolidinyl) phosphinic acid chloride (abbreviated to "BOPCl" hereinafter), and the like are preferably used. In the use of DCC, condensation can be carried out by using, as a base, a tertiary amine such as triethylamine, diisopropylethylamine, proton sponge, or the like, an organic base such as pyridine, dimethylaminopyridine, imidazole, or the like, in a reaction solvent such as a halogenated hydrocarbon solvent such as dichloromethane, chloroform, carbon tetrachloride, 1,2-dichloroethane, or the like, an ether solvent such as an ether, THF, DME, dioxane, or the like. Particularly, dimethylaminopyridine is preferably used in dichloromethane or chloroform. In the use of CDI, as a solvent, an ether solvent such as an ether, THF, DME, dioxane, or the like, a halogenated hydrocarbon solvent such as dichloromethane, chloroform, carbon tetrachloride, 1,2-dichloroethane, or the like can be used, and particularly THF is preferably used. In the use of BOPCl, as a solvent, a halogenated hydrocarbon solvent such as dichloromethane, chloroform, carbon tetrachloride, 1,2-dichloroethane, or the like, an ether solvent such as ether, THF, DME, dioxane, or the like can be used, and as a base, a tertiary amine such as triethylamine, diisopropylethylamine, proton sponge, N-ethylpiperidine, or the like; an organic base such as pyridine, dimethylaminopyridine, imidazole, or the like can be used. Particularly, N-ethylpiperidine is preferably used in dichloromethane or chloroform.

Condensation with isocyanate $R^9$-NCO or isothiocyanate $R^9$-NCS can be carried out directly in a halogenated hydrocarbon solvent such as dichloromethane, chloroform, carbon tetrachloride, 1,2-dichloroethane, or the like; an ether solvent such as an ether, THF, DME, dioxane, or the like. Particularly, chloroform is preferably used.

Compounds represented by formula (If4) can be produced directly by formylation using formic acid or formate (methyl or ethyl ester). However, it is possible to use any one of general known formylation methods such as a method using formic acid and acetic anhyride, a method using formate and a base such as triethylamine, or the like, a method using mixed acid anhydride such as mixed formic, mixed acetic anhydride or the like, a method using DMF and phosphorus oxychloride or sodium methoxide, etc.

In the steps shown in Scheme 12, of compounds represented by formula (Id2), when $R^3$ is hydroxyl, condensation products in which the phenolic hydroxyl groups are reacted at the same time are sometimes produced. In this case, hydrolysis under basic conditions after the condensation reaction can produce target compounds represented by formulae (If1), (If2), (If3) and (If4) in which $R^3$ is hydroxyl. Hydrolysis reaction can be effected by using as a base an inorganic base such as, potassium carbonate, sodium carbonate, sodium bicarbonate, sodium hydroxide, potassium hydroxide, or the like, particularly potassium carbonate or sodium hydroxide, in water, an alcohol solvent such as methanol, ethanol, or the like, an ether solvent such as an ether, THF, DME, dioxane, or the like, or a solvent mixture thereof. With insufficient solubility, hydrolysis reaction can be effected in a solvent to which a halogenated hydrocarbon solvent such as dichloromethane, chloroform, or the like is appropriately added.

Of the compounds represented by formula (I) of the present invention, compounds represented by formulae (If5) and (If6) ($R^1$, $R^2$, $R^3$, $R^5$ and m are defined as the same as the above) wherein $R^4$ is $(CH_2)_i$-$R^{16}$ (i is defined as the same as the above) wherein $R^{16}$ is $NH(C=Y)NR^8R^9$ and $NH(C=Y)O—R^9$ ($R^8$, $R^9$ and Y are defined as the same as the above), respectively, can also be produced by condensation of isocyanate or isothiocyanate represented by formula (Ie) ($R^1$, $R^2$, $R^3$, $R^5$, m, i and Y are defined as the same as the above) with an amine $R^8R^9NH$ or alcohol $R^9OH$, for example, as shown in Scheme 13. The condensation reaction can be generally effected directly in a halogenated hydrocarbon solvent such as dichloromethane, chloroform, carbon tetrachloride, 1,2-dichloroethane, or the like, an ether solvent such as an ether, THF, DME, dioxane, or the like.

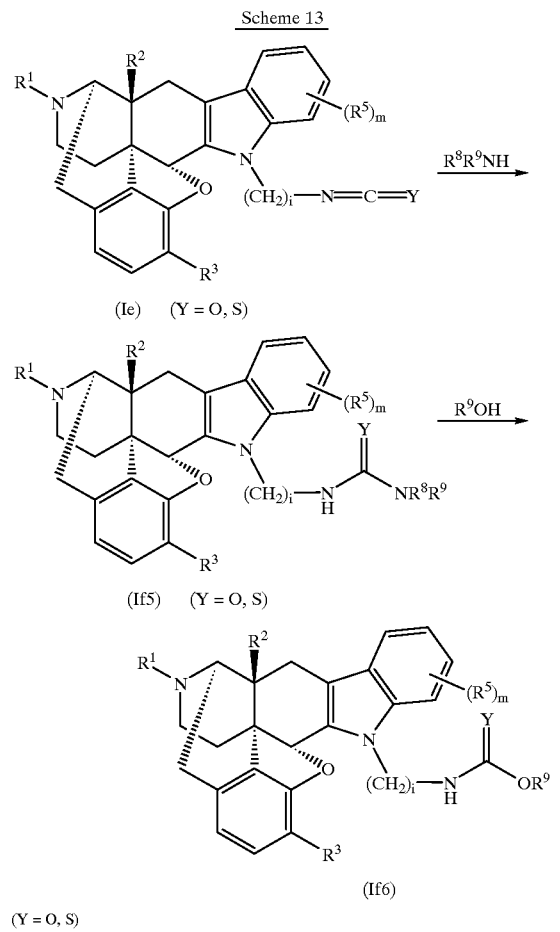

Scheme 13

(Ie)  (Y = O, S)

(If5)  (Y = O, S)

(If6)

(Y = O, S)

Of the compounds represented by formula (I) of the present invention, compounds ($R^1$, $R^2$, $R^3$, $R^5$ and m are defined as the same as the above) represented by formula (Iha) ($R^7$ is hydrogen) or (Ihb) ($R^7$ is alkyl having a carbon number of 1 to 5) wherein $R^4$ is $(CH_2)_i$-$R^{16}$ (i is defined as the same as the above) wherein $R^{16}$ is $COOR^7$ ($R^7$ is defined as the same as the above) can be produced by solvolysis of compounds represented by formula (Ig) wherein in compounds represented by formula (Id), $R^4$ is $(CH_2)_i$-$R^{16}$ (i is defined as the same as the above), and $R^{16}$ is cyano, by using water or alcohol $R^7OH$, as shown in Scheme 14. Esterification of the thus-obtained carboxylic acids of formula (Iha) wherein $R^7$ is hydrogen can produce esters of formula (Ihb) wherein $R^7$ is alkyl, and conversely hydrolysis of the esters of formula (Ihb) wherein $R^7$ is alkyl can produce carboxylic acids of formula (Iha).

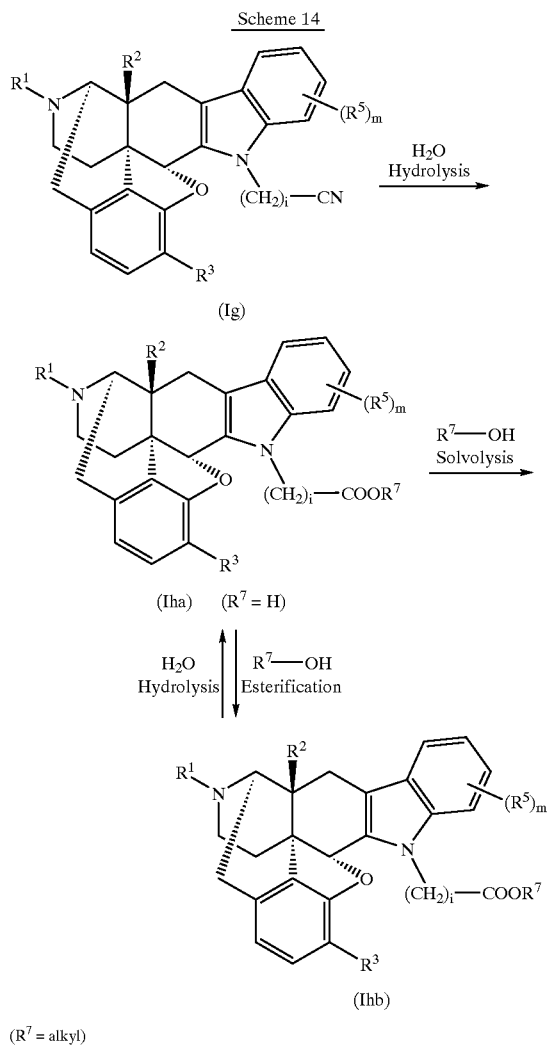

Scheme 14

(Ig)

(Iha)  ($R^7$ = H)

(Ihb)

($R^7$ = alkyl)

Although any one of general known methods can be used for solvolysis, particularly, hydrolysis to products of formula (Iha) can sufficiently be effected in an aqueous solution or a hydrous alcohol under acidic conditions using hydrochloric acid, sulfuric acid, phosphoric acid, acetic acid, or the like, or basic conditions using a base such as sodium hydroxide, potassium hydroxide, or the like.

Solvolysis to products of formula (Ihb) can be effected by using an acid such as hydrochloric acid, sulfuric acid, p-toluenesulfonic acid, or the like in alcohol.

Esterification can be effected by any one of general methods such as a method using alcohol $R^7OH$, an appropriate acid or base, and if required, an appropriate condensation agent, a method comprising conversion to acid chloride or acid anhydride, and then condensation with alcohol $R^7OH$, etc. Hydrolysis of esters can be sufficiently effected by a method using an appropriate acid or base in the same manner as the above hydrolysis.

Of the compounds represented by formula (I) of the present invention, compounds ($R^1$, $R^2$, $R^4$, $R^5$ and m are defined as the same as the above) represented by formula (Ii) wherein $R^3$ is methoxy can be converted to compounds ($R^1$, $R^2$, $R^4$, $R^5$ and m are defined as the same as the above) represented by formula (Ij) wherein $R^3$ is hydroxyl by general demethylation reaction of phenolic methyl ether, as shown in Scheme 15.

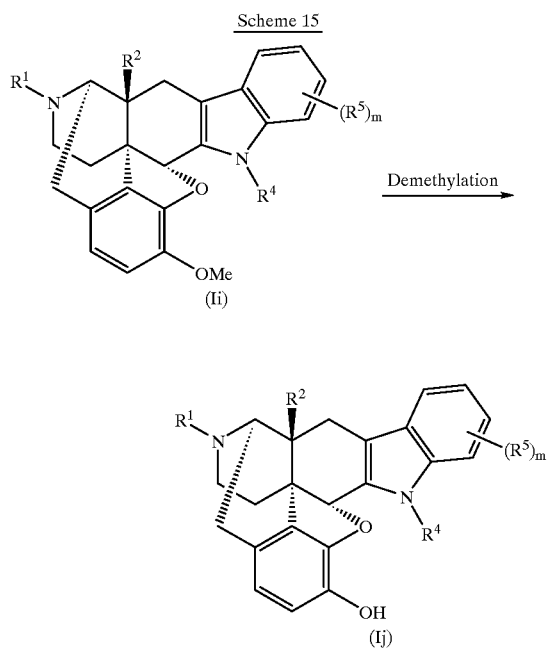

Although general known conditions can be applied to demethylation reaction, particularly, demethylation reaction can be effected by a method using boron tribromide [Document: Tetrahedron, Vol. 24, 2289 (1968)] or boron trichloride in a solvent such as dichloromethane, chloroform, or 1,2-dichloroethane, a method using thioalkoxide, particularly sodium thioethoxide [Document: Tetrahedron Lett., 1327 (1970)] in DMF, or the like.

Conversely, of the compounds represented by formula (I) of the present invention, compounds ($R^1$, $R^2$, $R^4$, $R^5$ and m are defined as the same as the above) represented by formula (Ii) wherein $R^3$ is methoxy can also be produced by methylation of phenolic hydroxy groups of compounds ($R^1$, $R^2$, $R^4$, $R^5$ and m are defined as the same as the above) represented by formula (Ij) wherein $R^3$ is hydroxy by a general method, as shown in Scheme 16.

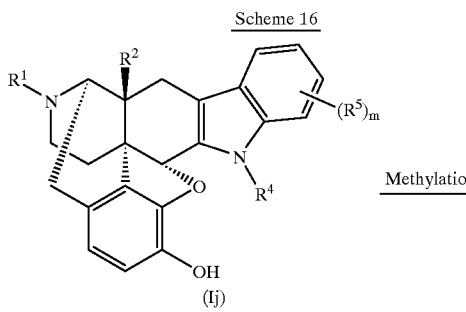

Although any general known conditions can be applied to the methylation, particularly, a method using methyl iodide in a solvent such as DMF or acetone in the presence of an inorganic base such as sodium carbonate, potassium carbonate, lithium carbonate, or the like, a method using diazomethane in a solvent such as diethyl ether or the like in the presence of silica gel, and the like are preferably used.

As a result of in vitro and in vivo pharmacological evaluation, the indolomorphinan derivatives of the present invention represented by formula (I) exhibit excellent effects on disorders of the cerebral nerve cells, as described in the examples below. Therefore, the compounds of the present invention can be used as agents for curing and preventing cerebral disorders, i.e., medicines useful for ameliorating various cerebral diseases and aftereffects thereof, and preventing recurrence thereof. Specifically it was made apparent that the compounds of the present invention can be used as therapeutic agents for cerebral stroke, therepeutic agents for traumatic cerebral diseases, therapeutic agents for cerebral edema, therapeutic agents for ischemic diseases, therapeutic agents for cerebral neurodegenerative diseases, and therapeutic agents for aftereffects of cerebral diseases. The compounds of the present invention exhibited the excellent neuroprotetive action on damages of the cerebral nerve cells, and it was thus found that the compounds of the present invention are useful as cerebral neuroprotective agents which inhibit ischemic or hemorrhagic cerebrovascular diseases, traumatic cerebral diseases and various cerebral neurodegenerative diseases by the protecting action on the cerebral nerve cells.

The therapeutic agents for cerebral stroke are medicines used for curing, ameliorating or preventing ischemic or hemorrhagic cerebral stroke, specifically, cerebral infarction (cerebral embolism, cerebral thrombosis), cerebral hemorrhage, subarachnoid hemorrhage, transient ischemic attack (TIA), hypertensive encephalophathy, etc. The therapeutic agents for traumatic cerebral diseases are medicines used for ameliorating cerebral disorder caused by trauma and functional disorder of the brain accompanied thereby, and ameliorating aftereffects. The therapeutic agents for cerebral edema are medicines used for ameliorating, curing or preventing cerebral edema caused by a lesion of hemorrhage, infarction, tumor, trauma, or the like which occurs in the brain, or an increase in intracranial pressure to ameliorate disorders of the cerebral nerve cells due to cerebral edema. The therapeutic agents for ischemic diseases are medicines used for curing, emeliorating or preventing the cerebral disorders caused by insufficient supply of oxygen and glucose to the cerebral nerve cells on the basis of ischemia due to hypoxia, hypoglycemia, drug poisoning, or the like. The therapeutic agents for cerebral neurodegenerative diseases are medicines used for curing, ameliorating or preventing cerebral diseases such as Alzheimer's disease, Parkinson's disease, Huntington's chorea, diffuse Lewy's bodies, Creutzfeldt-Jakob's disease, and the like, which cause disorders of the cerebral nerve cells accompanied with degeneration of the nerve cells. The therapeutic agents for aftereffects of cerebral diseases are medicines used for curing, ameliorating or preventing aftereffects caused by the above cerebral disorders, such as cerebrovascular dementia, amnesia, disorder of consciousness, motor paralysis, allophasis, sensory disorder, mental disorder, memory disorder, and the like.

In the clinical use of the agent for curing and preventing cerebral disorder of the present invention, a free base or salt thereof may be used, and additives such as an excipient, a stabilizer, a preservative, a buffer, a solubilizer, an emulsifier, a diluent, an isotonizing agent, etc. may be appropriately mixed. As an administration form, either parenteral administration or oral administration produces sufficient effects. Administration formulations include an injection, a tablet, a liquid, a capsule, granules, a powder, and the like, and these formulations can be produced by known formulation techniques. Although the dosage is appropriately selected in accordance with the symptoms, age and body weight of a patient, the administration method, etc., the amount of the effective component per adult is 0.0001 mg to 10 g per day, preferably 0.001 mg to 1 g per day, and the agent can be administered once or divided into several doses.

EXAMPLES

Although the present invention is described in detail with reference to reference examples and examples, the present invention is not limited to these example.

Reference Example 1

17-cyclopropylmethyl-3,14β-dihydroxy-6,7-dehydro-4, 5α-epoxy-6,7,2',3'-indolomorphinan 1 • methanesulfonate This compound was synthesized in accordance with the method disclosed in U.S. Pat. No. 4,816,586 and International Unexamined Patent Publication No. WO 94/14445. 150 g (40 mmol) of 17-cyclopropylmethyl-6-oxo-4,5α-epoxy-3,14β-dihydroxymorphinan (nartrexone) hydrochloride, and 45.1 g (42 mol) of phenylhydrazine were added to 2.5 L of ethanol, and 381 g (4 mol) of methanesulfonic acid was added to the resultant mixture, followed by heating under reflux for 1.5 hours. The reaction solution was cooled to room temperature, and the precipitated crystals were filtered off. 140 g of the crude crystals obtained were recrystallized from methanol to obtain 140 g (yield 68%) of title compound.

Reference Examples 2–14

Indole synthesis reaction was effected by using nartrexone as a raw material in accordance with the method of Reference Example 1. Namely, 17-cyclopropylmethyl-3,14β-dihydroxy-6,7-dehydro-4,5α-epoxy-6,7,2',3'-(1'-phenylindolo)morphinan 4 was obtained by using 1,1-diphenylhydrazine in place of phenylhydrazine. 17-cyclopropylmethyl-3,14β-dihydroxy-6,7-dehydro-4,5α-epoxy-6,7,2',3'-(6'-cyclohexylindolo)morphinan 5 was obtained by using 3-cyclohexylphenylhydrazine (prepared from 3-cyclophexylaniline). 17-cyclopropylmethyl-3,14β-dihydroxy-6,7-dehydro-4,5α-epoxy-6,7,2',3'-(4'-heptylindolo)morphinan 6 and 17-cyclopropylmethyl-3, 14β-dihydroxy-6,7-dehydro-4,5α-epoxy-6,7,2',3'-(6'-heptylindolo)morphinan 7 were obtained by using 3-heptylphenylhydrazine (prepared from 3-heptylaniline). 17-cyclopropylmethyl-3,14β-dihydroxy-6,7-dehydro-4,5α-epoxy-6,7,2',3'-(6',7'-benzoindolo)morphinan 2 and 17-cyclopropylmethyl-3,14β-dihydroxy-6,7-dehydro-4,5α-epoxy-6,7,2',3'-(4',5'-benzoindolo)morphinan 8 were obtained by using 1-naphthylhydrazine (prepared from 1-bromonaphthalene). 17-cyclopropylmethyl-3,14β-dihydroxy-6,7-dehydro-4,5α-epoxy-6,7,2',3'-(5'-bromo-6', 7'-benzoindolo)morphinan 9 was obtained by using 4-bromo-1-napthylhydrazine (prepared from 4-bromo-1-aminonaphthalene). 17-cyclopropylmethyl-3,14β-dihydroxy-6,7-dehydro-4,5α-epoxy-6,7,2',3'-(5'-chloro-6', 7'-benzoindolo)morphinan 10 was obtained by using 4-chloro-1-naphthylhydrazine (prepared from 4-chloro-1-aminonaphthalene). 17-cyclopropylmethyl-3,14β-dihydroxy-6,7-dehydro-4,5α-epoxy-6,7,2',3'-(5'-cyano-6', 7'-benzoindolo)morphian 11 was obtained by using 4-cyano-1-naphthylhydrazine (prepared from 4-cyano-1-aminonaphthalene). 17-cyclopropylmethyl-3,14β-dihydroxy-6,7-dehydro-4,5α-epoxy-6,7,2',3'-(3"-chloro-6', 7'-benzoindolo)morphinan 12 was obtained by using 8-chloro-1-naphthylhydrazine (prepared from 8-chloro-1-aminonaphthalene). 17-cyclopropylmethyl-3,14β-dihydroxy-6,7-dehydro-4,5α-epoxy-6,7,2',3'-(5'-methyl-6', 7'-benzoindolo)morphinan 13 was obtained by using 4-methyl-1-naphthylhydrazine (prepared from 4-bromo-1-methylnaphthalene). 17-cyclopropylmethyl-3,14β-dihydroxy-6,7-dehydro-4,5α-epoxy-6,7,2',3'-(5'-fluoro-6', 7'-benzoindolo)morphinan 14 was obtained by using 4-fluoro-1-naphthylhydrazine (prepared from 4-bromo-1-fluoronaphthalene). 17-cyclopropylmethyl-3,14β-dihydroxy-6,7-dehydro-4,5α-epoxy-6,7,2',3'-(5'-phenyl-6', 7'-benzoindolo)morphinan 15 was obtained by using 4-phenyl-1-naphthylhydrazine (prepared from 4-bromo-1-phenylnaphthalene).

Reference Examples 15–16

In accordance with the method of Reference Example 1, indole synthesis reaction was effected by using 17-cyclopropylmethyl-6-oxy-4,5α-epoxy-3-methoxy-14β-hydroxymorphinan (nartrexone-3-methyl ether) as a raw material in place of nartrexone, and 4-t-butylphenylhydrazine (prepared from 4-t-butylaniline) and 1-naphthylhydrazine as hydrazine derivatives to obtain 17-cyclopropylmethyl-3-methoxy-14β-hydroxy-6,7-dehydro-4,5α-epoxy-6,7,2',3'-(5'-t-butylindolo)morphinan 16 and 17-cyclopropylmethyl-3-methoxy-14β-hydroxy-6,7-dehydro-4,5α-epoxy-6,7,2',3'-(6',7'-benzoindolo)morphinan 17, respectively.

Reference Example 17

In accordance with the method of Reference Example 1, indole synthesis reaction was effected by using 17-cyclopropylmethyl-6-oxy-4,5α-epoxy-14β- hydroxymorphinan as a raw material in place of nartrexone, and 1-naphthylhydrazine as a hydrazine derivative to obtain 17-cyclopropylmethyl-14β-hydroxy-6,7-dehydro-4,5α-epoxy-6,7,2',3'-(6',7'-benzoindolo)morphinan 18.

Examples 1–9

Indole synthesis reaction was effected by using nartrexone as a raw material in accordance with the method of Reference Example 1. Namely, 5-hydrazinoacenaphthene (prepared from 5-nitroacenaphthene), 3-hydrazinofluoranthene (prepared from 3-aminofluoranthene), 1-hydrazinofluorene (prepared from 1-aminofluorene), 1-hydrazinoanthracene (prepared from 1-aminoanthracene), 4-hydrazinofluorene (prepared from 4-acetoamino-9-fluorenone), 9-hydrazinophenanthrene (prepared from 9-bromophenanthrene), 1-phenylpyrazoline (prepared by the method disclosed in J. Pharmceut. Sci., Vol. 68, 377 (1979)), 1-(1-naphthyl)pyrazoline (prepared by the method disclosed in the same document), and 1-(2-cyanoethyl)-1-phenylhydrazine (prepared by the method disclosed in Chem. Abst., 81084w (1969)) were used in place of phenylhydrazine to obtain 17-cyclopropylmethyl-3,14β-dihydroxy-6,7-dehydro-4,5α-epoxy-6,7,2',3'-(5',6"-ethano-6',7'-benzoindolo)morphinan 3, 17-cyclopropylmethyl-3,14β-dihydroxy-6,7-dehydro-4,5α-epoxy-6,7,2',3'-(5',6"-benzeno-6',7'-benzoindolo)morphinan 19, 17-cyclopropylmethyl-3,14β-dihydroxy-6,7-dehydro-4,5α-epoxy-6,7,2',3'-(6',7',3",2"-indenoindolo)morphinan 20, 17-cyclopropylmethyl-3,14β-dihydroxy-6,7-dehydro-4,5α-epoxy-6,7,2',3'-(6',7',2",3"-naphthoindolo)morphinan 21, 17-cyclopropylmethyl-3,14β-dihydroxy-6,7-dehydro-4,5α-epoxy-6,7,2',3'-(6',7',2",3"-indenoindolo)morphinan 22, 17-cyclopropylmethyl-3,14β-dihydroxy-6,7-dehydro-4,5α-epoxy-6,7,2',3'-(4',5',6',7'-debenzoindolo)morphinan 23, 17-cyclopropylmethyl-3,14β-dihydroxy-6,7-dehydro-4,5α-epoxy-6,7,2',3'-[1'-(3-aminopropyl)indolo]morphinan 24, 17-cyclopropylmethyl-3,14β-dihydroxy-6,7-dehydro-4,5α-epoxy-6,7,2',3'-[1'-(3-aminopropyl)-6',7'-benzoindolo]morphinan 25, and 17-cyclopropylmethyl-3,14β-dihydroxy-6,7-dehydro-4,5α-epoxy-6,7,2',3'-[1'-(2-cyanoethyl)indolo]morphinan 26, respectively.

Example 10

In accordance with the method of Reference Example 1, indole synthesis reaction was effected by using 17-cyclopropylmethyl-6-oxy-4,5α-epoxy-3-methoxy-14β-hydroxymorphinan as a raw material in place of nartrexone, and 3-hydrazinofluoranthene as a hydrazine derivative to obtain 17-cyclopropylmethyl-3-methoxy-14β-hydroxy-6,7-dehydro-4,5α-epoxy-6,7,2',3'-(5',6"-benzeno-6',7'-benzoindolo)morphinan 27.

Reference Example 18

In accordance with the method of Reference Example 1, indole synthesis reaction was effected by using 6-oxy-4,5α-epoxy-3-methoxy-14β-hydroxymorphinan (noroxycodone) as a raw material in place of nartrexone, and 1-naphthylhydrazine as a hydrazine derivative to obtain 3-methoxy-14β-hydroxy-6,7-dehydro-4,5α-epoxy-6,7,2',3'-(6',7"-benzoindolo)morphinan 28.

Reference Example 19

17-methyl-3-methoxy-14β-hydroxy-6,7-dehydro-4,5α-epoxy-6,7,2',3'-(6',7'-benzoindolo)morphinan 29 • methanesulfonate 951 mg (2,24 mmol) of 3-methoxy-14β-hydroxy-6,7-dehydro-4,5α-epoxy-6,7,2',3'-(6',7'-benzoindolo)morphinan 28 was dissolved in 12 ml of DMF, and 464 mg (3.36 mmol) of potassium carbonate and 0.15 ml (2.41 mmol) of methyl iodide were added to the resultant solution, followed by stirring at room temperature for 2 hours. After reaction was completed, water was added to the residue obtained by concentration under reduced pressure, followed by extraction with chloroform. The organic layer obtained was dried over anhydrous sodium sulfate, concentrated and then purified by silica gel column chromatography (ammonia saturated chloroform-methanol (50:1)) to obtain 904 mg (yield 92%) of a salt-free title compound. The thus-obtained compound was dissolved in methanol, and methanesulfonic acid was added to the solution to isolate methanesulfonate.

Reference Example 20

17-(2-phenylethyl)-3-methoxy-14β-hydroxy-6,7-dehydro-4,5α-epoxy-6,7,2',3'-(6',7'-benzoindolo)morphinan 30 1.33 g (3.13 mmol) of 3-methoxy-14β-hydroxy-6,7-dehydro-4,5α-epoxy-6,7,2',3'-(6',7'-benzoindolo)morphinan 28 was dissolved in 20 ml of dichloromethane, and 1.3 ml (9.33 mmol) of triethylamine was added to the resultant solution, followed by cooling to 0° C. 0.62 ml (4.69 mmol) of phenylacetyl chloride was added to the solution, and the resultant mixture was stirred at 0° C. for 5 hours. 0.43 ml (3.06 mmol) of triethylamine and 0.2 ml (1.51 mmol) of phenylacetyl chloride were further added to the solution, followed by stirring at 0° C. for 3 hours. 70 ml of saturated aqueous sodium bicarbonate solution was added to the reaction solution, followed by extraction with chloroform (70 ml×3). The organic layers together were dried over anhydrous sodium sulfate, and then concentrated. The thus-obtained crude product was purified twice by silica gel column chromatography (ammonia saturated chloroform→ammonia saturated chloroform-methanol (100:1→50:1)) to obtain 851 mg (yield 50%) of 17-phenylacetyl-3-methoxy-14β-hydroxy-6,7-dehydro-4,5α-epoxy-6,7,2',3'-(6',7'-benzoindolo)morphinan as an intermediate amide.

842 mg (1.56 mmol) of the thus-obtained amide was dissolved in 30 ml of anhydrous THF, and 1.04 ml (10.5 mmol) of a solution of borane dimethyl sulfide complex in THF was added to the resultant solution, followed by heating under reflux for 4 hours. The reaction solution was cooled to 0° C., and 10 ml of 6 N hydrochloric acid was added to the resultant solution, followed by stirring at room temperature for 1 hour. The reaction solution was made basic by adding a 2 N aqueous sodium hydroxide solution and an aqueous saturated sodium bicarbonate solution, followed by extraction with chloroform. The organic layers together were dried over anhydrous sodium sulfate, and concentrated. The thus-obtained crude product was purified by silica gel column chromatography (ammonia saturated chloroform→ammonia saturated chloroform-methanol (100:1→40:1)) to obtain 412 mg (yield 50%) of title compound. The compound was recrystallized from methanol to obtain 140 mg of crystal.

Reference Example 21

In accordance with the method of Reference Example 20, cyclobutylcarbonyl chloride was used as an amidation agent in place of phenylacetyl chloride to obtain 17-cyclobutylmethyl-3-methoxy-14β-hydroxy-6,7-dehydro-4,5α-epoxy-6,7,2',3'-(6',7'-benzoindolo)morphinan 31.

Reference Example 22

17-cyclopropylmethyl-3-methoxy-14β-hydroxy-6,7-dehydro-4,5α-epoxy-6,7,2',3'-(5'-methyl-6',7'-benzoindolo)morphinan 32 • methanesulfonate 0.28 g of 17-cyclopropylmethyl-3,14β-dihydroxy-6,7-dehydro-4,5α-epoxy-6,7,2',3'-(5'-methyl-6',7'-benzoindolo)morphinan 13 was dissolved in 7 ml of anhydrous DMF, and 0.24 g of potassium carbonate and 54.6 µl of methyl iodide were added the resultant solution, followed by reaction at room temperature for 4 hours. Although the reaction solution was fractionated by pouring into 70 ml of water and 40 ml of ether, precipitation was observed in an organic layer. Therefore, the extraction was carried out with additional 30 ml of ethyl acetate. The extract was dried with 30 ml of saturated brine, dried and then concentrated. The thus-obtained crude product was purified by medium-pressure silica gel column chromatography (first: 50 g; chloroform→chloroform/methanol=30/1, second: 50 g; chloroform→chloroform/methanol=30/1) to obtain 273 mg of a salt-free title compound. The compound was dissolved in 10 ml of methanol and 5 ml of chloroform, and 34.1 µl of methanesulfonic acid was added to the resultant solution to form methanesulfonate. After evaporation of methanol solution 5 ml×2, the product was suspended in ether, and then filtered off to obtain 251 mg (yield 73%) of title compound.

Reference Example 23

In accordance with the method of Reference Example 22, 17-cyclopropylmethyl-3,14β-dihydroxy-6,7-dehydro-4,5α-epoxy-6,7,2',3'-indolomorphinan 1 was used as a raw material in place of 17-cyclopropylmethyl-3,14β-dihydroxy-6,7-dehydro-4,5α-epoxy-6,7,2',3'-(5'-methyl-6',7'-benzoindolo)morphinan 13 to obtain 17-cyclopropylmethyl-3-methoxy-14β-hydroxy-6,7-dehydro-4,5α-epoxy-6,7,2',3'-indolomorphinan 33.

Examples 11–13

In accordance with the method of Reference Example 22, 17-cyclopropylmethyl-3,14β-dihydroxy-6,7-dehydro-4,5α-epoxy-6,7,2',3'-(5',6"-benzeno-6',7'-benzoindolo)morphinan 19, 17-cyclopropylmethyl-3,14β-dihydroxy-6,7-dehydro-4,5α-epoxy-6,7,2',3'-(6',7'3",2"-indenoindolo)morphinan 20, and 17-cyclopropylmethyl-3,14β-dihydroxy-6,7-dehydro-4,5α-epoxy-6,7,2',3'-(5',6"-ethano-6',7'-benzoindolo)morphinan 3 were used as raw materials in place of 17-cyclopropylmethyl-3,14β-dihydroxy-6,7-dehydro-4,5α-epoxy-6,7,2',3'-(5'-methyl-6',7'-benzoindolo)morphinan 13 to obtain 17-cyclopropylmethyl-3-methoxy-14β-hydroxy-6,7-dehydro-4,5α-epoxy-6,7,2',3'-(1'-methyl-5',6"-benzeno-6',7'-benzoindolo)morphinan 34, 17-cyclopropylmethyl-3-methoxy-14β-hydroxy-6,7-dehydro-4,5α-epoxy-6,7,2',3'-(6',7',3",2"-indenoindolo)morphinan 35, and 17-cyclopropylmethyl-3-methoxy-14β-hydroxy-6,7-dehydro-4,5α-epoxy-6,7,2',3'-(5',6"-ethano-6',7'-benzoindolo)morphinan 36, respectively.

Reference Example 24

17-cyclopropylmethyl-3-methoxy-14β-hydroxy-6,7-dehydro-4,5α-epoxy-6,7,2',3'-(1'-benzyl-6',7'-benzoindolo)morphinan 37 • methanesulfonate 38.4 mg (0.463 mmol) of 17-cyclopropylmethyl-3-methoxy-14β-hydroxy-6,7-dehydro-4,5α-epoxy-6,7,2',3'-(6',7'-benzoindolo)morphinan 17 was dissolved in 0.4 ml of DMSO, and 29.1 mg (0.441 mmol) of powdered potassium hydroxide was added to the resultant solution. After stirring at room temperature for 5 minutes, 0.015 ml (0.126 mmol) of benzyl bromide was added to the resultant mixture, followed by stirring at room temperature for 30 minutes. After completion of reaction, 20 ml of water was added to the reaction solution, followed by extraction with ethyl acetate (20 ml×4). The organic layers together were dried over anhydrous sodium sulfate, concentrated and then purifed by silica gel column chromatography (10 g; chloroform-methanol (200:1→100:1)) to obtain 33.3 mg (yield 73%) of a salt-free title compound. The thue-obtained compound was dissolved in methanol, and methanesulfonic acid was added to the solution to isolate methanesulfonate.

Reference Examples 25–26

In accordance with the method of Reference Example 24, 4-fluorobenzyl bromide and 4-methylbenzyl bromide were used as alkylation agents in place of benzyl bromide to obtain 17-cyclopropylmethyl-3-methoxy-14β-hydroxy-6,7-dehydro-4,5α-epoxy-6,7,2',3'-[1'-(4-fluorobenzyl)indolo]morphinan 38 and 17-cyclopropylmethyl-3-methoxy-14β-hydroxy-6,7-dehydro-4,5α-epoxy-6,7,2',3'-[1'-(4-methylbenzyl)indolo]morphinan 39, respectively.

Example 14

In accordance with the method of Reference Example 24, 17-cyclopropylmethyl-3-methoxy-14β-hydroxy-6,7-dehydro-4,5α-epoxy-6,7,2',3'-(5',6"-benzeno-6',7'-benzoindolo)morphinan 27 was used as a raw material in place of 17-cyclopropylmethyl-3-methoxy-14β-dihydroxy-6,7-dehydro-4,5α-epoxy-6,7,2',3'-(6',7'-benzoindolo)morphinan 17 to obtain 17-cyclopropylmethyl-3-methoxy-14β-hydroxy-6,7-dehydro-4,5α-epoxy-6,7,2',3'-(1'-benzyl-5',6"-benzeno-6',7'-benzoindolo)morphinan 40

Reference Example 27

17-cyclopropylmethyl-3-methoxy-14β-hydroxy-6,7-dehydro-4,5α-epoxy-6,7,2',3'-[1'-(2-phenylethyl-6',7'-benzoindolo)morphinan 41 • methanesulfonate 53.1 mg (0.111 mmol) of 17-cyclopropylmethyl-3-methoxy-14β-hydroxy-6,7-dehydro-4,5α-epoxy-6,7,2',3'-(6',7'-benzoindolo)morphinan 17 was dissolved in 0.7 ml of benzene, and 46.0 mg (0.17 mmol) of 2-phenylethyl p-toluenesulfonate, 0.2 ml of 50% aqueous sodium hydroxide solution and 18.8 mg (0.0554 mmol) of tetrabutylammonium hydrogensulfate were added to the resultant solution, followed by stirring at room temperature for 16 hours. 46.0 mg (0.17 mmol) of 2-phenylethyl p-toluensulfonate was further added to the resultant mixture, followed by stirring at 40° C. for 48 hours. To the reaction mixture was added 5 ml of water, followed by extraction with ethyl acetate (5 ml×4). The organic layers together were dried over anhydrous sodium sulfate, concentrated and then purifed by silica gel column chromatography (5 g: chloroform-methanol (100:1)) to obtain 64.6 mg (yield 100%) of title compound. The thus-obtained compound was dissolved in methanol, and methanesulfonate acid was added to the solution to isolate methanesulfonate.

Reference Examples 28–29

In accordance with the method of Reference Example 27, methyl iodide was used as an alkylation agent in place of 2-phenylethyl p-toluenesulfonate to obtain 17-cyclopropylmethyl-3-methoxy-14β-hydroxy-6,7-dehydro-4,5α-epoxy-6,7,2',3'-[1'-methyl-6',7'-benzoindolo]morphinan 42 , 17-cyclopropylmethyl-3-methoxy-14β- hydroxy-6,7-dehydro-4,5α-epoxy-6,7,2',3'-indolomorphinan 33 was used as a raw material in place of 17-cyclopropylmethyl-3-methoxy-14β-hydroxy-6,7-dehydro-4,5α-epoxy-6,7,2',3'-(6',7'-benzoindolo)morphinan 17, and benzyl chloride was used as an alkylation agent to obtain 17-cyclopropylmethyl-3-methoxy-14β-hydroxy-6,7-dehydro-4,5α-epoxy-6,7,2',3'-(1'-benzoindolo)morphinan 43.

Examples 15–21

In accordance with the method of Reference Example 27, 2-methoxyethyl p-toluesulfonate, 5-bromovaleronitrile, and 4-bromobutyronitrile were used as alkylation agents in place of 2-phenylethyl p-toluenesulfonate to obtain 17-cyclopropylmethyl-3-methoxy-14β-hydroxy-6,7-dehydro-4,5α-epoxy-6,7,2',3'-[1'(2-methoxyethyl)-6',7'-benzoindolo]morphinan 44, 17-cyclopropylmethyl-3-methoxy-14β-hydroxy-6,7-dehydro-4,5α-epoxy-6,7,2',3'-[1'-(4-cyanobutyl)-6',7'-benzoindolo]morphinan 45, 17-cyclopropylmethyl-3-methoxy-14β-hydroxy-6,7-dehydro-4,5α-epoxy-6,7,2',3'-[1'-(3-cyanoproppyl)-6',7'-benzoindolo]morphinan 46, respectively. 17-cyclopropylmethyl-3-methoxy-14β-hydroxy-6,7-dehydro-4,5α-epoxy-6,7,2',3'-(5'-methyl-6',7'-benzoindolo)morphinan 32 was used as a raw material in place of 17-cyclopropylmethyl-3-methoxy-14β-hydroxy-6,7-dehydro-4,5α-epoxy-6,7,2',3'-(6',7'-benzoindolo)morphinan 17, and 4-bromobutyronitrile and 3-bromopropylamine hydrobromide were used as alkylation agents to obtain 17-cyclopropylmethyl-3-methoxy-14β-hydroxy-6,7-dehydro-4,5α-epoxy-6,7,2',3'-[1'-(3-cyanopropyl)-5'-methyl-6',7'-benzoindolo)morphinan 47 and 17-cyclopropylmethyl-3-methoxy-14β-hydroxy-6,7-dehydro-4,5α-epoxy-6,7,2',3'-[1'-(3-aminopropyl)-5'-methyl-6',7'-benzoindolo]morphinan 48, respectively. 17-cyclopropylmethyl-3-methoxy-14β-hydroxy-6,7-dehydro-4,5α-epoxy-6,7,2',3'-(5',6"-ethano-6',7'-benzoindolo]morphinan 36 was used as a raw material, and benzyl chloride and methyl iodide were used as alkylation agents to obtain 17-cyclopropylmethyl-3-methoxy-14β-hydroxy-6,7-dehydro-4,5α-epoxy-6,7,2',3'-(1'-benzyl-5',6"-ethano-6',7'-benzoindolo]morphinan 49, and 17-cyclopropylmethyl-3-methoxy-14β-hydroxy-6,7-dehydro-4,5α-epoxy-6,7,2',3'-(1'-methyl-5',6"-ethano-6',7'-benzoindolo]morphinan 50, respectively.

Example 22

17-cyclopropylmethyl-3-methoxy-14β-hydroxy-6,7-dehydro-4,5α-epoxy-6,7,2',3'-(1'-benzoylindolo)morphinan 51·methanesulfonate 285 mg of 17-cyclopropylmethyl-3-methoxy-14β-hydroxy-6,7-dehydro-4,5α-epoxy-6,7,2',3'-indolomorphinan 33 was dissolved in 5.7 ml of dichloroethane, and 72.6 mg of powdered sodium hydroxide, and 2.5 mg of tetrabutylammonium hydrogensulfate were added to the resultant solution. Then, 0.12 ml of benzoyl chloride was added to the solution, followed by stirring at room temperature for 6.5 hours. 44.9 mg of powdered sodium hydroxide and 0.06 ml of benzoyl chloride were further added to the solution, followed by stirring at room temperature for 2.5 days. To the reaction solution was poured 8 ml of water to fractionate the solution, and the aqueous layer was extracted with 5 ml of chloroform. The organic layers together were dried and concentrated, and 389 mg of the obtained crude product was purified by silica gel column chromatography (first: 25 g; chloroform-methanol (50:1), second: 20 g; chloroform-methanol (100:1)) to obtain 220 mg of salt-free title compound. The thus-obtained compound was dissolved in chloroform-methanol, and methanesulfonic acid was added to the solution to form a salt. The solid obtained by concentration was suspended in ethyl acetate, and then filtered off to obtain 227 mg (yield 54%) of title compound.

Example 23

17-cyclopropylmethyl-3-methoxy-14β-hydroxy-6,7-dehydro-4,5α-epoxy-6,7,2',3'-(1'-methylsulfonyl-6',7'-benzoindolo)morphinan 52·methanesulfonate 120 mg of sodium hydride (60%) was suspended in anhydrous THF, and a THF solution (10+5 ml) of 453 mg of 17-cyclopropylmethyl-3-methoxy-14β-hydroxy-6,7-dehydro-4,5α-epoxy-6,7,2',3'-(6',7'-benzoindolo)morphinan 17 was added to the resultant suspension, followed by stirring at 100° C. for 30 minutes. After cooling to room temperature, 88 μl of methanesulfonyl chloride was added to the resultant mixture, followed by stirring for 20 minutes. To the reaction solution was added 50 ml of water, followed by extraction with chloroform (50 ml×2). The organic layers together were dried over anhydrous sodium sulfate, and then concentrated. The thus-obtained crude product was purified by medium-pressure silica gel column chromatography (cyclohexane:ethyl acetate=2:1), and then recrystallized from ethyl acetate to obtain 211 mg (yield 40%) of a salt-free title compound. The thus-obtained compound was converted to methanesulfonate to isolate.

Examples 24–28

In accordance with the method of Example 23, 17-cyclopropylmethyl-3-methoxy-14β-hydroxy-6,7-dehydro-4,5α-epoxy-6,7,2',3'-(6'-phenylindolo)morphinan, 17-cyclopropylmethyl-3-methoxy-14β-hydroxy-6,7-dehydro-4,5α-epoxy-6,7,2',3'-(5',6"-benzeno-6',7'-benzoindolo)morphinan 27, and 17-cyclopropylmethyl-3-methoxy-14β-hydroxy-6,7-dehydro-4,5α-epoxy-6,7,2',3'-indolomorphinan 33 were used as raw materials in place of 17-cyclopropylmethyl-3-methoxy-14β-hydroxy-6,7-dehydro-4,5α-epoxy-6,7,2',3'-(6',7'-benzoindolo)morphinan 17 to obtain 17-cyclopropylmethyl-3-methoxy-14β-hydroxy-6,7-dehydro-4,5α-epoxy-6,7,2',3'-(1'-methylsulfonyl-6'-phenylindolo)morphinan 53, 17-cyclopropylmethyl-3-methoxy-14β-hydroxy-6,7-dehydro-4,5α-epoxy-6,7,2',3'-(1'-methylsulfonyl-5',6"-benzeno-6',7'-benzoindolo)morphinan 54, and 17-cyclopropylmethyl-3-methoxy-14β-hydroxy-6,7-dehydro-4,5α-epoxy-6,7,2',3'-(1'-methylsulfonylindolo)morphinan 55, respectively. 17-cyclopropylmethyl-3-methoxy-14β-hydroxy-6,7-dehydro-4,5α-epoxy-6,7,2',3'-indolomorphinan 33 was used as a raw material, and p-toluenesulfonyl chloride and α-toluenesulfonyl chloride were used as sulfonylation agents in place of methanesulfonyl chloride to obtain 17-cyclopropylmethyl-3-methoxy-14β-hydroxy-6,7-dehydro-4,5α-epoxy-6,7,2',3'-[1'-(4- tolylsulfonyl)indolo]morphinan 56, and 17-cyclopropylmethyl-3-methoxy-14β-hydroxy-6,7-dehydro-4,5α-epoxy-6,7,2',3'-(1'-benzylsulfonylindolo) morphinan 57, respectively.

Example 29

In accordance with the method of Example 23, 17-cyclopropylmethyl-3-methoxy-14β-hydroxy-6,7-dehydro-4,5α-epoxy-6,7,2',3'-indolomorphinan 33 was used as a raw material in place of 17-cyclopropylmethyl-3-methoxy-14β-hydroxy-6,7-dehydro-4,5α-epoxy-6,7,2',3'-(6',7'-benzoindolo)morphinan 17, and acetyl chloride as a acylation agent in place of methanesulfonyl chloride as a sulfonylation agent to obtain 17-cyclopropylmethyl-3-methoxy-14β-hydroxy-6,7-dehydro-4,5α-epoxy-6,7,2',3'-(1'-acetylindolo)morphinan 58.

Example 30

17-cyclopropylmethyl-3,14β-dihydroxy-6,7-dehydro-4,5α-epoxy-6,7,2',3'-[1'-(3-isothiocyanatopropyl)indolo]morphinan 59·methanesulfonate 241 mg of 17-cyclopropylmethyl-3,14β-dihydroxy-6,7-dehydro-4,5α-epoxy-6,7,2',3'-[1'-(3aminopropyl)indolo]morphinan 24 was dissolved in 4 ml of dichloromethane, and 120 mg of di-2-pyridyl thionocarbonate was added to the resultant solution, followed by stirring at room temperature for 15 minutes. To the reaction solution was added 4 ml of ammonia saturated chloroform, followed by stirring for 5 minutes. The organic layer was washed with water (4 ml×2), dried and then concentrated. 253 mg of the thus-obtained crude product was purified by silica gel column chromatography (25 g; chloroform-methanol (50:1→30:1)) to obtain 227 mg of a salt-free title compound. The thus-obtained compound was dissolved in chloroform-methanol, and methanesulfonic acid was added to the resultant solution to form a salt. The solid obtained after concentration was suspended in ethyl acetate, and filtered off to obtain 240 mg (yield 77%) of the title compound.

Example 31

In accordance with the method of Example 30, 17-cyclopropylmethyl-3,14β-dihydroxy-6,7-dehydro-4,5α-epoxy-6,7,2',3'-[1'-(3-aminopropyl)-6',7'-benzoindolo]morphinan 25 was used as a raw material in place of 17-cyclopropylmethyl-3,14β-dihydroxy-6,7-dehydro-4,5α-epoxy-6,7,2',3'-[1'-(3-aminopropyl)indolo]morphinan 24 to obtain 17-cyclopropylmethyl-3,14β-dihydroxy-6,7-dehydro-4,5α-epoxy-6,7,2',3'-[1'-(3-isothiocyanatopropyl)-6',7'-benzoindolo)morphinan 60.

Example 32

17-cyclopropylmethyl-3,14β-dihydroxy-6,7-dehydro-4,5α-epoxy-6,7,2',3'-[1'-(3-benzamidopropyl)indolo]morphinan 61·methanesulfonate 229 mg of 17-cyclopropylmethyl-3,14β-dihydroxy-6,7-dehydro-4,5α-epoxy-6,7,2',3'-[1'-(3-aminopropyl)indolo]morphinan 24 was dissolved in 3.5 ml of chloroform, and 0.203 ml of triethylamine and 0.118 ml of benzoyl chloride were added to the resultant solution, followed by stirring at room temperature for 1 hour. The reaction solution was concentrated, and then dissolved in 3 ml of methanol, and 1 ml of 3N aqueous sodium hydroxide solution was added to the resultant solution, followed by stirring at room temperature for 40 minutes. The reaction solution was concentrated, and 5 ml of water was added to the concentrated solution, followed by extraction with chloroform (5 ml×2). The organic layers together were dried and then concentrated. 279 mg of the thus-obtained crude product was purified by silica gel column chromatography (20 g; chloroform-methanol (20:1)) to obtain 266 mg of a salt-free title compound. The thus-obtained compound was dissolved in methanol, and a solution of hydrogen chloride in methanol was added to the solution to form a salt. The solid obtained after concentration was suspended in ethyl acetate and filtered off to obtain 199 mg (yield 67%) of the title compound.

Examples 33–38

In accordance with the method of Example 32, 6-phenylhexanoyl chloride and 3-trifluoromethylcinnamoyl chloride were used as acylation agents in place of benzoyl chloride to obtain 17-cyclopropylmethyl-3,14β-dihydroxy-6,7-dehydro-4,5α-epoxy-6,7,2',3'-[1'-[3-(6-phenylhexanoamido)propyl]indolo]morphinan 62, and 17-cyclopropylmethyl-3,14β-dihydroxy-6,7-dehydro-4,5α-epoxy-6,7,2',3'-[1'-[3-(3-trifluoromethylcinnamido)propyl]indolo]morphinan 63, respectively. 17-cyclopropylmethyl-3,14β-dihydroxy-6,7-dehydro-4,5α-epoxy-6,7,2',3'-[1'-(3-aminopropyl)-6',7'-benzoindolo]morphinan 25 was used as a raw material in place of 17-cyclopropylmethyl-3,14β-dihydroxy-6,7-dehydro-4,5α-epoxy-6,7,2',3'-[1'-(3-aminopropyl)indolo]morphinan 24, and benzoyl chloride, 3-trifluoromethylcinnamoyl chloride, nicotinoyl chloride and benzyl isothiocyanate were used as acylation agents to obtain 17-cyclopropylmethyl-3,14β-dihydroxy-6,7-dehydro-4,5α-epoxy-6,7,2',3'-[1'-(3-benzamidopropyl)-6',7'-benzoindolo)morphinan 64, 17-cyclopropylmethyl-3,14β-dihydroxy-6,7-dehydro-4,5α-epoxy-6,7,2',3'-[1'-(3-(3-trifluoromethylcinnamamido)propyl)-6',7'-benzoindolo]morphinan 65, 17-cyclopropylmethyl-3,14β-dihydroxy-6,7-dehydro-4,5α-epoxy-6,7,2',3'-[1'-(3-nicotinamidopropyl)-6',7'-benzoindolo]morphinan 66, and 17-cyclopropylmethyl-3,14β-dihydroxy-6,7-dehydro-4,5α-epoxy-6,7,2',3'-[1'-[3-(N'-benzylthioureido)propyl]-6',7'-benzoindolo]morphinan 67, respectively.

Reference Example 30

17-cyclopropylmethyl-3,14β-dihydroxy-6,7-dehydro-4,5α-epoxy-6,7,2',3'-(1'-benzylindolo)morphinan 68·methanesulfonate 160 mg of 17-cyclopropylmethyl-3-methoxy-14β-hydroxy-6,7-dehydro-4,5α-epoxy-6,7,2',3'-(1'-benzylindolo)morphinan 43 was dissolved in 8 ml of dichloromethane, and the resultant solution was cooled to 0° C. To the solution was added dropwise 1.2 ml of a 1.0M solution of boron tribromide in dichloromethane, followed by stirring at 0° C. for 1 hour. To the reaction solution were added 30 ml of water and 5 ml of ammonia water, followed by extraction with chloroform 50 ml×2. The organic layers together were dried over anhydrous sodium sulfate, and concentrated, and the thus-obtained crude product was purified by medium-pressure silica gel column chromatography (chloroform-methanol (50:1)) to obtain 112 mg (yield 72%) of a salt-free title compound. The thus-obtained compound was isolated as methanesulfonate.

Reference Examples 31–38

In accordance with the method of Reference Example 30, 17-cyclopropylmethyl-3-methoxy-14β-hydroxy-6,7-dehydro-4,5α-epoxy-6,7,2',3'-(1'-benzyl-6',7'-benzoindolo) morphinan 37, 17-cyclopropylmethyl-3-methoxy-14β-hydroxy-6,7-dehydro-4,5α-epoxy-6,7,2',3'-[1'-(4-fluorobenzyl)indolo]morphinan38, 17-cyclopropylmethyl-3-methoxy-14β-hydroxy-6,7-dehydro-4,5α-epoxy-6,7,2',3'-[1'-(4-methylbenzyl)indolo]morphinan 39, 17-cyclopropylmethyl-3-methoxy-14β-hydroxy-6,7-dehydro-4,5α-epoxy-6,7,2',3'-(1'-methyl-6',7'-benzoindolo) morphinan 42, 3-methoxy-14β-hydroxy-6,7-dehydro-4,5α-epoxy-6,7,2',3'-(6',7'-benzoindolo)morphinan 28, 17-methyl-3-methoxy-14β-hydroxy-6,7-dehydro-4,5α-epoxy-6,7,2',3'-(6',7'-benzoindolo)morphinan 29, 17-(2-phenylethyl)-3-methoxy-14β-hydroxy-6,7-dehydro-4,5α-epoxy-6,7,2',3'-(6',7'-benzoindolo)morphinan 30, and 17-cyclobutylmethyl-3-methoxy-14β-hydroxy-6,7-dehydro-4,5α-epoxy-6,7,2',3'-(6',7'-benzoindolo)morphinan 31 were uses as raw materials in place of 17-cyclopropylmethyl-3-methoxy-14β-hydroxy-6,7-dehydro-4,5α-epoxy-6,7,2',3'-(1'-benzylindolo)morphinan 43 to obtain 17-cyclopropylmethyl-3,14β-dihydroxy-6,7-dehydro-4,5α-epoxy-6,7,2',3'-(1'-benzyl-6',7'-benzoindolo) morphinan 69, 17-cyclopropylmethyl-3,14β-dihydroxy-6,7-dehydro-4,5α-epoxy-6,7,2',3'-[1'-(4-fluorobenzyl)indolo] morphinan 70, 17-cycloproylmethyl-3,14β-dihydroxy-6,7-dehydro-4,5α-epoxy-6,7,2',3'-[1'-(4-methylbenzyl)indolo] morphinan 71, 17-cyclopropylmethyl-3,14β-dihydroxy-6,7-dehydro-4,5α-epoxy-6,7,2',3'-(1'-methyl-6',7'-benzoindolo) morphinan 72, 3, 14β-dihydroxy-6,7-dehydro-4,5α-epoxy-6,7,2',3'-(6',7'-benzoindolo)morphinan 73, 17-methyl-3,14β-dihydroxy-6,7-dehydro-4,5α-epoxy-6,7,2',3'-(6',7'-benzoindolo)morphinan 74, 17-(2-phenylethyl)-3,14β-dihydroxy-6,7-dehydro-4,5α-epoxy-6,7,2',3'-(6',7'-benzoindolo)morphinan 75, and 17-cyclobutylmethyl-3,14β-dihydroxy-6,7-dehydro-4,5α-epoxy-6,7,2',3'-(6',7'-benzoindolo)morphinan 76, respectively.

Examples 39–48

In accordance with the method of Reference Example 30, 17-cyclopropylmethyl-3-methoxy-14β-hydroxy-6,7-dehydro-4,5α-epoxy-6,7,2',3'-(1'-methyl-5',6"-benzeno-6',7'-benzoindolo(morphinan 34, 17-cyclopropylmethyl-3-methoxy-14β-hydroxy-6,7-dehydro-4,5α-epoxy-6,7,2',3'-(1'-methylsulfonyl-6',7'-benzoindolo)morphinan 52, 17-cyclopropylmethyl-3-methoxy-14β-hydroxy-6,7-dehydro-4,5α-epoxy-6,7,2',3'-(1'-benzyl-5',6"-benzeno-6',7'-benzoindolo)morphinan 40, 17-cyclopropylmethyl-3-methoxy-14β-hydroxy-6,7-dehydro-4,5α-epoxy-6,7,2',3'-[1'-(2-phenylethyl)-6',7'-benzoindolo]morphinan 41, 17-cyclopropylmethyl3-methoxy-14β-hydroxy-6,7-dehydro-4,5α-epoxy-6,7,2',3'-[1'-(2-methoxyethyl)-6',7'-benzoindolo)morphinan 44, 17-cyclopropylmethyl-3-methoxy-14β-hydroxy-6,7-dehydro-4,5α-epoxy-6,7,2',3'-[1'-(4-cyanobutyl)-6',7'-benzoindolo]morphinan 45, 17-cyclopropylmethyl-3-methoxy-14β-hydroxy-6,7-dehydro-4,5α-epoxy-6,7,2',3'-(1'-benzyl-5',6"-ethano-6',7'-benzoindolo)morphinan 49, 17-cyclopropylmethyl-3-methoxy-14β-hydroxy-6,7-dehydro-4,5α-epoxy-6,7,2',3'-(1'-methyl-5',6"-ethano-6',7'-benzoindolo)morphinan 50, 17-cyclopropylmethyl-3-methoxy-14β-hydroxy-6,7-dehydro-4,5α-epoxy-6,7,2',3'-[1'-(3-cyanopropyl)-6',7'-benzoindolo]morphinan 46, and 17-cyclopropylmethyl-3-methoxy-14β-hydroxy-6,7-dehydro-4,5α-epoxy-6,7,2',3'-[1'-(3-cyanopropyl)-5'-methyl-6',7'-benzoindolo]morphinan 47 were used as raw materials in place of 17-cyclopropylmethyl-3-methoxy-14β-hydroxy-6,7-dehydro-4,5α-epoxy-6,7,2',3'-(1'-benzylindolo)morphinan 43 to obtain 17-cyclopropylmethyl-3,14β-dihydroxy-6,7-dehydro-4,5α-epoxy-6,7,2',3'-(1'-methyl-5',6"-benzeno-6',7'-benzoindolo)morphinan 77, 17-cyclopropylmethyl-3,14β-dihydroxy-6,7-dehydro-4,5α-epoxy-6,7,2',3'-(1'-methylsulfonyl 6',7'-benzoindolo)morphinan 78, 17-cyclopropylmethyl-3,14β-dihydroxy-6,7-dehydro-4,5α-epoxy-6,7,2',3'-(1'-benzyl-5',6"-benzeno-6',7'-benzoindolo) morphinan79, 17-cyclopropylmethyl-3,14β-dihydroxy-6,7-dehydro-4,5α-epoxy-6,7,2',3'-[1'-(2-phenylethyl)-6',7'-benzoindolo]morphinan 80, 17-cyclopropylmethyl-3,14β-dihydroxy-6,7-dehydro-4,5α-epoxy-6,7,2',3'-[1'-(2-hydroxyethyl)-6',7'-benzoindolo]morphinan 81, 17-cyclopropylmethyl-3,14β-dihydroxy-6,7-dehydro-4,5α-epoxy-6,7,2',3'-[1'-(4-cyanobutyl)-6',7'-benzoindolo] morphinan 82, 17-cyclopropylmethyl-3,14β-dihydroxy-6,7-dehydro-4,5α-epoxy-6,7,2',3'-(1'-benzyl-5',6"-ethano-6',7'-benzoindolo)morphinan 83, 17-cyclopropylmethyl-3,14β-dihydroxy-6,7-dehydro-4,5α-epoxy-6,7,2',3'-(1'-methyl-5',6"-ethano-6',7'-benzoindolo)morphinan 84, 17-cyclopropylmethyl-3,14β-dihydroxy-6,7-dehydro-4,5α-epoxy-6,7,2',3'-[1'-(3-cyanopropyl)-6',7'-benzoindolo] morphinan 85, and 17-cyclopropylmethyl-3,14β-dihydroxy-6,7-dehydro-4,5α-epoxy-6,7,2',3'-[1'-(3-cyanopropyl)-5'-methyl-6',7'-benzoindolo]morphinan 86, respectively.

Examples 49–50

In accordance with the method of Reference Example 27, 17-cyclopropylmethyl-3-methoxy-14β-hydroxy-6,7-dehydro-4,5α-epoxy-6,7,2',3'-(5'-methyl-6',7'-benzoindolo) morphinan 32 was used as a raw material in place of 17-cyclopropylmethyl-3-methoxy-14β-hydroxy-6,7-dehydro-4,5α-epoxy-6,7,2',3'-(6',7'-benzoindolo)morphinan 17, and 4-bromobutyronitrile and ethyl 4-bromobutyrate were used as alkylation agents in place of 2-phenylethyl p-toluenesulfonate to obtain 17-cyclopropylmethyl-3-methoxy-14β-hydroxy-6,7-dehydro-4,5α-epoxy-6,7,2',3'-[1'-(4-cyanobutyl)-5'-methyl-6',7'-benzoindolo]morphinan 87 and 17-cyclopropylmethyl-3-methoxy-14β-hydroxy-6,7-dehydro-4,5α-epoxy-6,7,2',3'-1'-[3-(ethoxycarbonyl) propyl]-5'-methyl-6',7'-benzoindolo]morphinan 88, respectively.

Examples 51–52

In accordance with the method of Reference Example 30, 17-cyclopropylmethyl-3-methoxy-14β-hydroxy-6,7-dehydro-4,5α-epoxy-6,7,2',3'-[1'-(3-aminopropyl)-5'-methyl-6',7'-benzoindolo]morphinan 48, and 17-cyclopropylmethyl-3-methoxy-14β-hydroxy-6,7-dehydro-4,5α-epoxy-6,7,2',3'-[1'-(4-cyanobutyl)-5'-methyl-6',7'-benzoindolo]morphinan 87 were used as raw materials in place of 17-cyclopropylmethyl-3-methoxy-14β-hydroxy-6,7-dehydro-4,5α-epoxy-6,7,2',3'-(1'-benzylindolo)morphinan 43 to obtain 17-cyclopropylmethyl-3,14β-dihydroxy-6,7-dehydro-4,5α-epoxy-6,7,2',3'-[1'-(3-aminopropyl)-5'-methyl-6',7'-benzoindolo]morphinan 89, and 17-cyclopropylmethyl-3,14β-dihydroxy-6,7-dehydro-4,5α-epoxy-6,7,2',3'-[1'-(4-cyanobutyl)-5'-methyl-6',7'-benzoindolo]morphinan 90, respectively.

Example 53

In accordance with the method of Example 30, 17-cyclopropylmethyl-3,14β-dihydroxy-6,7-dehydro-4,5α-epoxy-6,7,2',3'-[1'-(3-aminopropyl)-5'-methyl-6',7'-benzoindolo]morphinan 89 was used as a raw material in place of 17-cyclopropylmethyl-3,14β-dihydroxy-6,7-dehydro-4,5α-epoxy-6,7,2',3'-[1'-(3-aminopropyl)indolo]morphinan 24 to obtain 17-cyclopropylmethyl-3,14β-dihydroxy-6,7-dehydro-4,5α-epoxy-6,7,2',3'-[1'-(3-isothiocyanatopropyl)-5'-methyl-6',7'-benzoindolo]morphinan 91.

Example 54

17-cyclopropylmethyl-3,14β-dihydroxy-6,7-dehydro-4,5α-epoxy-6,7,2',3'-[1'-(3-formamidopropyl)-6',7'-benzoindolo]morphinan 92·methanesulfonate 1.7 g (3.26 mmol) of 17-cyclopropylmethyl-3,14β-dihydroxy-6,7-dehydro-4,5α-epoxy-6,7,2',3'-[1'-(3-aminopropyl)-6',7'-benzoindolo]morphinan 25 was dissolved in 30 ml of ethyl formate and 20 ml of ethanol, and the resultant solution was heated under reflux for 25 hours. The reaction mixture was concentrated, and the thus-obtained crude product was purified by silica gel column chromatography (100 g:ASC/methanol:50/1→20/1) to obtain 1.31 g (66%) of a salt-free title compound. The thus-obtained compound was isolated as methanesulfonate.

Example 55

17-cyclopropylmethyl-3-methoxy-14β-hydroxy-6,7-dehydro-4,5α-epoxy-6,7,2',3'-[1'-(3-carboxypropyl)-6',7'-benzoindolo]morphinan 93

74.8 mg (0.137 mmol) of 17-cyclopropylemethyl-3-methoxy-14β-hydroxy-6,7-dehydro-4,5α-epoxy-6,7,2',3'-[1'-(3-cyanopropyl)-6',7'-benzoindolo]morphinan 46 was dissolved in 3 ml of methanol and 8 ml of tetrahydrofuran, and 2 ml of a 2N aqueous sodium hydroxide solution was added to the resultant solution, followed by heating under reflux for 98 hours. To the reaction mixture was added 30 ml of water, followed by extraction with chloroform (40 ml×3). The organic layers together were dried over anhydrous sodium sulfate, and concentrated. The thus-obtained crude product was purified by silica gel column chromatography (10 g:chloroform/methanol:50/1→20/1→10/1→1/1) to obtain 66 mg (85%) of the title compound.

The structural formulae, acid addition salts, production yields, and various spectral data of the compounds of the above reference examples and examples of the present invention are shown in the table below.

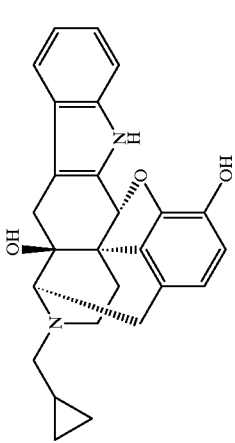
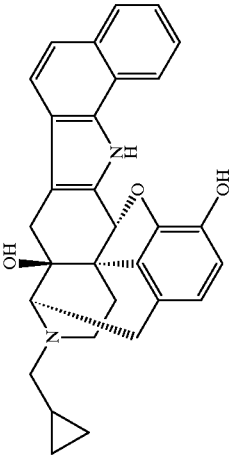

Compound 1
Methanesulfonate
Yield: 68(%)

NMR (ppm)(400 MHz, DMSO-$d_6$)
0.43(m, 1H), 0.49(m, 1H), 0.62(m, 1H), 0.73(m, 1H), 1.10 (m, 1H), 1.82(br d, 1H, J=11.2Hz), 2.31(s, 3H), 2.54(d, 1H, J=16.1Hz), 2.60(m, 1H), 2.71(m, 1H), 2.94(m, 1H), 2.95(d, 1H, J=16.1Hz), 3.12(m, 1H), 3.25(dd, 1H, J=20.0, 6.3Hz), 3.37(m, 1H), 3.44(d, 1H, J=20.0Hz), 4.08(d, 1H, J=6.3Hz), 5.69(s, 1H), 6.33(s, 1H, OH), 6.59(d, 1H, J=8.1Hz), 6.64(d, 1H, J=8.1Hz), 6.97(dd, 1H, J=8.3, 7.8Hz), 7.11(dd, 1H, J=8.3, 7.8Hz), 7.35(d, 1H, J=7.8Hz), 7.36(d, 1H, J=8.3Hz), 8.92(m, 1H, NH$^+$), 9.22(s, 1H, OH), 11.32(s, 1H, NH).

Melting Point(not measured)(° C.).
Elemental Analysis
as $C_{26}H_{26}N_2O_3 \cdot MeSO_3H \cdot 0.3H_2O$
Calculated: C, 62.85; H, 5.95; N, 5.43; S, 6.21.
Found: C, 62.88; H, 6.24; N, 5.44; S, 6.24.
IR (cm$^{-1}$) (KBr) (data of salt-free compound) 3392, 2926, 2838, 1638, 1622, 1504, 1458.
Mass(FAB) 415 ((M+H)$^+$).

Compound 2
Hydrochloride
Yield: 56 (%)

NMR (ppm) (400 MHz, DMSO-$d_6$)
0.45(1H, m), 0.51(1H, m), 0.64(1H, m), 0.74(1H, m), 1.11 (1H, m), 1.86(1H, br d, J=11.7Hz), 2.63(1H, d, J=16.1Hz), 2.65–2.80(2H, m), 2.96(1H, m), 3.06(1H, d, J=16.1Hz), 3.12 (1H, m), 3.25–3.40(2H, m), 3.46(1H, d, J=20.0Hz), 4.12(1H, d, J=6.4Hz), 5.80(1H, s), 6.43(1H, s), 6.60(1H, d, J=8.3Hz), 6.66(1H, d, J=8.3Hz), 7.41(1H, t, J=7.8Hz), 7.43(1H, d, J=8.8Hz), 7.48(1H, d, J=8.8Hz), 7.55(1H, t, J=7.8Hz), 7.90 (1H, d, J=8.3Hz), 8.44(1H, d, J=8.3Hz), 8.98(1H, br s), 9.26 (1H, s), 12.30(1H, s).

Melting Point 190 (dec) (° C.)
Elemental Analysis
as $C_{30}H_{28}N_2O_3 \cdot HCl \cdot 0.5H_2O$
Calculated: C, 70.65; H, 5.93; N, 5.49; Cl, 6.95.
Found: C, 70.42; H, 5.97; N, 5.63; Cl, 6.79.
IR (cm$^{-1}$) (KBr)
3210, 1638, 1620, 1504, 1462, 1427, 1390, 1317, 1245, 1172, 1116, 855, 810, 750.
Mass(FAB) 465((M+H)$^+$).

Compound 3
Methanesulfonate
Yield: 66 (%)

NMR (ppm) (400 MHz, DMSO-$d_6$)
0.45(m, 1H), 0.51(m, 1H), 0.63(m, 1H), 0.75(m, 1H), 1.12 (m, 1H), 1.83(m, 1H), 2.30(s, 3H), 2.61(d, 1H, J=15.8Hz), 2.62(m, 1H), 2.73(m, 1H), 2.93(m, 1H), 3.01(d, 1H, J=15.8 Hz), 3.12(m, 1H), 3.23–3.49(m, 7H), 4.09(br d, J=6.8Hz), 5.78(s, 1H), 6.37(s, 1H, OH), 6.60(d, 1H, J=8.3Hz), 6.64(d, 1H, J=8.3Hz), 7.21(s, 1H), 7.23(d, 1H, J=7.8Hz), 7.47(dd, 1H, J=7.8, 7.8Hz), 8.02(d, 1H, J=7.8Hz), 8.93(m, 1H, NH$^+$), 9.20(s, 1H, OH), 12.12(s, 1H, NH).

Melting Point >260 (dec) (° C.).
Elemental Analysis
as $C_{32}H_{30}N_2O_3 \cdot CH_3SO_3H \cdot 0.4H_2O$
Calculated: C, 66.74; H, 5.91; N, 4.72; S, 5.40.
Found: C, 66.63; H, 6.12; N, 4.68; S, 5.39.
IR (cm$^{-1}$) (KBr)
3570, 1638, 1626, 1508, 1460, 1408, 1328, 1199, 1152, 1044, 928, 861, 779.
Mass (FAB) 490 ((M+H)$^+$).

-continued

| | | |
|---|---|---|
| Compound 4<br>Methanesulfonate<br>Yield: 43 (%)<br>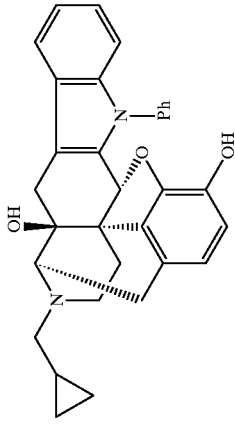 | NMR (ppm) (400 MHz, DMSO-$d_6$)<br>0.40–0.53(2H, m), 0.64(1H, m), 0.75(1H, m), 1.10(1H, m), 1.78(1H, br d, J=10.7Hz), 2.29(3H, s), 2.57(1H, m), 2.64 (1H, d, J=16.1Hz), 2.71(1H, m), 2.96(1H, m), 3.03(1H, d, J=16.1Hz), 3.10(1H, m), 3.25–3.42(2H, m), 3.46(1H, d, J=20.0Hz), 4.13(1H, d, J=6.8Hz), 5.62(1H, s), 6.40(1H, s), 6.62(1H, d, J=8.3Hz), 6.65(1H, d, J=8.3Hz), 7.11(1H, dd, J=7.8, 2.0Hz), 7.15–7.22(2H, m), 7.48(1H, d, J=7.8Hz), 7.55 (1H, m), 7.63–7.70(4H, m), 8.94(1H, br s), 9.20(1H, s). | Melting Point 220 (dec) (° C.).<br>Elemental Analysis<br>as $C_{32}H_{30}N_2O_3 \cdot CH_3SO_3H \cdot 0.4H_2O$<br>Calculated: C, 66.14; H, 5.91; N, 4.72; S, 5.40.<br>Found: C, 66.81; H, 6.05; N, 4.69; S, 5.30.<br>IR (cm$^{-1}$) (KBr)<br>3400, 2928, 1502, 1460, 1377, 1187, 1116, 1044, 934, 845, 748.<br>Mass (FAB) 491 ((M+H)$^+$). |
| Compound 5<br>Methanesulfonate<br>Yield: 16 (%)<br>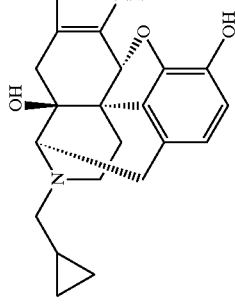 | NMR (ppm) (400 MHz, DMSO-$d_6$)<br>0.39–0.55(2H, m), 0.58–0.78(2H, m), 1.93–1.16(1H, m), 1.18–1.31(1H, m), 1.30–1.50(4H, m), 1.71(1H, br d, J=11.7Hz), 1.71–1.87(5H, m), 2.30(3H, s), 2.61(1H, dt, J=4.4, 13.2Hz), 2.64–2.77(1H, m), 2.85–2.98(2H, m), 3.10(1H, br d, J=10.3Hz), 3.25(1H, dd, J=6.6, 19.8Hz), 4.07(1H, d, J=6.3Hz), 5.66(1H, s), 6.28(1H, br s), 6.58(1H, d, J=8.3Hz), 6.63(1H, d, J=7.8Hz), 6.86(1H, d, J=8.3Hz), 7.15(1H, s), 7.23(1H, d, J=8.3Hz), 8.91(1H, br s), 9.20(1H, br s), 11.16(1H, s). | Melting Point 180 (dec) (° C.).<br>Elemental Analysis<br>as $C_{32}H_{36}N_2O_3 \cdot CH_3SO_3H \cdot 0.8H_2O$<br>Calculated: C, 65.28; H, 6.91; N, 4.61; S, 5.28.<br>Found: C, 65.18; H, 6.73; N, 4.79; S, 5.38.<br>IR (cm$^{-1}$) (KBr)<br>3395, 3280, 2924, 2852, 1462, 1330, 1210, 1168, 1114, 1044, 861, 777.<br>Mass (FAB) 497 ((M+H)$^+$). |
| Compound 6<br>methanesulfonate<br>Yield: 20 (%)<br>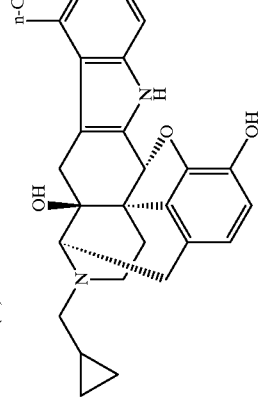 | NMR (ppm) (400 MHz, DMSO-$d_6$)<br>0.39–0.56(2H, m), 0.59–0.78(2H, m), 0.85(3H, t, J=6.8Hz), 1.07–1.38(9H, m), 1.43–1.64(2H, m), 1.81(1H, br d, J=11.2Hz), 2.30(3H, s), 2.59(1H, dt, J=4.4, 13.2Hz), 2.65–2.76(1H, m), 2.74(1H, d, J=15.6Hz), 2.76–2.85(2H, m), 2.86–2.96(1H, m), 3.11(1H, br s), 3.16(1H, d, J=16.1Hz), 3.24(1H, dd, J=6.6, 19.8Hz), 4.04(1H, d, J=6.8Hz), 5.66(1H, s), 6.37(1H, br s), 6.59(1H, d, J=8.3Hz), 6.63(1H, d, J=8.3Hz), 6.70(1H, d, J=7.3Hz), 6.98(1H, t, J=7.6Hz), 7.17(1H, d, J=7.8Hz), 8.91(1H, br s), 9.21(1H, br s), 11.31(1H, s). | Melting Point 195 (dec) (° C.).<br>Elemental Analysis<br>as $C_{33}H_{40}N_2O_3 \cdot CH_3SO_3H \cdot 0.3H_2O$<br>Calculated: C, 66.49; H, 7.32; N, 4.56; S, 5.22.<br>Found: C, 66.38; H, 7.27; N, 4.67; S, 5.32.<br>IR (cm$^{-1}$) (KBr)<br>3258, 2930, 2858, 1640, 1622, 1464, 1331, 1194, 1116, 1045, 779, 553.<br>Mass (FAB) 512 ((M+H)$^+$). |

-continued

| | | |
|---|---|---|
| Compound 7<br>Methansulfonate<br>Yield: 51 (%) | 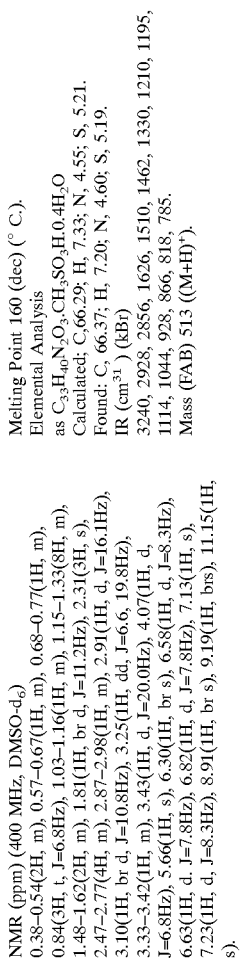 | NMR (ppm) (400 MHz, DMSO-d$_6$) 0.38–0.54(2H, m), 0.57–0.67(1H, m), 0.68–0.77(1H, m), 0.84(3H, t, J=6.8Hz), 1.03–1.16(1H, m), 1.15–1.33(8H, m), 1.48–1.62(2H, m), 1.81(1H, br d, J=11.2Hz), 2.31(3H, s), 2.47–2.77(4H, m), 2.87–2.98(1H, d, J=16.1Hz), 2.91(1H, d, J=6.6, 19.8Hz), 3.10(1H, br d, J=10.8Hz), 3.25(1H, dd, J=6.6, 19.8Hz), 3.33–3.42(1H, m), 3.43(1H, d, J=20.0Hz), 4.07(1H, d, J=6.8Hz), 5.66(1H, s), 6.30(1H, br s), 6.58(1H, d, J=8.3Hz), 6.63(1H, d, J=7.8Hz), 6.82(1H, d, J=7.8Hz), 7.13(1H, s), 7.23(1H, d, J=8.3Hz), 8.91(1H, br s), 9.19(1H, brs), 11.15(1H, s). | Melting Point 160 (dec) (° C.).<br>Elemental Analysis<br>as C$_{33}$H$_{40}$N$_2$O$_3$·CH$_3$SO$_3$H·0.4H$_2$O<br>Calculated; C, 66.29; H, 7.33; N, 4.55; S, 5.21.<br>Found; C, 66.37; H, 7.20; N, 4.60; S, 5.19.<br>IR (cm$^{-1}$) (kBr)<br>3240, 2928, 2856, 1626, 1510, 1462, 1330, 1210, 1195, 1114, 1044, 928, 866, 818, 785.<br>Mass (FAB) 513 ((M+H)$^+$) |
| Compound 8<br>Methanesulfonate<br>Yield: 35 (%) | 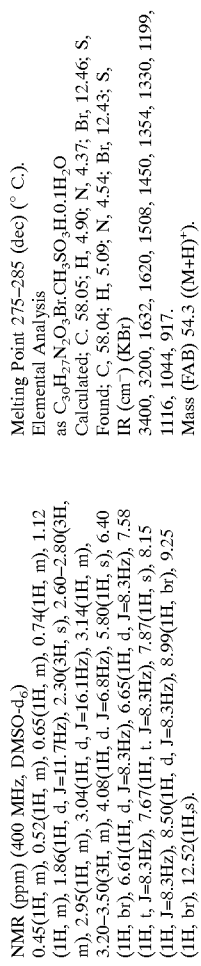 | NMR (ppm) (400 MHz, CD$_3$OD) 0.52–0.60(2H, m), 0.76–0.84(1H, m), 0.87–0.94(1H, m), 1.15–1.22(1H, m), 1.95–2.01(1H, m), 2.69(3H, m), 2.74–2.83 (1H, m), 2.92–3.04(2H, m), 3.13(1H, d, J=16.2Hz), 3.16–3.23 (1H, m), 3.35–3.42(1H, m), 3.45–3.50(2H, m), 3.58(1H, d, J=16.2Hz), 4.29(1H, br s), 5.81(1H, s), 6.67(1H, d, J=8.0 Hz), 6.70(1H, d, J=8.0Hz), 7.29–7.34(1H, m), 7.42–7.47(1H, m), 7.52(1H, d, J=5.0Hz), 7.55(1H, d, J=5.0Hz), 7.84(1H, d, J=8.0Hz), 8.24(1H, d, J=8.0Hz). | Melting Point 245 (dec) (° C.).<br>Elemental Analysis<br>as C$_{30}$H$_{28}$N$_2$O$_3$·CH$_3$SO$_3$H·0.3H$_2$O<br>Calculated; C, 65.78; H, 5.80; N, 4.95; S, 5.66.<br>Found; C, 65.61; H, 5.86; N, 5.00; S, 5.59.<br>IR (cm$^{-1}$) (KBr)<br>3300, 1620, 1504, 1462, 1363, 1330, 1207, 1116, 1046, 862, 8 |
| Compound 9<br>Methanesulfonate<br>Yield: 58 (%) | 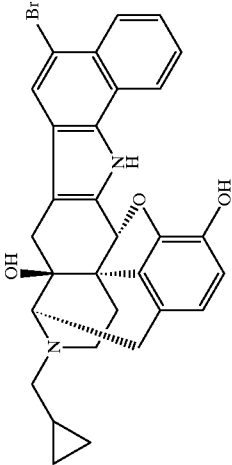 | NMR (ppm) (400 MHz, DMSO-d$_6$) 0.45(1H, m), 0.52(1H, m), 0.65(1H, m), 0.74(1H, m), 1.12 (1H, m), 1.86(1H, d, J=11.7Hz), 2.30(3H, s), 2.60–2.80(3H, m), 2.95(1H, m), 3.04(1H, d, J=16.1Hz), 3.14(1H, m), 3.20–3.50(3H, m), 4.08(1H, d, J=6.8Hz), 5.80(1H, s), 6.40 (1H, br), 6.61(1H, d, J=8.3Hz), 6.65(1H, d, J=8.3Hz), 7.58 (1H, t, J=8.3Hz), 7.67(1H, t, J=8.3Hz), 7.87(1H, s), 8.15 (1H, d, J=8.3Hz), 8.50(1H, d, J=8.3Hz), 8.99(1H, br), 9.25 (1H, br), 12.52(1H,s). | Melting Point 275–285 (dec) (° C.).<br>Elemental Analysis<br>as C$_{30}$H$_{27}$N$_2$O$_3$Br·CH$_3$SO$_3$H·0.1H$_2$O<br>Calculated; C, 58.04; H, 4.90; N, 4.37; Br, 12.46; S, 4.54.<br>Found; C, 58.04; H, 5.09; N, 4.54; Br, 12.43; S,<br>IR (cm$^{-1}$) (KBr)<br>3400, 3200, 1632, 1620, 1508, 1450, 1354, 1330, 1199, 1116, 1044, 917.<br>Mass (FAB) 54.3 ((M+H)$^+$) |

-continued

| | | |
|---|---|---|
| Compound 10<br>Methanesulfonate<br>Yield: 85 (%)<br>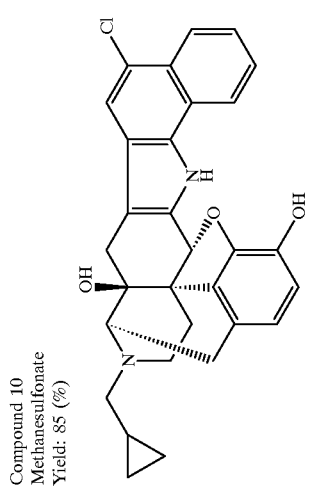 | NMR (ppm) (400 MHz, DMSO-$d_6$)<br>0.45(1H, m), 0.52(1H, m), 0.64(1H, m), 0.74(1H, m), 1.12 (1H, m), 1.87(1H, d, J=12.7Hz), 2.30(3H, s), 2.60–2.80(3H, m), 2.95(1H, m), 3.03(1H, d, J=16.1Hz), 3.14(1H, m), 3.20–3.50(3H, m), 4.08(1H, d, J=6.4Hz), 5.80(1H, s), 6.41 (1H, br), 6.61(1H, d, J=8.3Hz), 6.65(1H, d, J=8.3Hz), 7.57 (1H, t, J=7.3Hz), 7.68(1H, t, J=7.5Hz), 7.69(1H, s), 8.19 (1H, d, J=8.3Hz), 8.52(1H, d, J=8.3Hz), 8.96(1H, br), 9.25 (1H, br), 12.51(1H, s). | Melting Point 275–285(dec) (° C.).<br>Elemental Analysis<br>as $C_{30}H_{27}N_3O_3Cl.CH_3SO_3H.0.2H_2O$<br>Calculated: C, 62.19; H, 5.29; N, 4.68; Cl, 5.92; S, 5.58.<br>Found: C, 61.80; H, 5.58; N, 4.93; Cl, 5.95; S, 5.62.<br>IR (cm$^{-1}$) (KBr)<br>3400, 3200, 1632, 1620, 1510, 1460, 1357, 1330, 1202, 1116, 1044, 857.<br>Mass (FAB) 499 ((M+H)$^+$). |
| Compound 11<br>Methansulfonate<br>Yield: 80 (%)<br>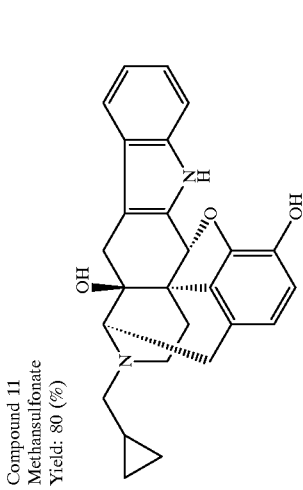 | NMR (ppm) (400 MHz, DMSO-$d_6$)<br>0.46(1H, m), 0.52(1H, m), 0.65(1H, m), 0.75(1H, m), 1.13 (1H, m), 1.88(1H, d, J=11.7Hz), 2.32(3.15H, s), 2.60–2.80 (3H, m), 2.96(1H, m), 3.14(1H, d, J=14.2Hz), 3.17(1H, m), 3.20–3.50(3H, m), 4.10(1H, d, J=6.3Hz), 5.82(1H, s), 6.45 (1H, br), 6.62(1H, d, J=8.3Hz), 6.66(1H, d, J=8.3Hz), 7.68 (1H, t, J=8.3Hz), 7.75(1H, t, J=6.8Hz), 8.11(1H, d, J=7.8 Hz), 8.24(1H, s), 8.60(1H, d, J=8.3Hz), 8.97(1H, br), 9.26 (1H, br), 12.91(1H, s). | Melting Point 260–280 (dec) (° C.).<br>Elemental Analysis<br>as $C_{31}H_{27}N_3O_3.1.05CH_3SO_3H.0.7H_2O$<br>Calculated: C, 63.83; H, 5.45; N, 6.97; S, 5.58.<br>Found: C, 63.92; H, 5.57; N, 6.80; S, 5.62.<br>IR (cm$^{-1}$) (KBr)<br>3400, 3200, 2218, 1630, 1620, 1508, 1460, 1375, 1330, 1209, 1116, 1046.<br>Mass (FAB) 490((M+H)$^+$). |
| Compound 12<br>Methanesulfonate<br>Yield: 60 (%)<br>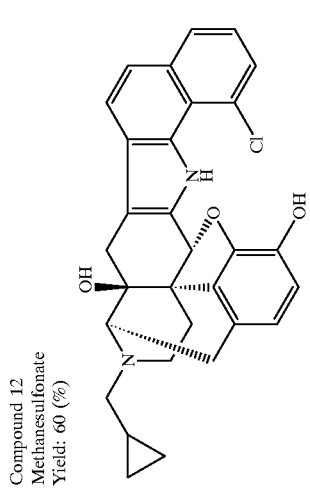 | NMR (ppm) (400 MHz, DMSO-$d_6$)<br>0.41–0.56(2H, m), 0.58–0.69(1H, m), 0.69–0.79(1H, m), 1.04–1.16(1H, m), 1.88(1H, d, J=12Hz), 2.56–2.69(2H, m), 2.69–2.83(1H, m), 2.89–3.00(1H, m), 3.06(1H, d, J=16Hz), 3.08–3.18(1H, m), 3.22–3.35(1H, m), 3.36–3.47(2H, m), 4.11 (1H, d, J=6.4Hz), 5.90(1H, s), 6.40(1H, br s), 6.61(1H, d, J=7.8Hz), 6.65(1H, d, J=8.3Hz), 7.43(1H, t, J=7.8Hz), 7.57 (1H, d, J=7.8Hz), 7.62(1H, d, J=8.3Hz), 7.66(1H, d, J=7.3 Hz), 7.95(1H, d, J=7.8Hz), 8.97(1H, br s), 9.25(1H, br s). | Melting Point 257 (dec) (° C.).<br>Elemental Analysis<br>as $C_{29}H_{27}N_3O_3Cl.1.2CH_3SO_3H.0.5H_2O$<br>Calculated: C, 61.00; H, 5.22; N, 4.56; Cl, 5.77; S, 5.79.<br>Found: C, 60.83; H, 5.41; N, 4.20; Cl, 5.79; S,<br>IR (cm$^{-1}$) (KBr)<br>3400, 3012, 1626, 1545, 1508, 1466, 1429, 1369, 1317, 1197, 1116, 1050, 948, 928, 901, 868, 822, 799, 785.<br>Mass (FAB) 499 ((M+H)$^+$). |

-continued

| | | |
|---|---|---|
| Compound 13<br>Methanesulfonate<br>Yield: 79 (%) | NMR (ppm) (400 MHz, DMSO-$d_6$)<br>0.45(1H, m), 0.51(1H, m), 0.64(1H, m), 0.74(1H, m), 1.12 (1H, m), 1.85(1H, d, J=12.2Hz), 2.30(3H, s), 2.60–2.80(3H, m), 2.61(3H, s), 2.95(1H, m), 3.00(1H, d, J=16.1Hz), 3.13 (1H, m), 3.25–3.50(3H, m), 4.09(1H, d, J=5.9Hz), 5.78(1H, s), 6.37(1H, s), 6.60(1H, d, J=8.3Hz), 6.64(1H, d, J=8.3Hz), 7.32(1H, s), 7.47(1H, t, J=7.3Hz), 7.57(1H, t, J=7.3Hz), 7.97(1H, d, J=8.3Hz), 8.43(1H, d, J=8.3Hz), 8.94(1H, br), 9.20(1H, s), 12.15(1H, s). | Melting Point 270–280,(dec) (° C.).<br>Elemental Analysis<br>as $C_{31}H_{31}N_2O_3 \cdot CH_3SO_3H \cdot 0.7H_2O$<br>Calculated: C, 65.44; H, 6.08; N, 4.77; S, 5.46.<br>Found: C, 65.51; H, 6.28; N, 4.52; S, 5.13.<br>IR (cm$^{-1}$) (KBr)<br>3400, 3200, 1632, 1620, 1508, 1460, 1330, 1201, 1160, 1116, 1044, 859.<br>Mass (FAB) 479 ((M+H)$^+$). |
| Compound 14<br>Methanesulfonate<br>Yield: 43 (%) | NMR (ppm) (400 MHz, DMSO-$d_6$)<br>0.45(1H, m), 0.51(1H, m), 0.64(1H, m), 0.75(1H, m), 1.12 (1H, m), 1.86(1H, d, J=11.7Hz), 2.30(3H, s), 2.55–2.75(3H, m), 2.95(1H, m), 3.01(1H, d, J=16.1Hz), 3.13(1H, m), 3.25–3.50(3H, m), 4.09(1H, d, J=6.4Hz), 5.79(1H, s), 6.40 (1H, s), 6.61(1H, d, J=8.3Hz), 6.65(1H, d, J=8.3Hz), 7.30 (1H, d, J=11.2Hz), 7.53(1H, t, J=7.3Hz), 7.67(1H, t, J=7.3 Hz), 8.02(1H, d, J=8.3Hz), 8.47(1H, d, J=8.3Hz), 8.95(1H, br), 9.22(1H, br), 12.38(1H, s). | Melting Point 265–275(dec) (° C.).<br>Elemental Analysis<br>as $C_{30}H_{27}FN_2O_3 \cdot H \cdot CH_3SO_3H \cdot 0.5H_2O \cdot 0.2AcOEt$<br>Calculated: C, 63.10; H, 5.60; N, 4.63; F, 3.14; S, 5.30.<br>Found: C, 62.99; H, 5.89; N, 4.43; F, 3.13; S, 5.16.<br>IR (cm$^{-1}$) (KBr)<br>3400, 3200, 1638, 1510, 1460, 1381, 1330, 1205, 1156, 1116, 1046, 857.<br>Mass (FAB) 483 ((M+H)$^+$). |
| Compound 15<br>Methanesulfonate<br>Yield: 48 (%) | NMR (ppm) (400 MHz, DMSO-$d_6$)<br>0.40–0.51(2H, m), 0.51–0.63(1H, m), 0.63–0.72(2H, m), 1.88 (1H, d, J=12Hz), 2.60–2.82(3H, m), 2.88–2.99(1H, m), 3.04 (1H d J=16Hz), 3.10–3.18(1H, m), 3.21–3.31(1H, m), 3.36–3.53(4H, m), 4.07(1H, d, J=6.8Hz), 5.83(1H, s), 6.39 (1H, br s), 6.61(1H, d, J=8.3Hz), 6.65(1H, d, J=8.3Hz), 7.36–7.44(5H, m), 7.50(2H, t, J=7.8Hz), 7.58(1H, t, J=7.8 Hz), 7.76(1H, d, J=8.8Hz), 8.52(1H, d, J=7.8Hz), 8.96(1H, br s), 9.24(1H, br s) | Melting Point 261 (dec) (° C.).<br>Elemental Analysis<br>as $C_{36}H_{32}N_2O_3 \cdot 1.25CH_3SO_3H \cdot 0.2H_2O$<br>Calculated: C, 67.04; H, 5.96; N, 4.20; S, 6.01.<br>Found: C, 67.04; H, 5.85; N, 4.46; S, 5.75.<br>IR (cm$^{-1}$) (KBr)<br>3400,1638, 1562, 1543, 1510, 1460, 1330, 1203, 1116, 1048, 901, 857, 777, 704, 634.<br>Mass (FAB) 541 ((M+H)$^+$). |

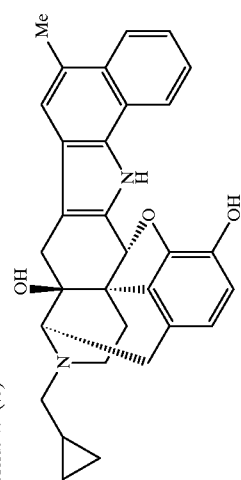

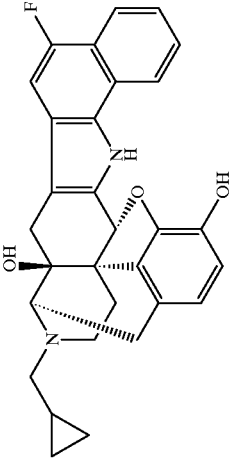

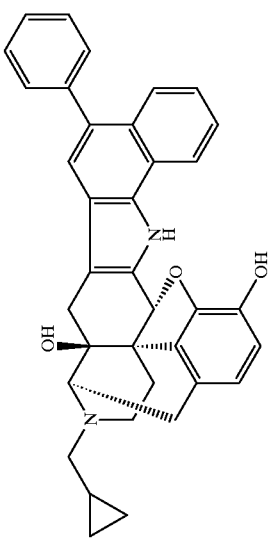

| | |
|---|---|
| Compound 16<br>Methanesulfonate<br>Yield: 74 (%)<br>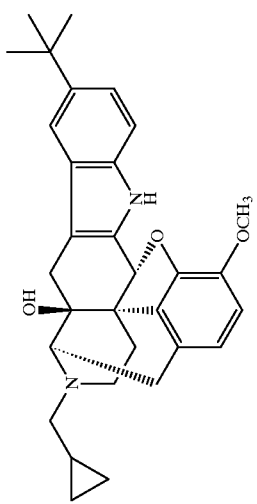 | NMR (ppm) (400 MHz, DMSO-d$_6$) 0.40–0.56(2H, m), 0.57–0.68(1H, m), 0.69–0.80(1H, m), 1.02–1.15(1H, m), 1.28(9H, s), 1.84(1h, d, J=12.2Hz), 2.32(3.6H, s), 2.51–2.77 (3H, m), 2.91–3.07(2H, m), 3.08–3.19(1H, m), 3.23–3.58(4H, m), 3.67(3H, s), 4.10(1H, d, J=6.35Hz), 5.73(1H, s), 6.31 (1H, d, J=8.3Hz), 6.72(1H, d, J=8.3Hz), 6.81(1H, d, J=8.3Hz), 7.18–7.29(3H, m), 8.97(1H, br s), 11.19(1.2H, s).<br>Melting Point 217–219 (° C.).<br>Elemental Analysis<br>as C$_{31}$H$_{36}$N$_2$O$_3$.1.2CH$_3$SO$_3$.0.5H$_2$O<br>Calculated: C, 63.31; H, 6.92; N, 4.78; S, 6.32.<br>Found: C, 63.31; H, 6.94; N, 4.78; S, 6.55.<br>IR (cm$^{-1}$) (KBr)<br>2962, 1636, 1560, 1543, 1508,1460, 1197, 1122, 1054, 895, 812, 561.<br>Mass (FAB) 485 ((M+H)$^+$). |
| Compound 17<br>Hydrochloride<br>Yield: 81 (%)<br>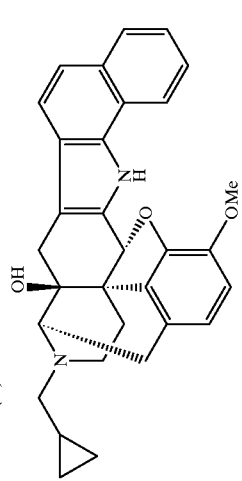 | NMR (ppm) (400 MHz, DMSO-d$_6$) 0.47(1H, m), 0.53(1H, m), 0.66(1H, m), 0.75(1H, m), 1.14 (1H, m), 1.86(1H, d, J=9.8Hz), 2.61(1H, d, J=16.1Hz), 2.65–2.75(2H, m), 3.00(1H, m), 3.10(1H, d, J=16.1Hz), 3.15 (1H, m), 3.30–3.45(2H, m), 3.51(1H, d, J=20.0Hz), 3.67(3H, s), 4.18(1H, d, J=5.9Hz), 5.87(1H, s), 6.52(1H, s), 6.73(1H, d, J=8.3Hz), 6.81(1H, d, J=8.3Hz), 7.40–7.50(3H, m), 7.54 (1H, t, J=7.3Hz), 7.89(1H, d, J=7.8Hz), 8.44(1H, d, J=8.3Hz), 9.05(1H, br), 12.34(1H, s).<br>Melting Point 245–255 (dec) (° C.).<br>Elemental Analysis<br>as C$_{31}$H$_{32}$N$_2$O$_3$.HCl.0.3H$_2$O<br>Calculated: C, 71.54; H, 6.12; N, 5.38; Cl, 6.88.<br>Found: C, 71.49; H, 6.29; N, 5.56; Cl, 6.57.<br>IR (cm$^{-1}$) (KBr)<br>3400, 3200, 1632, 1611, 1508, 1444, 1390, 1332, 1174, 1122, 1050, 893.<br>Mass (FAB) 479 ((M+H)$^+$). |
| Compound 18<br>Phosphate<br>Yield: 77 (%)<br>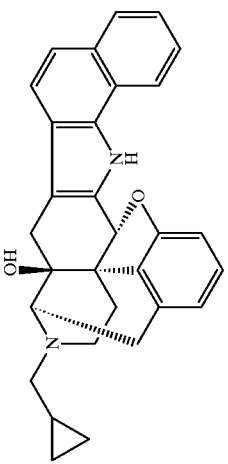 | NMR (ppm) (400 MHz, DMSO-d$_6$) 0.25–0.35(2H, m), 0.50–0.65(2H, m), 0.99(1H, m), 1.70(1H, d, J=11.7Hz), 2.36(1H, m), 2.45(1H, m), 2.56(1H, d, J=16.1 Hz), 2.62(1H, m), 2.75–2.95(3H, m), 3.05(1H, m), 3.32(1H, m), 3.63(1H, br), 5.73(1H, s), 6.54(1H, d, J=7.8Hz), 6.72 (1H, d, J=7.8Hz), 7.01(1H, t, J=7.8Hz), 7.40(1H, t, J=8.3 Hz), 7.41(1H, d, J=8.3Hz), 7.48(1H, d, J=8.8Hz), 7.53(1H, (1H,s).<br>Melting Point 265–280 (dec) (° C.).<br>Elemental Analysis<br>as C$_{30}$H$_{28}$N$_2$O$_2$.1.2H$_3$PO$_4$.0.6H$_2$O.0.2Et$_2$O<br>Calculated: C, 62.51; H, 5.93; N, 4.73; P, 6.28.<br>Found: C, 62.51; H, 6.95; N, 4.60; P. 6.30.<br>IR (cm$^{-1}$) (KBr)<br>3400, 3200, 1620, 1607, 1462, 1354, 1390, 1104.<br>Mass (FAB) 449 ((M+H)$^+$). |

| | |
|---|---|
| Compound 19<br>Methanesulfonate<br>Yield: 88 (%)<br>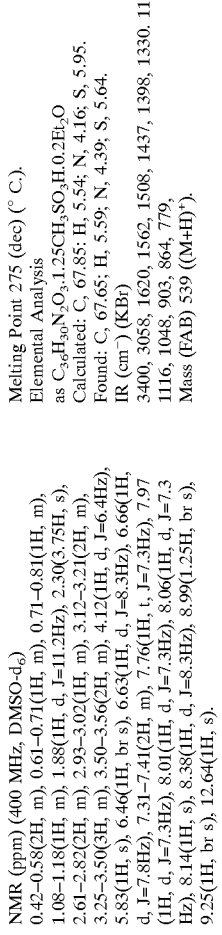 | NMR (ppm) (400 MHz, DMSO-d$_6$)<br>0.42–0.58(2H, m), 0.61–0.71(1H, m), 0.71–0.81(1H, m), 1.08–1.18(1H, m), 1.88(1H, d, J=11.2Hz), 2.30(3.75H, s), 2.61–2.82(2H, m), 2.93–3.02(1H, m), 3.12–3.21(2H, m), 3.25–3.50(3H, m), 3.50–3.56(2H, m), 4.12(1H, d, J=6.4Hz), 5.83(1H, s), 6.46(1H, br s), 6.63(1H, d, J=8.3Hz), 6.66(1H, d, J=7.8Hz), 7.31–7.41(2H, m), 7.76(1H, t, J=7.3Hz), 7.97 (1H, d, J=7.3Hz), 8.01(1H, d, J=7.3Hz), 8.06(1H, d, J=7.3 Hz), 8.14(1H, s), 8.38(1H, d, J=8.3Hz), 8.99(1.25H, br s), 9.25(1H, br s), 12.64(1H, s). | Melting Point 275 (dec) (° C.).<br>Elemental Analysis<br>as C$_{34}$H$_{30}$N$_2$O$_3$·1.25CH$_3$SO$_3$H·0.2Et$_2$O<br>Calculated: C, 67.85; H, 5.54; N, 4.16; S, 5.95.<br>Found: C, 67.65; H, 5.59; N, 4.39; S, 5.64.<br>IR (cm$^{-1}$) (KBr)<br>3400, 3058, 1620, 1562, 1508, 1437, 1398, 1330, 1180, 1116, 1048, 903, 864, 779,<br>Mass (FAB) 539 ((M+H)$^+$). |
| Compound 20<br>Hydrochloride<br>Yield: 73 (%)<br>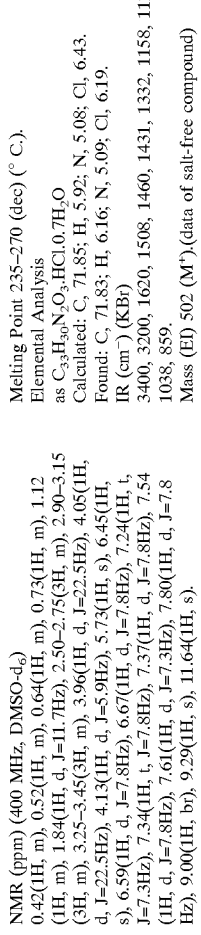 | NMR (ppm) (400 MHz, DMSO-d$_6$)<br>0.42(1H, m), 0.52(1H, m), 0.64(1H, m), 0.73(1H, m), 1.12 (1H, m), 1.84(1H, d, J=11.7Hz), 2.50–2.75(3H, m), 2.90–3.15 (3H, m), 3.25–3.45(3H, m), 3.96(1H, d, J=22.5Hz), 4.05(1H, d, J=22.5Hz), 4.13(1H, d, J=5.9Hz), 5.73(1H, s), 6.45(1H, s), 6.59(1H, d, J=7.8Hz), 6.67(1H, d, J=7.8Hz), 7.24(1H, t, J=7.3Hz), 7.34(1H, t, J=7.8Hz), 7.37(1H, d, J=7.8Hz), 7.54 (1H, d, J=7.8Hz), 7.61(1H, s), 7.80(1H, d, J=7.3Hz), 7.8 Hz), 9.00(1H, br), 9.29(1H, s), 11.64(1H, s). | Melting Point 235–270 (dec) (° C.).<br>Elemental Analysis<br>as C$_{33}$H$_{30}$N$_2$O$_3$·HCl·0.7H$_2$O<br>Calculated: C, 71.85; H, 5.92; N, 5.08; Cl, 6.43.<br>Found: C, 71.83; H, 6.16; N, 5.09; Cl, 6.19.<br>IR (cm$^{-1}$) (KBr)<br>3400, 3200, 1620, 1508, 1460, 1431, 1332, 1158, 1114, 1038, 859,<br>Mass (EI) 502 (M$^+$).(data of salt-free compound) |
| Compound 21<br>Methanesulfonate<br>Yield: 83 (%)<br>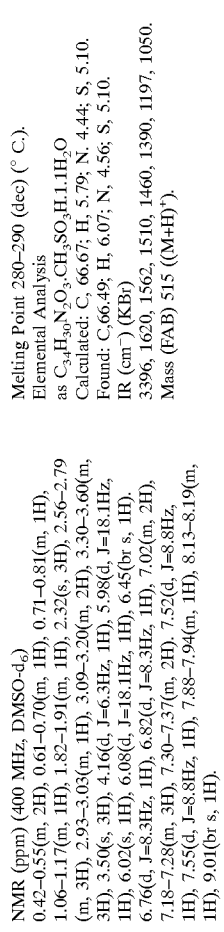 | NMR (ppm) (400 MHz, DMSO-d$_6$)<br>0.42–0.55(m, 2H), 0.61–0.70(m, 1H), 0.71–0.81(m, 1H), 1.06–1.17(m, 1H), 1.82–1.91(m, 1H), 2.32(s, 3H), 2.56–2.79 (m, 3H), 2.93–3.03(m, 1H), 3.09–3.20(m, 2H), 3.30–3.60(m, 3H), 3.50(s, 3H), 4.16(d, J=6.3Hz, 1H), 5.98(d, J=18.1Hz, 1H), 6.02(s, 1H), 6.08(d, J=18.1Hz, 1H), 6.45(br s, 1H), 6.76(d, J=8.3Hz, 1H), 6.82(d, J=8.3Hz, 1H), 7.02(m, 2H), 7.18–7.28(m, 3H), 7.30–7.37(m, 2H), 7.52(d, J=8.8Hz, 1H), 7.55(d, J=8.8Hz, 1H), 7.88–7.94(m, 1H), 8.13–8.19(m, 1H), 9.01(br s, 1H). | Melting Point 280–290 (dec) (° C.).<br>Elemental Analysis<br>as C$_{34}$H$_{30}$N$_2$O$_3$·CH$_3$SO$_3$H·1.1H$_2$O<br>Calculated: C, 66.67; H, 5.79; N, 4.44; S, 5.10.<br>Found: C,66.49; H, 6.07; N, 4.56; S, 5.10.<br>IR (cm$^{-1}$) (KBr)<br>3396, 1620, 1562, 1510, 1460, 1390, 1197, 1050, Mass (FAB) 515 ((M+H)$^+$). |

-continued

| | | |
|---|---|---|
| Compound 22<br>Methanesulfonate<br>Yield: 60 (%)<br>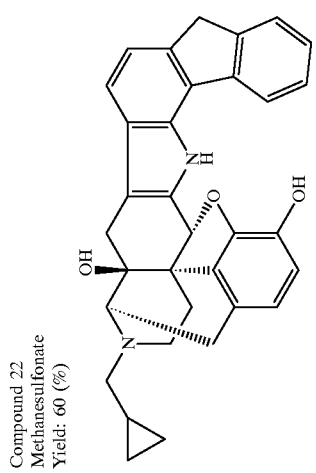 | NMR (ppm) (300 MHz, DMSO-$d_6$)<br>0.43–0.57(2H, m), 0.61–0.70(1H, m), 0.70–0.79(1H, m), 1.06–1.17(1H, m), 1.18(0.03H, t, J=7.1Hz), 1.89(1H, d, J=13.2Hz), 1.99(0.03H, s), 2.31(3.3H, s), 2.57–2.83(3H, m), 2.91–3.17(4H, m), 3.24–3.34(2H, m), 3.97–3.99(2H, m), 4.11 (1H, d, J=6.0Hz), 5.79(1H, s), 6.42(1H, br s), 6.61(1H, d, J=8.2Hz), 6.66(1H, d, J=8.0Hz), 7.27–7.38(3H, m), 7.45–7.50(1H, m), 7.61(1H, d, J=7.4Hz), 8.51(1H, d, J=7.4Hz), 8.97(1.1H, br s), 9.23(1H, br s), 11.65(1H, s). | Melting Point >290 (dec) (° C.).<br>Elemental Analysis<br>as $C_{35}H_{30}N_2O_3 \cdot 1.1CH_3SO_3H \cdot 1.1H_2O \cdot 0.01EtOAc$<br>Calculated: C, 65.19; H, 5.88; N, 4.45; S, 5.61.<br>Found: C, 65.09; H, 5.98; N, 4.62; S, 5.52.<br>IR (cm$^{-1}$) (KBr)<br>3400, 2928, 1620, 1562, 1510, 1462, 1162, 1116, 1046, 777.<br>Mass (EI) 502 (M$^+$) (data of salt-free compound) |
| Compound 23<br>Methanesulfonate<br>Yield: 87 (%)<br>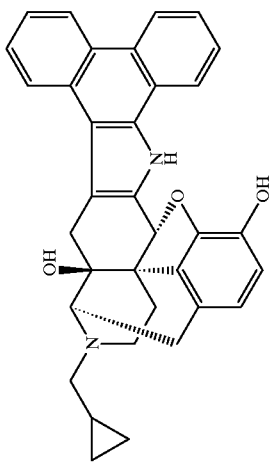 | NMR (ppm) (300 MHz, DMSO-$d_6$)<br>0.43–0.56(2H, m), 0.62–0.83(2H, m), 1.11(1H, m), 1.88(1H, d, J=11.8Hz), 2.30(3H, s), 2.60–2.73(2H, m), 2.93–3.03(2H, m), 3.13(1H, m), 3.34–3.52(4H, m), 4.19(1H, m), 4.41(1H, d, J=4.1Hz), 5.82(1H, s), 6.42(1H, br s), 6.61–6.67(2H, m), 7.50(1H, m), 7.54–7.61(2H, m), 7.68(1H, m), 8.21(1H, d, J=7.4Hz), 8.48 (1H, d, J=8.0Hz), 8.78(2H, d, J=8.0Hz), 8.98(1H, br s), 9.22 (1H, br s), 12.43(1H, s). | Melting Point >250 (dec) (° C.).<br>Elemental Analysis<br>as $C_{39}H_{32}N_2O_3 \cdot 1.1CH_3SO_3H \cdot 0.6H_2O$<br>Calculated: C, 66.80; H, 5.69; N, 4.44; S, 5.59.<br>Found: C, 66.64; H, 5.80; N, 4.69; S, 5.61.<br>IR (cm$^{-1}$) (KBr)<br>3400, 1638, 1200, 1048, 758, 559.<br>Mass (FAB) 515 ((M+H)$^+$). |
| Compound 24<br>Hydrochloride<br>Yield: 44 (%)<br>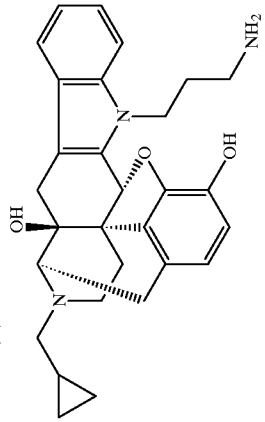 | NMR (ppm) (500 MHz, DMSO-$d_6$)<br>0.45(m, 1H), 0.52(m, 1H), 0.63(m, 1H), 0.73(m, 1H), 1.12 (m, 1H), 1.83(1H, m), 2.12(m, 1H), 2.22(m, 1H), 2.55(d, 1H, J=16.2Hz), 2.62–2.78(m, 2H), 2.88(m, 1H), 2.93–3.07 (m, 3H), 3.13(m, 1H), 3.23–3.42(m, 2H), 3.45(d, 1H, J=18.5 Hz), 4.15(d, 1H, J=5.8Hz), 4.34–4.45(m, 2H), 5.95(s, 1H), 6.46(s, 1H, OH), 6.60(d, 1H, J=8.2Hz), 6.66(d, 1H, J=8.2 Hz), 7.03(br t, 1H, J=7.6Hz), 7.19(br t, 1H, J=7.6Hz), 7.38 (d, 1H, J=7.9Hz), 7.58(d, 1H, J=8.2Hz), 8.19(br s, 3H, NH$_3^+$), 9.02(br s, 1H, NH$^+$), 9.23 (s, 1H, OH). | Melting Point >225 (dec) (° C.).<br>Elemental Analysis<br>as $C_{29}H_{33}N_3O_3 \cdot 1.95HCl \cdot 0.4H_2O$<br>Calculated: C, 63.34; H, 6.55; Cl, 12.57; N, 7.64.<br>Found: C, 63.35; H, 6.66; Cl, 12.54; N, 7.50.<br>IR (cm$^{-1}$) (KBr)<br>3380, 3210, 1626, 1506, 1466, 1379, 1328, 1296, 1210, 1191, 1156, 1116, 1056, 1031, 930, 855, 799, 748.<br>Mass (FAB) 472 ((M+H)$^+$). |

| | NMR (ppm) (400 MHz, DMSO-d6) | |
|---|---|---|
| Compound 25 Hydrochloride Yield: 73 (%) 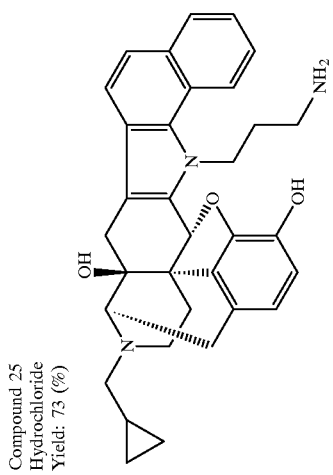 | 0.47(m, 1H), 0.52(m, 1H), 0.64(m, 1H), 0.74(m, 1H), 1.13 (m, 1H), 1.87(1H, m), 2.17–2.37(m, 2H), 2.63(d, 1H, J=16.1 Hz), 2.63–2.80(m, 2H), 2.96–3.20(m, 5H), 3.24–3.44(m, 2H), 3.47(d, 1H, J=19.5Hz), 4.17(d, 1H, J=5.4Hz), 4.77–4.88(m, 2H), 6.07(s, 1H), 6.48(s, 1H, OH), 6.62(d, 1H, J=8.3Hz), 6.67(d, 1H, J=8.3Hz), 7.46–7.56(m, 3H), 7.63(dd, 1H, J=7.8, 7.3Hz), 7.98(d, 1H, J=7.8Hz), 8.19(brs, 3H, NH3+), 8.43(d, 1H, J=7.8Hz), 9.95(br s, 1H, NH+), 9.24(s, 1H, OH). | Melting Point >220 (dec) (° C.). Elemental Analysis as C33H35N3O3.1.95 HCl.0.9H2O Calculated: C, 65.09; H, 6.41; Cl, 11.35; N, 6.90. Found: C, 65.02;H, 6.51; Cl, 11.15; N, 7.02. IR (cm−1) (KBr) 3376, 1620, 1506, 1462, 1425, 1392, 1328, 1309, 1270, 1247, 1189, 1160, 1116, 1048, 1031, 946, 903, 851, 806, 748. Mass (FAB) 522 ((M+H)+). |
| Compound 26 Methanesulfonate Yield: 80 (%) 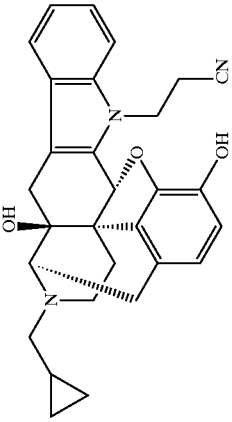 | 0.44(m, 1H), 0.49(m, 1H), 0.64(m, 1H), 0.73(m, 1H), 1.10 (m, 1H), 1.86(br d, 1H, J=10.7Hz), 2.29(s, 3H), 2.56(d, 1H, J=16.1Hz), 2.62(ddd, 1H, J=13.2, 4.4, 4.4Hz), 2.73(m, 1H), 2.95(m,1H), 2.99(d, 1H, J=16.1Hz), 3.06–3.18(m, 3H), 3.27 (dd, 1H, J=20.0, 6.8Hz), 3.39(m, 1H), 3.44(d, 1H, J=20.0 Hz), 4.09(d, 1H, J=6.3Hz), 4.59–4.73(m, 2H), 6.03(s, 1H), 6.33(br s, 1H, OH), 6.61(d, 1H, J=8.3Hz), 6.64(d, 1H, J=8.3 Hz), 7.05(br t, 1H, J=7.3Hz), 7.20(br t, 1H, J=7.6Hz), 7.38 (d, 1H, J=7.8Hz), 7.62(d, 1H, J=8.3Hz), 8.94(brs, 1H, NH+), 9.25(br s, 1H, OH). | Melting Point 285–295 (dec) (° C.). Elemental Analysis as C29H29N3O3.MeSO3H #Calculated: C, 63.93; H, 5.90; N, 7.45; S, 5.69. Found: C, 63.68; H, 5.92; N, 7.45; S, 5.62. IR (cm−1) (KBr) 3528, 3030, 2254, 1649, 1618, 1506, 1470, 1437, 1377, 1330, 1193, 1152, 1114, 1038, 1011, 940, 868, 843, 801, 772. Mass (FAB) 468 ((M+H)+). |
| Compound 27 Phosphate Yield: 89 (%) 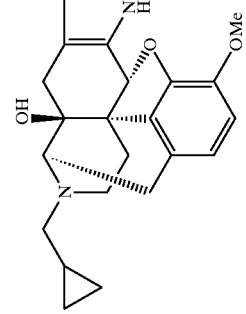 | 0.24–0.32(2H, m), 0.54–0.65(2H, m), 0.95–1.04(1H, m), 1.73 (1H, d, J=11.7Hz), 2.32–2.42(1H, m), 2.43–2.51(1H, m), 2.57–2.67(1H, m), 2.64(1H, d, J=15.6Hz), 2.70–2.79(1H, m), 2.84–2.91(1H, m), 2.96–3.06(1H, m), 3.03(1H, d, J=15.6Hz), 3.28(1H, d, J=19.5Hz), 3.62–3.66(2H, m), 3.66(3H, s), 5.77 (1H, s), 6.70(1H, d, J=8.3Hz), 6.76(1H, d, J=8.3Hz), 7.31–7.46(2H, m), 7.76(1H, dd, J=8.3, 7.3Hz), 7.97(1H, d, J=6.8Hz), 8.01(1H, d, J=6.8Hz), 8.05(1H, d, J=6.8Hz), 8.16 (1H, s), 8.36(1H, d, J=7.8Hz), 12.64(1H, s). | Melting Point 282 (dec) (° C.). Elemental Analysis as C37H32N2O3.H3PO4.0.1Et2O Calculated: C, 66.44; H,5.67; N, 4.14; P, 4.58. Found: C, 66.37; H, 5.76; N, 4.33; P, 4.37. IR (cm−1) (KBr) 3400, 1611, 1562, 1508, 1439, 1398, 1284, 1255, 1154, 1122, 1050, 944, 897, 799, 723. Mass (FAB) 552 ((M+H)+). |

-continued

Compound 28
Methanesulfonate
Yield: 56 (%)

NMR (ppm) (500 MHz, DMSO-d₆)
1.80–1.83(m, 1H), 2.31(s, 2.9H), 2.54(d, J=16.1Hz, 1H), 2.60(dd, J=13.2, 4.9Hz, 1H), 2.74(td, J=13.2, 3.4Hz, 1H), 2.98(d, J=16.1Hz, 1H), 3.12(dd, J=13.2, 4.9Hz, 1H), 3.23(d, J=19.0Hz, 1H), 3.42(d, J=19.0, 6.8Hz, 1H), 3.67(s, 3H), 3.86(d, J=6.8Hz, 1H), 5.81(s, 1H), 6.11(s, 1H), 6.75(d, J=8.3Hz, 1H), 6.80(d, J=8.3Hz, 1H), 7.41(dd, J=6.8, 1.5Hz, 1H), 7.43(d, J=8.8Hz, 1H), 7.47(d, J=8.8Hz, 1H), 7.54(dd, J=6.8, 1.5Hz, 1H), 7.89(d, J=7.8Hz, 1H), 8.41(d, J=7.8Hz, 1H), 8.58(br s, 1H), 8.88(brs, 1H).

Melting Point 260–266 (° C.).
Elemental Analysis
as C₂₇H₂₄N₂O₃·0.9CH₃SO₃H·0.6H₂O
Calculated: C, 64.22; H, 5.56; N, 5.37; S, 5.53.
Found: C, 64.22; H, 5.71; N, 5.36; S, 5.41.
IR (cm⁻¹) (KBr) (data of salt-free compound)
3422, 1634, 1506, 1456, 1203, 1174, 1046, 893
Mass (FAB) 425 ((M+H)+)

Compound 29
Methanesulfonate
Yield: 92.9%

NMR (ppm) (500 MHz, DMSO-d₆)
1.86(dd, J=13.7, 2.4Hz, 1H), 2.30(s, 3.2H), 2.59–2.66(m, 2H), 2.73–2.75(m, 1H), 2.91(s, 3H), 2.98(d, J=15.6Hz, 1H), 3.12–3.19(m, 1H), 3.28(dd, J=20.4, 6.4Hz, 1H), 3.53(d, J=20.4Hz, 1H), 3.68(s, 3H), 3.52–3.87(m, 1H), 5.85(s, 1H), 6.37(br s, 1H), 6.75(d, J=8.3Hz, 1H), 6.82(d, J=8.3Hz, 1H), 7.41(td, J=6.8, 1.0Hz, 1H), 7.43(d, J=8.8Hz, 1H), 7.49(d, J=8.8Hz, 1H), 7.55(td, J=6.8, 1.0Hz, 1H), 7.90(d, J=8.3Hz, 1H), 8.41(d, J=8.3Hz, 1H), 9.27(br s, 1H), 12.3(br s, 1H).

Melting Point 260–263 (° C.).
Elemental Analysis
as C₂₈H₂₆N₂O₃·CH₃SO₃H·0.5H₂O
Calculated: C, 64.07; H, 5.75; N, 5.15; S, 5.90.
Found: C, 64.12; H, 6.03; N, 5.05;S, 5.77.
IR (cm⁻¹) (KBr)
3400, 1636, 1508, 1454, 1390, 1332, 1205, 1174, 1046, 812.
Mass (FAB) 439 ((M+H)⁺).

Compound 30
Yield: 25 (%)

NMR (ppm) (300 MHz, CDCl₃)
1.66–1.78(m, 1H), 1.80–1.94(m, 2H), 2.32–2.46(m, 2H), 2.66 (d, J=15.9Hz, 1H), 2.68–2.98(m, 4H), 3.10–3.20(m, 1H), 3.22 (d, J=18.6Hz, 1H), 3.66–3.74(m, 1H), 3.75(s, 3H), 4.65(br s, 1H), 5.77(s, 1H), 6.62(m, 2H), 7.18–7.52(m, 9H), 7.85(d, J=7.9Hz, 1H), 7.93(d, J=7.9Hz, 1H), 8.95(br s, 1H).

Melting Point (not measured) (° C.).
Elemental Analysis
as(not measured)
Calculated:
Found:
IR (cm⁻¹) (not measured)
Mass (EI) 528 (M⁺)

-continued

NMR (ppm) (400 MHz, DMSO-d₆)
1.82–2.27(m, 7H), 2.29(s, 3H), 2.57(d, J=15.6Hz, 1H), 2.62–2.69(m, 1H), 2.70–2.81(m, 2H), 3.02(d, J=15.6Hz, 1H), 3.05–3.18(m, 2H), 3.23–3.30(m, 1H), 3.43–3.54(m, 2H), 3.62–3.68(m, 1H), 3.67(s, 3H), 5.84(s, 1H), 6.33(s, 1H), 6.75(d, J=8.3Hz, 1H), 6.83(d, J=8.3Hz, 1H), 7.38–7.48(m, 3H), 7.52–7.57(m, 1H), 7.89(d, J=8.3Hz, 1H), 8.41(d, J=8.3Hz, 1H), 8.91(br s, 1H), 12.3(s, 1H).

Melting Point 231–247 (dec) (° C.).
Elemental Analysis
as $C_{31}H_{32}N_2O_3 \cdot CH_3SO_3H \cdot 0.2H_2O$
Calculated: C, 66.92; H, 6.19; N, 4.73; S, 5.41.
Found: C, 66.84; H, 6.35; N, 4.77; S, 5.34.
IR (cm⁻¹) (KBr)
3400, 1638, 1508, 1454, 1390, 1332, 1205, 1122, 1048, 893.
Mass (FAB) 493 ((M+H)⁺).

NMR (ppm) (400 MHz, DMS)-d₆)
0.46(1H, m), 0.51(1H, m), 0.65(1H, m), 0.75(1H, m), 1.12 (1H, m), 1.87(1H, d, J=11.7Hz), 2.30(3H, s), 2.60–2.75(3H, m), 2.61(3H, s), 2.96(1H, m), 3.02(1H, d, J=16.1Hz), 3.15 (1H, m), 3.30–3.45(2H, m), 3.51(1H, d, J=20.0Hz), 3.67(3H, s), 4.11(1H, d, J=6.4Hz), 5.84(1H, s), 6.42(1H, br), 6.74 (1H, d, J=8.3Hz), 6.82(1H, d, J=8.3Hz), 7.31(1H, s), 7.47 (1H, t, J=7.3Hz), 7.57(1H, t, J=6.8Hz), 7.97(1H, d, J=8.3 Hz), 8.43(1H, d, J=8.3Hz), 8.98(1H, br), 12.17(1H, s).

Melting Point 235–250 (dec) (° C.).
Elemental Analysis
as $C_{32}H_{32}N_2O_3 \cdot CH_3SO_3H \cdot 0.6H_2O$
Calculated: C, 66.11; H, 6.25; N, 4.67; S, 5.35.
Found: C, 65.15; H, 6.41; N, 4.72; S, 5.31.
IR (cm⁻¹) (KBr)
3400, 3200, 1655, 1636, 1610, 1508, 1444, 1332, 1284, 1200, 1168, 1122, 1052, 893.
Mass (FAB) 493 ((M+H)⁺).

NMR (ppm) (500 MHz, DMSO-d₆)
0.45(1H, m), 0.50(1H, m), 0.64(1H, m), 0.74(1H, m), 1.10 (1H, m), 1.82(1H, br d, J=13.4Hz), 2.31(3H, s), 2.54(1H, d, J=15.9Hz), 2.58–2.80(2H,m), 2.91–3.2(1H, m), 2.97(1H, d, J=15.9Hz), 3.12(1H, m), 3.31(1H, dd, J=20.1, 6.7Hz), 3.39 (1H, m), 3.49(1H, d, J=20.1Hz), 3.68(3H, s), 4.11(1H, d, J=6.7 Hz), 5.75(1H, s), 6.37(1H,br s), 6.73(1H, d, J=8.5Hz), 6.81 (1H, d, J=8.5Hz), 6.97(1H, t, J=7.9Hz), 7.11(1H, dd, J=7.9, 7.3Hz), 7.35(2H, d, J=9.15Hz), 8.95(1H, br s), 11.34 (1H, s).

Melting Point >300 (dec) (° C.).
Elemental Analysis
as $C_{27}H_{28}N_2O_3 \cdot 1.05CH_3SO_3H \cdot 0.4H_2O$
Calculated: C, 62.78; H, 6.20; N, 5.22; S, 6.27.
Found: C, 62.65; H, 6.19; N, 5.20; S, 6.42.
IR (cm⁻¹) (KBr)
3252, 1636, 1510, 1456, 1328, 1191, 1122, 1044, 859, 797, 774.
Mass (FAB) 429 ((M+H)⁺).

Compound 31
Methanesulfonate
Yield: 50 (%)

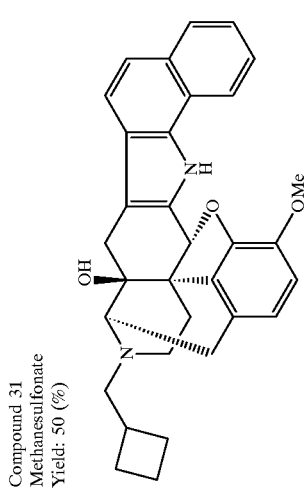

Compound 32
Methanesulfonate
Yield: 73 (%)

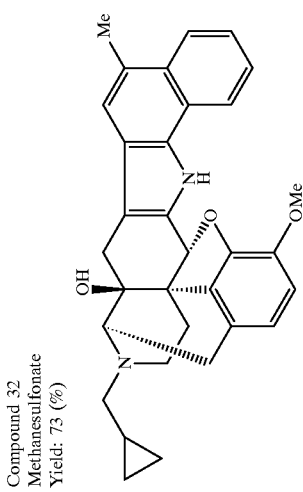

Compound 33
Methanesulfonate
Yield: 47 (%)

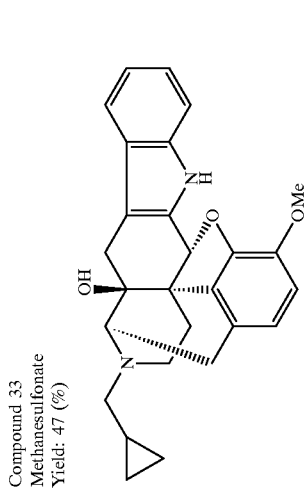

| | |
|---|---|
| Compound 34<br>Methanesulfonate<br>Yield: 64 (%)<br>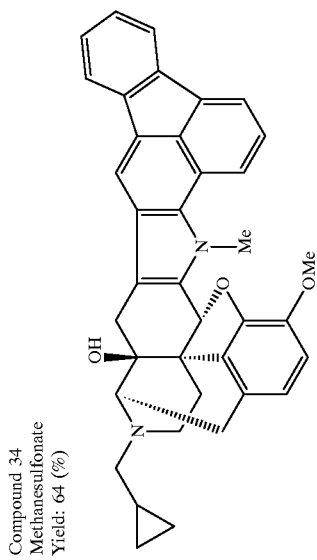 | NMR (ppm) (400 MHz, DMSO-d$_6$)<br>0.44–0.56(2H, m), 0.63–0.70(1H, m), 0.74–0.80(1H, m), 1.08–1.18(1H, m), 1.94(1H, d, J=12.2Hz), 2.31(3.75H, s), 2.64–2.81(2H, m), 2.74(1H, d, J=16.1Hz), 2.97–3.04(1H, m), 3.17(1H, d, J=11.2Hz), 3.22(1H, d, J=16.1Hz),3.33–3.46(2H, m), 3.51–3.59(3H, m), 3.70(3H, s), 4.16(1H, d, J=6.4Hz), 4.33(3H, s), 6.14(1H, s), 6.46(1H, br s), 6.78(1H, d, J=8.3 Hz), 6.84(1H, d, J=8.8Hz), 7.34–7.43(2H, m), 7.82(1H, dd, J=8.3, 7.3Hz), 7.99(1H, d, J=6.8Hz), 8.03(1H, d, J=7.3Hz), 8.14(1H, d, J=6.8Hz), 8.19(1H, s), 8.51(1H, d, J=8.3Hz), 9.04(1.3H,br s). | Melting Point 255–257 (° C.).<br>Elemental Analysis<br>as C$_{38}$H$_{34}$N$_2$O$_3$·1.3CH$_3$SO$_3$H·0.3H$_2$O<br>#Calculated: C, 67.72; H, 5.76; N, 4.02; S, 5.98.<br>Found: C, 67.64; H, 5.85; N, 4.14; S, 6.17.<br>IR (cm$^{-1}$) (KBr)<br>3400, 2914, 1738, 1636, 1502, 1452, 1396, 1261, 1118, 1050, 951, 893, 859, 797, 770, 611.<br>Mass (FAB) 566 ((M+H)$^+$). |
| Compound 35<br>Methanesulfonate<br>Yield: 81 (%)<br>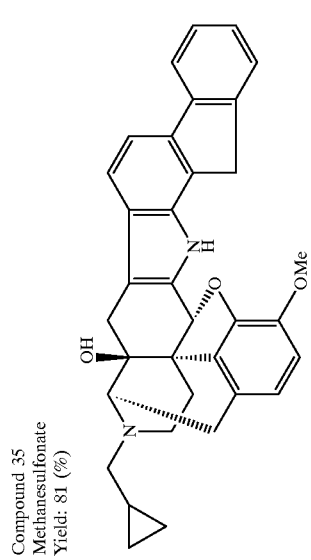 | NMR (ppm) (400 MHz, DMSO-d$_6$)<br>0.46(1H, m), 0.51(1H, m), 0.65(1H, m), 0.75(1H, m), 1.11 (1H, m), 1.87(1H, d, J=12.2Hz), 2.34(3H, s), 2.50–2.75(3H, m), 2.96(1H, m), 3.02(1H, d, J=16.1Hz), 3.14(1H, m), 3.30 (1H, m), 3.51(1H, d, J=20.0Hz), 3.69(3H, s), 3.96(1H, d, J=22.5Hz), 4.06(1H, d, J=22.5Hz), 4.12(1H, d, J=6.8Hz), 5.79(1H, s), 6.42(1H, brs), 6.74(1H, d, J=8.3Hz), 6.83(1H, d, J=8.3Hz), 7.24(1H, t, J=7.8Hz), 7.35(1H, t, J=7.8Hz), 7.37(1H, d, J=8.3Hz), 7.55(1H, d, J=6.8Hz), 7.61(1H, d, J=7.3Hz), 7.81(1H, d, J=7.3Hz), 8.98(1H, br), 11.64(1H, s). | Melting Point 250–260 (dec) (° C.),<br>Elemental Analysis<br>as C$_{34}$H$_{32}$N$_2$O$_3$·CH$_3$SO$_3$H·0.6H$_2$O<br>Calculated: C, 67.42; H,6.01; N, 4.49; S, 5.14.<br>Found: C, 67.29; H, 6.17; N, 4.60; S, 5.28.<br>IR (cm$^{-1}$) (KBr)<br>3350, 1636, 1508, 1433, 1334, 1195, 1122, 1052, 973, 891.<br>Mass (EI) 516 (M$^+$). (data of salt-free compound) |
| Compound 36<br>Yield: 87 (%)<br>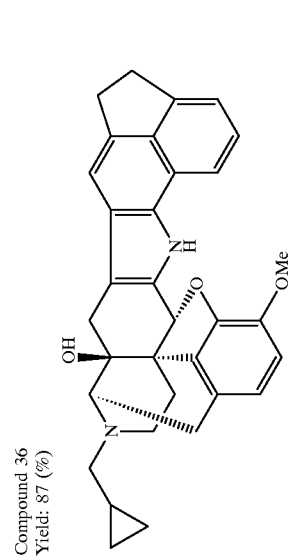 | NMR (ppm) (400 MHz, CDCl$_3$)<br>0.14–0.22(m, 2H), 0.54–0.64(m, 2H), 0.93(m, 1H), 1.84(m, 1H), 2.32(ddd, 1H, J=11.7, 11.7, 3.4Hz), 2.42–2.51(m, 3H), 2.69(d, 1H, J=15.6Hz), 2.77(dd, 1H, J=11.7, 4.4Hz), 2.85 (dd, 1H, J=18.1, 6.4Hz), 2.95(d, 1H, J=15.6Hz), 3.17(d, 1H, J=18.1Hz), 3.25–3.45(m, 5H), 3.74(s, 3H), 5.00(br s, 1H, OH), 5.78(s, 1H), 6.60(d, 1H, J=8.1Hz), 6.63(d, 1H, J=8.1 Hz), 7.20(s, 1H), 7.21(d, 1H, J=7.8Hz), 7.42(dd, 1H, J=7.8, 7.8Hz), 7.62(d, 1H, J=7.8Hz), 8.88(s, 1H, NH). | Melting Point (not measured) (° C.).<br>Elemental Analysis<br>as(not measured)<br>Calculated:<br>Found:<br>IR (cm$^{-1}$) (KBr)<br>3260, 1632, 1605, 1506, 1439, 1406, 1388, 1332, 1284, 1195, 1147, 1123, 1054, 1021, 888, 864, 791, 756.<br>Mass (EI) 504 (M$^+$) |

| | |
|---|---|
| Compound 37<br>Methanesulfonate<br>Yield: 73 (%)<br>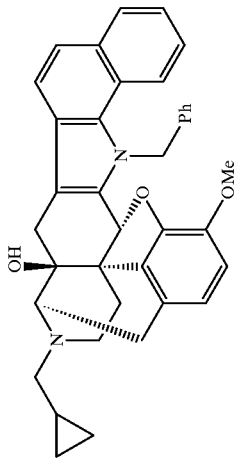 | NMR (ppm) (400 MHz, DMSO-d$_6$)<br>0.42–0.55(m, 2H), 0.61–0.70(m, 1H), 0.71–0.81(m, 1H), 1.06–1.17(m, 1H), 1.82–1.91(m, 1H), 2.32(s, 3H), 2.56–2.79 (m, 3H), 2.93–3.03(m, 1H), 3.09–3.20(m, 2H), 3.30–3.60(m, 3H), 3.50(s, 3H), 4.16(d, J=6.3Hz, 1H), 5.98(d, J=18.1Hz, 1H), 6.02(s, 1H), 6.08(d, J=18.1Hz, 1H), 6.45(br s, 1H), 6.76(d, J=8.3Hz, 1H), 6.82(d, J=8.3Hz, 1H), 7.02(m, 2H), 7.18–7.28(m, 3H), 7.30–7.37(m, 2H), 7.52(d, J=8.8Hz, 1H), 7.55(d, J=8.8Hz, 1H), 7.88–7.94(m, 1H), 8.13–8.19(m, 1H), 9.01(brs, 1H). | Melting Point 190–197 (dec) (° C.).<br>Elemental Analysis<br>as C$_{38}$H$_{36}$N$_2$O$_3$·1.15CH$_3$SO$_3$H·0.8H$_2$O<br>Calculated: C, 67.79; H, 6.13; N, 4.04; S, 5.32.<br>Found: C, 67.67; H, 6.24; N, 4.17; S, 5.42.<br>IR (cm$^{-1}$) (KBr)<br>3382, 1499, 1452, 1396, 1284, 1158, 1125, 1056, 893.<br>Mass (FAB) 569 ((M+H)$^+$). |
| Compound 38<br>Methanesulfonate<br>Yield: 57 (%)<br>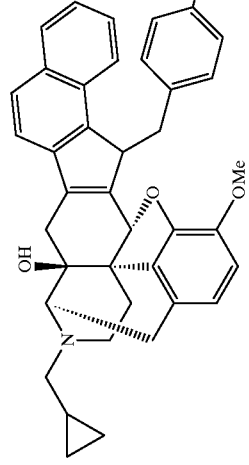 | NMR (ppm) (300 MHz, DMSO-d$_6$)<br>0.53–066(2H, m), 0.62–0.80(2H, m), 1.12(1H; m), 1.86(1H, d, J=11.3Hz), 2.30(3H, s), 2.55–2.77(3H, m), 2.99(1H, m), 3.11–3.19(2H, m), 3.31–3.45(3H, m), 3.51(3H, s), 4.16(1H, d, J=6.0Hz), 6.02(1H, s), 6.04(2H, d, J=14.0Hz), 6.46(1H, s, OH), 6.75–6.84(2H, m), 6.99–7.11(4H, m), 7.34(1H, d, J=3.3Hz), 7.36(1H, d, J=3.3Hz), 7.51–7.58(2H, m), 7.91 (1H, m), 8.15(1H, m), 9.01(1H, s). | Melting Point >200 (dec) (° C.).<br>Elemental Analysis<br>as C$_{38}$H$_{35}$FN$_2$O$_3$·CH$_3$SO$_3$H·1.2H$_2$O<br>Calculated: C, 66.50; H, 5.92; F, 2.70; N, 3.98; S, 4.55.<br>Found: C, 66.27; H, 5.91; F, 2.77; N, 3.91; S, 4.90.<br>IR (cm$^{-1}$) (KBr)<br>3400, 1636, 1607, 1510, 1439, 1396, 1201,1123, 1044, 851, 810.<br>Mass (FAB) 587 ((M+H)$^+$). |
| Compound 39<br>Methanesulfonate<br>Yield: 78 (%)<br>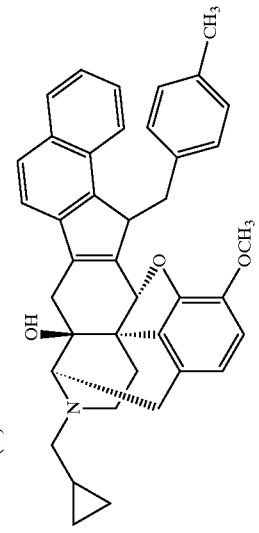 | NMR (ppm) (300 MHz, DMSO-d$_6$)<br>0.42–0.56(2H, m), 0.62–0.80(2H, m), 1.12(1H, m), 1.86(1H, d, J=11.3Hz), 2.23(3H, s), 2.30(3H, s), 2.54–2.77(3H, m), 2.98(1H, m), 3.09–3.21(2H, m), 3.31–3.57(6H, m), 4.16(1H, d, J=5.8Hz), 5.93(1H, d, J=17.9Hz), 6.00(1H, s), 6.03(1H, d, J=17.9Hz), 6.44(1H, br s), 6.76(1H, d, J=8.2Hz), 6.82 (1H, d, J=8.2Hz), 6.91(2H, d, J=8.0Hz), 7.05(2H, d, J=8.0 Hz), 7.32–7.35(2H, m), 7.52(1H, d, J=8.8Hz), 7.56(1H, d, J=8.8Hz), 7.89–7.92(1H, m), 8.15–8.19(1H, m), 9.02(1H, br s). | Melting Point 196–200 (dec) (° C.).<br>Elemental Analysis<br>as C$_{39}$H$_{38}$N$_2$O$_3$·1.05CH$_3$SO$_3$H·1.3H$_2$O<br>Calculated: C, 68.03; H, 6.39; N, 3.96; S, 4.76.<br>Found: C, 67.93; H, 6.31;N, 4.25; S, 4.89.<br>IR (cm$^{-1}$) (KBr)<br>3400, 1508, 1454, 1439, 1396, 1197, 1123, 1052, 804, 561.<br>Mass (FAB) 583 ((M+H)$^+$). |

| | | |
|---|---|---|
| Compound 40<br>Methanesulfonate<br>Yield: 76 (%) | 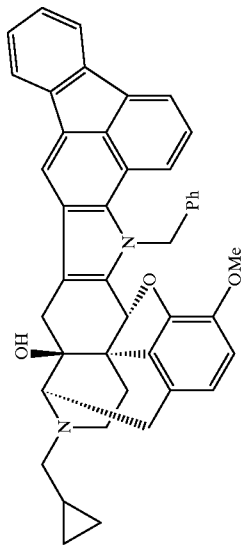 | NMR (ppm) (400 MHz, DMSO-d₆)<br>0.46–0.56(2H, m), 0.65–0.73(1H, m), 0.73–0.82(1H, m), 1.11–1.19(1H, m), 1.89(1H, d, J=12.7Hz), 2.30(3.75H, s), 2.59–2.81(2H,m), 2.85(1H, d, J=16.1Hz), 2.96–3.06(1H, m), 3.13–3.19(1H, m), 3.31(1H, d, J=16.1Hz), 3.31–3.48(2H, m), 3.53(3H, s), 3.55–3.63(1H, m), 4.18(1H, d, J=6.3Hz), 5.99 (1H, d, J=18.1Hz), 6.07(1H, s), 6.12(1H, d, J=18.1Hz), 6.52 (1H, br s), 6.77(1H, d, J=8.3Hz), 6.84(1H, d, J=8.3Hz), 7.07 (2H, d, J=7.3Hz), 7.19–7.29(1H, m), 7.25(2H, d, J=7.3Hz), 7.31–7.42(2H, m), 7.57(1H, dd, J=8.3, 7.3Hz), 8.00(2H, d, J=7.3Hz), 8.02(2H, d, J=7.3Hz), 8.04(1H, d, J=7.3Hz), 8.25 (1H, s), 9.05(1.25H, br s). | Melting Point 208–210 (° C.).<br>Elementa Analysis<br>as C₄₁H₃₈N₂O₃·1.2SCH₃SO₃H·1.1H₂O<br>Calculated: C, 69.43; H, 5.82; N, 3.58; S, 5.12.<br>Found: C, 69.51; H, 5.86; N, 3.38; S, 5.05.<br>IR (cm⁻¹) (KBr)<br>3400, 2928, 1736, 1719, 1702, 1686, 1649, 1636, 1562, 1543, 1510, 1454, 1396, 1340, 1284, 1149, 1125, 1056, 893, 774, 754.<br>Mass (FAB) 643 (M+H)⁺. |
| Compound 41<br>Methanesulfonate<br>Yield: 100 (%) | 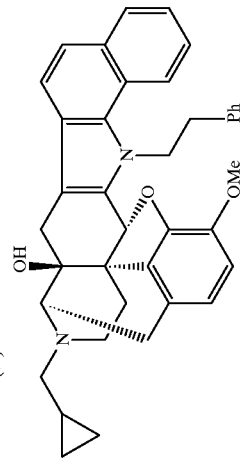 | NMR (ppm) (500 MHz, DMSO-d₆)<br>0.42–0.49(m, 1H), 0.49–0.56(m, 1H), 0.62–0.69(m, 1H), 0.72–0.81(m, 1H), 1.06–1.16(m, 1H), 1.81–1.88(m, 1H), 2.34 (s, 5.4H); 2.50–2.61(m, 1H), 2.65(d, J=16.1Hz, 1H), 2.67–2.76(m, 1H), 2.94–3.02(m, 1H), 3.12(d, J=16.1Hz, 1H), 3.10–3.26(m, 3H), 3.29–3.45(m, 2H), 3.51(d, J=20.0Hz, 1H), 3.68(s, 3H), 4.13(d, J=6.3Hz, 1H), 4.87–4.98(m, 2H), 5.81 (s, 1H), 6.34(br s, 1H), 6.76(d, J=8.3Hz, 1H), 6.84(d, J=8.3 Hz, 1H), 7.30–7.36(m, 1H), 7.40–7.58(m, 7H), 7.68–7.74(m, 1H), 8.01(d, J=7.8Hz, 1H), 8.55(d, J=7.8Hz, 1H), 8.99(br s, 1H). | Melting Point 130–137 (° C.).<br>Elemental Analysis<br>as C₃₉H₃₈N₂O₃·2.0CH₃SO₃H<br>Calculated: C, 63.55; H, 5.98; N, 3.61; S, 8.28.<br>Found: C, 63.33; H, 6.22; N, 3.82; S, 8.35.<br>IR (cm⁻¹) (KBr)<br>3400, 1607, 1506, 1441, 1394, 1284, 1193, 1156, 1123, 1054, 1021, 893.<br>Mass (EI) 582 (M⁺). (data of salt-free compound) |
| Compound 42<br>Methanesulfonate<br>Yield: 100 (%) | 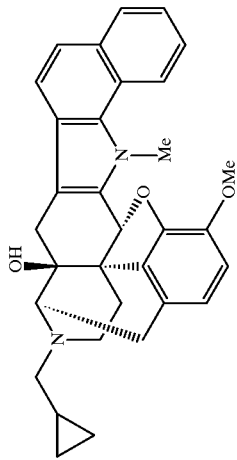 | NMR (ppm) (300 MHz, DMSO-d₆)<br>0.40–0.57(m, 2H), 0.59–0.68(m, 1H), 0.68–0.80(m, 1H), 1.04–1.18(m, 1H), 1.85–1.95(m, 1H), 2.29(s, 3H), 2.60–2.81 (m, 2H), 2.64(d, J=15.7Hz, 1H), 2.90–3.02(m, 1H), 3.09(d, J=15.7Hz, 1H), 3.11–3.20(m, 1H), 3.26–3.50(m, 2H), 3.52(d, J=20.0Hz, 1H), 3.69(s, 1H), 4.10–4.16(m, 1H), 4.32(s, 1H), 6.10(s, 1H), 6.39(s, 1H), 6.74(d, J=8.5Hz, 1H), 6.82(d, J=8.5Hz, 1H), 7.43–7.52(m, 3H), 7.55–7.63(m, 1H), 7.97(d, J=9Hz, 1H), 8.62(d, J=8.5Hz, 1H), 9.00(br s, 1H). | Melting Point 300–305 (dec) (° C.).<br>Elemental Analysis<br>as C₃₂H₃₂N₂O₃·CH₃SO₃H·0.5H₂O<br>Calculated: C, 66.31; H, 6.24; N, 4.69; S, 5.36.<br>Found: C, 66.47; H, 6.29; N, 4.58; S,5.22.<br>IR (cm⁻¹) (KBr)<br>3400, 1499, 1437, 1398, 1257, 1019.<br>Mass (EI) 492 (M⁺). (data of salt-free compound) |

| | |
|---|---|
| Compound 43<br>Methanesulfonate<br>Yield: 96 (%)<br>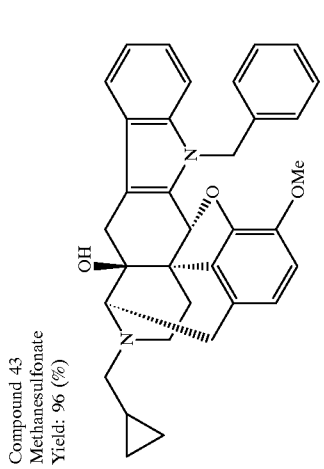 | NMR (ppm) (400 MHz, DMSO-$d_6$)<br>0.42–0.54(2H, m), 0.61–0.79(2H, m), 1.11(1H, m), 1.87(1H, d, J=11.7Hz), 2.29(3H, s), 2.57–2.77(2H, m), 2.62(1H, d, J=16.1Hz), 2.98(1H, m), 3.04(1H, d, J=16.1Hz), 3.14(1H, m), 3.31–3.43(2H, m), 3.51(1H, m), 3.65(3H, s), 4.13(1H, d, J=6.4Hz), 5.40(1H, d, J=16.6Hz), 5.65(1H, d, J=16.6Hz), 5.96(1H, s), 6.40 (1H, s), 6.77(1H, d, J=8.3Hz), 6.85(1H, d, J=8.3Hz), 7.00(1H, m), 7.09(1H, m), 7.22–7.31(6H, m), 7.40(1H, d, J=7.8Hz), 8.98(1H, br s).<br>Melting Point 171–176 (dec) (°C).<br>Elemental Analysis<br>as $C_{34}H_{34}N_2O_3 \cdot CH_3SO_3H \cdot 1.2H_2O$<br>Calculated: C, 66.06; H, 6.40; N, 4.40; S, 5.04.<br>Found: C, 66.03; H, 6.41; N, 4.43; S, 5.12.<br>IR ($cm^{-1}$)(KBr)<br>3400, 1510, 1452, 1197, 1052, 779, 741.<br>Mass (FAB) 519 ((M+H)$^+$). |
| Compound 44<br>Hydrochloride<br>Yield: 117 (%)<br>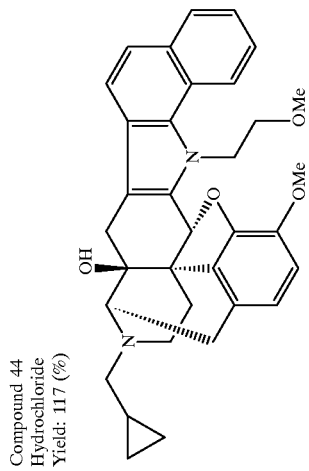 | NMR (ppm) (500 MHz, DMSO-$d_6$)<br>0.42–0.49(m, 1H), 0.49–0.56(m, 1H), 0.60–0.69(m, 1H), 0.71–0.79(m, 1H), 1.09–1.18(m, 1H), 1.86–1.93(m, 1H), 2.59–2.77(m, 2H), 2.62(d, J=15.6Hz, 1H), 2.96–3.04(m, 1H), 3.10–3.18(m, 1H), 3.14(d, J=15.6Hz, 1H), 3.30–3.44(m, 2H), 3.32(s, 3H), 3.51(d, J=20.0Hz, 1H), 3.70(s, 3H), 3.81–3.95 (m, 2H), 4.18(d, J=6.4Hz, 1H), 4.86–4.99(m, 2H), 6.10(s, 1H), 6.46(s, 1H), 6.75(d, J=8.3Hz, 1H), 6.83(d, J=8.3Hz, 1H), 7.43–7.55(m, 3H), 7.57–7.63(m, 1H), 7.98(d, J=7.8Hz, 1H), 8.43(d, J=7.8Hz, 1H), 9.05(br s, 1H).<br>Melting Point 185–190 (°C).<br>Elemental Analysis<br>as $C_{34}H_{36}N_2O_4 \cdot 1.17HCl \cdot 0.2H_2O$<br>Calculated: C, 70.06; H, 6.50; N, 4.81; Cl, 7.12.<br>Found: C, 69.83; H, 6.63; N, 5.02; Cl, 6.96.<br>IR ($cm^{-1}$) (KBr)<br>3400, 1609, 1506, 1439, 1394, 1284, 1195, 1160, 1123, 1054, 1021, 893.<br>Mass (EI) 536 (M$^+$). (data of salt-free compound) |
| Compound 45<br>Methanesulfonate<br>Yield: 47 (%)<br>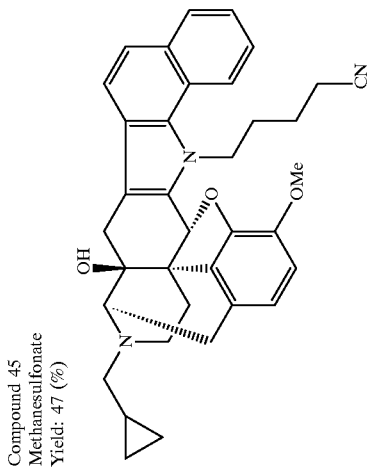 | NMR (ppm) (300 MHz, DMS)-$d_6$)<br>0.41–0.58(m, 2H), 0.60–0.70(m, 1H), 0.70–0.81(m, 1H), 1.50–1.21(m, 1H), 1.73–2.07(m, 5H), 2.30(s, 3,6H), 2.53–2.81(m, 5H), 2.91–3.05(m, 1H), 3.10(d, J=16.5Hz, 1H), 3.12–3.22(m, 1H), 3.25–3.57(m, 3H), 3.69(s, 3H), 4.13(d, J=6.1Hz, 1H), 4.65–4.85(m, 2H), 6.08(s, 1H), 6.40 (br s, 1H), 6.75(d, J=8.5Hz, 1H), 6.83(d, J=8.5Hz, 1H), 7.43–7.55(m, 3H), 7.57–7.67(m, 1H), 7.97(d, J=8.2Hz, 1H), 8.39(d, J=8.2Hz), 1H), 9.00(br s, 1H).<br>Melting Point 169–179 (°C)<br>Elemental Analysis<br>as $C_{36}H_{37}N_3O_3 \cdot 1.2CH_3SO_3H \cdot 0.2H_2O$<br>Calculated: C, 65.84; H, 6.27; N, 6.19; S, 5.67.<br>Found: C, 66.02; H, 6.47; N, 6.25; S, 5.39.<br>IR ($cm^{-1}$) (KBr)<br>3400, 2926, 2250, 1636, 1609, 1506, 1452, 1364, 1282, 1125, 1054, 1023, 891, 851.<br>Mass (EI) 559 (M$^+$). (data of salt-free compound) |

-continued

| | NMR (ppm) | |
|---|---|---|
| Compound 46
Methanesulfonate
Yield: 50 (%) | NMR (ppm) (300 MHz, DMSO-$d_6$) 0.40–0.58(m, 2H), 0.59–0.70(m, 1H), 0.70–0.83(m, 1H), 1.03–1.20(m, 1H), 1.84–1.99(m, 1H), 2.10–2.29(m, 2H), 2.30 (s, 3.6H), 2.64(d, J=16.4Hz, 1H), 2.65–2.91(m, 4H), 2.91–3.03(m, 1H), 3.08(d, J=16.4Hz, 1H), 3.11–3.23(m, 1H), 3.26–3.50(m, 3H), 3.69(s, 3H), 4.14(d, J=5.5Hz, 1H), 4.66–4.90(m, 2H), 6.11(s, 1H), 6.41(br s, 1H), 6.76(d, J=8.0 Hz, 1H), 6.84(d, J=8.0Hz, 1H), 7.40–7.68(m, 4H), 7.99(d, J=7.7Hz, 1H), 8.42(d, J=8.8Hz, 1H), 8.90(br s, 1H). | Melting Point 175–182 (° C.).
Elemental Analysis
as $C_{35}H_{35}N_3O_3 \cdot 1.2CH_3SO_3H \cdot 0.3H_2O$
Calculated: C, 65.24; H, 6.11; N, 6.31; S, 5.77.
Found: C, 65.31; H, 6.29; N, 6.36; S, 5.60.
IR (cm$^{-1}$) (KBr) (data of salt-free compound)
3388, 2932, 2246, 1636, 1611, 506, 1452, 1392, 1282, 1160, 1125, 1054, 1021, 893.
Mass (EI) 545 (M$^+$) (data of salt-free compound) |
| Compound 47
Methanesulfonate
Yield: 99 (%) | NMR (ppm) (300 MHz, DMSO-$d_6$) 0.40–0.58(m, 2H), 0.58–0.70(m, 1H), 0.70–0.80(m, 1H), 1.04–1.18(m, 1H), 1.86–1.95(m, 1H), 2.11–2.25(m, 2H), 2.31 (s, 3.8H), 2.62(s, 3H), 2.57–2.92(m, 5H), 2.93–3.23(m, 3H), 3.24–3.58(m, 3H), 3.69(s, 3H), 4.08–4.16(m, 1H), 4.66–4.87 (m2H), 6.09(s, 1H), 6.37(br s, 1H), 6.75(d, J=8.2Hz, 1H), 6.84(d, J=8.2Hz, 1H), 7.36(s, 1H), 7.50–7.58(m, 1H), 7.60–7.68(m, 1H), 8.06(d, J=7.1Hz, 1H), 8.44(d, J=7.1Hz, 1H), 9.00(br s, 1H). | Melting Point 175 (° C.).
Elemental Analysis
as $C_{35}H_{37}N_3O_3 \cdot 1.4CH_3SO_3H \cdot 0.1H_2O$
Calculated: C, 64.54; H, 6.20; N, 6.04; S, 6.45.
Found: C, 64.58; H, 6.27; N, 6.04; S, 6.32.
IR (cm$^{-1}$) (KBr)
3404, 2250, 1760, 1638, 1599, 1508, 1491, 1452, 1203, 1122, 1089.
Mass (EI) 559 (data of salt-free compound) |
| Compound 48
Methanesulfonate
Yield: 96 (%) | NMR (ppm) (300 MHz, CD$_3$OD) 0.40–0.46(m, 2H), 0.58–0.75(m, 2H), 0.96–1.08(m, 1H), 1.84–1.92(m, 1H), 2.32(q, J=7.1Hz, 2H), 2.52–2.60(m, 2H), 2.64(s, 3H), 2.68(s, 3H), 2.64–2.74(m, 2H), 2.70–3.24(m, 6H), 3.31–3.40(m, 1H), 3.77(s, 3H), 4.72–5.02(m, 2H), 5.95 (s, 1H), 6.75(d, J=8.5Hz, 1H), 6.82(d, J=8.2Hz, 1H), 7.40(s, 1H), 8.06(d, J=8.2Hz, 1H), 8.43(d, J=8.2Hz, 1H). | Melting Point 200 (° C.).
Elemental Analysis
as $C_{35}H_{39}N_3O_3 \cdot 1.4SCH_3SO_3H \cdot 0.6EtOAc$
Calculated: C, 62.89; H, 6.74; N, 5.66; S, 6.27.
Found: C, 62.71; H, 6.56; N, 6.01; S, 6.08.
IR (cm$^{-1}$) (KBr)
3410, 1655, 1636, 1508, 1450, 1386, 1207, 1052.
Mass (EI) 549 (M$^+$) (data of salt-freecompound) |

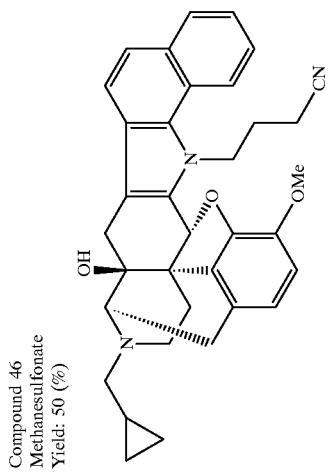
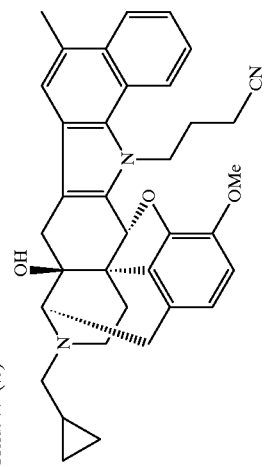
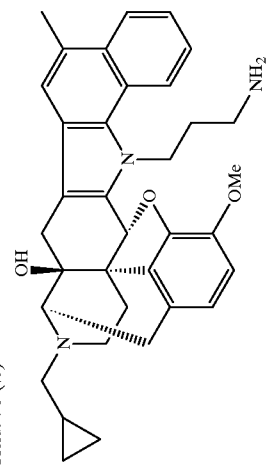

-continued

Compound 49
Yield: 99 (%)

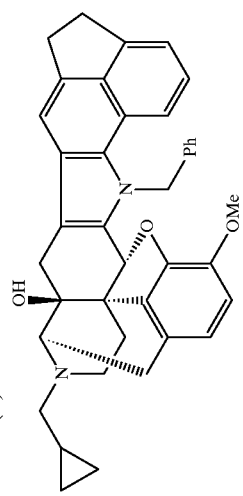

NMR (ppm) (400 MHz, CDCl₃)
0.17(m, 2H), 0.58(m, 1H), 0.91(m, 1H), 1.77(m, 1H), 2.29 (m, 1H), 2.37(m, 1H), 2.41–2.48(m, 2H), 2.73(m, 1H), 2.79 (d, 1H, J=15.4Hz), 2.86(dd, 1H, J=18.6, 6.4Hz), 3.00(d, 1H, J=15.4Hz), 3.17(d, 1H, J=18.6Hz), 3.30–3.40(m, 5H), 3.62 (s, 3H), 4.93(br s, 1H, OH), 5.74(s, 1H), 5.95(d, 1H, J=17.3 Hz), 6.03(d, 1H, J=17.3Hz), 6.59(d, 1H, J=8.3Hz), 6.62(d, 1H, J=8.3Hz), 7.06(d, 2H, J=7.3Hz), 7.13(d, 1H, J=6.8Hz), 7.17–7.27(m, 4H), 7.37(s, 1H), 7.63(d, 1H, J=8.3Hz).

Melting Point (not measured) (° C.).
Elemental Analysis
as (not measured)
Calculated:
Found:
IR (cm⁻¹) (KBr)
3376, 1605, 1499, 1450, 1412, 1336, 1284, 1259, 1193, 1164, 1122, 1054, 1019, 971, 917, 890, 864, 791, 748.
Mass (EI) 594 (M⁺)

Compound 50
Yield: 87 (%)

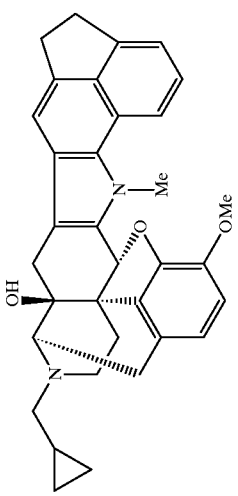

NMR (ppm) (400 MHz, CDCl₃)
0.18(m, 2H), 0.58(m, 2H), 0.92(m, 1H), 1.86(m, 1H), 2.32 (m, 1H), 2.39–2.52(m, 3H), 2.72(d, 1H, J=15.1Hz), 2.75(m, 1H), 2.84(dd, 1H, J=18.6, 6.4Hz), 3.16(d, 1H, J=18.6Hz), 3.25–3.44(m, 5H), 3.76(s, 3H), 4.32(s, 3H), 4.95(br s, 1H, OH), 5.85(s, 1H), 6.59(d, 1H, J=8.3Hz), 6.63(d, 1H, J=8.3 Hz), 7.22(d, 1H, J=6.8Hz), 7.25(s, 1H), 7.44(d, 1H, J=8.3, 6.8Hz), 8.10(d, 1H, J=8.3Hz).

Melting Point (not measured) (° C.).
Elemental Analysis
as (not measured)
Calculated:
Found:
IR (cm⁻¹) (KBr)
3378, 1632, 1620, 1605, 1508, 1450, 1404, 1379,1284, 1265, 1193, 1164, 1122, 1054, 890, 789, 750.
Mass (EI) 518 (M⁺)

Compound 51
Methanesulfonate
Yield: 54 (%)

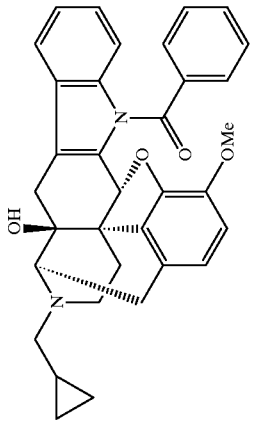

NMR (ppm) (400 MHz, DMSO-d₆)
0.48(m, 1H), 0.51(m, 1H), 0.66(m, 1H), 0.76(m, 1H), 1.12 (m, 1H), 1.82(m, 1H), 2.30(s, 3H), 2.56–2.78(m,2H), 2.63(d, 1H, J=17.3Hz), 2.99(m, 1H), 3.08(d, 1H, J=17.3Hz), 3.14 (m, 1H), 3.27–3.44(m, 2H), 3.52(d, 1H, J=20.0Hz), 3.63(s, 3H), 4.17(d, 1H, J=6.4Hz), 6.09(s, 1H), 6.61(1H, d, J=8.3 Hz), 6.65(br s, 1H, OH), 6.75(1H, d, J=8.3Hz), 6.81(1H, d, J=8.3Hz), 7.11(1H, dd, J=8.3, 7.3Hz), 7.18(1H, dd, J=7.3, 7.3Hz), 7.47(1H, d, J=7.8Hz), 7.58–7.69(m, 4H), 7.78(m, 1H), 9.04(m, 1H, NH⁺).

Melting Point >180 (dec) (° C.)
Elemental Analysis
as C₃₄H₃₂N₂O₄·CH₃SO₃H·0.6H₂O
Calculated: C, 65.55; H, 5.88; N, 4.37; S, 5.00.
Found: C, 65.50; H, 5.87; N, 4.40; S, 5.30.
IR (cm⁻¹) (KBr)
3418, 1686, 1638, 1607, 1508, 1456, 1412, 1357, 1292, 1203, 1176, 1123, 1042, 932, 891, 748.
Mass (FAB) 533 ((M+H)⁺).

-continued

| | NMR (ppm) | Melting Point, Elemental Analysis, IR, Mass |
|---|---|---|
| Compound 52<br>Methanesulfonate<br>Yield: 40 (%)<br>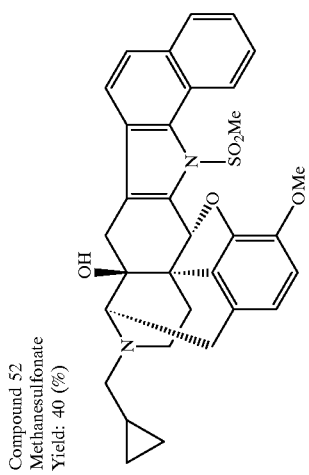 | NMR (ppm) (300 MHz, DMSO-d$_6$)<br>0.42–0.57(2H, m), 0.61–0.80(2H, m), 1.12(1H, m), 1.89(1H, m), 2.30(3H, s), 2.62(1H, d, J=17.0Hz), 2.62–2.77(2H, m), 3.00(1H, m), 3.16(1H, m), 3.17(1H, d, J=17.0Hz), 3.27–3.58 (3H, m), 3.68(3H, s), 3.78(3H, s), 4.17(1H, d, J=5.8Hz), 6.29(1H, s), 6.69–6.80(1H, br s), 6.78(2H, m), 7.52–7.65 (3H, m), 7.86(1H, d, J=8.2Hz), 8.04(1H, m), 8.73(1H, d, J=8.8Hz), 9.08(1H, br s). | Melting Point >190 (dec) (° C.).<br>Elemental Analysis<br>as C$_{32}$H$_{32}$N$_2$O$_5$S.1.05CH$_3$SO$_3$H.H$_2$O<br>Calculated: C, 58.76; H, 5.70; N, 4.15; S, 9.73.<br>Found: C, 58.48; H:5.66; N, 4.21; S, 10.02.<br>IR (cm$^{-1}$) (KBr)<br>3400, 1638, 1510, 1456, 1365, 1207, 1174, 1050, 553.<br>Mass (FAB) 557(M+H)$^+$). |
| Compound 53<br>Methanesulfonate<br>Yield: 6 (%)<br>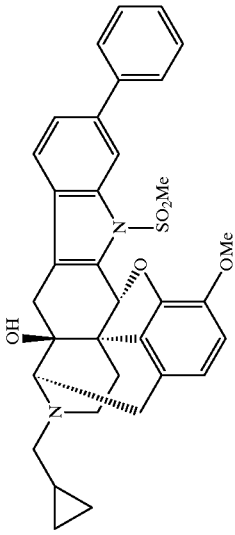 | NMR (ppm) (400 MHz, DMSO-d$_6$)<br>0.46(1H, m), 0.52(1H, m), 0.65(1H, m), 0.75(1H, m), 1.10 (1H, m), 1.91(1H, m), 2.30(2.85H, s), 2.50–2.75(3H, m), 2.95–3.20(3H, m), 3.30–3.55(3H, m), 3.65(3H, s), 3.69(3H, s), 4.17(1H, m), 6.11(1H, s), 6.67(1H, s), 6.78(1H, d, J=7.8 Hz), 6.87(1H, d, J=7.8Hz), 7.39(1H, t, J=7.3Hz), 7.50(2H, t, J=7.3Hz), 7.56(1H, d, J=7.3Hz), 7.61(1H, d, J=8.3Hz) 7.68(2H, d, J=7.3Hz), 8.18(1H, s), 9.05(0.95H, br). | Melting Point 200–210 (dec) (° C.).<br>Elemental Analysis<br>as C$_{34}$H$_{34}$N$_2$O$_5$S.0.95CH$_3$SO$_3$H.0.2Et$_2$O<br>Calculated: C, 62.34; H, 5.82; N, 4.07; S, 9.08.<br>Found: C, 62.33; H, 5.63; N, 4.27; S, 8.90.<br>IR (cm$^{-1}$) (KBr)<br>3400, 1638, 1508, 1458, 1421, 1367,1270, 1166, 1123, 1054, 984, 888.<br>Mass (EI) 582 (M$^+$). (data of salt-free compound) |
| Compound 54<br>Methanesulfonate<br>Yield: 66 (%)<br>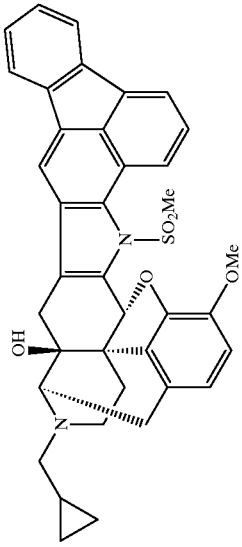 | NMR (ppm) (400 MHz, DMSO-d$_6$)<br>0.45–0.56(2H, m), 0.64–0.71(1H, m), 0.78–0.81(1H, m), 1.11–1.19(1H, m), 1.93(1H, d, J=10.8Hz), 2.31(3.6H, s), 2.67–2.77(3H, m), 3.00–3.07(1H, m), 3.18–3.47(4H, m), 3.56 (1H, d, J=20.5Hz), 3.68(3H, s), 3.92(3H, s), 4.19 9H, d, J=6.4Hz), 6.33(1H, s), 6.77(1H, d, J=8.3Hz), 6.84(1H, d, J=8.3Hz), 7.39–7.46(2H, m), 7.80–7.82(1H, m), 7.99–8.04 (2H, m), 8.16(1H, d, J=6.8Hz), 8.22(1H, s), 8.81(1H, d, J=8.8Hz), 9.12(1.2H, s br). | Melting Point 255 (dec) (° C.).<br>Elemental Analysis<br>as C$_{38}$H$_{34}$N$_2$O$_3$S.1.2CH$_3$SO$_3$H.1.5H$_2$O<br>Calculated: C, 60.90; H, 5.45; N, 3.62; S, 9.15.<br>Found: C, 60.79; H, 5.33; N, 3.74; S, 9.15.<br>IR (cm$^{-1}$)(KBr)<br>3400, 1702, 1638, 1560, 1543, 1510, 1450, 1363, 1199, 1176, 1125, 1050, 967, 895, 779, 756.<br>Mass (FAB) 630 ((M+H)$^+$). |

| | | |
|---|---|---|
| Compound 55<br>Methanesulfonate<br>Yield: 66 (%)<br>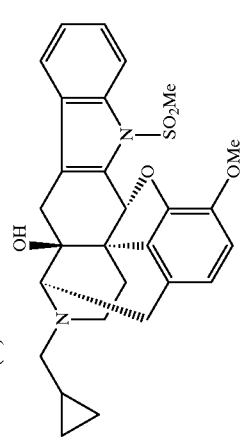 | NMR (ppm) (300 MHz, DMSO-$d_6$)<br>0.39–0.56(2H, m), 0.59–0.80(2H, m), 1.04–1.17(1H, m),<br>1.91(1H, d, J=10.7Hz), 2.30(3H, s), 2.50–2.81(3H, m),<br>2.94–3.03(1H, m), 3.02(1H, d, J=17.3Hz), 3.15(1H, br d,<br>J=9.6Hz), 3.24–3.52(3H, m), 3.56(3H, s), 3.69(3H, s), 4.15(1H,<br>d, J=6.0Hz), 6.10(1H, s), 6.23(1H, s), 6.78(1H, d, J=8.5Hz),<br>6.87(1H, d, J=8.5Hz), 7.31(1H, t, J=7.1Hz), 7.42(1H, dt, J=1.3,<br>7.8Hz), 7.49(1H, d, J=7.4Hz), 7.96(1H, d, J=8.2Hz), 9.04(1H,<br>br s). | Melting Point 270 (dec) (° C.).<br>Elemental Analysis<br>as $C_{29}H_{30}N_2O_5S.CH_3SO_3H.1.1H_2O$<br>Calculated: C, 55.95; H, 5.86; N, 4.50; S, 10.30.<br>Found: C, 55.78; H, 5.77; N, 4.67; S, 10.38.<br>IR (cm$^{-1}$) (KBr)<br>3418, 1510, 1454, 1365, 1209, 1197, 1174, 1154, 1052,<br>775, 538.<br>Mass (EI) 506 (M$^+$) (data of salt-free compound) |
| Compound 56<br>Methanesulfonate<br>Yield: 48 (%)<br>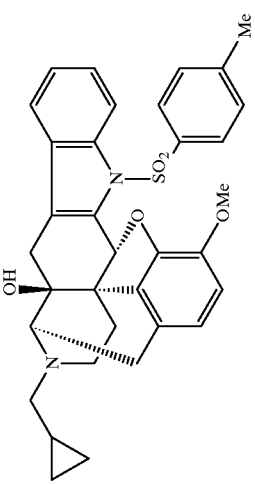 | NMR (ppm) (300 MHz, DMSO-$d_6$)<br>0.38–0.57(2H, m), 0.57–0.80(2H, m), 1.02–1.17(1H, m),<br>1.95(1H, d, J=12.1Hz), 2.34(5.4H, s), 2.36(3H, s),<br>2.45–2.55(1H, m), 2.60–2.83(2H, m), 2.91–3.05(2H, m),<br>3.11–3.52(3H, m), 3.53(1H, d, J=20.0Hz), 3.82(3H, s),<br>4.13(1H, d, J=6.6Hz), 6.25(1H, s), 6.51(1H, br s), 6.78(1H, d,<br>J=8.2Hz), 6.90(1H, d, J=8.2Hz), 7.22–7.30(1H, m),<br>7.33–7.47(4H, m), 7.97(1H, d, J=8.2Hz), 8.28(2H, d, J=8.2Hz),<br>9.04(1H, br s). | Melting Point 140 (dec) (° C.).<br>Elemental Analysis<br>as $C_{34}H_{34}N_2O_5S.1.8CH_3SO_3H.0.8H_2O$<br>Calculated: C, 55.83; H, 5.60; N, 3.64; S, 11.66.<br>Found: C, 55.58; H, 5.70; N, 3.84; S, 11.86.<br>IR (cm$^{-1}$) (KBr)<br>3414,1638, 1510, 1454, 1369, 1210, 1195, 1176, 1125,<br>1060, 785, 665, 578, 561, 538.<br>Mass (EI) 582 (M$^+$) (data of salt-free compound) |
| Compound 57<br>Methanesulfonate<br>Yield: 42 (%)<br>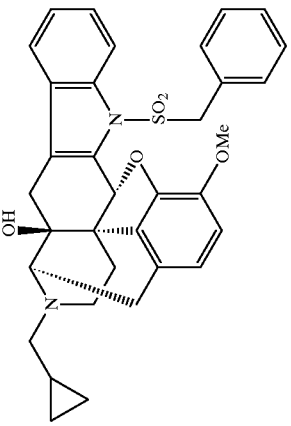 | NMR (ppm) (300 MHz, DMSO-$d_6$)<br>0.40–0.58(2H, m), 0.58–0.81(2H, m), 1.04–1.17(1H, m),<br>1.96(1H, d, J=11.5Hz), 2.32(4.2H, s), 2.57–2.84(3H, m),<br>2.95–3.06(2H, m), 3.18(1H, br d, J=11.0Hz), 3.30–3.49(2H, m),<br>3.49–3.63(1H, m), 3.61(3H, s), 4.16(1H, d, J=6.6Hz), 5.15(1H,<br>d, J=13.6Hz), 5.23(1H, d, J=13.6Hz), 6.14(1H, s), 6.62(1H, br<br>s), 6.84(1H, d, J=8.5Hz), 6.95(1H, d, J=8.5Hz), 7.00–7.25(7H,<br>m), 7.28(1H, d, J=8.2Hz), 7.36(1H, d, J=7.7Hz), 9.07(1H, br s). | Melting Point 155 (dec) (° C.).<br>Elemental Analysis<br>as $C_{34}H_{34}N_2O_5S.1.4CH_3SO_3H.0.9H_2O$<br>Calculated: C, 57.97; H, 5.69; N, 3.82; S, 10.49.<br>Found: C, 57.77; H, 5.75; N, 3.96; S, 10.76.<br>IR (cm$^{-1}$)(KBr)<br>3430, 1638, 1611, 1508, 1454, 1369, 1199, 1170, 1151,<br>1123, 1052, 785, 534.<br>Mass (EI) 582 (M$^+$) (data of salt-free compound) |

-continued

| | | |
|---|---|---|
| Compound 58<br>Methanesulfonate<br>Yield: 53 (%)<br>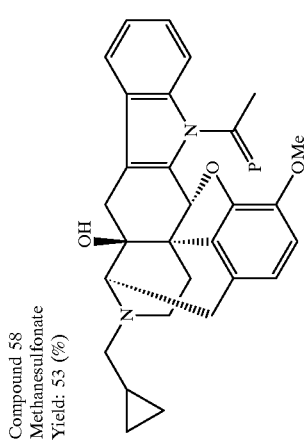 | NMR (ppm) (400 MHz, DMSO-d$_6$)<br>0.38–0.56(2H, m), 0.59–0.79(2H, m), 1.03–1.17(1H, m), 1.88(1H, d, J=11.2Hz), 2.29(3.3H, s), 2.56(1H, d, J=17.1Hz), 2.58–2.77(2H, m), 2.92(3H, s), 2.93–3.03(1H, m), 3.01(1H, d, J=17.1Hz), 3.15(1H, br d, J=10.3Hz), 3.24–3.46(2H, m), 3.51(1H, d, J=20.0Hz), 3.68(3H, s), 4.14(1H, d, J=6.3Hz), 6.29(1H, s), 6.48(1H, s), 6.75(1H, d, J=8.3Hz), 6.82(1H, d, J=8.3Hz), 7.28(1H, t, J=7.3Hz), 7.39(1H, t, J=7.3Hz), 7.45(1H, d, J=7.3Hz), 8.15(1H, d, J=8.3Hz), 9.02(1H, br s). | Melting Point 185 (dec) (° C.).<br>Elemental Analysis<br>as C$_{29}$H$_{30}$N$_2$O$_4$·1.1CH$_3$SO$_3$H·0.8H$_2$O·0.2Et$_2$O<br>Calculated: C, 61.25; H, 6.24; N, 4.68; S, 5.90.<br>Found: C, 61.26; H, 6.20; N, 4.86; S, 5.94.<br>IR (cm$^{-1}$) (KBr)<br>3426, 1698, 1510, 1454, 1377, 1209, 1195, 1052.<br>Mass (FAB) 471 ((M+H)$^+$). |
| Compound 59<br>Methanesulfonate<br>Yield: 77 (%)<br>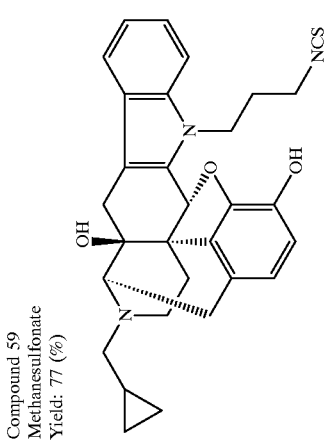 | NMR (ppm) (400 MHz, DMSO-d$_6$)<br>0.45(m, 1H), 0.49(m, 1H), 0.64(m, 1H), 0.73(m, 1H), 1.10.(m, 1H), 1.86(br d, 1H, J=11.2Hz), 2.19(m, 1H), 2.27(m, 1H), 2.30(s, 3H), 2.56(d, 1H, J=16.1Hz), 2.63(m, 1H), 2.72(m, 1H), 2.95(m, 1H), 2.97(d, 1H, J=16.1Hz), 3.14(m, 1H), 3.26(dd, 1H, J=20.0, 6.8Hz), 3.39(m, 1H), 3.45(d, 1H J=20.0Hz), 3.77(dt, 1H, J=14.6, 6.8Hz), 3.86(dt, 1H, J=14.6, 6.8Hz), 4.09(d, 1H, J=6.4Hz), 4.37(br t, 2H, J=7.3Hz), 5.91 (s, 1H), 6.33(br s, 1H, OH), 6.61(d, 1H, J=8.1Hz), 6.64(d, 1H, J=8.1Hz), 7.04(br t, 1H, J=7.6Hz), 7.21(br t, 1H, J=7.6 Hz), 7.39(d,1H, J=7.8Hz), 7.49(d, 1H, J=8.3Hz), 8.92(br s, 1H, NH$^+$), 9.23(br s, 1H, CH). | Melting Point 135–180 (° C.).<br>Elemental Analysis<br>as C$_{40}$H$_{39}$N$_3$O$_4$·1.05MeSO$_3$H·1.0 H$_2$O<br>Calculated: C, 66.21; H, 6.12; N, 5.64; S, 4.52.<br>Found: C, 66.16; H, 6.14; N, 5.73; S, 4.69.<br>IR (cm$^{-1}$) (KBr)<br>3380, 3254, 2188, 2116, 1649, 1638, 1628, 1508, 1644, 1433, 1377, 1330, 1189, 1116, 1044, 949, 924, 777, 746.<br>Mass (FAB) 514 ((M+H)$^+$). |
| Compound 60<br>Methanesulfonate<br>Yield: 69 (%)<br>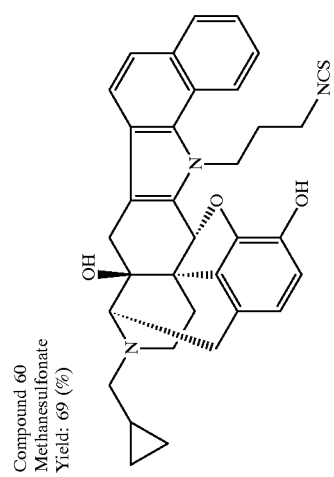 | NMR (ppm) (400 MHz, DMSO-d$_6$)<br>0.47(m, 1H), 0.50(m, 1H), 0.65(m, 1H), 0.74(m, 1H), 1.12 (m, 1H), 1.90(br d, 1H, J=12.2Hz), 2.26(m, 1H), 2.29(s, 3H), 2.38(m, 1H), 2.64(d, 1H, J=16.1Hz), 2.67(m, 1H), 2.76 (m, 1H), 2.96(m, 1H), 3.07(d, 1H, J=16.1Hz), 3.16(br d, 1H, J=10.2Hz), 3.29(dd, 1H, J=20.0, 6.8Hz), 3.39(m, 1H), 3.48 (d, 1H, J=20.0Hz), 3.93–4.07(m, 2H), 4.12(d, 1H, J=6.3Hz), 4.74–4.92(m, 2H), 6.02(d, 1H), 6.38(s, 1H, OH), 6.62(d, 1H, J=8.1Hz), 6.64(d, 1H, J=8.1Hz), 7.46–7.56(m, 3H), 7.65(br t, 1H, J=7.6Hz), 7.99(d, 1H, J=7.8Hz), 8.43(d, 1H, J=8.8 Hz), 8.96(br s, 1H, NH$^+$), 9.25(br s, 1H, OH). | Melting Point >205 (dec) (° C.).<br>Elemental Analysis<br>as C$_{34}$H$_{33}$N$_3$O$_3$S·MeSO$_3$H·1.0 H$_2$O<br>Calculated C, 62.02; H, 5.80; N, 6.20; S, 9.46.<br>Found: C, 62.07; H, 5.86; N, 6.12; S, 9.51.<br>IR (cm$^{-1}$) (KBr)<br>3392, 3280, 2188, 2114, 1638, 1620, 1058, 1466, 1423, 1396, 1379, 1328, 1180, 1114, 1046, 853, 808, 779, 748.<br>Mass (FAB) 564 (M+H)$^+$). |

-continued

| | | |
|---|---|---|
| Compound 61<br>Hydrochloride<br>Yield: 67 (%)<br>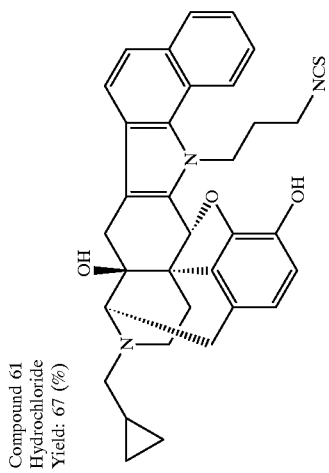 | NMR (ppm) (400 MHz, DMSO-$d_6$)<br>0.43(m, 1H), 0.51(m, 1H), 0.63(m, 1H), 0.73(m, 1H), 1.11 (m, 1H), 1.78(br d, 1H, J=11.2Hz), 2.03–2.22(m, 2H), 2.54 (d, 1H, J=16.1Hz), 2.58–2.78(m, 2H), 2.97(m, 1H), 2.99(d, 1H, J=16.1Hz), 3.11(m, 1H), 3.22–3.50(m, 5H), 4.12(d, 1H, J=5.9Hz), 4.28–4.43(2H, m), 5.90(s, 1H), 6.40(s, 1H, OH), 6.60(d, 1H, J=8.1Hz), 6.63(d, 1H, J=8.1Hz), 7.01(br t, 1H, J=7.3Hz), 7.16(br t, 1H, J=7.3Hz), 7.37(d, 1H, J=7.8Hz), 7.45–7.57(m, 4H), 7.88(br d, 2H, J=6.8Hz), 8.66(t, 1H, J=5.4Hz, CONH), 8.99(br s, 1H, NH$^+$), 9.23(s, 1H, OH). | Melting Point >195 (dec) (° C.).<br>Elemental Analysis<br>as $C_{36}H_{37}N_3O_4 \cdot HCl \cdot 0.9H_2O$<br>Calculated: C, 68.81; H, 6.38; Cl, 5.64; N, 6.69.<br>Found: C, 68.87; H, 6.45; Cl, 5.63; N, 6.73.<br>IR (cm$^{-1}$) (KBr)<br>3380, 3162, 1638, 1576, 1543, 1462, 1377, 1309, 1243, 1189, 1116, 1058, 1029, 1013, 949, 928, 866, 845, 801, 745, 706.<br>Mass (FAB) 576 ((M+H)$^+$). |
| Compound 62<br>Hydrochloride<br>Yield: 73 (%)<br>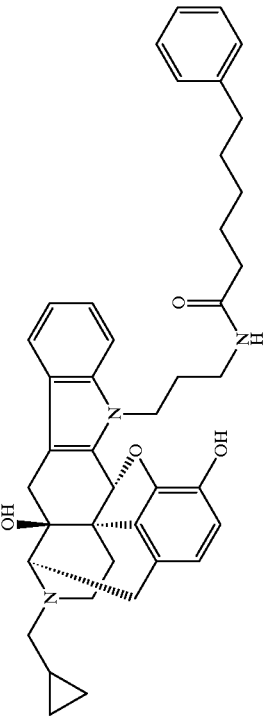 | NMR (ppm) (400 MHz, DMSO-$d_6$)<br>0.43(m, 1H), 0.51(m, 1H), 0.63(m, 1H), 0.73(m, 1H), 1.11 (m, 1H), 1.25–1.35(m, 2H), 1.52–1.63(m, 4H), 1.81(br d, 1H, J=10.8Hz), 1.90–2.05(m, 2H), 2.12(t, 2H, J=7.3Hz), 2.53–2.75(m, 4H), 2.97(m, 1H), 2.99(d, 1H, J=16.1Hz), 3.07–3.48(m, 7H), 4.12(d, 1H, J=6.3Hz), 4.20–4.34(2H, m), 5.87(s, 1H), 6.40(s, 1H, OH), 6.60(d, 1H, J=8.1Hz), 6.64(d, 1H, J=8.1Hz), 7.01(br t, 1H, J=7.5Hz), 7.12–7.27(m, 6H), 7.37(d, 1H, J=7.8Hz), 7.46(d, 1H, J=8.3Hz), 8.02(t, 1H, J=5.4Hz, CONH), 8.99(br s, 1H, NH$^+$), 9.22(s, 1H, OH). | Melting Point 166–175 (° C.).<br>Elemental Analysis<br>as $C_{41}H_{47}N_3O_4 \cdot HCl \cdot 0.35H_2O$<br>Calculated: C, 71.51; H, 7.13; Cl, 5.15; N, 6.10.<br>Found: C, 71.30; H, 7.09; Cl, 5.42; N, 6.35.<br>IR (cm$^{-1}$) (KBr)<br>3380, 3196, 1638, 1543, 1508, 1460, 1377, 1328, 1394, 1243, 1189, 1116, 1060, 1029, 1013, 948, 926, 862, 799, 743.<br>Mass (FAB) 646 (M+H)$^+$). |

-continued

| | | |
|---|---|---|
| Compound 63<br>Methanesulfonate<br>Yield: 60 (%)<br>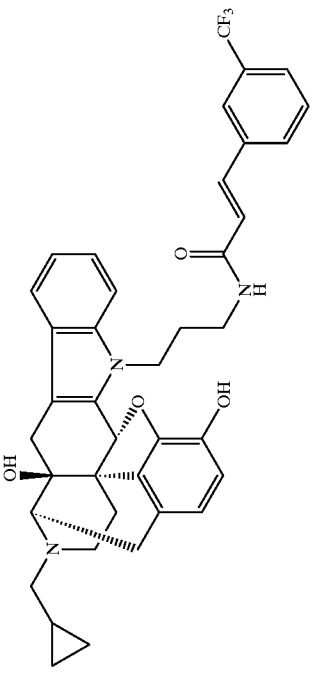 | NMR (ppm) (400 MHz, DMSO-d$_6$)<br>0.45(m, 1H), 0.48(m, 1H), 0.63(m, 1H), 0.73(m, 1H), 1.09 (m, 1H), 1.83(br d, 1H, J=11.7Hz), 1.97–2.15(m, 2H), 2.32 (s, 3H), 2.57(d, 1H, J=16.1Hz), 2.63(m, 1H), 2.72(m, 1H), 2.96(m, 1H), 2.97(d, 1H, J=16.1Hz), 3.12(br d, 1H, J=10.3 Hz), 3.27(dd, 1H, J=20.0, 6.3Hz), 3.32–3.42(m, 3H), 3.44(d, 1H, J=20.0Hz), 4.09(d, 1H, J=6.4Hz), 4.28–4.40(m, 2H), 5.91(s, 1H), 6.34(br s, 1H, OH), 6.60(d, 1H, J=8.3Hz), 6.63 (d, 1H, J=8.3Hz), 6.85(d, 1H, J=16.1Hz), 7.02(t, 1H, J=7.3 Hz), 7.19(t, 1H, J=7.8Hz), 7.38(d, 1H, J=7.8Hz), 7.50 (d, 1H, J=8.3Hz), 7.55(d,1H, J=16.1Hz), 7.67(t, 1H, J=7.8Hz), 7.74(d, 1H, J=8.3Hz), 7.91(d, 1H, J=7.8Hz), 7.95(s, 1H), 8.36(t, 1H, J=5.4Hz, NH), 8.94(br s, 1H, NH$^+$), 9.20(br s, 1H, OH). | Melting Point 160–185 (° C.).<br>Elemental Analysis<br>as C$_{39}$H$_{38}$F$_3$N$_3$O$_4$·1.2MeSO$_3$H·0.7H$_2$O<br>Calculated: C, 60.53; H, 5.59.; F, 7.15; N, 5.27; S, 4.82.<br>Found: C, 60.36; H, 5.72; F, 7.20; N, 5.35; S, 4.92.<br>IR (cm$^{-1}$) (KBr)<br>3252, 1663, 1620, 1560, 1510, 1462, 1437, 1377, 1336, 1170, 1118, 1071, 1044, 978, 862, 801, 775, 746<br>Mass (FAB) 670 ((M+H)$^+$). |
| Compound 64<br>Methanesulfonate<br>Yield: 73 (%)<br>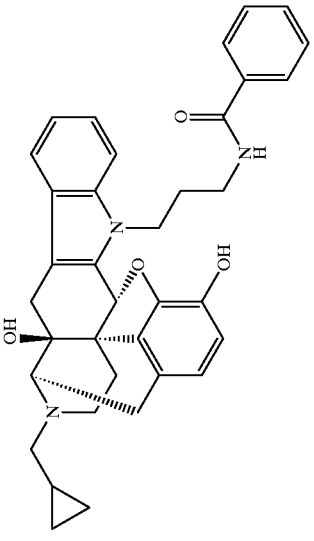 | NMR (ppm) (400 MHz, DMSO-d$_6$)<br>0.46(m, 1H), 0.50(m, 1H), 0.64(m, 1H), 0.74(m, 1H), 1.12 (m, 1H), 1.83(1H, br d, J=11.2Hz), 2.18(m, 1H), 2.30(s, 3H), 2.31(m, 1H), 2.59–2.80(m, 2H), 2.64(d, 1H, J=16.1Hz), 2.96(m, 1H), 3.06(d, 1H, J=16.1Hz), 3.13(m, 1H), 3.28(dd, 1H, J=20.0, 6.2Hz), 3.39(m, 1H), 3.46(d, 1H, J=20.0Hz), 3.55–3.64(m, 2H), 4.11(d, 1H, J=6.4Hz), 4.72–4.88(m, 2H), 6.03(s, 1H), 6.35(s, 1H, OH), 6.61(d, 1H, J=8.3Hz), 6.64(d, 1H, J=8.3Hz), 7.23(t, 1H, J=7.3Hz), 7.38(t, 1H, J=7.3Hz), 7.49–7.61(m, 5H), 7.93–7.98(m, 3H), 8.37(d, 1H, J=8.3Hz), 8.87(t, 1H, J=5.6Hz, NH), 8.96(br s, 1H, NH$^+$), 9.23(s, 1H, OH). | Melting Point 185–225 (° C.).<br>Elemental Analysis<br>as C$_{40}$H$_{39}$N$_3$O$_4$·1.0SMeSO$_3$H·1.0H$_2$O<br>Calculated: C, 66.16; H, 6.14; N, 5.73; S, 4.69.<br>Found: C, 66.21; H, 6.12; N, 5.64; S, 4.52.<br>IR (cm$^{-1}$) (KBr)<br>3296, 1638, 1543, 1510, 1491, 1460, 1423, 1396, 1379, 1315, 1162, 1116, 1044, 853, 804.<br>Mass (FAB) 626 ((M+H)$^+$). |

| | |
|---|---|
| Compound 65<br>Methanesulfonate<br>Yield: 62 (%)<br>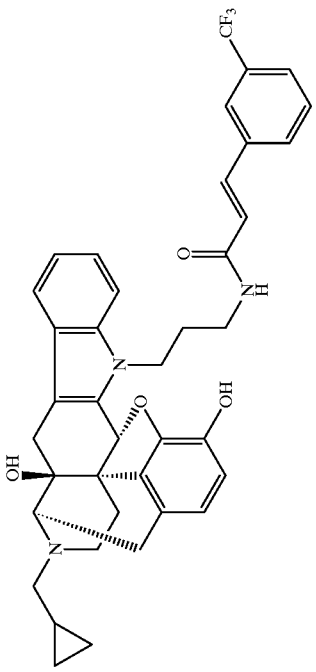 | NMR (ppm) (400 MHz, DMSO-d$_6$)<br>(0.45(m, 1H), 0.51(m, 1H), 0.65(m, 1H), 0.74(m, 1H), 1.12 (m, 1H), 1.83(br d, 1H, J=11.7Hz), 2.14(m, 1H), 2.26(m, 1H), 2.30(s, 3H), 2.64(d, 1H, J=16.1Hz), 2.63–2.80(m, 2H), 2.96(m, 1H), 3.07(d, 1H, J=16.1Hz), 3.13(br d, 1H, J=9.8 Hz), 3.27(dd, 1H, J=20.0, 6.4Hz), 3.36–3.53(m, 4H), 4.11(d, 1H, J=6.3Hz), 4.69–4.88(m, 2H), 6.03(s, 1H), 6.36(br s, 1H, OH), 6.61(d, 1H, J=8.3Hz), 6.64(d, 1H, J=8.3Hz), 6.91(d, 1H, J=16.1Hz), 7.41(br t, 1H, J=7.6Hz), 7.47–7.56(m, 3H), 7.61(d, 1H, J=16.1Hz), 7.68(t, 1H, J=7.8Hz), 7.76(d, 1H, J=7.8Hz), 7.92–7.98(m, 3H), 8.40,(d, 1H, J=8.8Hz), 8.54(t, 1H, J=5.9Hz, NH), 8.96(br s, 1H, NH$^+$), 9.22(br s, 1H, OH). | Melting Point 200–215 (° C.).<br>Elemental Analysis<br>as C$_{43}$H$_{40}$F$_3$N$_3$O$_4$.1.1MeSO$_3$H.0.7H$_2$O<br>Calculated: C, 63.20; H, 5.51; F, 6.80; N. 5.01; S, 4.21.<br>Found: C, 63.00; H, 5.62; F, 6.97; N, 5.06; S, 4.23.<br>IR (cm$^{-1}$) (KBr)<br>3242, 1663, 1620, 1560, 1510, 1460, 1437, 1396, 1334, 1274, 1125, 1071, 1044, 980, 903, 853, 804, 775, 748.<br>Mass (FAB) 720 ((M+H)$^+$). |
| Compound 66<br>Methanesulfonate<br>Yield: 88 (%)<br>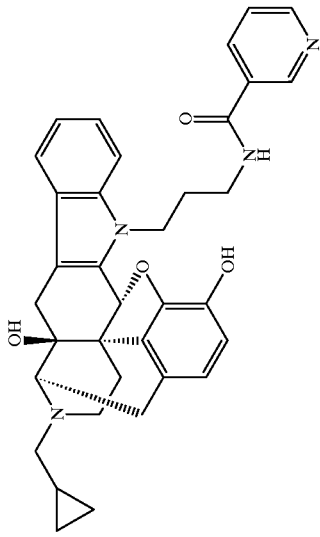 | NMR (ppm) (400 MHz, DMSO-d$_6$)<br>0.46(m, 1H), 0.51(m, 1H), 0.66(m, 1H), 0.75(m, 1H), 1.12 (m, 1H), 1.83(1H, br d, J=11.2Hz), 2.22(m, 1H), 2.32(m, 1H), 2.35(s, 6H), 2.60–2.82(m, 2H), 2.64(d, 1H, J=16.1Hz), 2.97(m, 1H), 3.07(d, 1H, J=16.1Hz), 3.15(m, 1H), 3.29(dd, 1H, J=19.5, 6.8Hz), 3.40(m, 1H), 3.47(d, 1H, J=19.5Hz), 3.58–3.67(m, 2H), 4.11(d, 1H, J=6.4Hz), 4.74–4.90(m, 2H), 6.04(s, 1H), 6.30–7.20(m, 3H, 2OH, NH+), 6.61(d, 1H, J=8.3 Hz), 6.64(d, 1H, J=8.3Hz), 7.32(t, 1H, J=7.8Hz), 7.41(t, 1H, J=7.8Hz), 7.47–7.53(m, 2H), 7.82(dd, 1H, J=7.8, 5.4Hz), 7.96(d, 1H, J=7.8Hz), 8.39(d, 1H, J=7.8Hz), 8.55(br d, 1H, J=7.8Hz), 8.88(dd, 1H, J=5.4, 1.5Hz), 8.95(m, 1H, NH$^+$), 9.17(t, 1H, J=5.6Hz, NH), 9.20(d, 1H, J=1.5Hz). | Melting Point >175 (dec) (° C.).<br>Elemental Analysis<br>as C$_{39}$H$_{38}$N$_4$O$_4$.2.3MeSO$_3$H.0.7H$_2$O.0.9EtOAc<br>Calculated: C, 57.39; H, 5.99; N, 5.96; S, 8.03.<br>Found: C, 57.35; H, 5.78; N, 6.05; S, 8.03.<br>IR (cm$^{-1}$) (KBr)<br>3380, 1663, 1636, 1543, 1508, 1460, 1423, 1377, 1317, 1197, 1116, 1052, 853, 810, 785.<br>Mass (FAB) 627 ((M+H)$^+$). |

-continued

| | | |
|---|---|---|
| Compound 67<br>Methanesulfonate<br>Yield: 73 (%)<br>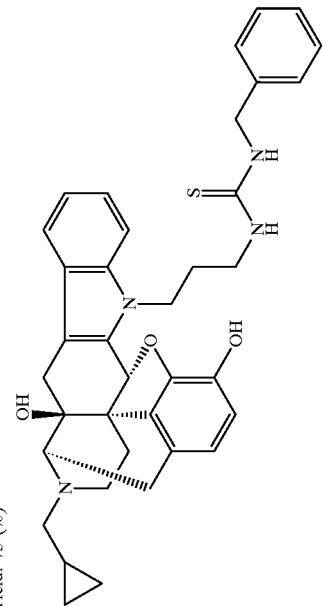 | NMR (ppm) (400 MHz, DMSO-d$_6$)<br>0.46(m, 1H), 0.51 (m, 1H), 0.65(m, 1H), 0.75(m, 1H), 1.11 (m, 1H), 1.85(1H, br d, J=11.6Hz), 2.13–2.33(m, 2H), 2.30 (s, 3H), 2.64(d, 1H, J=16.2Hz), 2.62–2.80(m, 2H), 2.97(m, 1H), 3.07(d, 1H, J=16.2Hz), 3.14(m, 1H), 3.29(dd, 1H, J=19.8, 6.8Hz), 3.41(m, 1H), 3.47(d, 1H, J=19.8Hz), 3.75 (m, 2H), 4.11(d, 1H, J=6.4Hz), 4.65–4.85(m, 4H), 6.01(s, 1H), 6.36(br s, 1H, OH), 6.61(d, 1H, J=8.1Hz), 6.64(d, 1H, J=8.1Hz), 7.18–7.36(m, 5H), 7.42–7.60(m, 3H), 7.87(br s, 1H, NH), 7.96(br d, 1H, J=8.1Hz), 8.08(br s, 1H, NH), 8.40 (d, 1H, J=8.5Hz), 8.95(br s, 1H,NH$^+$), 9.21(br s, 1H, OH). | Melting Point 180–205 (° C.).<br>Elemental Analysis<br>as C$_{39}$H$_{38}$N$_4$O$_4$·2.3MeSO$_3$H·0.7H$_2$O·0.9EtOAc<br>Calculated: C, 57.39; H, 5.99; N, 5.96; S, 8.03.<br>Found: C, 57.35; H, 5.78; N, 6.05; S, 8.03.<br>IR (cm$^{-1}$) (KBr)<br>3260, 1638, 1620, 1551, 1508, 1460, 1423, 1396, 1377, 1328, 1200, 1156, 1114, 1042, 948, 851, 806, 777, 745.<br>Mass (FAB) 671 ((M+H)$^+$). |
| Compound 68<br>Methanesulfonate<br>Yield: 72 (%)<br>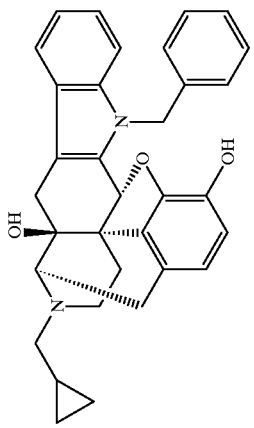 | NMR (ppm) (400 MHz, DMSO-d$_6$)<br>0.42–0.54(2H, m), 0.61–0.78(2H, m), 1.10(1H, m), 1.85(1H, d, J=11.2Hz), 2.30(3H, s), 2.54–2.78(3H, m), 2.96(1H, m), 3.03(1H, d, J=16.1Hz), 3.13(1H, d, J=11.7Hz), 3.27–3.49 (3H, m), 4.10(1H, d, J=6.3Hz), 5.41(1H, d, J=16.1Hz), 5.64 (1H, d, J=16.6Hz), 5.85(1H, s), 6.36(1H, br s), 6.64(1H, d, J=16.6Hz), 6.66(1H, d, J=16.1Hz), 7.00(1H, m), 7.09(1H, m), 7.23–7.34(6H, m), 7.40(1H, d, J=7.8Hz), 8.94(1H, br s), 9.26(1H, br s). | Melting Point 262–278 (dec) (° C.).<br>Elemental Analysis<br>as C$_{33}$H$_{32}$N$_2$O$_3$·CH$_3$SO$_3$H·1.5H$_2$O<br>Calculated: C, 65.05; H, 6.26; N, 4.46; S, 5.11.<br>Found: C, 64.90; H, 6.29; N, 4.38; S, 5.40.<br>IR (cm$^{-1}$) (KBr)<br>3400, 15008, 1460, 1193, 1044, 779, 743, 549.<br>Mass (FAB) 505 ((M+H)$^+$). |
| Compound 69<br>Methanesulfonate<br>Yield: 62 (%)<br>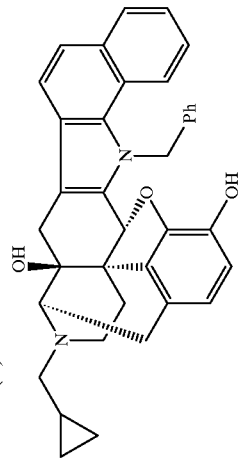 | NMR (ppm) (400 MHz, DMSO-d$_6$)<br>0.42–0.55(m, 2H), 0.60–0.69(m, 1H), 0.71–0.80(m, 1H), 1.06–1.18(m, 1H), 1.81–1.89(m, 1H), 2.29(s, 3H), 2.54–2.65 (m, 1H), 2.67–2.80(m, 2H), 2.93–3.02(m, 1H), 3.09–3.20(m, 2H), 3.28–3.53(m, 3H), 4.13(d, J=6.3Hz, 1H), 5.89(s, 1H), 5.98(d, J=18.1Hz, 1H), 6.11(d, J=18.1Hz, 1H), 6.39(br s, 2H), 6.65(m, 2H), 7.06–7.12(m, 2H), 7.18–7.37(m, 5H), 7.52 (d, J=8.3Hz, 1H), 7.56(d, J=8.3Hz, 1H), 7.87–7.93(m, 1H), 8.15–8.22(m, 1H), 8.96(brs, 1H), 9.16(brs, 1H). | Melting Point 291–306 (dec) (° C.).<br>Elemental Analysis<br>as C$_{37}$H$_{34}$N$_2$O$_3$·CH$_3$SO$_3$H·1.6H$_2$O<br>Calculated: C, 67.16; H, 6.09; N, 3.92; S, 4.72.<br>Found: C, 67.20; H, 6.09; N, 3.92; S, 4.74.<br>IR (cm$^{-1}$) (KBr)<br>3410, 1655, 1636, 1510, 1460, 1398.<br>Mass (FAB) 555 ((M+H)$^+$). |

-continued

| | | |
|---|---|---|
| Compound 70<br>Methanesulfonate<br>Yield: 61 (%) | 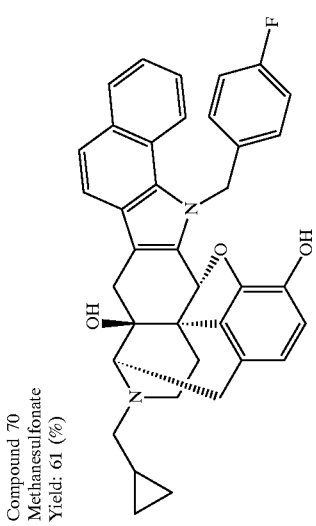 | NMR (ppm) (360 MHz, DMSO-$d_6$) 0.51–0.58(2H, m), 0.60–0.80(2H, m), 1.12(1H, m), 1.85(1H, d, J=11.0Hz), 2.29(3H, s), 2.53–2.80(3H, m), 2.97(1H, m), 3.03–3.19(2H, m), 3.27–3.52(3H, m), 4.13(1H, d, J=4.9Hz), 5.95(1H, s), 5.98(1H, d, J=17.9Hz), 6.07(1H, d, J=17.9Hz), 6.41(1H, s), 6.62–6.67(2H, m), 7.04–7.09(4H, m), 7.34(1H, d, J=3.3Hz), 7.36(1H, d, J=3.3Hz), 7.51–7.58(2H, m), 7.91 (1H, dd, J=6.0, 3.6Hz), 8.16–8.19(1H, m), 8.97(1H, br s), 9.16(1H, s). | Melting Point >200 (dec) (° C.). Elemental Analysis as $C_{37}H_{33}FN_2O_3 \cdot CH_3SO_3H \cdot 0.7H_2O$ Calculated: C, 66.98; H, 5.68; F, 2.79; N, 4.11; S, 4.71. Found: C, 66.81; H, 5.90; F, 2.83; N, 4.34; S, 4.72. IR (cm$^{-1}$) (KBr) 3400, 1516, 1396, 1328, 1222, 1160, 1118, 1046, 853, 808. Mass (FAB) 573 ((M+H)$^+$). |
| Compound 71<br>Methanesulfonate<br>Yield: 71 (%) | 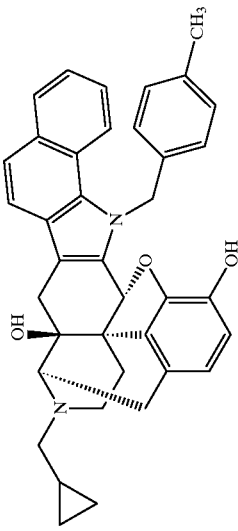 | NMR (ppm) (300 MHz, DMSO-$d_6$) 0.42–0.55(2H, m), 0.60–0.80(2H, m), 1.12(1H, m), 1.85(1H, d, J=11.8Hz), 2.23(3H, s), 2.29(3H, s), 2.44–2.80(3H, m), 2.97(1H, m), 3.09–3.26(2H, m), 3.27–3.54(3H, m), 4.13(1H, J=6.3Hz), 5.87(1H, s), 5.90–6.08(2H, m), 6.40(1H, s), 6.62–6.68(2H, m), 6.98(2H, d, J=8.0Hz), 7.07(2H, d, J=8.0 Hz), 7.33(1H, d, J=3.3Hz), 7.35(1H, d, J=3.3Hz), 7.52(1H, d, J=8.5Hz), 7.56(1H, d, J=8.5Hz), 7.90(1H, dd, J=6.0, 3.6 Hz), 8.19(1H, dd, J=6.3, 3.6Hz), 8.97(1H, br s), 9.20(1H, s). | Melting Point >250 (dec) (° C.). Elemental Analysis as $C_{38}H_{36}N_2O_3 \cdot 1.05CH_3SO_3H \cdot 1.5H_2O$ Calculated: C, 67.33; H, 6.25; N, 4.02; S, 4.83. Found: C, 67.07; H, 6.24; N, 4.33; S, 4.68. IR (cm$^{-1}$) (KBr) 3400, 1514, 1460, 1392, 1365, 1307, 1253, 1195, 1180, 1048, 1033, 810, 748. Mass (FAB) 569 ((M+H)$^+$). |
| Compound 72<br>Methanesulfonate<br>Yield: 77 (%) | 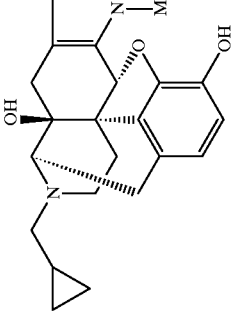 | NMR (ppm) (400 MHz, DMSO-$d_6$) 0.40–0.56(m, 2H), 0.60–0.69(m, 1H), 0.70–0.80(m, 1H), 1.05–1.16(m, 1H), 1.84–1.93(m, 1H), 2.29(s, 3H), 2.59–2.81 (m, 2H), 2.64(d, J=16.1Hz, 1H), 2.90–3.00(m, 1H), 3.07(d, J=16.1Hz, 1H), 3.11–3.18(m, 1H), 3.23–3.32(m, 1H), 3.37–3.46(m, 1H), 3.47(d, J=19.5Hz, 1H), 4.11(d, J=6.8Hz, 1H), 4.33(s, 3H), 6.03(s, 1H), 6.34(s, 1H), 6.61(d, J=8.3Hz, 1H), 6.64(d, J=8.3Hz, 1H), 7.43–7.53(m, 3H), 7.55–7.62(m, 1H), 7.97(d, J=7.8Hz, 1H), 8.63(d, J=7.8Hz, 1H), 8.96(br s, 1H), 9.23(s, 1H). | Melting Point 267–274 (° C.). Elemental Analysis as $C_{31}H_{30}N_2O_3 \cdot CH_3SO_3H \cdot 0.8H_2O$ Calculated: C, 65.24; H, 6.11; N, 4.62; S, 5.44. Found: C, 65.24; H, 6.09; N, 4.76; S, 5.39. IR (cm$^{-1}$) (KBr) 3410, 1622, 1510, 1460, 1398, 1207, 1048. Mass (FAB) 479 ((M+H)$^+$). |

-continued

| | NMR (ppm) | |
|---|---|---|
| Compound 73<br>Methanesulfonate<br>Yield: 31 (%)<br>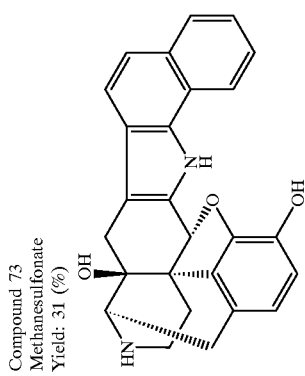 | NMR (ppm) (400 MHz, DMSO-$d_6$)<br>1.79(m, 1H), 2.31(s, 2.9 H), 2.50–2.61(m, 2H), 2.70–2.80 (m, 1H), 2.96(d, J=15.6Hz, 1H), 3.08–3.15(m, 1H), 3.16(d, J=19.5Hz, 1H), 3.38(dd, J=19.5, 6.8Hz, 1H), 3.83(d, J=6.8 Hz, 1H), 5.75(s, 1H), 6.06(br s, 1H), 6.60(d, J=8.3Hz, 1H), 6.63(d, J=8.3Hz, 1H), 7.41(dd, J=7.3, 1.0Hz, 1H), 7.43(d, J=8.8Hz, 1H), 7.48(d, J=8.8Hz, 1H), 7.54(dd, J=7.3, 1.0Hz, 1H), 7.89(d, J=8.3Hz, 1H), 8.42(d, J=8.3Hz, 1H), 8.44–8.84 (br s, 2H), 9.20(br s, 1H) 12.2(br s, 1H). | Melting Point 273–279 (° C.).<br>Elemental Analysis<br>as $C_{27}H_{22}N_2O_3 \cdot CH_3SO_3H \cdot 0.7H_2O \cdot 0.65EtOAc$<br>Calculated: C, 61.67; H, 5.70; N, 4.86; S, 5.56.<br>Found: C, 61.95; H, 5.81; N, 4.59; S, 5.34.<br>IR (cm$^{-1}$) (KBr)<br>3200, 1707, 1638, 1620, 1508, 1464, 1377, 1323, 1280, 1214, 1199, 1172, 1154, 1040, 868.<br>Mass (FAB) 411 ((M+H)$^+$) |
| Compound 74<br>Methanesulfonate<br>Yield: 56 (%)<br>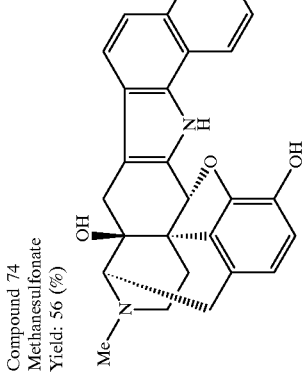 | NMR (ppm) (300 MHz, DMSO-$d_6$)<br>1.79(m, 1H), 2.31(s, 2.9 H), 2.50–2.61(m, 2H), 2.70–2.80 (m, 1H), 2.96(d, J=15.6Hz, 1H), 3.08–3.15(m, 1H), 3.16(d, J=19.5Hz, 1H), 3.38(dd, J=19.5, 6.8Hz, 1H), 3.83(d, J=6.8 Hz, 1H), 5.75(s, 1H), 6.06(br s, 1H), 6.60(d, J=8.3Hz, 1H), 6.63(d, J=8.3Hz, 1H), 7.41(dd, J=7.3, 1.0Hz, 1H), 7.43(d, J=8.8Hz, 1H), 7.48(d, J=8.8Hz, 1H), 7.54(dd, J=7.3, 1.0Hz, 1H), 7.89(d, J=8.3Hz, 1H), 8.60(br s, 1H), 9.20(br s, 1H), 12.2(br s, 1H). | Melting Point 334–340 (° C.).<br>Elemental Analysis<br>as $C_{27}H_{24}N_2O_3 \cdot CH_3SO_3H \cdot 0.4H_2O$<br>Calculated: C, 63.72; H, 5.50; N, 5.31; S, 6.08.<br>Found: C, 63.78; H, 5.68; N, 5.22; S, 6.02.<br>IR (cm$^{-1}$) (KBr)<br>3384, 3232, 1626, 1508, 1468, 1392, 1325, 1207, 1174, 1042, 818.<br>Mass (FAB) 411 ((M+H)$^+$). |
| Compound 75<br>Methanesulfonate<br>Yield: 60 (%)<br>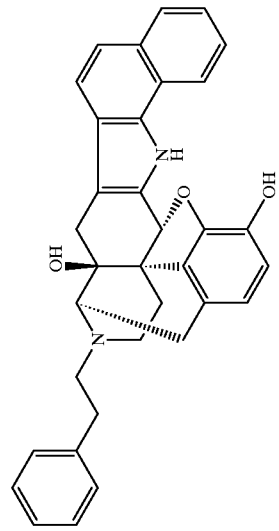 | NMR (ppm) (400 MHz, DMSO-$d_6$)<br>1.84–1.93(m, 1H), 2.30(s, 3.2H), 2.59–2.72(m, 1H), 2.63(d, J=15.6Hz, 1H), 2.76–2.95(m, 2H), 3.02(d, J=15.6Hz, 1H), 3.44–3.34(m, 4H), 3.57(d, J=20.0Hz, 1H), 3.56–3.69(m, 1H), 4.00(d, J=6.4Hz, 1H), 5.81(s, 1H), 6.36(s, 1H), 6.62(d, J=8.3Hz, 1H), 6.65(d, J=8.3Hz, 1H), 7.26–7.59(m, 1H), 7.90 (d, J=7.8Hz, 1H), 8.43(d, J=7.8Hz, 1H), 9.17(br s, 1H), 9.20 (s, 1H), 12.2(s, 1H). | Melting Point 273–280 (dec) (° C.).<br>Elemental Analysis<br>as $C_{34}H_{30}N_2O_3 \cdot CH_3SO_3H \cdot 0.3H_2O$<br>Calculated: C, 68.23; H, 5.66; N, 4.55; S, 5.20.<br>Found: C, 68.21; H, 5.75; N, 4.37; S, 5.31.<br>IR (cm$^{-1}$) (KBr)<br>3400, 1638, 1508, 1460, 1390, 1325, 1199, 1048, 812.<br>Mass(FAB) 515 ((M+H)$^+$). |

-continued

| | |
|---|---|
| Compound 76<br>Methanesulfonate<br>Yield: 54 (%)<br>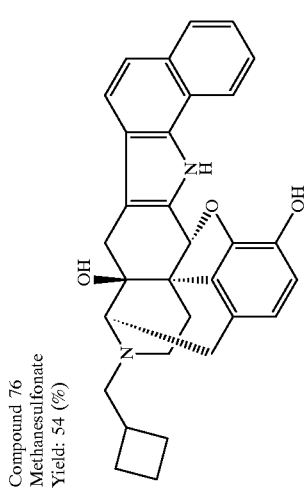 | NMR (ppm) (400 MHz, DMSO-$d_6$)<br>1.80–1.98(m, 5H), 2.02–2.12(m, 1H), 2.14–2.23(m, 1H), 2.29 (s, 3H), 2.58(d, J=16.1Hz, 1H), 2.60–2.69(m, 1H), 2.69–2.83, (m, 2H), 3.00(d, J=16.1Hz, 1H), 3.05–3.18(m, 2H), 3.23(dd, J=19.5, 6.8Hz, 1H), 3.40–3.53(m, 1H), 3.45(d, J=19.5Hz, 1H), 3.62(d, J=6.8Hz, 1H), 5.78(s, 1H), 6.29(s, 1H), 6.60(d, J=8.3Hz, 1H), 6.64(d, J=8.3Hz, 1H), 7.48–7.50(m, 3H), 7.55 (t, J=7.8Hz, 1H), 7.89(d, J=7.8Hz, 1H), 8.42(d, J=7.8Hz, 1H), 8.88(br s, 1H), 9.21(br s, 1H), 12.3(s, 1H). | Melting Point 274 (dec) (° C.).<br>Elemental Analysis<br>as $C_{31}H_{30}N_2O_3 \cdot CH_3SO_3H \cdot 0.2H_2O$<br>Calculated: C, 66.46; H, 6.00; N, 4.84; S, 5.54.<br>Found: C, 66.56; H, 6.22; N, 4.91; S, 5.42.<br>IR (cm$^{-1}$) (KBr)<br>3400, 1626, 1508, 1464, 1427, 1390, 1328, 1199, 1116, 1046, 872.<br>Mass (FAB) 479 ((M+H)$^+$). |
| Compound 77<br>Phosphate<br>Yield: 83 (%)<br>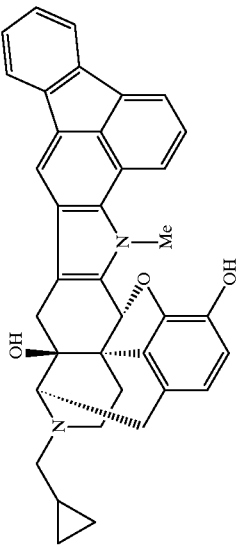 | NMR (ppm) (400 MHz, DMSO-$d_6$)<br>0.22–0.30(2H, m), 0.50–0.63(2H, m), 0.93–1.04(1H, m), 1.74 (1H, d, J=11.2Hz), 2.33–2.49(2H, m), 2.55–2.77(2H, m), 2.67 (1H, d, J=15.6Hz), 2.81–3.00(2H, m), 3.02(1H, d, J=16.1Hz), 3.22(1H, d, J=19.1Hz), 3.58(1H, m), 4.31(3H, s), 5.00–6.00 (2H, br), 5.95(1H, s), 6.54–6.58(2H, m), 7.32–7.41(2H, m), 7.79(1H, dd, J=8.3, 6.8Hz), 7.98(1H, d, J=7.3Hz), 8.01(1H, d, J=7.3Hz), 8.11(1H, d, J=7.3Hz), 8.21(1H, d), 8.49(1H, d, J=8.3Hz). | Melting Point 294 (dec) (° C.).<br>Elemental Analysis<br>as $C_{37}H_{32}N_2O_3 \cdot H_3PO_4 \cdot 0.8H_2O \cdot 0.2Et_2O$<br>Calculated: C, 66.78; H, 5.72; N, 4.12; P, 4.56.<br>Found: C, 66.74; H, 5.76; N, 4.32; P, 4.36.<br>IR (cm$^{-1}$) (KBr)<br>3408, 2968, 1620, 1562, 1510, 1452, 1394, 1315, 1263, 1176, 1031, 915, 859, 801, 565. |
| Compound 78<br>Methanesulfonate<br>Yield: 61 (%) | NMR (ppm) (300 MHz, DMSO-$d_6$)<br>0.40–0.54(2H, m), 0.60–0.80(2H, m), 1.08(1H, m), 1.85(1H, m), 2.35(3H, s), 2.58(1H, d, J=17.3Hz), 2.63–2.78(2H, m), 2.95(1H, m), 3.08–3.18(1H, m), 3.13(1H, d, J=17.3Hz), 3.22–3.44(3H, m), 3.80(3H, s), 4.16(1H, d, J=6.3Hz), 6.24 (1H, s), 6.57–6.63(2H, m), 7.50–7.63(2H, m), 7.56(1H, d, J=8.5Hz), 7.84(1H, d, J=8.5Hz), 8.02(1H, d, J=7.7Hz), 8.67 (1H, d, J=8.5Hz), 9.05(1H, br s), 9.34(1H, br s). | Melting Point 232–243 (dec) (° C.).<br>Elemental Analysis<br>as $C_{31}H_{30}N_2O_5S \cdot 1.15CH_3SO_3H \cdot 1.8H_2O$<br>Calculated: C, 56.32; H, 5.62; N, 4.09; S, 10.06.<br>Found: C, 56.02; H, 5.58; N, 3.99; S, 10.28.<br>IR (cm$^{-1}$) (KBr)<br>3400, 1626, 1508, 1466, 1365, 1334, 117, 1118, 1046, 803, 766, 551, 518.<br>Mass (FAB) 543 (M+H)$^+$). |

| | |
|---|---|
| Compound 79<br>Methanesulfonate<br>Yield: 78 (%)<br>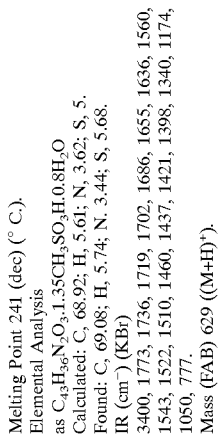 | NMR (ppm) (400 MHz, DMSO-d$_6$)<br>0.45–0.56(2H, m), 0.65–0.72(1H, m), 0.76–0.82(1H, m), 1.10–1.19(1H, m), 1.88(1H, d, J=12.2Hz), 2.32(4.05H, s), 2.59–2.69(1H, m), 2.73–2.87(2H, m), 2.97–3.03(1H, m), 3.14–3.18(1H, m), 3.30(1H, d, J=16.1Hz), 3.55–3.51(3H, m), 4.18(1H, d, J=6.4Hz), 5.94(1H, s), 5.99(1H, d, J=18.1Hz), 6.13(1H, d, J=17.6Hz), 6.47(1H, br s), 6.67–6.71(1H, m), 7.13–7.15(2H, m), 7.21–7.41(5H, m), 7.58(1H, dd, J=8.3, 7.3Hz), 7.97–8.02(3H, m), 8.07(1H, d, J=8.8Hz), 8.25(1H, s), 9.00(1.35H, br s), 9.20(1H, br s). | Melting Point 241 (dec) (° C.).<br>Elemental Analysis<br>as C$_{43}$H$_{46}$N$_2$O$_3$·1.35CH$_3$SO$_3$H·0.8H$_2$O<br>Calculated: C, 68.92; H, 5.61; N, 3.62; S, 5.<br>Found: C, 69.08; H, 5.74; N, 3.44; S, 5.68.<br>IR (cm$^{-1}$) (KBr)<br>3400, 1773, 1736, 1719, 1702, 1686, 1655, 1636, 1560, 1543, 1522, 1510, 1460, 1437, 1421, 1398, 1340, 1174, 1050, 777.<br>Mass (FAB) 629 ((M+H)$^+$). |
| Compound 80<br>Methanesulfonate<br>Yild: 59 (%)<br>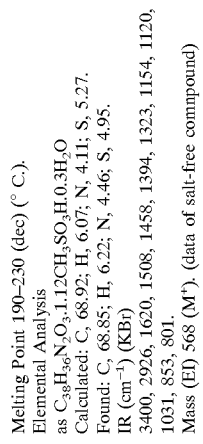 | NMR (ppm) (400 MHz, DMSO-d$_6$)<br>0.40–0.56(m, 2H), 0.60–0.69(m, 1H), 0.70–0.79(m, 1H), 1.04–1.16(m, 1H), 1.79–1.88(m, 1H), 2.30(s, 3.3H), 2.50–2.62(m, 1H), 2.66(d, J=15.6Hz, 1H), 2.68–2.80(m, 1H), 2.91–3.00(m, 1H), 3.11(d, J=15.6Hz, 1H), 3.12–3.22(m, 2H), 3.22–3.48(m, 4H), 3.46(d, J=19.5Hz, 1H), 4.10(d, J=6.4Hz, 1H), 4.85–4.98(m, 1H), 5.75(s, 1H), 6.31(br s, 1H), 6.61 (d, J=8.3Hz, 1H), 6.64(d, J=8.3Hz, 1H), 7.30–7.36(m, 1H), 7.39–7.45(m, 2H), 7.45–7.58(m, 5H), 7.67–7.74(m, 1H), 8.01 (dd, J=8.3, 1.0Hz, 1H), 8.50(d, J=8.3Hz, 1H), 8.97(br s, 1H), 9.25(br s, 1H). | Melting Point 190–230 (dec) (° C.),<br>Elemental Analysis<br>as C$_{38}$H$_{46}$N$_2$O$_3$·1.12CH$_3$SO$_3$H·0.3H$_2$O<br>Calculated: C, 68.92; H, 6.07; N, 4.11; S, 5.27.<br>Found: C, 68.85; H, 6.22; N, 4.46; S, 4.95.<br>IR (cm$^{-1}$) (KBr)<br>3400, 2926, 1620, 1508, 1458, 1394, 1323, 1154, 1120, 1031, 853, 801.<br>Mass (EI) 568 (M$^+$) (data of salt-free compound) |
| Compound 81<br>Methanesulfonate<br>Yield: 54 (%)<br>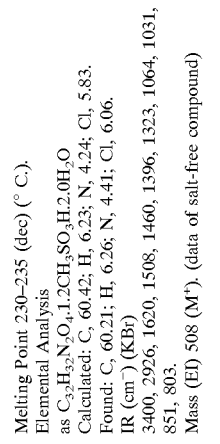 | NMR (ppm) (500 MHz, DMSO-d$_6$)<br>0.42–0.54(m, 2H), 0.60–0.68(m, 1H), 0.71–0.78(m, 1H), 1.06–1.15(m, 1H), 1.85–1.92(m, 1H), 2.31(s, 3.8H), 2.58–2.68(m, 1H), 2.63(d, J=15.6Hz, 1H), 2.69–2.79(m, 1H), 2.92–3.00(m, 1H), 3.07(d, J=15.6Hz, 1H), 3.11–3.17(m, 1H), 3.28(dd, J=19.5, 6.8Hz, 1H), 3.36–3.46(m, 2H), 3.46(d, J=19.5Hz, 1H), 3.84–3.92(m, 1H), 4.02–4.10(m, 1H), 4.11(d, J=6.8Hz, 1H), 4.74–4.88(m, 2H), 6.06(s, 1H), 6.30(br s, 1H), 6.61(d, J=7.8Hz, 1H), 6.64(d, J=7.8Hz, 1H), 7.44–7.54 (m, 3H), 7.58–7.64(m, 1H), 7.97(d, J=8.3Hz, 1H), 8.45(d, J=8.3Hz, 1H), 8.97(br s, 1H), 9.26(br s, 1H). | Melting Point 230–235 (dec) (° C.),<br>Elemental Analysis<br>as C$_{32}$H$_{32}$N$_2$O$_4$·1.2CH$_3$SO$_3$H·2.0H$_2$O<br>Calculated: C, 60.42; H, 6.23; N, 4.24; Cl, 5.83.<br>Found: C, 60.21; H, 6.26; N, 4.41; Cl, 6.06.<br>IR (cm$^{-1}$) (KBr)<br>3400, 2926, 1620, 1508, 1460, 1396, 1323, 1064, 1031, 851, 803.<br>Mass (EI) 508 (M$^+$) (data of salt-free compound) |

-continued

| | |
|---|---|
| Compound 82<br>Methanesulfonate<br>Yield: 81 (%)<br>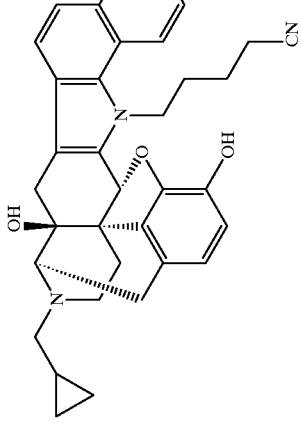 | NMR (ppm) (300 MHz, DMSO-$d_6$)<br>0.40–0.57(m, 2H), 0.57–0.70(m, 1H), 0.70–0.80(m, 1H), 1.03–1.15(m, 1H), 1.80–2.08(m, 5H), 2.29(s, 3H), 2.54–2.80(m, 5H), 2.90–3.02(m, 1H), 3.07(d, J=15.9Hz, 1H), 3.10–3.21(m, 1H), 3.21–3.53(m, 3H), 4.11(d, J=5.5Hz, 1H), 4.64–4.86(m, 1H), 6.02(s, 1H), 6.37(br s, 1H), 6.61(d, J=8.2 Hz, 1H), 6.64(d, J=8.2Hz, 1H), 7.43–7.51(m, 3H), 7.59–7.64(m, 1H), 7.98(d, J=8.0Hz, 1H), 8.40(d, J=8.8Hz, 1H), 8.96 (br s, 1H), 9.23(s, 1H).<br>Melting Point 181–206 (° C.).<br>Elemental Analysis<br>as $C_{35}H_{35}N_3O_3 \cdot CH_3SO_3H \cdot 0.7H_2O$<br>Calculated: C, 66.49; H, 6.39; N, 6.29; S, 4.80.<br>Found: C, 66.34; H, 6.29; N, 6.40; S, 5.06.<br>IR (cm$^{-1}$) (KBr)<br>3400, 2926, 2252, 1638, 1620, 1504, 1460, 1394, 1323, 1290, 1154, 1118, 1031, 907, 853.<br>Mass (EI) 545 (M$^+$) (data of salt-free compound) |
| Compound 83<br>Phosphate<br>Yield: 42 (%)<br>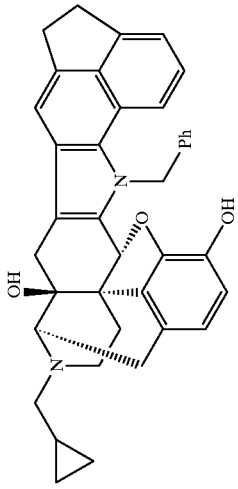 | NMR (ppm) (400 MHz, DMSO-$d_6$)<br>0.26(m, 2H), 0.50–0.63(m, 2H), 0.98(m, 1H), 1.70(m, 1H), 2.25–2.42(m, 2H), 2.50–2.74(m, 2H), 2.64(d, 1H, J=15.6Hz), 2.81(m, 1H), 2.92(d, 1H, J=15.6Hz), 2.94(m, 1H), 3.14–3.37 (m, 5H), 3.53(m, 1H), 5.69(s, 1H), 5.85(br s, 5H, OH, NH$^+$), 5.90(d, 1H, J=18.1Hz), 6.04(d, 1H, J=18.1Hz), 6.63–6.58(m, 2H), 7.02(d, 2H, J=7.3Hz), 7.14–7.22(m, 2H), 7.22–7.30(m, 3H), 7.31(s, 1H), 7.75(d, 1H, J=8.3Hz).<br>Melting Point >230 (dec) (° C.).<br>Elemental Analysis<br>as $C_{39}H_{36}N_2O_3 \cdot 0.95H_3PO_4 \cdot 1.4H_2O$<br>Calculated: C, 67.01; H, 5.84; N, 4.01; P, 4.21<br>Found: C, 67.23; H, 5.84; N, 3.89; P, 4.04.<br>IR (cm$^{-1}$) (KBr)<br>3332, 1638, 1620, 1510, 1460, 1412, 1315, 1245, 1168, 1118, 1060, 1031, 948, 926, 864, 797, 752.<br>Mass (FAB) 581 ((M+H)$^+$). |
| Compound 84<br>Phosphate<br>Yield: 63 (%)<br>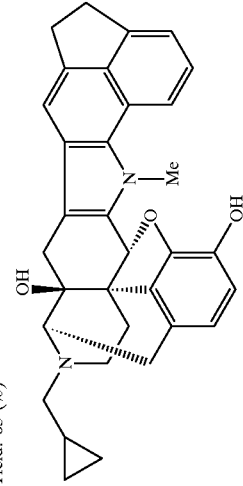 | NMR (ppm) (400 MHz, DMSO-$d_6$)<br>0.26(m, 2H), 0.49–0.65(m, 2H), 0.97(m, 1H), 1.71(m, 1H), 2.32–2.98(m, 6H), 2.55(d, 1H, J=15.6Hz), 2.84(d, 1H, J=15.6Hz), 3.15–3.32(m, 3H), 3.33–3.42(m, 2H), 3.55(m, 1H), 4.25(s, 3H), 4.92(br s, 5H, OH, NH$^+$), 5.88(s, 1H), 6.52(d, 1H, J=8.3Hz), 6.55(d, 1H, J=8.3Hz), 7.25(s, 1H), 7.27(d, 1H, J=7.3Hz), 7.49(dd, 1H, J=8.3, 7.3Hz), 8.19(d, 1H, J=8.3 Hz).<br>Melting Point >230 (dec) (° C.).<br>Elemental Analysis<br>as $C_{33}H_{32}N_2O_3 \cdot 1.05H_3PO_4 \cdot 1.4H_2O$<br>Calculated: C, 62.64; H, 6.05; N, 4.43; P, 5.14.<br>Found: C, 62.90; H, 5.79; N, 4.28; P, 4.98.<br>IR (cm$^{-1}$) (KBr)<br>3350, 1638, 1620, 1508, 1450, 1406, 1313, 1243, 1170, 1116, 1062, 1031, 926, 859, 752,<br>Mass (FAB) 505 ((M+H)$^+$). |

| | |
|---|---|
| Compound 85<br>Methanesulfonate<br>Yield: 36 (%)<br>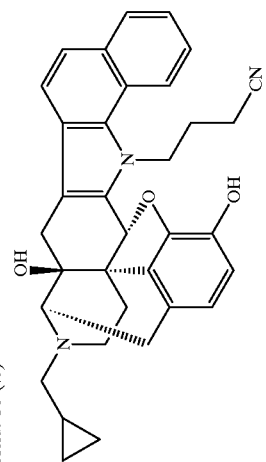 | NMR (ppm) (500 MHz, DMSO-$d_6$)<br>0.42–0.48(m, 1H), 0.48–0.55(m, 1H), 0.62–0.68(m, 1H), 0.72–0.79(m, 1H), 1.07–1.15(m, 1H), 1.86–1.92(m, 1H), 2.14–2.24(m, 1H), 2.30(s, 3.6H), 2.26–2.36(nn, 2H), 2.64(d, J=16.1Hz, 1H), 2.63–2.70(m, 2H), 2.70–2.81(m, 2H), 2.83–2.92(m, 1H), 2.93–3.00(m, 1H), 3.40–3.50(m, 1H), 3.07 (d, J=16.1Hz, 1H), 3.12–3.19(m, 1H), 3.28(dd, J=20.2, 6.8 Hz, 1H), 4.11(d, J=6.8Hz, 1H), 4.70–4.86(m, 2H), 6.04(s, 1H), 6.36(br s, 1H), 6.62(d, J=8.3Hz, 1H), 6.64(d, J=8.3Hz, 1H), 7.46–7.56(m, 3H), 7.59–7.64(m, 1H), 7.99(d, J=8.0Hz, 1H), 8.42(d, J=8.0Hz, 1H), 8.90(br s, 1H), 9.27(br s, 1H). | Melting Point 217–220 (° C.).<br>Elemental Analysis<br>as $C_{31}H_{33}N_3O_3 \cdot 1.2CH_3SO_3H \cdot 0.8H_2O$<br>Calculated: C, 63.92; H, 6.00; N, 6.35; S, 5.82.<br>Found: C, 63.87; H, 6.24; N, 6.23; S, 5.87.<br>IR (cm$^{-1}$) (KBr)<br>3400, 2250, 1638, 1626, 1508, 1462, 1423, 1396, 1328, 1313, 1195, 1060.<br>Mass (FAB) 532 ((M+H)$^+$). |
| Compound 86<br>Methanesulfoante<br>Yield: 31 (%)<br>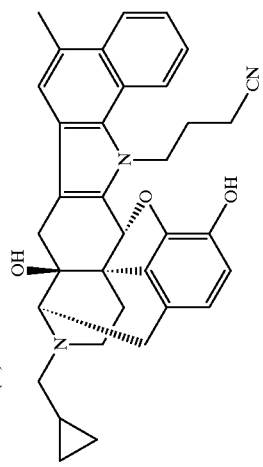 | NMR (ppm) (300 MHz, DMSO-$d_6$)<br>0.40–0.57(m, 2H), 0.58–0.69(m, 1H), 0.69–0.80(m, 1H), 1.03–1.18(m, 1H), 1.82–1.92(m, 1H), 2.09–2.30(m, 2H), 2.31 (s, 3.75H), 2.62(s, 3H), 2.56–3.09(m, 8H), 3.10–3.35(m, 3H), 4.05–4.07(m, 1H), 4.05–4.07(m, 1H), 4.64–4.89(m, 2H), 6.01 (s, 1H), 6.36(br s, 1H), 6.59–6.68(m, 2H), 7.37(s, 1H), 7.49–7.58(m, 1H), 7.60–7.68(m, 1H), 8.96(d, J=8.5Hz, 1H), 8.44(d, J=8.5Hz, 1H), 8.96(br s, 1H), 9.26(br s, 1H). | Melting Point 190 (° C.).<br>Elemental Analysis<br>as $C_{35}H_{35}N_3O_3 \cdot 1.4CH_3SO_3H \cdot 0.2H_2O$<br>Calculated: C, 63.93; H, 6.15; N, 6.04; S, 6.14; S, 6.56.<br>Found: C, 64.09; H, 6.15; N, 6.04; S, 6.22.<br>IR (cm$^{-1}$) (KBr)<br>3400, 2252, 1640, 1622, 1508,1460, 1423, 1400, 1317, 1209, 1116, 1058, 1050.<br>Mass (EI) 545 (M$^+$) (data of salt-free compound) |
| Compound 87<br>Methanesulfonate<br>Yield: 97 (%)<br>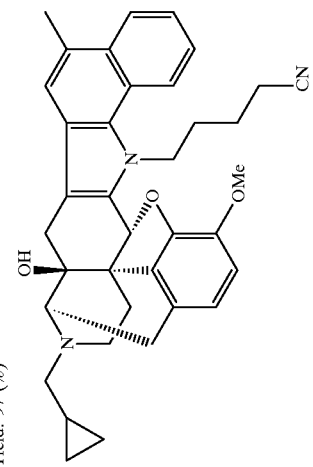 | NMR (ppm) (300 MHz, DMSO-$d_6$).<br>0.40–0.56(m, 2H), 0.60–0.70(m, 1H), 0.70–0.80(m, 1H), 1.04–1.18(m, 1H), 1.70–2.04(m, 5H), 2.30(S, 4.6H), 2.53–2.80(m, 5H), 2.82(S, 3H), 2.88–3.05(m, 1H), 3.06(d, J=16.4Hz, 1H), 3.10–3.21(m, 1H), 3.32(dd, J=19.5, 6.0Hz, 1H), 3.33–3.47(m, 1H), 3.53(d, J=19.5Hz, 1H), 3.69(S, 3H), 4.12(d, J=6.0Hz, 1H), 4.60–4.82(m, ,2H), 6.06(s, 1H), 6.37 (br s, 1H), 6.75(d, J=8.2Hz, 1H), 6.83(d, J=8.2Hz, 1H), 7.35 (s, 1H), 7.52(t, J=7.4Hz, 1H), 7.64(t, J=8.3Hz, 1H), 8.04(d, J=7.7Hz, 1H), 8.41(d, J=7.7Hz, 1H), 9.00(br s, 1H). | Melting Point 150 (° C.).<br>Elemental Analysis<br>as $C_{37}H_{39}N_3O_3 \cdot 1.5CH_3SO_3H \cdot 0.1H_2O$<br>Calculated: C, 64.25; H, 6.33; N, 5.84; S, 6.68.<br>Found: C, 64.23; H, 6.48; N, 5.86; S, 6.49.<br>IR (cm$^{-1}$) (KBr)<br>3450, 3248, 1638, 1508, 1454, 1423, 1402, 1209, 1197, 1123, 1054, 893.<br>Mass (EI) 573 (M$^+$) (data of salt-free compound) |

| | | |
|---|---|---|
| Compound 88<br>Yield: 6 (%)<br>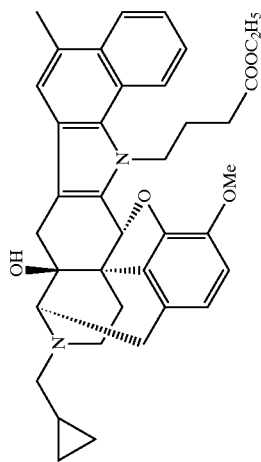 | NMR (ppm) (300 MHz, CDCl$_3$) (data of salt-free compound) 0.12–0.23(m, 2H), 0.51–0.64(m, 2H), 0.84–0.98(m, 1H), 1.28 (t, J=7.1Hz, 3H), 1.81–1.91(m, 1H), 2.24–2.63(m, 8H), 2.65 (s, 3H), 2.66–2.69(m, 1H), 2.70(d, J=15.6Hz, 1H), 2.72–2.80 (m, 1H), 2.84(dd, J=18.4, 6.0Hz, 1H), 2.95(d, J=15.6Hz, 1H), 3.16(d, J=18.4Hz, 1H), 3.39(d, J=6.0Hz, 1H), 3.74(s, 3H), 4.18(q, J=7.1Hz, 2H), 4.60–4.74(m, 1H), 4.78–4.91(m, 1H), 5.83(s, 1H), 6.60(d, J=8.4Hz, 1H), 6.62(d, J=8.4Hz, 1H), 1.36(s, 1H), 7.41–7.51(m, 1H), 7.51–7.62(m, 1H), 8.04 (d, J=8.4Hz, 1H), 8.43(d, J=8.4Hz, 1H). | Melting Point (° C.),<br>Elemental Analysis<br>as<br>Calculated:<br>Found:<br>IR (cm$^{-1}$)<br>Mass (EI) 606 (M$^+$) (data of salt-free compound) |
| Compound 89<br>Methanesulfonate<br>Yield: 81 (%)<br>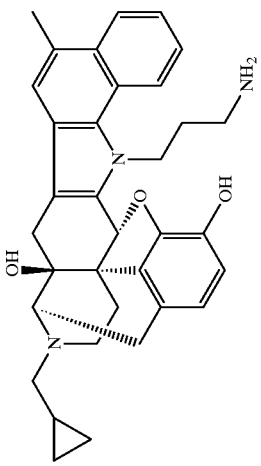 | NMR (ppm) (300 MHz, DMSO-d$_6$) 0.40–0.56(m, 2H), 0.57–0.60(m, 1H), 0.60–0.80(m, 1H), 1.03–1.20(m, 1H), 1.81–1.92(m, 1H), 2.10–2.25(m, 2H), 2.30 (S, 6H), 2.52–2.82(m, 3H), 2.62(S, 3H), 2.90–3.04(m, 3H), 3.03(d, J=15.6Hz, 1H), 3.04–3.20(m, 1H), 3.16(d, J=7.8 Hz, 1H), 3.21–3.31(m, 1H), 3.31–3.42(m, 1H), 3.48(d, J=15.6 Hz, 1H), 4.10(d, J=7.8Hz, 1H), 4.68–4.88(m, 2H), 6.00(s, 1H), 6.33(s, 1H), 6.61(d, J=7.8Hz, 1H), 6.67(d, J=7.8Hz, 1H), 7.37(s, 1H), 7.54(t, J=7.8Hz, 1H), 7.65(t, J=8.3Hz, 1H), 7.80(br s, 2H), 8.05(d, J=7.8Hz, 1H), 8.42(d, J=7.8Hz, 1H), 8.96(br s), 1H), 9.22(s, 1H). | Melting Point 200 (° C.),<br>Elemental Analysis<br>as C$_{34}$H$_{37}$N$_3$O$_3$·2.00CH$_3$SO$_3$H·0.4MeOH<br>Calculated: C, 59.02; H, 6.34; N, 5.67; S, 8.66.<br>Found: C, 58.90; H, 6.59; N, 5.64; S, 8.73.<br>IR (cm$^{-1}$) (KBr)<br>3400, 1626, 1506, 1462, 1403, 1396, 1330, 1183, 1116, 1050, 864.<br>Mass (FAB) 536 ((M+H)$^+$). |
| Compound 90<br>Methanesulfonate<br>Yield: 41 (%)<br>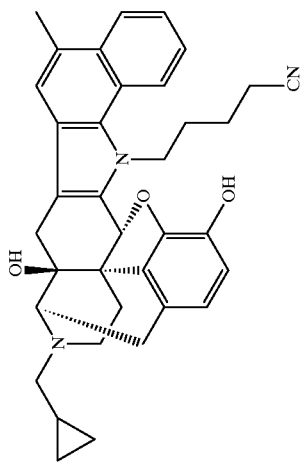 | NMR (ppm) (400 MHz, DMSO-d$_6$) 0.41–0.56(m, 2H), 0.60–0.69(m, 1H), 0.70–0.79(m, 1H), 1.04–1.14(m, 1H), 1.77–1.93(m, 3H), 1.94–2.05(m, 2H), 2.30 (S, 3H), 2.54–2.81(m, 5H), 2.62(S, 3H), 2.92–3.01(m, 1H), 3.05(d, J=16.1Hz, 1H), 3.28(dd, J=19.5, 6.4Hz, 1H), 3.34–3.44(m, 2H), 3.46(d, J=19.5Hz, 1H), 4.05(d, J=6.4Hz, 1H), 4.63–4.81(m, 2H), 5.95(s, 1H), 6.34(br s, 1H), 6.61(d, J=8.3Hz, 1H), 6.64(d, J=8.3Hz, 1H), 7.36(s, 1H), 7.52(t, J=7.8Hz, 1H), 7.64(t, J=7.8Hz, 1H), 8.05(d, J=8.3Hz, 1H), 8.42(d, J=8.3Hz, 1H), 8.95(br s, 1H), 9.21(br s, 1H). | Melting Point 180 (° C.),<br>Elemental Analysis<br>as C$_{36}$H$_{37}$N$_3$O$_3$·1.2CH$_3$SO$_3$H·0.2H$_2$O<br>Calculated: C, 65.84; H, 6.27; N, 6.19, S, 5.67.<br>Found: C, 65.85; H, 6.40; N. 6.19; S. 5.67.<br>IR (cm$^{-1}$) (KBr)<br>3412, 2370, 2300, 1638, 1510, 1460, 1423, 1400, 1315, 1189, 1048.<br>Mass (EI) 559 (M$^+$) (data of salt-free compound) |

| Compound 91 Methanesulfonate Yield: 88 (%) 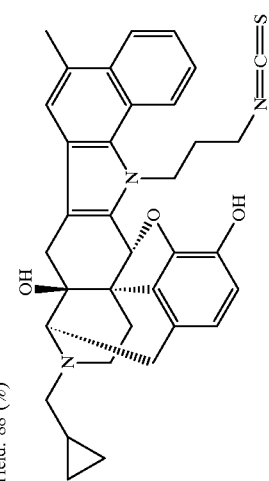 | NMR (ppm) (400 MHz, DMSO-$d_6$) 0.41–0.56(m, 2H), 0.60–0.69(m, 1H), 0.70–0.79(m, 1H), 1.06–1.17(m, 1H), 1.84–1.92(m, 1H), 2.18–2.24(m, 1H), 2.30 (s, 3H), 2.31–2.42(m, 1H), 2.58–2.81(m, 3H), 2.63(S, 3H), 2.92–3.06(m, 1H), 3.04(d, J=16.1Hz, 1H), 3.12–3.20(m, 1H), 3.22–3.32(m, 1H), 3.35–3.45(m, 1H), 3.47(d, J=19.5Hz, 1H), 3.88–4.05(m, 2H), 4.11 (d, J=6.3Hz, 1H), 4.70–4.90(m, 2H), 6.00 (s, 1H), 6.36(s, 1H), 6.61(d, J=7.8Hz, 1H), 6.64(d, J=7.8Hz, 1H), 7.37(s, 1H), 7.54(t, J=7.8Hz, 1H), 7.68(t, J=7.8Hz, 1H), 8.06(d, J=7.8Hz, 1H), 8.45(d, J=7.8Hz, 1H), 8.95(br s,1H), 9.23(br s, 1H). | Melting Point 214 (° C.). Elemental Analysis as $C_{35}H_{35}N_3O_3$·$1.1CH_3SO_3H$·$0.6H_2O$ Calculated: C, 62.45; H, 5.89; N, 6.05; S, 9.70. Found: C, 62.53; H, 6.04; N, 6.03; S, 9.49. IR (cm$^{-1}$) (KBr) (data of salt-free compound) 3400, 2926, 2192, 2114, 1636, 1620, 1506, 1454, 1398, 1379, 1321, 1218, 1149, 1116, 1033. Mass (EI) 577 (M$^+$) (data of salt-free compound) |
| Compound 92 Methanesulfonate Yield: 66 (%) 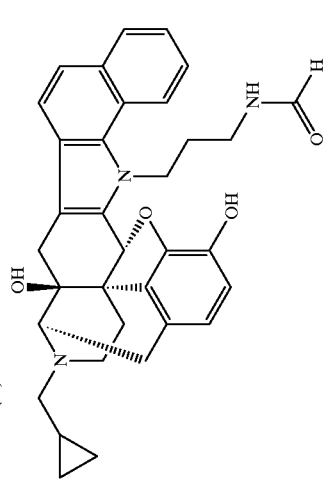 | NMR (ppm) (500 MHz, DMSO-$d_6$) 0.40–0.48(m, 1H), 0.48–0.54(m, 1H), 0.60–0.70 (m, 1H), 0.73–0.80(m, 1H), 1.05–1.17(m, 1H), 1.83–1.93(m, 1H), 2.03–2.12(m, 1H), 2.13–2.26(m, 1H), 2.30(s, 3.5H), 2.64(d, J=16.1Hz, 1H), 2.62–2.80(m, 2H), 2.93–3.00(m, 1H), 3.07(d, J=16.1Hz, 1H), 3.12–3.19(m, 1H), 3.28(dd, J=20.0, 6.8Hz, 1H), 3.36–3.43(m, 3H), 3.46(d, J=20.0Hz, 1H), 4.11 (d, J=6.8Hz, 1H), 4.66–4.79(m, 2H), 6.01(s, 1H), 6.35(br s, 1H), 6.61(d, J=7.8Hz, 1H), 6.64(d, J=7.8Hz, 1H), 7.46(t, J=7.8Hz, 1H), 7.47–7.54(m, 1H), 7.50(d, J=1.4Hz, 1H), 7.60 (td, J=6.8,1.4Hz, 1H), 7.97(d, J=6.8Hz, 1H), 8.18(d, J=1.4 Hz, 1H), 8.31–8.35(m, 1H), 8.39(d, J=7.8Hz, 1H), 8.95(br s, 1H), 9.19(br s, 1H). | Melting Point 207 (° C.). Elemental Analysis as $C_{34}H_{35}N_3O_4$·$1.2CH_3SO_3H$·$0.2H_2O$ Calculated: C, 63.23; H, 6.06; N, 6.20; S, 5.76. Found: C, 63.25; H, 6.22; N, 6.28; S, 5.73. IR (cm$^{-1}$) (KBr) (data of salt-free compound) 3400, 1663, 1508, 1462, 1394, 1330, 1201, 1116, 1048. Mass (FAB) 550 ((M+H)$^+$). |
| Compound 93 Yield: 85 (%) 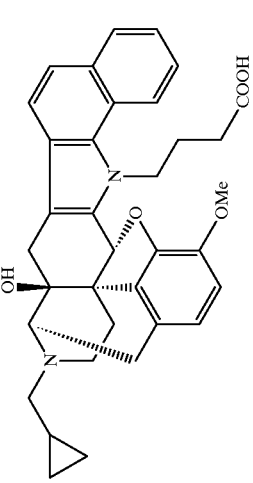 | NMR (ppm) (300 MHz, DMSO-$d_6$) (data of salt-free compound) 0.09–0.22(m, 1H), 0.44–0.60 (m, 2H), 0.81–0.97(m, 1H), 1.00–1.70(m, 1H), 2.00–2.24(m, 3H), 2.28–2.58(m, 6H), 2.64–2.74(m, 2H), 2.73(d, J=15.6Hz, 1H), 3.10(d, J=20.0Hz, 1H), 3.30–3.51(m, 3H), 3.64(s, 3H), 4.60–4.80(m, 2H), 5.93 (s, 1H), 6.62(d, J=7.8Hz, 1H), 6.68(d, J=7.8Hz, 1H), 7.40–7.62(m, 4H), 7.94(d, J=7.8Hz, 1H), 8.56(d, J=7.8Hz, 1H) | Melting Point (° C.). Elemental Analysis as Calculated: Found: IR (cm$^{-1}$) (neat) (data of salt-free compound) 3400, 2366, 1636, 1611, 1562, 1508, 1421, 1386, 1286, 1158, 1123, 1052, 893. Mass (EI) 564 (M$^+$) (data of salt-free compound) |

Example 56

Action of protecting cultured nerve cells from glutamic acid toxicity

It is known that when the blood flow to the brain is temporarily clogged due to cerebral ischemia, hypoxia, or an trauma, delayed cerebral neuronal death is induced [Document: Brain Research, Vol. 239, 57 (1982)]. A possible cause of such damage of the cerebral nerve cells is excitatory toxicity due to an excitatory neutotransmitter such as glutamic acid or the like, which is excessively released with ischemia [Document: Trends in Neuroscience, vol. 10, 299 (1987)]. A compound having the action to protect the nerve cells from the cytotoxicity of glutamic acid exhibits the action to inhibit various ischemic, hemorrhagic or traumatic cerebral disorders, and disorders of the cerebral nerve cells caused by various nerve degeneration, and is useful as an agent for curing and preventing cerebral stroke, traumatic cerebral diseases, cerebral edema, and cerebral neurodegenerative diseases by protecting the cerebral nerve cells from these disorders. This is a problem to be solved by the invention. This action was evaluated by using the in vitro evaluation system which will be described below.

A fetus was taken from the abdomen of a Wistar female rat on the 18 to 19th day of pregnancy under aseptic conditions, and the head of the fetus was opened to extract the brain. The brain was placed in an ice-cooled L-15 medium, and the cerebral cortex was separated under a microscope. The cerebral cortexes of about 30 rats were cut into pieces, and then suspended in 10 ml of a 0.25% trypsin solution and 0.2 ml of a 0.01% DNase solution, followed by culture at 37° C. for 30 minutes. Then, 2 ml of serum was added to the solution, and immediately the resultant mixture was centrifuged at 120 rpm for 2 minutes to separate the precipitates. To the precipitates was added 7 ml of a DF medium (a medium obtained by adding 20 nM of transferrin, 5 μg/ml of insulin, 20 nM of progesterone, 60 nM of selenite, 50 U/ml of penicillin, and 50 U/ml of streptomycin to a mixture equivalent amounts of Dulbecco modified Eagle medium and F-12 medium), followed by 20 pipetting operations using a 10-ml plastic pipette to obtain a cell suspension. The cell suspension was filtered with nylon mesh (pore diameter 43 μm) to fractionate isolated cells. The thus-obtained isolated cells were diluted with a DF medium to a concentration of $6.0 \times 10^5$ cells/ml, and 500 μl of the diluted cells was inoculated in each of the 48 wells of a 48-well culture plate precoated with polylysine, followed by culture at 37° C. for 1 day in the presence of 5% of $CO_2$. On the 2nd day, the medium was changed to a new DF medium, and 10 μl of a solution of 0.5M glutamic acid in distilled water was added to each of the wells (the final glutamic acid concentration was 10 mM), followed by further culture at 37° C. for 24 hours in the presence 5% of $CO_2$. A test compound was dissolved in distilled water, 10% or 100% DMSO or 10% methanol, and 5 μl of the solution was added to each of the wells immediately before glutamic acid was added. As an index of nerve cell damage, the enzyme activity of lactic acid dehydrogenase (LDH) leaking from the damaged cells into the medium was measured. For each of the test compounds, the LDH leakage was measured at each of concentrations to determine a dose-response curve by the modified Cochran-Armitige method. The 50% effective dose ($ED_{50}$) of each of the test compounds we determined from the curve. The results are shown in Table 1.

TABLE 1

Action to protect cultured nerve cells from glutamic acid toxicity

| Compound | $ED_{50}$ (μM) | Compound | $ED_{50}$ (μM) | Compound | $ED_{50}$ (μM) |
|---|---|---|---|---|---|
| 2 | 0.033 | 17 | 0.12 | 67 | 0.027 |
| 3 | 0.053 | 18 | 0.9 | 68 | 0.091 |
| 4 | 0.08 | 19 | 0.2 | 69 | 0.0093 |
| 5 | 0.12 | 20 | 0.027 | 70 | 0.015 |
| 6 | 0.4 | 22 | 0.05 | 71 | 0.019 |
| 7 | 0.2 | 24 | 0.8 | 72 | 0.026 |
| 8 | 0.2 | 25 | 0.3 | 77 | 0.16 |
| 9 | 0.11 | 59 | 0.11 | 79 | 0.19 |
| 11 | 0.138 | 60 | 0.093 | 80 | 0.037 |
| 12 | 0.035 | 61 | 0.14 | 81 | 0.067 |
| 13 | 0.093 | 63 | 0.15 | 83 | 0.073 |
| 14 | 0.086 | 65 | 0.11 | 84 | 0.039 |
| 15 | 0.15 | 66 | 0.4 | | |

These results indicate that the compounds of the present invention have the action to protect the nerve cells from the cytotoxicity of glutamic acid, and are useful as agents for curing and preventing cerebral stroke, traumatic cerebral diseases, cerebral edema, and cerebral neurodegenerative diseases.

Example 57

Infarction inhibiting action in middle cerebral artery ischemia model of rat It is the well known fact that, in the acute stage of human cerebral infarction, significant cerebral edema is caused by cerebral ischemia accompanied with a grave lesion of the intracerebral blood vessels, and that when the blood flow is reopened in the acute stage of cerebral infarction, cerebral edema is significantly worsened. It is also known that, in this way, in the acute stage of cerebral infarction, the lesion proceeds to the peripheral tissue from the core of infarction, and death of the nerve cells is extended with the passage of several days. This possible not only extends and creates grave aftereffects, and causes loss of motor and mental function, but also finally critically influences on the life. As an in vivo experimental model of cerebral infarction which is capable of precisely evaluating the clinical effect of a medicine in conformity with clinical conditions of the disease of a patient of cerebral infarction, the middle cerebral artery occlusion (MCAo)-recirculation model comprising an embolus with a yarn using Wister rates may be used [Document: Japan Journal of Stroke, vol. 8, 1 (1986)]. It is apparent that, in this model, a compound exhibiting the infarction inhibiting action is useful as an agent for curing and preventing cerebral stroke, traumatic cerebral diseases, cerebral edema, and cerebral neurodegenerative diseases. This action was evaluated by applying the MCAo model by the method which will be described below.

In rats of 10 weeks old, after etherization, a median incision of the cervical region was made up to the right carotid artery bifurcation under 1.0% halothane anesthetization with care to preserve the vagus nerves. The common carotid artery and the external carotid artery were separated from the periphery connective tissue with the right carotid artery bifurcation as the center, and each of the arteries was ligated by a 6-0 silk yarn (Eto yarn). Further, a yarn was wound on the internal carotid artery origin in preparation for ligation and fixing after insertion of the embolus. Next, the common carotid artery was incised, and the embolus was inserted from the common carotid artery to the internal carotid artery by about 15 to 16 mm, and ligated and fixed to the internal carotid artery by the silk yarn at the end thereof near the nylon yarn. In this operation, the end of the embolus was inserted into the anterior cerebral artery by about 1 to 2 mm beyond the middle cerebral artery bifurcation, and the inlet of the middle cerebral artery was occluded by the body (resin part) of the embolus for 1 hours. In recirculation, the embolus with a yarn was removed to recirculate the blood flow to the middle cerebral artery. 3 mg/kg of each of test compounds was intraperitoneally administered 10 minutes before occlusion and 1 hour after recirculation of the blood flow. One day after occlusion and recirculation, the whole body was perfused with physiologic saline through the heart, and the brain was extracted. The extracted brain was cooled with ice and water for 5 minutes, and cut at intervals of 2.0 mm to form 7 sections of the cerebral coronal surface. Each of the sections was stained with TTC (Triphenyltetrazolium Chloride), and fixed by a 5% neutral buffer formalin solution. In each of the sections, the infarction area in the right cerebral hemisphere was measured by an image analyzer (Olympus), and the infarction was evaluated by volume (mm$^3$). The infarction volume was compared with the infarction volume of a control group to calculate the rate of inhibition of infarction. The results obtained are shown in Table 2.

for curing or preventing cerebral disorders. Namely, it was apparent that the compounds of the present invention can be used as medicines useful for curing and preventing cerebral stroke, traumatic cerebral diseases, cerebral edema, and cerebral neurodegenerative diseases by inhibiting various ischemic, hemorrhagic or traumatic cerebral disorders, and damage of the cerebral nerve cells caused by various nerve degenerations to protect the cerebral nerve cells.

What is claimed is:

1. An indolomorphinan derivative or pharmacologically acceptable acid addition salt thereof represented by the following formula (II):

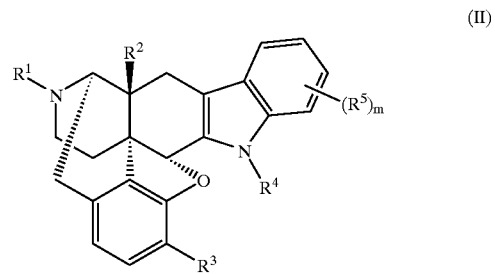

(II)

wherein $R^1$ is hydrogen, alkyl having a carbon number of 1 to 5, cycloalkylalkyl having a carbon number of 4 to 7, cycloalkenylalkyl having a carbon number of 5 to 7, aryl having a carbon number of 6 to 12, aralkyl having a carbon number of 7 to 13, alkenyl having a carbon number of 2 to 7, furan-2-ylalkyl (wherein an alkyl moiety has a carbon number of 1 to 5), or thiophene-2-ylalkyl (wherein an alkyl moiety has a carbon number of 1 to 5);

$R^2$ represents hydrogen, hydroxy, alkoxy having a carbon number of 1 to 5, alkanoyloxy having a carbon number

TABLE 2

Action to inhibit infarction in rat model of middle cerebral artery ischemia

| Compound | Rate of inhibition of infarction (%) | Compound | Rate of inhibition of infarction (%) | Compound | Rate of inhibition of infarction (%) |
|---|---|---|---|---|---|
| 1 | 23 | 17 | 56 | 70 | 34 |
| 2 | 72 | 18 | 23 | 72 | 85 |
| 3 | 54 | 19 | 29 | 73 | 34 |
| 5 | 31 | 20 | 10 | 74 | 27 |
| 6 | 33 | 23 | 79 | 75 | 30 |
| 8 | 49 | 25 | 15 | 76 | 65 |
| 9 | 9 | 61 | 29 | 77 | 84 |
| 10 | 15 | 62 | 10 | 78 | 55 |
| 12 | 67 | 66 | 25 | 79 | 26 |
| 14 | 29 | 67 | 39 | 80 | 29 |
| 16 | 22 | 69 | 69 | 81 | 11 |

These results indicate that these compounds of the present invention have the action to protect the cerebral nerve cells from various damage caused by occurrence of cerebral ischemia to inhibit evolution of infarction, and the action to prevent increase in disease conditions of cerebral infarction. Therefore, it was found that the compounds of the present invention are useful as agents for curing and preventing cerebral stroke, traumatic cerebral diseases, cerebral edema, and cerebral neurodegenerative diseases.

Industrial Applicability

As described in the examples, it was made apparent that the compounds of the present invention are useful as agents of 1 to 5, aralkyloxy having a carbon number of 7 to 13, or arylcarbonyloxy having a carbon number of 7 to 13 (wherein when $R^1$ is cycloalkylalkyl having a carbon number of 4 to 7, cycloalkenylalkyl having a carbon number of 5 to 7, aralkyl having a carbon number of 7 to 13, or alkenyl having a carbon number of 2 to 7, $R^2$ represents hydroxyl);

$R^3$ represents hydrogen, hydroxy, alkoxy having a carbon number of 1 to 5, alkanoyloxy having a carbon number of 1 to 5, aralkyloxy having a carbon number of 7 to 13, or arylcarbonyloxy having a carbon number of 7 to 13 (wherein when $R^1$ is cycloalkylalkyl having a carbon number of 4 to 7, cycloalkenylalkyl having a carbon number of 5 to 7, aralkyl having a carbon number of 7 to 13, or alkenyl having a carbon number of 2 to 7, $R^3$ is not hydrogen);

$R^4$ represents hydrogen, alkyl having a carbon number of 1 to 8, aralkyl having a carbon number of 7 to 13 (which may be substituted by at least one substituent $R^{15}$), alkanoyl having a carbon number of 1 to 5 or $R^6$;

$R^6$ represents arylcarbonyl having a carbon number of 7 to 13 (which may be substituted by at least one substituent $R^{15}$), alkylsulfonyl having a carbon number of 1 to 5, arylsulfonyl having a carbon number of 6 to 12 (which may be substituted by at least one substituent $R^{15}$), aralkylsulfonyl having a carbon number of 7 to 13 (which may be substituted by at least one substituent $R^{15}$), or $(CH_2)_i—R^{16}$;

$R^{15}$ represents fluoro, chloro, bromo, iodo, nitro, amino, hydroxy, alkyl having a carbon number of 1 to 5, alkoxy having a carbon number of 1 to 5, isothiocyanato, trifluoromethyl, trifluoromethoxy, or cyano;

i represents an integer of 1 to 8;

$R^{16}$ represents $OR^7$, $NR^7R^{7'}$, nitro, cyano, isocyano, isocyanato, isothiocyanato, $COOR^7$, $CONR^7R^{7'}$, $NR^7CHO$, $NR^7(CO)—R^9$, $NR^7(CO)NR^8R^9$, $NR^7(C=S)NR^8R^9$, $NR^7(CO)O—R^9$, or $NR^7(C=S)O—R^9$ (wherein $R^7$, $R^{7'}$, $R^8$ independently represent hydrogen or alkyl having a carbon number of 1 to 5); and $R^9$ represents alkyl having a carbon number of 1 to 5, aryl having a carbon number of 6 to 12 (which may be substituted by at least one substituent $R^{15}$), heteroaryl having a hetero atom number of 1 to 3 and a carbon number of 3 to 11 (wherein a hetero atom is O, N or S, and which may be substituted by at least one substituent $R^{15}$), aralkyl having a carbon number of 7 to 13 (which may be substituted by at least one substituent $R^{15}$), or arylalkenyl having a carbon number of 8 to 15 (wherein an aryl moiety may be substituted by at least one substituent $R^{15}$);

m represents an integer of 0 to 4;

$R^5$ represents a substituent selected from the group consisting of fluoro, chloro, bromo, amino, alkyl having a carbon number of 1 to 8, cycloalkyl having a carbon number of 3 to 7, and alkoxy having a carbon number of 1 to 5 (wherein when $R^4$ is $R^6$, $R^5$ represents $R^{11}$), and two $R^5$ groups substituted at adjacent carbons may form together a fused ring structure A (wherein residual 0 to 2 substituents $R^5$ each represent $R^{11}$ or form another fused ring structure A);

said fused ring structure A representing a benzo, indeno or naphtho structure which is unsubstituted or substituted by 1 to 4 substituents $R^{10}$;

$R^{10}$ and $R^{11}$ independently represent (1) fluoro, chloro, bromo, iodo, nitro, alkyl having a carbon number of 6 to 8, alkoxy having a carbon number of 1 to 5, isothiocyanato, trifluoromethyl, trifluoromethoxy, cyano, phenyl, hydroxyalkyl having a carbon number of 1 to 3, $SR^{12}$, $SOR^{12}$, $SO_2R^{12}$, $(CH_2)_kCO_2R^{12}$, $SO_2NR^{13}R^{14}$, $CONR^{13}R^{14}$, $(CH_2)_kNR^{13}R^{14}$, or $(CH_2)_kN(R^{13})COR^{14}$ (wherein K represents an integer of 0 to 5, $R^{12}$ represents alkyl having a carbon number of 1 to 5, $R^{13}$ and $R^{14}$ independently represent hydrogen, alkyl having a carbon number of 1 to 5, or cycloalkylalkyl having a carbon number of 4 to 6), and/or (2) $R^{10}$ and $R^{11}$ substituted at adjacent carbons with a ring junction therebetween form together any one of ethano, propano and o-benzeno bridged structures $R^{10}–R^{11}$; and wherein when $R^4$ is hydrogen, alkyl having a carbon number of 1 to 8, aralkyl having a carbon number of 7 to 13 (which may be substituted by at least one substituent $R^{15}$), or alkanoyl having a carbon number of 1 to 5, m is an integer of 2 to 4, two $R^5$ groups form together fused ring structure A, and each of the residual 0 to 2 $R^5$ groups must be $R^{11}$ (wherein when the fused ring structure A is benzo, at least one $R^{10}$ and one $R^{11}$ substituted at adjacent carbons with a ring junction therebetween must form together a bridged structure $R^{10}–R^{11}$ which must be any one of ethano, propano and o-benzo), or must form together another fused ring structure A, and formula (II) includes (+) form, (−) form and (±) form.

2. The indolomorphinan derivative or pharmacologically acceptable acid addition salt thereof according to claim 1, wherein in formula (II), $R^4$ is hydrogen, alkyl having a carbon number of 1 to 8, or aralkyl having a carbon number of 7 to 13 which may be substituted by at least one substituent $R^{15}$ or alkanoyl having a carbon number of 1 to 5.

3. The indolomorphinan derivative or a pharmacologically acceptable acid addition salt thereof according to claim 1, wherein in formula (II), $R^4$ is $R^6$.

4. The indolomorphinan derivative or a pharmacologically acceptable acid addition salt thereof according to claim 2, wherein formula (II), m is an integer of 2 to 4, two $R^5$ groups form together a fused ring structure A, and the residual 0 to 2 $R^5$ groups are each $R^{11}$ or form together another fused ring structure A.

5. The indolomorphinan derivative or a pharmacologically acceptable acid addition salt thereof according to claim 3, wherein in formula (II), $R^5$ is $R^{11}$ which is independently fluoro, chloro, bromo, iodo, nitro, alkyl having a carbon number of 1 to 8, alkoxy having a carbon number of 1 to 5, isothiocyanato, trifluoromethyl, trifluoromethoxy, cyano, phenyl, hydroxyalkyl having a carbon number of 1 to 3, $SR^{12}$, $SOR^{12}$, $SO_2R^{12}$, $(CH_2)_kCO_2R^{12}$, $SO_2NR^{13}R^{14}$, $CONR^{13}R^{14}$, $(CH_2)_kNR^{13}R^{14}$, or $(CH_2)_kN(R^{13})COR^{14}$.

6. The indolomorphinan derivative or a pharmacologically acceptable acid addition salt thereof according to claim 3, wherein in formula (II), m is an integer of 2 to 4, two $R^5$ groups form together a fused ring structure A, and residual 0 to 2 $R^5$ groups are each $R^{11}$ or form together another fused ring structure A.

7. The indolomorphinan derivative or a pharmacologically acceptable acid addition salt thereof according to claim 4, wherein in formula (II), m is an integer of 2 to 4, two $R^5$ groups form together a fused ring structure A which is a benzo structure, and the residual 0 to 2 $R^5$ groups are each $R^{11}$.

8. The indolomorphinan derivative or a pharmacologically acceptable acid addition salt thereof according to claim 4, wherein in formula (II), m is an integer of 2 to 4, two $R^5$ groups form together the fused ring structure A which is an indeno or naphtho structure, and the residual 0 to 2 $R^5$ groups are each $R^{11}$.

9. The indolomorphinan derivative or a pharmacologically acceptable acid addition salt thereof according to claim 4, wherein in formula (II), m is 4, two $R^5$ groups form together a fused ring structure A, and the residual two $R^5$ groups form together another fused ring structure A.

10. The indolomorphinan derivative or a pharmacologically acceptable acid addition salt thereof according to claim 5, wherein in formula (II), m is an integer of 2 to 4, two $R^5$ groups form together a fused ring structure A which is a benzo structure, and the residual 0 to 2 $R^5$ groups are each $R^{11}$.

11. The indolomorphinan derivative or a pharmacologically acceptable acid addition salt thereof according to claim 5, wherein in formula (II), m is an integer of 3 to 4, two $R^5$ groups form together a fused ring structure A which is an indeno or naphtho structure, and the residual 0 to 2 $R^5$ groups are each $R^{11}$.

12. The indolomorphinan derivative or a pharmacologically acceptable acid addition salt thereof according to claim 5, wherein in formula (II), m is 4, two $R^5$ groups form together a fused ring structure A, and the residual two $R^5$ groups form together another fused ring structure A.

13. A pharmaceutical composition comprising a therapeutically effective amount of an indolomorphinan derivative or pharmacologically acceptable acid addition salt thereof represented by the following formula (II):

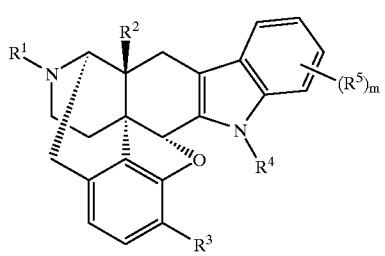

(II)

wherein $R^1$ is hydrogen, alkyl having a carbon number of 1 to 5, cycloalkylalkyl having a carbon number of 4 to 7, cycloalkenylalkyl having a carbon number of 5 to 7, aryl having a carbon number of 6 to 12, aralkyl having a carbon number of 7 to 13, alkenyl having a carbon number of 2 to 7, furan-2-ylalkyl (wherein an alkyl moiety has a carbon number of 1 to 5), or thiophene-2-ylalkyl (wherein an alkyl moiety has a carbon number of 1 to 5);

$R^2$ represents hydrogen, hydroxy, alkoxy having a carbon number of 1 to 5, alkanoyloxy having a carbon number of 1 to 5, aralkyloxy having a carbon number of 7 to 13, or arylcarbonyloxy having a carbon number of 7 to 13 (wherein when $R^1$ is cycloalkylalkyl having a carbon number of 4 to 7, cycloalkenylalkyl having a carbon number of 5 to 7, aralkyl having a carbon number of 7 to 13, or alkenyl having a carbon number of 2 to 7, $R^2$ represents hydroxyl);

$R^3$ represents hydrogen, hydroxy, alkoxy having a carbon number of 1 to 5, alkanoyloxy having a carbon number of 1 to 5, aralkyloxy having a carbon number of 7 to 13, or arylcarbonyloxy having a carbon number of 4 to 7, cycloalkenylalkyl having a carbon number of 5 to 7, aralkyl having a carbon number of 7 to 13, or alkenyl having a carbon number of 2 to 7, $R^3$ is not hydrogen);

$R^4$ represents hydrogen, alkyl having a carbon number of 1 to 8, aralkyl having a carbon number of 7 to 13 (which may be substituted by at least one substituent $R^{15}$), alkanoyl having a carbon number of 1 to 5 or $R^6$;

$R^6$ represents arylcarbonyl having a carbon number of 7 to 13 (which may be substituted by at least one substituent $R^{15}$), alkylsulfonyl having a carbon number of 1 to 5, arylsulfonyl having a carbon number of 6 to 12 (which may be substituted by at least one substituent $R^{15}$), aralkylsulfonyl having a carbon number of 7 to 13 (which may be substituted by at least one substituent $R^{15}$), or $(CH_2)_i-R^{16}$;

$R^{15}$ represents fluoro, chloro, bromo, iodo, nitro, amino, hydroxy, alkyl having a carbon number of 1 to 5, alkoxy having a carbon number of 1 to 5, isothiocyanato, trifluoromethyl, trifluoromethoxy, or cyano;

i represents an integer of 1 to 8;

$R^{16}$ represents $OR^7$, $NR^7R^7$, nitro, cyano, isocyano, isocyanato, isothiocyanato, $COOR^7$, $CONR^7R^7$, $NR^7CHO$, $NR^7(CO)-R^9$, $NR^7(CO)NR^8R^9$, $NR^7(C=S)NR^8R^9$, $NR^7(CO))-R^9$, or $NR^7(C=S)O-R^9$ (wherein $R^7$, $R^7$, $R^8$ independently represent hydrogen or alkyl having a carbon number of 1 to 5); and $R^9$ represents alkyl having a carbon number of 1 to 5, aryl having a carbon number of 6 to 12 (which may be substituted by at least one substituent $R^{15}$), heteroaryl having a hetero atom number of 1 to 3 and a carbon number of 3 to 11 (wherein a hetero atom is O, N or S, and which may be substituted by at least one substituent $R^{15}$), aralkyl having a carbon number of 7 to 13 (which may be substituted by at least one substituent $R^{15}$), or arylalkenyl having a carbon number of 8 to 15 (wherein an aryl moiety may be substituted by at least one substituent $R^{15}$);

m represents an integer of 0 to 4;

$R^5$ represents a substituent selected from the group consisting of fluoro, chloro, bromo, amino, alkyl having a carbon number of 1 to 8, cycloalkyl having a carbon number of 3 to 7, and alkoxy having a carbon number of 1 to 5 (wherein when $R^4$ is $R^6$, $R^5$ represents $R^{11}$), and two $R^5$ groups substituted at adjacent carbons may form together a fused ring structure A (wherein residual 0 to 2 substituents $R^5$ each represent $R^{11}$ or form another fused ring structure A);

said fused ring structure A representing a benzo, indeno or naphtho structure which is unsubstituted or substituted by 1 to 4 substituents $R^{10}$;

$R^{10}$ and $R^{11}$ independently represent (1) fluoro, chloro, bromo, iodo, nitro, alkyl having a carbon number of 6 to 8, alkoxy having a carbon number of 1 to 5, isothiocyanato, trifluoromethyl, trifluoromethyoxy, cyano, phenyl, hydroxyalkyl having a carbon number of 1 to 3, $SR^{12}$, $SOR^{12}$, $SO_2R^{12}$, $(CH_2)_kCO_2R^{12}$, $SO_2NR^{13}R^{14}$, $CONR^{13}R^{14}$, $(CH_2)_kNR^{13}R^{14}$, or $(CH_2)_kN(R^{13})COR^{14}$ (wherein K represents an integer of 0 to 5, $R^{12}$ represents alkyl having a carbon number of 1 to 5, $R^{13}$ and $R^{14}$ independently represent hydrogen, alkyl having a carbon number of 1 to 5, or cycloalkylalkyl having a carbon number of 4 to 6), and/or (2) $R^{10}$ and $R^{11}$ substituted at adjacent carbons with a ring junction therebetween form together any one of ethano, propano and o-benzeno bridged structures $R^{10}-R^{11}$; and wherein when $R^4$ is hydrogen, alkyl having a carbon number of 1 to 8, aralkyl having a carbon number of 7 to 13 (which may be substituted by at least one substituent $R^{15}$), or alkanoyl having a carbon number of 1 to 5, m is an integer of 2 to 4, two $R^5$ groups form together fused ring structure A, and each of the residual 0 to 2 $R^5$ groups must be $R^{11}$ (wherein when the fused ring structure A is benzo, at least one $R^{10}$ and one $R^{11}$ substituted at adjacent carbons with a ring junction therebetween must form together a bridged structure $R^{10}$–$R^{11}$ which is any one of ethano, propano and o-benzo), or must form together another fused ring structure A, and formula (II) includes (+) form, (−) form and (±) form.

14. A method of preventing damage of cerebral nerve cells due to cerebral ischemia or cerebral hemorrhage and treating cerebral disorder comprising administering an effective amount of an indolomorphinan derivative or a pharmacologically acceptable acid addition salt thereof which is represented by the following formula (II):

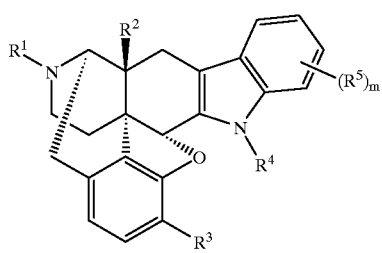

(II)

wherein $R^1$ is hydrogen, alkyl having a carbon number of 1 to 5, cycloalkylalkyl having a carbon number of 4 to 7, cycloalkenylalkyl having a carbon number of 5 to 7, aryl having a carbon number of 6 to 12, aralkyl having a carbon number of 7 to 13, alkenyl having a carbon number of 2 to 7, furan-2-ylalkyl (wherein an alkyl moiety has a carbon number of 1 to 5), or thiophene-2-ylalkyl (wherein an alkyl moiety has a carbon number of 1 to 5);

$R^2$ represents hydrogen, hydroxy, alkoxy having a carbon number of 1 to 5, alkanoyloxy having a carbon number of 1 to 5, aralkyloxy having a carbon number of 7 to 13, or arylcarbonyloxy having a carbon number of 7 to 13 (wherein when $R^1$ is cycloalkylalkyl having a carbon number of 4 to 7, cycloalkenylalkyl having a carbon number of 5 to 7, aralkyl having a carbon number of 7 to 13, or alkenyl having a carbon number of 2 to 7, $R^2$ represents hydroxyl);

$R^3$ represents hydrogen, hydroxy, alkoxy having a carbon number of 1 to 5, alkanoyloxy having a carbon number of 1 to 5, aralkyloxy having a carbon number of 7 to 13, or arylcarbonyloxy having a carbon number of 7 to 13 (wherein when $R^1$ is cycloalkylalkyl having a carbon number of 4 to 7, cycloalkenylalkyl having a carbon number of 5 to 7, aralkyl having a carbon number of 7 to 13, or alkenyl having a carbon number of 2 to 7, $R^3$ is not hydrogen);

$R^4$ represents hydrogen, alkyl having a carbon number of 1 to 8, aralkyl having a carbon number of 7 to 13 (which may be substituted by at least one substituent $R^{15}$), alkanoyl having a carbon number of 1 to 5 or $R^6$;

$R^6$ represents arylcarbonyl having a carbon number of 7 to 13 (which may be substituted by at least one substituent $R^{15}$), alkylsulfonyl having a carbon number of 1 to 5, arylsulfonyl having a carbon number of 6 to 12 (which may be substituted by at least one substituent $R^{15}$), aralkylsulfonyl having a carbon number of 7 to 13 (which may be substituted by at least one substituent $R^{15}$), or $(CH_2)_i$—$R^{16}$;

$R^{15}$ represents fluoro, chloro, bromo, iodo, nitro, amino, hydroxy, alkyl having a carbon number of 1 to 5, alkoxy having a carbon number of 1 to 5, isothiocyanato, trifluoromethyl, trifluoromethoxy, or cyano;

i represents an integer of 1 to 8;

$R^{16}$ represents $OR^7$, $NR^7R^7$, nitro, cyano, isocyano, isocyanato, isothiocyanato, $COOR^7$, $CONR^7R^7$, $NR^7CHO$, $NR^7(CO)$—$R^9$, $NR^7(CO)NR^8R^9$, $NR^7(C=S)NR^8R^9$, $NR^7(CO)O$—$R^9$, or $NR^7(C=SO$—$R^9$ (wherein $R^7$, $R^{7'}$, $R^8$ independently represent hydrogen or alkyl having a carbon number of 1 to 5); and $R^9$ represents alkyl having a carbon number of 1 to 5, aryl having a carbon number of 6 to 12 (which may be substituted by at least one substituent $R^{15}$), heteroaryl having a hetero atom number of 1 to 3 and a carbon number of 3 to 11 (wherein a hetero atom is O, N or S, and which may be substituted by at least one substituent $R^{15}$), aralkyl having a carbon number of 7 to 13 (which may be substituted by at least one substituent $R^{15}$), or arylalkenyl having a carbon number of 8 to 15 (wherein an aryl moiety may be substituted by at least one substituent $R^{15}$);

m represents an integer of 0 to 4;

$R^5$ represents a substituent selected from the group consisting of fluoro, chloro, bromo, amino, alkyl having a carbon number of 1 to 8, cycloalkyl having a carbon number of 3 to 7, and alkoxy having a carbon number of 1 to 5 (wherein when $R^4$ is $R^6$, $R^5$ represents $R^{11}$), and two $R^5$ groups substituted at adjacent carbons may form together a fused ring structure A (wherein residual 0 to 2 substituents $R^5$ each represent $R^{11}$ or form another fused ring structure A);

said fused ring structure A representing a benzo, indeno or naphtho structure which is unsubstituted or substituted by 1 to 4 substituents $R^{10}$;

$R^{10}$ and $R^{11}$ independently represent (1) fluoro, chloro, bromo, iodo, nitro, alkyl having a carbon number of 6 to 8, alkoxy having a carbon number of 1 to 5, isothiocyanato, trifluoromethyl, trifluoromethoxy, cyano, phenyl, hydroxyalkyl having a carbon number of 1 to 3, $SR^{12}$, $SOR^{12}$, $SO_2R^{12}$, $(CH_2)_kCO_2R^{12}$, $SO_2NR^{13}R^{14}$, $CONR^{13}R^{14}$, $(CH_2)_kNR^{13}R^{14}$, or $(CH_2)_kN(R^{13})COR^{14}$ (wherein K represents an integer of 0 to 5, $R^{12}$ represents alkyl having a carbon number of 1 to 5, $R^{13}$ and $R^{14}$ independently represent hydrogen, alkyl having a carbon number of 1 to 5, or cycloalkylalkyl having a carbon number of 4 to 6), and/or (2) $R^{10}$ and $R^{11}$ substituted at adjacent carbons with a ring junction therebetween form together any one of ethano, propano and o-benzeno bridged structures $R^{10}$–$R^{11}$ (wherein when $R^4$ is hydrogen, alkyl having a carbon number of 1 to 8, aralkyl having a carbon number of 7 to 13 (which may be substituted by at least one substituent $R^{15}$), or alkanoyl having a carbon number of 1 to 5, m is an integer of 2 to 4, two $R^5$ groups form together fused ring structure A, and each of the residual 1 to 2 $R^5$ groups must be $R^{11}$ (wherein when the fused ring structure A is benzo, at least one $R^{10}$ and one $R^{11}$ substituted at adjacent carbons with a ring junction therebetween must form together a bridged structure $R^{10}$–$R^{11}$ which must be any one of ethano, propano and o-benzo), or must form together another fused ring structure A), and formula (II) includes (+) form, (−) form and (±) form.

15. The method of preventing damage of cerebral nerve cells due to cerebral ischemia or cerebral hemorrhage and treating cerebral disorder according to claim 14, wherein the cerebral disorder is selected from the group consisting of cerebral stroke, a traumatic cerebral disease, cerebral edema, and a cerebral neurodegenerative disease, an ischemic cerebral disease, or aftereffect of a cerebral disease.

16. The method of preventing damage of cerebral nerve cells due to cerebral ischemia or cerebral hemorrhage and treating cerebral disorder according to claim 15, wherein the cerebral disorder is cerebral stroke.

17. The method of preventing damage of cerebral nerve cells due to cerebral ischemia or cerebral hemorrhage and treating cerebral disorder according to claim 14 comprising administering an effective amount of a cerebral neuroprotective agent capable of inhibiting damage to cerebral nerve cells in various ischemic, hemorrhagic or traumatic cerebral disorders, or cerebral neurodegenerative diseases.

* * * * *